United States Patent
Zhang et al.

(10) Patent No.: US 9,527,851 B2
(45) Date of Patent: Dec. 27, 2016

(54) PYRROLE SIX-MEMBERED HETEROARYL RING DERIVATIVE, PREPARATION METHOD THEREOF, AND MEDICINAL USES THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Xuejun Zhang, Shanghai (CN); Qing Dong, Shanghai (CN); Bonian Liu, Shanghai (CN); Yaoping Zhu, Shanghai (CN); Xiaotao Li, Shanghai (CN); Jiong Lan, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

(*) Notice: Subject to any disclaimer, the term of this patent is extended or adjusted under 35 U.S.C. 154(b) by 33 days.

(21) Appl. No.: 14/365,497

(22) PCT Filed: Dec. 19, 2012

(86) PCT No.: PCT/CN2012/086922
§ 371 (c)(1),
(2) Date: Jun. 13, 2014

(87) PCT Pub. No.: WO2013/091539
PCT Pub. Date: Jun. 27, 2013

(65) Prior Publication Data
US 2014/0336207 A1 Nov. 13, 2014

(30) Foreign Application Priority Data
Dec. 21, 2011 (CN) .......................... 2011 1 0434071

(51) Int. Cl.
| | | |
|---|---|---|
| C07D 487/04 | (2006.01) |
| A61K 31/519 | (2006.01) |
| A61P 35/00 | (2006.01) |
| A61K 45/06 | (2006.01) |
| C07D 471/04 | (2006.01) |
| A61K 31/437 | (2006.01) |
| C07D 217/06 | (2006.01) |
| C07D 221/04 | (2006.01) |
| C07D 209/44 | (2006.01) |
| C07D 209/52 | (2006.01) |
| C07D 403/04 | (2006.01) |

(52) U.S. Cl.
CPC ............. *C07D 487/04* (2013.01); *A61K 45/06* (2013.01); *C07D 209/44* (2013.01); *C07D 209/52* (2013.01); *C07D 217/06* (2013.01); *C07D 221/04* (2013.01); *C07D 403/04* (2013.01); *C07D 471/04* (2013.01)

(58) Field of Classification Search
CPC ........................... C07D 487/04; A61K 31/519
See application file for complete search history.

(56) References Cited

U.S. PATENT DOCUMENTS

2007/0066607 A1 3/2007 Fairhurst et al.
2007/0161666 A1 7/2007 Blumenkopf et al.

FOREIGN PATENT DOCUMENTS

| | | |
|---|---|---|
| CN | 1439010 A | 8/2003 |
| CN | 1798559 A | 7/2006 |
| EP | 2 246 347 A1 | 11/2010 |
| WO | 01/42246 A2 | 6/2001 |
| WO | 02/00661 A1 | 1/2002 |
| WO | 2004/103980 A1 | 12/2004 |

(Continued)

OTHER PUBLICATIONS

K. Suzuki et al., "Role of Common cytokine receptor g chain (gc)- and Jak3-dependent signaling in the proliferation and survival of murine mast cells," blood, vol. 96, pp. 2172-2180, 2000.
K. Malaviya et al., "Genetic and Biochemical Evidence for a Critical Role of Janus Kinase (JAK)-3 in Mast Cell-Mediated Type 1 Hypersensitivity Reactions," Biochem. Biophys. Res. Commun., vol. 257, pp. 807-813, 1999.
R. Malaviya et al., "Targeting Janus Kinase 3 in Mast Cells Prevents Immediate Hypersensitivity Reactions and Anaphylaxis," J. Biol. Chem., vol. 274, pp. 27028-27038, 1999.

(Continued)

*Primary Examiner* — Susanna Moore
(74) *Attorney, Agent, or Firm* — Panitch Schwarze Belisario & Nadel LLP

(57) ABSTRACT

The present invention relates to a pyrrole six-membered heteroaryl ring derivative, the preparation method therefor, and the medicinal uses thereof. Specifically, the present invention relates to a new pyrrole six-membered heteroaryl ring derivative as represented by formula (I), the preparation method therefor, a medicinal composition comprising the derivative, and a therapeutic method using same, and, in particular, the uses as a JAK inhibitor and an immunosuppressor. Substituents in formula (I) have the same definitions as in the description.

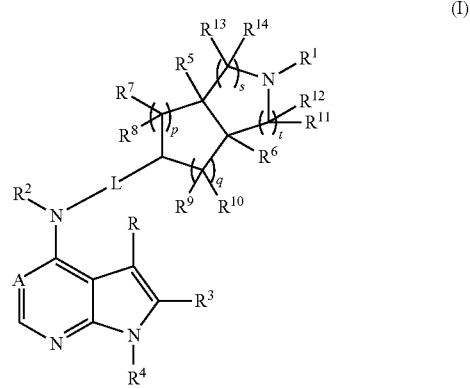

21 Claims, No Drawings

(56) References Cited

FOREIGN PATENT DOCUMENTS

| WO | 2009054941 A1 | 4/2009 |
|---|---|---|
| WO | 2012171863 A1 | 12/2012 |

OTHER PUBLICATIONS

R. A. Kirken, "Targeting JAK3 for Immune Suppression and Allograft Acceptance," Transpl. Proc., vol. 33, pp. 3268-3270, 2001.

S. Verstovsek et al., "Safty and Efficacy of INCB018424, a JAK1 and JAK2 Inhibitor, in Myelofibrosis," N. Engl. J. Med., vol. 363, pp. 1117-1127, 2010.

G. Vidari et al., "Desymmetrization of bicyclo[3.3.0]octane-3,7-dione by the Schmidt reaction: an easy synthesis of tecomanine," Tetrahedron: Asymmetry, vol. 8, No. 17, pp. 2893-2904, 1997.

H. Shulman et al., "Chemically Reactive Immunogen Lead to Functional Convergence of the Immune Response," Journal of the American Chemical Society, vol. 122, No. 44, pp. 10743-10753, 2000.

K. Bambridge et al., "Regio- and enantio-selective enolisations of cyclic ketones using chiral lithium amide bases," J. Chem. Soc. Perkin Trans., vol. 20, pp. 2535-2542, 1995.

M. Zbirovsky et al., "Organische Herbizide VI 3,5-Disubstituierte 1,2,4-Thiadiazole," Collection Czechoslov. Chem. Commun., vol. 36, pp. 4091-4098, 1971.

Int'l Search Report issued on Mar. 28, 2013 in Int'l Application No. PCT/CN2012/086922.

PYRROLE SIX-MEMBERED HETEROARYL RING DERIVATIVE, PREPARATION METHOD THEREOF, AND MEDICINAL USES THEREOF

FIELD OF THE INVENTION

The present invention relates to a new pyrrole six-membered heteroaryl ring derivative, the preparation method thereof, a medicinal composition comprising the derivative thereof, and a therapeutic agent using same, and, in particular, the pharmaceutical uses as a JAK inhibitor and in preparation of an immunosuppressor.

BACKGROUND OF THE INVENTION

Many protein kinases constitute a large family of kinases, which control various signal transduction in cells by catalysis. Many diseases are related to intracellular abnormal responses induced by the regulation of protein kinase, including autoimmune diseases, inflammatory diseases, bone diseases, metabolic diseases, neurological and neurodegenerative diseases, cancers and cardiovascular diseases.

Janus kinase (JAK) is a type of tyrosine kinase. There are four members of JAK, including JAK1, JAK2, JAK3 and TYK2. JAKs play an important role in signal transduction of a variety of cytokines. JAK1, JAK2 and TYK2 widely exist in various tissues and cells, while JAK3 is mainly found in lymphocytes. JAK3 can be bound specifically non-covalently to the common γ chain (Fcγ) of cytokine receptor, while JAK1 is bound to a beta chain. Both JAK3 and JAK1 are activated by IL-2, IL-4, IL-7, IL-9, and IL-15 cytokines. JAK2 plays an important role in the erythropoietin (EPO) signaling pathway, including promoting red blood cell differentiation and activating STATS.

Signal transducer and activator of transcription (STAT) is a group of cytoplasmic proteins which can be bound to DNA in the regulatory region of the target gene. As downstream substrates of JAKs, STATs can be self-activated by tyrosine phosphorylation under the stimulation of an external signal, and then transferred to the nucleus, where they regulates gene transcription.

Cytokine is bound to an associated receptor, resulting in dimerization of the receptor. JAKs coupled with the receptor are in proximity to each other and are activated by the phosphorylation of interactive tyrosine residues. Activated JAKs catalyze the phosphorylation of tyrosine residues of the receptor itself, thereby forming the corresponding "docking sites" for binding of STATs to the receptor complex. SH2 domains of STATs are bound to phosphotyrosine residues of the receptor, and the phosphorylation of C-terminal tyrosine residues is achieved under the role of JAKs. Two phosphorylated STAT molecules interact with each other to form homologous/heterologous dimers, which dissociate from receptor molecules in the cell nucleus, where they bind to promoter regions of a target gene and regulate gene transcription and expression.

Many abnormal immune responses, such as autoimmune diseases including allergies, asthma, (allogeneic) transplant rejection, rheumatoid arthritis, amyotrophic lateral sclerosis and multiple sclerosis, myeloproliferative disorders, and hematologic malignancies including leukemia and lymphoma, and their variations are associated with JAK/STAT signaling pathway.

A JAK3 deficiency is associated with a severe combined immunodeficiency immune (SCID) phenotype in both rodents and humans. The SCID phenotype of JAK3−/− mammals and the lymphoid cell specific expression of JAK3 are two advantageous properties that make JAK3 a target for immunosuppression. T cells of mice having a JAK3 deficiency cannot respond to IL-2, and T cells of mice having a JAK1 deficiency have a weak response to IL-2. IL-2 plays a critical role in T cell modulation. For example, when an antibody is bound to the extracellular part of the IL-2 receptor, the antibody bound IL-2 receptor could effectively prevent transplant rejection.

Further animal studies have indicated that JAK3 not only plays a critical role in B and T lymphocyte maturation, but that it is also essential to maintain T cell function. Modulation of immune activity through this novel mechanism can be useful for the treatment of T cell proliferative disorders such as transplant rejection and autoimmune diseases.

JAK kinase inhibitors, particularly JAK3 kinase inhibitors, could impede T-cell activation and prevent graft rejection after transplantation, and also could provide a therapeutic benefit for other autoimmune disorders. JAK3 is also involved in many biological processes. For example, the proliferation and survival of murine mast cells induced by IL-4 and IL-9 have been shown to be dependent on JAK3- and gamma chain-signaling (Suzuki et al., 2000, *Blood* 96: 2172-2180). JAK3 also plays an important role in IgE receptor-mediated mast cell degradation reactions. JAK3 inhibition also leads to immunosuppression in transplant rejection. JAK3 plays a pivotal role in IgE receptor-mediated mast cell degradation responses (Malaviya et al., 1999, *Biochem. Biophys. Res. Commun.* 257:807-813), and inhibition of JAK3 kinase activity has been demonstrated to prevent type I hypersensitivity, including anaphylaxis (Malaviya et al., 1999, *J. Biol. Chem.* 274: 27028-27038). JAK3 inhibition has also been shown to result in immune suppression for allograft rejection (Kirken, 2001, *Transpl. Proc.* 33:3268-3270). JAK3 kinases have also been involved in the mechanism of other diseases, such as early and late stages of rheumatoid arthritis; familial amyotrophic lateral sclerosis; leukemia; mycosis fungoides; and abnormal cell growth. As an important protein kinase, JAK3 can adjust the function of lymphocytes, macrophages, and mast cells. JAK3 inhibitors are expected to be involved in the treatment or prevention of lymphocytes, macrophages, or mast cell function-related diseases.

For JAK2 subtypes, JAK2 kinase-JAK2 V617F (mutation causes JAK2 kinase activity abnormal), a somatic cell gain-of-function mutation, was found in classic Philadelphia chromosome (Ph)-negative myeloproliferative neoplasms, which include primary thrombocytosis, polythemia vera, and primary myelofibrosis. Therefore, people had a strong interest in the development of JAK2-targeted therapies for these diseases. Some studies found that in patients suffering from marrow fibrosis, JAK2 kinase mutation was produced in more than 50% of patients in vivo, and disease-related symptoms such as anemia, splenomegaly, and the risk of transformation to acute myeloid leukemia (AML) were associated with the increased activity of, and hyperactive JAK-STAT signaling pathway resulting from JAK2 gene mutation. Meanwhile, JAK2 activity was increased abnormally in a variety of solid tumors and hematological tumors (glioblastoma, breast cancer, multiple myeloma, prostate cancer, AML, etc.). Therefore, the development of a selective inhibitor of JAK2 for myeloproliferative neoplasms and leukemia therapy has great medical value and market potential (it is estimated to be billions of dollars). Recently, a selective inhibitor of JAK2 named Ruxolitinib (INCB-018424), developed by INCYTE in cooperation with NOVARTIS, has been approved by the FDA, and appeared on the market successfully. (Safety and Efficacy of INCB018424, a JAK1 and JAK2 Inhibitor, in Myelofibrosis. Srdan Verstovsek, M. D., Ph.D., Hagop Kantarjian, M.D., Ruben A. Mesa, M.D, et al. N Engl J Med 2010; 363:1117-1127).

A series of JAK inhibitors have been disclosed by some patent applications, including WO2001042246, WO2002000661, WO2009054941, and WO2011013785 etc.

Although a series of JAK kinase inhibitors having function in immune diseases have been disclosed, there remains a need to develop new compounds with better efficacy. After continuous efforts, the present invention provides compounds of formula (I), and finds that the compounds having such structure exhibit excellent effects and actions.

SUMMARY OF THE INVENTION

The present invention is directed to provide a compound of formula (I) or a pharmaceutically acceptable salt thereof, and a tautomer, mesomer, racemate, enantiomer, or diastereomer thereof, and a mixture thereof, and a pharmaceutically acceptable salt thereof, as well as metabolites, metabolic precursors, or prodrugs thereof. The present invention provides a compound of formula (I) having the following structure:

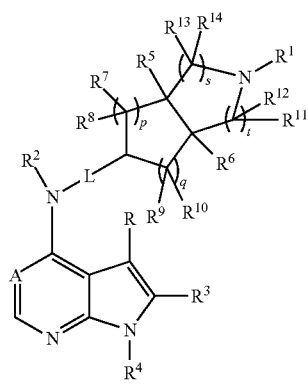

wherein:

A is CH or N;

L is a bond or alkyl;

$R^1$ is selected from the group consisting of hydrogen, alkyl, cycloalkyl, heterocyclyl, aryl, heteroaryl, —$(CH_2)_nC(O)OR^{15}$, —$OC(O)R^{15}$, —$C(O)R^{15}$, —$C(O)NR^{16}R^{17}$, —$NHC(O)R^{15}$, —$NR^{16}R^{17}$, —$OC(O)NR^{16}R^{17}$, —$NHC(O)NR^{16}R^{17}$ and —$S(O)_mR^{15}$, wherein the alkyl, cycloalkyl, heterocyclyl, aryl or heteroaryl is optionally substituted with one or more groups selected from the group consisting of halogen, hydroxy, cyano, nitro, alkyl, alkoxy, cycloalkyl, heterocyclyl, aryl, heteroaryl, —$(CH_2)_nC(O)OR^{15}$, —$OC(O)R^{15}$, —$C(O)R^{15}$, —$C(O)NR^{16}R^{17}$, —$NHC(O)R^{15}$, —$NR^{16}R^{17}$, —$OC(O)NR^{16}R^{17}$, —$NHC(O)NR^{16}R^{17}$, —$S(O)_mR^{15}$, —$NHC(O)(O)R^{15}$ and —$NHS(O)_mR^{15}$;

$R^2$ and $R^4$ are each independently selected from the group consisting of hydrogen and alkyl;

R and $R^3$ are each independently selected from the group consisting of hydrogen, halogen, and alkyl;

$R^5$ and $R^6$ are each independently selected from the group consisting of hydrogen, alkyl, and aryl, wherein the alkyl or aryl is optionally substituted with one or more groups selected from the group consisting of alkyl and halogen;

each of $R^7$, $R^8$, $R^9$ and $R^{10}$ are independently selected from the group consisting of hydrogen, alkyl, hydroxyalkyl, and halogen, or, $R^7$ and $R^8$ or $R^9$ and $R^{10}$ are taken together to form an oxo group;

either $R^{11}$, $R^{12}$, $R^{13}$ or $R^{14}$ is each independently selected from the group consisting of hydrogen, alkyl and halogen, or, $R^{11}$ and $R^{12}$ or $R^{13}$ and $R^{14}$ are taken together to form an oxo group;

$R^{15}$ is selected from the group consisting of hydrogen, alkyl, cycloalkyl, heterocyclyl, alkenyl, alkynyl, aryl, and heteroaryl, wherein the alkyl, cycloalkyl, heterocyclyl, aryl, or heteroaryl is optionally substituted with one or more groups selected from the group consisting of alkyl, halogen, hydroxy, cyano, amino, nitro, alkoxy, cycloalkyl, heterocyclyl, aryl, heteroaryl, —$(CH_2)_nC(O)OR^{18}$, —$OC(O)R^{18}$, —$C(O)R^{18}$, —$C(O)NR^{19}R^{20}$, —$NHC(O)R^{18}$, —$NR^{19}R^{20}$, —$OC(O)NR^{19}R^{20}$, —$NHC(O)NR^{19}R^{20}$, —$S(O)_mR^{18}$, —$NHC(O)OR^{18}$ and —$NHS(O)_mR^{18}$;

$R^{16}$ and $R^{17}$ are each independently selected from the group consisting of hydrogen, alkyl, cycloalkyl, heterocyclyl, aryl, and heteroaryl, wherein the alkyl, cycloalkyl, heterocyclyl, aryl or heteroaryl is optionally substituted with one or more groups selected from the group consisting of alkyl, halogen, hydroxy, cyano, amino, alkoxy, cycloalkyl, heterocyclyl, hydroxyalkyl, alkynyl, aryl, heteroaryl, carboxyl, alkoxycarbonyl, and —$OR^{18}$;

$R^{18}$ is selected from the group consisting of hydrogen, alkyl, cycloalkyl, heterocyclyl, hydroxyalkyl, aryl, and heteroaryl;

$R^{19}$ and $R^{20}$ are each independently selected from the group consisting of hydrogen, alkyl, cycloalkyl, heterocyclyl, aryl, and heteroaryl;

m is 0, 1, or 2;

n is 0, 1, or 2;

p is 0, 1, or 2;

q is 0, 1, or 2;

s is 0, 1, or 2; and t is 0, 1, or 2.

In a preferred embodiment of the invention, the compound of formula (I), or a tautomer, mesomer, racemate, enantiomer, diastereomer, or mixture thereof, or a pharmaceutically acceptable salt thereof, is selected from a compound of formula (II), or a pharmaceutically acceptable salt thereof:

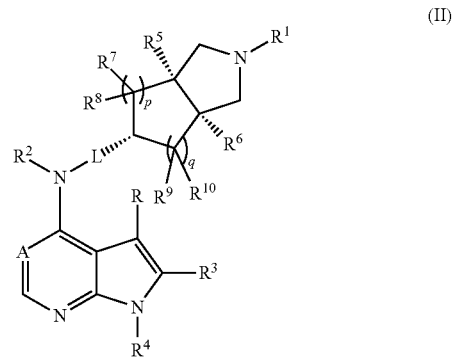

wherein A, L, R, $R^1$ to $R^{10}$, p and q are as described in formula (I).

In another preferred embodiment of the invention, the compound of formula (I), or a tautomer, mesomer, racemate, enantiomer, diastereomer, or mixture thereof, and a pharmaceutically acceptable salt thereof is selected from a compound of formula (III), or a pharmaceutically acceptable salt thereof:

(III)

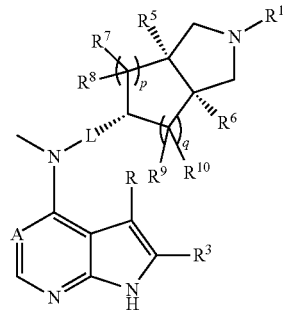

wherein A, L, R, $R^1$, $R^3$, $R^5$ to $R^{10}$, p and q are as described in formula (I).

In another preferred embodiment of the invention, the compound of formula (I), or a tautomer, mesomer, racemate, enantiomer, diastereomer, or mixture thereof, or a pharmaceutically acceptable salt thereof, is selected from a compound of formula (IV-a) or (IV-b), or a tautomer, mesomer, racemate, enantiomer, diastereomer, or mixture thereof, or a pharmaceutically acceptable salt thereof:

(IV-a)

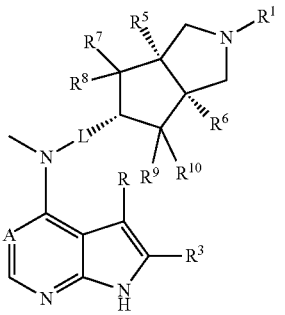

(IV-b)

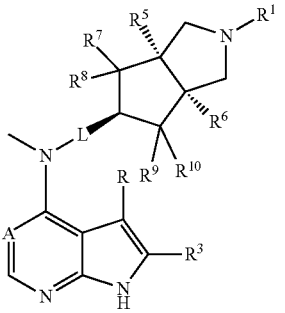

wherein A, L, R, $R^1$, $R^3$ and $R^5$ to $R^{10}$ are as described in formula (I).

In another preferred embodiment of the invention, the compound of formula (I), or a tautomer, mesomer, racemate, enantiomer, diastereomer, or mixture thereof, or a pharmaceutically acceptable salt thereof, is selected from a compound of formula (V-a) or (V-b), or a tautomer, mesomer, racemate, enantiomer, diastereomer, or mixture thereof, or a pharmaceutically acceptable salt thereof:

(V-a)

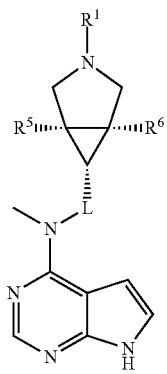

(V-b)

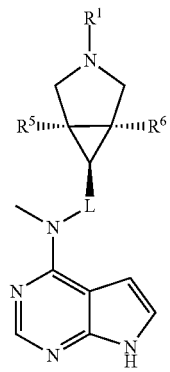

wherein $R^1$, $R^5$ to $R^{10}$ and L are as described in formula (I).

In another preferred embodiment of the invention, the compound of formula (I), or a tautomer, mesomer, racemate, enantiomer, diastereomer, or mixture thereof, or a pharmaceutically acceptable salt thereof, is selected from a compound of formula (VI-a) or (VI-b), or a pharmaceutically acceptable salt thereof:

(VI-a)

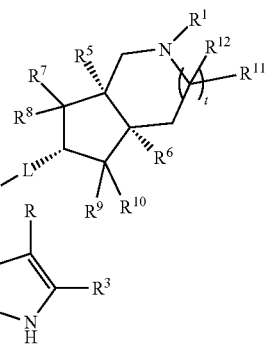

(VI-b)

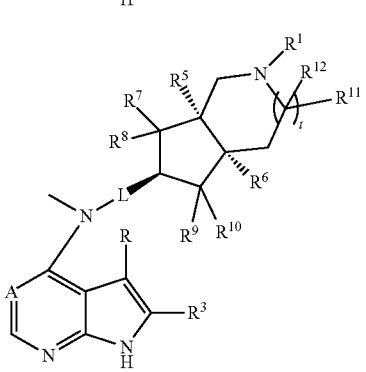

wherein A, L, R, R¹ and R⁵ to R¹² are as described in formula (I).

In another preferred embodiment of the invention, the compound of formula (I), or a tautomer, mesomer, racemate, enantiomer, diastereomer, or mixture thereof, or a pharmaceutically acceptable salt thereof, is selected from a compound of formula (VII-a) or (VII-b), or a pharmaceutically acceptable salt thereof:

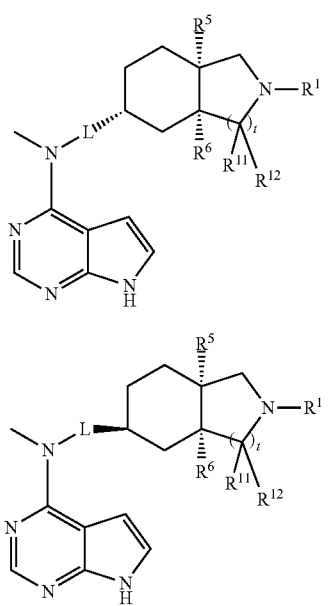

wherein $R^1$, $R^5$, $R^6$, $R^{11}$, $R^{12}$, L and t are as described in formula (I).

In another preferred embodiment of the invention, in the compound of formula (I), or a tautomer, mesomer, racemate, enantiomer, diastereomer, or mixture thereof, or a pharmaceutically acceptable salt thereof, L is a bond or alkyl, preferably a bond; and said alkyl is preferably —CH₂— or —CH(CH₃)—.

In another preferred embodiment of the invention, in the compound of formula (I), or a tautomer, mesomer, racemate, enantiomer, diastereomer, or mixture thereof, or a pharmaceutically acceptable salt thereof, $R^1$ is selected from the group consisting of alkyl, heteroaryl, —(CH₂)ₙC(O)OR¹⁵, —C(O)R¹⁵, —C(O)NR¹⁶R¹⁷ and —S(O)₂R¹⁵, wherein the alkyl or heteroaryl is optionally substituted with one or more groups selected from the group consisting of halogen, hydroxyl, cyano, and —(CH₂)ₙC(O)OR¹⁵;

$R^{15}$ is selected from the group consisting of hydrogen, alkyl, cycloalkyl, heterocyclyl, alkenyl, alkynyl, aryl, and heteroaryl, wherein the alkyl, cycloalkyl, heterocyclyl, aryl or heteroaryl is optionally substituted with one or more groups selected from the group consisting of alkyl, halogen, hydroxy, cyano, amino, nitro, alkoxy, cycloalkyl, heterocyclyl, aryl, heteroaryl, —(CH₂)ₙC(O)OR¹⁸, —OC(O)R¹⁸, —C(O)R¹⁸, —S(O)₂R¹⁸, —NHC(O)(O)R¹⁸, —NHS(O)₂R¹⁸, and —NR¹⁹R²⁰; preferably, $R^{11}$ is selected from the group consisting of alkyl and cycloalkyl, wherein said alkyl, cycloalkyl, or heterocyclyl is optionally substituted with one or more groups selected from the group consisting of alkyl, hydroxyl, cyano, amino, alkoxy, cycloalkyl, heterocyclyl, aryl, heteroaryl, —(CH₂)ₙC(O)OR¹⁸, —OC(O)R¹⁸, —C(O)R¹⁸, —S(O)₂R¹⁸, —NHC(O)OR¹⁸, —NHS(O)₂R¹⁸, and —NR¹⁹R²⁰.

$R^{16}$ and $R^{17}$ are each independently selected from the group consisting of hydrogen, alkyl, and heteroaryl; wherein said heteroaryl is optionally substituted with one or more groups selected from the group consisting of alkoxy, cycloalkyl, hydroxyalkyl, alkynyl, and —OR¹⁸;

$R^{18}$ is selected from the group consisting of hydrogen, alkyl, and hydroxyalkyl;

$R^{19}$ and $R^{20}$ are each independently selected from the group consisting of hydrogen and alkyl;

and n is 0, 1, or 2.

In another preferred embodiment of the invention, in the compound of formula (I), or a tautomer, mesomer, racemate, enantiomer, diastereomer, or mixture thereof, or a pharmaceutically acceptable salt thereof, $R^5$ and $R^6$ are each independently selected from the group consisting of hydrogen and alkyl, preferably hydrogen or methyl.

In another preferred embodiment of the invention, in the compound of formula (I), or a tautomer, mesomer, racemate, enantiomer, diastereomer, or mixture thereof, or a pharmaceutically acceptable salt thereof, $R^7$, $R^8$, $R^9$ and $R^{10}$ are each independently selected from the group consisting of hydrogen, alkyl, and hydroxyalkyl, preferably hydrogen, methyl, or hydroxymethyl, more preferably hydrogen.

In another preferred embodiment of the invention, in the compound of formula (I), or a tautomer, mesomer, racemate, enantiomer, diastereomer, or mixture thereof, or a pharmaceutically acceptable salt thereof, $R^{11}$, $R^{12}$, $R^{13}$ and $R^{14}$ are each independently hydrogen.

In another preferred embodiment of the invention, in the compound of formula (I), or a tautomer, mesomer, racemate, enantiomer, diastereomer, or mixture thereof, or a pharmaceutically acceptable salt thereof, $R^{11}$ and $R^{12}$, or $R^{13}$ and $R^{14}$ are taken together to form an oxo group.

In another preferred embodiment of the invention, the compound of formula (I), or a tautomer, mesomer, racemate, enantiomer, diastereomer, or mixture thereof, or a pharmaceutically acceptable salt thereof, A is N.

The compounds of the present invention include all conformational isomers, e.g. cis-isomers and trans-isomers; and all their optical isomers and stereoisomers and mixtures thereof. The compounds of the present invention have asymmetric centers, and therefore there are different enantiomeric and diastereomeric isomers. The present invention relates to the use of compounds of the invention and pharmaceutical compositions comprising compounds of the invention, and the therapeutic method thereof. On this point, the compounds of the present invention include Z-isomers and E-isomers. The compounds of formula (I) may exist as tautomers. The present invention relates to the use of all such tautomers and mixtures thereof.

Typical compounds of the present invention, or a tautomer, mesomer, racemate, enantiomer, diastereomer, or mixture thereof include, but are not limited to the following:

| Example No. | Structure and Name |
|---|---|
| 1 | 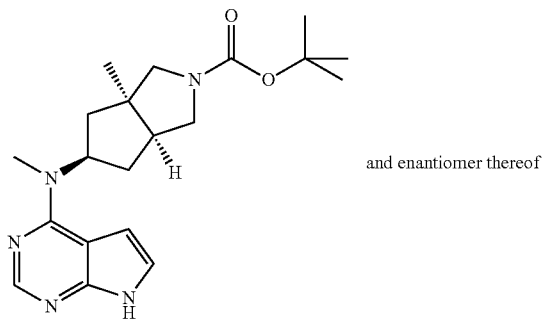 [SMILES: CN(c1ncnc2[nH]ccc12)[C@@H]1C[C@@H]2CN(C(=O)OC(C)(C)C)C[C@]2(C)C1] and enantiomer thereof (3aR,5R,6aS/3aS,5S,6aR)-tert-butyl-3a-methyl-5-(methyl(7H-pyrrolo[2,3-d]pyrimidin-4-yl)amino)hexahydrocyclopenta[c]pyrrole-2(1H)-carboxylate |
| 2 | 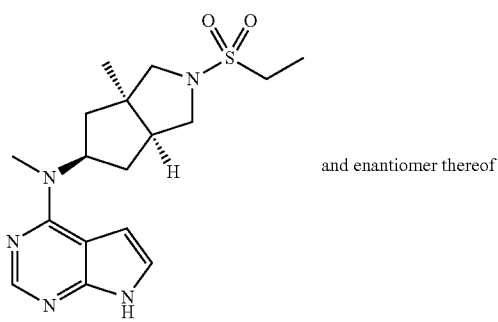 [SMILES: CCS(=O)(=O)N1C[C@H]2C[C@@H](N(C)c3ncnc4[nH]ccc34)C[C@@]2(C)C1] and enantiomer thereof N-((3aR,5R,6aS/3aS,5S,6aR)-2-(ethylsulfonyl)-3a-methyloctahydro-cyclopenta[c]pyrrol-5-yl)-N-methyl-7H-pyrrolo[2,3-d]pyrimidin-4-amine |
| 3 | 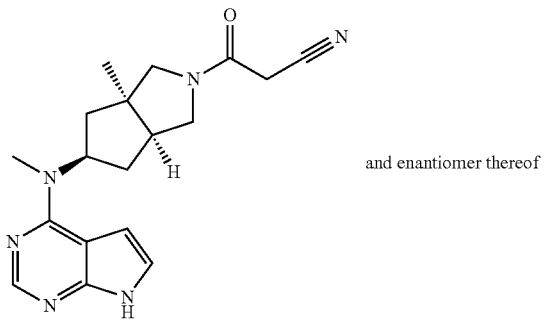 [SMILES: CN(c1ncnc2[nH]ccc12)[C@@H]1C[C@@H]2CN(C(=O)CC#N)C[C@]2(C)C1] and enantiomer thereof 3-((3aR,5R,6aS/3aS,5S,6aR)-3a-methyl-5-(methyl(7H-pyrrolo[2,3-d]pyrimidin-4-yl)amino)hexahydrocyclopenta[c]pyrrol-2(1H)-yl)-3-oxopropanenitrile |
| 4 | 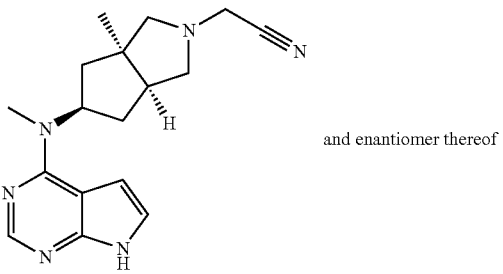 [SMILES: CN(c1ncnc2[nH]ccc12)[C@@H]1C[C@@H]2CN(CC#N)C[C@]2(C)C1] and enantiomer thereof 2-((3aR,5R,6aS/3aS,5S,6aR)-3a-methyl-5-(methyl(7H-pyrrolo[2,3-d]pyrimidin-4-yl)amino)hexahydrocyclopenta[c]pyrrol-2(1H)-yl)acetonitrile |

-continued

| Example No. | Structure and Name |
|---|---|
| 5 | 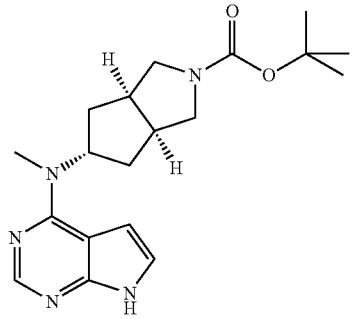 [SMILES: CN(c1ncnc2[nH]ccc12)[C@H]1C[C@@H]2CN(C(=O)OC(C)(C)C)C[C@@H]2C1]<br>(3aR,5S,6aS)-tert-butyl 5-(methyl(7H-pyrrolo[2,3-d]pyrimidin-4-yl)amino)hexahydrocyclopenta[c]pyrrole-2(1H)-carboxylate |
| 6 | 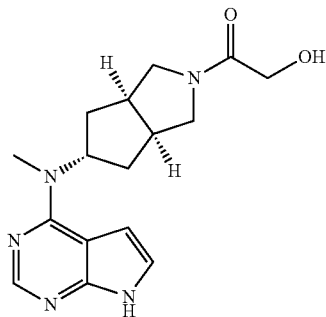 [SMILES: CN(c1ncnc2[nH]ccc12)[C@H]1C[C@@H]2CN(C(=O)CO)C[C@@H]2C1]<br>2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)ethanone |
| 7 | 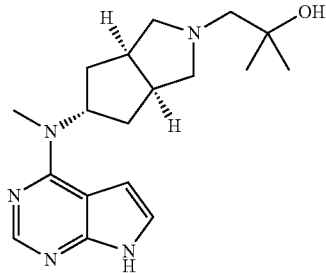 [SMILES: CN(c1ncnc2[nH]ccc12)[C@H]1C[C@@H]2CN(CC(C)(C)O)C[C@@H]2C1]<br>2-methyl-1-((3aR,5S,6aS)-5-(methyl(7H-pyrrolo[2,3-d]pyrimidin-4-yl)amino)hexahydrocyclopenta[c]pyrrol-2(1H)-yl)propan-2-ol |
| 8 | 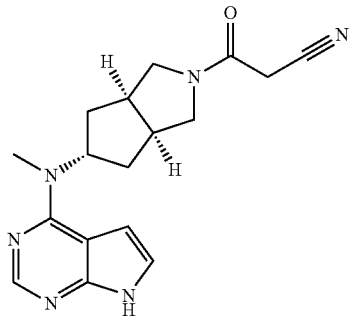 [SMILES: CN(c1ncnc2[nH]ccc12)[C@H]1C[C@@H]2CN(C(=O)CC#N)C[C@@H]2C1]<br>3-((3aR,5S,6aS)-5-(methyl(7H-pyrrolo[2,3-d]pyrimidin-4-yl)amino)hexahydrocyclopenta[c]pyrrol-2(1H)-yl)-3-oxopropanenitrile |

-continued

| Example No. | Structure and Name |
|---|---|
| 9 | 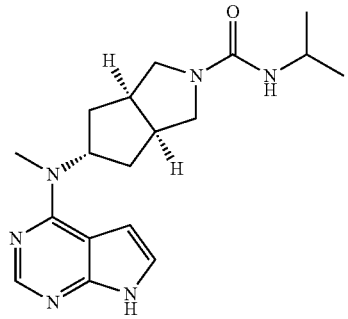 [SMILES: CC(C)NC(=O)N1C[C@H]2C[C@H](N(C)c3ncnc4[nH]ccc34)C[C@H]2C1]<br>(3aR,5S,6aS)-N-isopropyl-5-(methyl(7H-pyrrolo[2,3-d]pyrimidin-4-yl)amino)hexahydrocyclopenta[c]pyrrole-2(1H)-carboxamide |
| 10 | 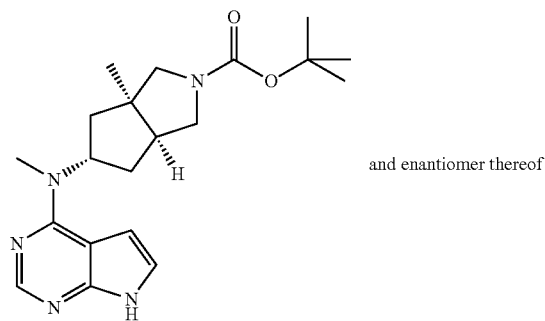 [SMILES: CN(c1ncnc2[nH]ccc12)[C@H]1C[C@@H]2CN(C(=O)OC(C)(C)C)C[C@]2(C)C1] and enantiomer thereof<br>(3aR,5S,6aS/3aS,5R,6aR)-tert-butyl 3a-methyl-5-(methyl(7H-pyrrolo[2,3-d]pyrimidin-4-yl)amino)hexahydrocyclopenta[c]pyrrole-2(1H)-carboxylate |
| 11 | 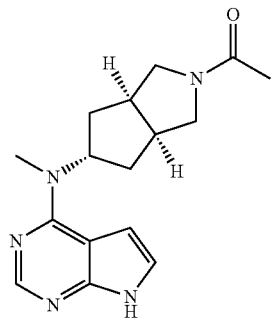 [SMILES: CC(=O)N1C[C@H]2C[C@H](N(C)c3ncnc4[nH]ccc34)C[C@H]2C1]<br>1-((3aR,5S,6aS)-5-(methyl(7H-pyrrolo[2,3-d]pyrimidin-4-yl)amino)hexahydrocyclopenta[c]pyrrol-2(1H)-yl)ethanone |
| 12 | 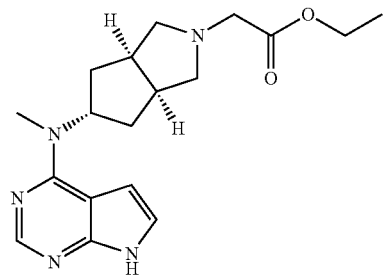 [SMILES: CCOC(=O)CN1C[C@H]2C[C@H](N(C)c3ncnc4[nH]ccc34)C[C@H]2C1]<br>ethyl 2-((3aR,5S,6aS)-5-(methyl(7H-pyrrolo[2,3-d]pyrimidin-4-yl)amino)hexahydrocyclopenta[c]pyrrol-2(1H)-yl)acetate |

| Example No. | Structure and Name |
|---|---|
| 13 | 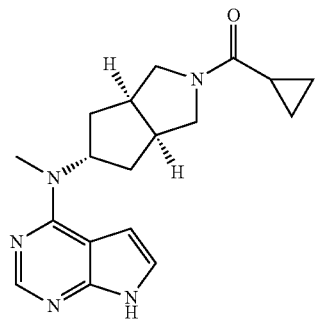 [SMILES: CN(c1ncnc2[nH]ccc12)[C@H]1C[C@@H]2CN(C(=O)C3CC3)C[C@@H]2C1]

cyclopropyl((3aR,5S,6aS)-5-(methyl(7H-pyrrolo[2,3-d]pyrimidin-4-yl)amino)hexahydrocyclopenta[c]pyrrol-2(1H)-yl)methanone |
| 14 | 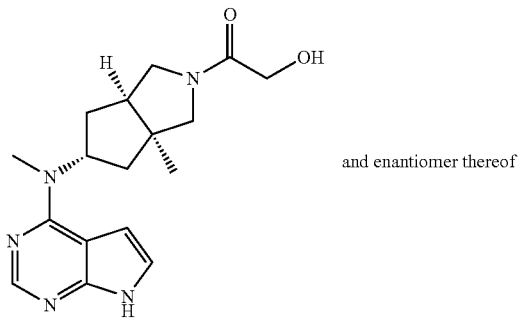 [SMILES: CN(c1ncnc2[nH]ccc12)[C@@H]1C[C@H]2CN(C(=O)CO)C[C@@]2(C)C1]

and enantiomer thereof 2-hydroxy-1-((3aS,5R,6aR/3aS,5R,6aR)-3a-methyl-5-(methyl(7H-pyrrolo[2,3-d]pyrimidin-4-yl)amino)hexahydrocyclopenta[c]pyrrol-2(1H)-yl)ethanone |
| 15 | 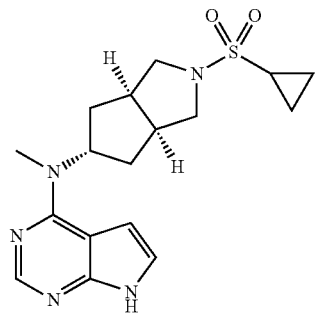 [SMILES: CN(c1ncnc2[nH]ccc12)[C@H]1C[C@@H]2CN(S(=O)(=O)C3CC3)C[C@@H]2C1]

N-((3aR,5S,6aS)-2-(cyclopropylsulfonyl)octahydrocyclopenta[c]pyrrol-5-yl)-N-methyl-7H-pyrrolo[2,3-d]pyrimidin-4-amine |
| 16 | 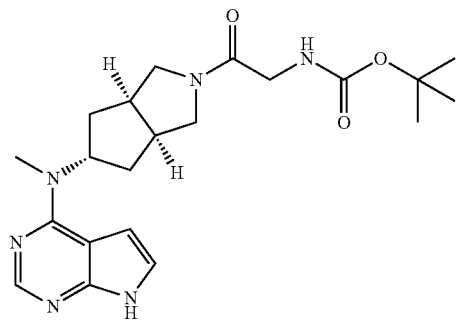 [SMILES: CN(c1ncnc2[nH]ccc12)[C@H]1C[C@@H]2CN(C(=O)CNC(=O)OC(C)(C)C)C[C@@H]2C1]

tert-butyl (2-((3aR,5S,6aS)-5-(methyl(7H-pyrrolo[2,3-d]pyrimidin-4-yl)amino)hexahydrocyclopenta[c]pyrrol-2(1H)-yl)-2-oxoethyl)carbamate |

-continued

| Example No. | Structure and Name |
|---|---|
| 17 | 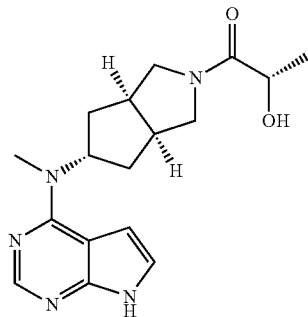 [SMILES: C[C@H](O)C(=O)N1C[C@H]2C[C@H](N(C)c3ncnc4[nH]ccc34)C[C@H]2C1]<br>(S)-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)propan-1-one |
| 18 | 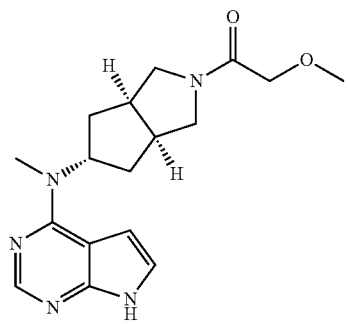 [SMILES: COCC(=O)N1C[C@H]2C[C@H](N(C)c3ncnc4[nH]ccc34)C[C@H]2C1]<br>2-methoxy-1-((3aR,5S,6aS)-5-(methyl(7H-pyrrolo[2,3-d]pyrimidin-4-yl)amino)hexahydrocyclopenta[c]pyrrol-2(1H)-yl)ethanone |
| 19 | 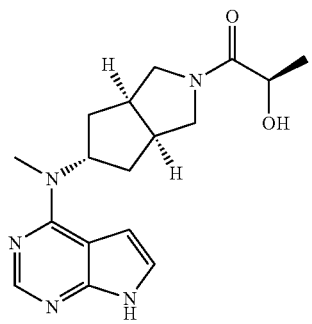 [SMILES: C[C@@H](O)C(=O)N1C[C@H]2C[C@H](N(C)c3ncnc4[nH]ccc34)C[C@H]2C1]<br>(R)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |
| 20 | 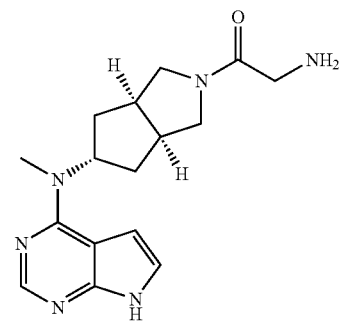 [SMILES: CN(c1ncnc2[nH]ccc12)[C@H]1C[C@@H]2CN(C(=O)CN)C[C@@H]2C1]<br>2-amino-1-((3aR,5S,6aS)-5-(methyl(7H-pyrrolo[2,3-d]pyrimidin-4-yl)amino)hexahydrocyclopenta[c]pyrrol-2(1H)-yl)ethanone |

| Example No. | Structure and Name |
|---|---|
| 21 | 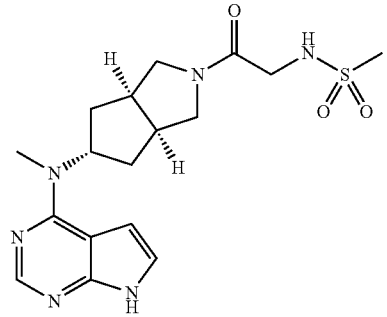<br>N-(2-((3aR,5S,6aS)-5-(methyl(7H-pyrrolo[2,3-d]pyrimidin-4-yl)amino)hexahydrocyclopenta[c]pyrrol-2(1H)-yl)-2-oxoethyl)methanesulfonamide |
| 22 | 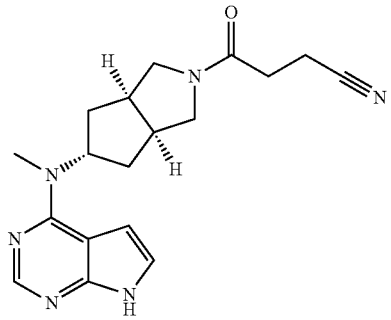 [SMILES: CN(c1ncnc2[nH]ccc12)[C@H]1C[C@@H]2CN(C(=O)CCC#N)C[C@@H]2C1]<br>4-((3aR,5S,6aS)-5-(methyl(7H-pyrrolo[2,3-d]pyrimidin-4-yl)amino)hexahydrocyclopenta[c]pyrrol-2(1H)-yl)-4-oxobutanenitrile |
| 23 | 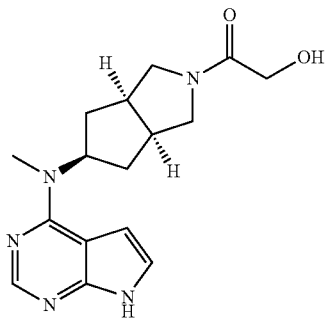 [SMILES: CN(c1ncnc2[nH]ccc12)[C@@H]1C[C@@H]2CN(C(=O)CO)C[C@@H]2C1]<br>2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)ethanone |
| 24 | 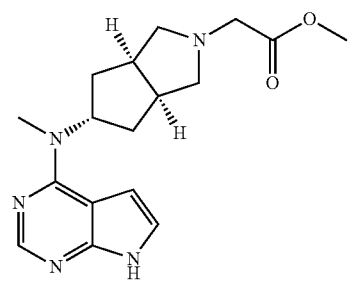 [SMILES: COC(=O)CN1C[C@H]2C[C@H](N(C)c3ncnc4[nH]ccc34)C[C@H]2C1]<br>methyl 2-((3aR,5S,6aS)-5-(methyl(7H-pyrrolo[2,3-d]pyrimidin-4-yl)amino)hexahydrocyclopenta[c]pyrrol-2(1H)-yl)acetate |

-continued

| Example No. | Structure and Name |
|---|---|
| 25 | 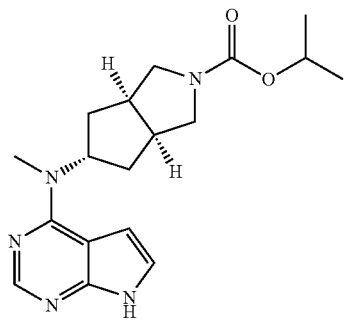 [SMILES: CC(C)OC(=O)N1C[C@H]2C[C@H](N(C)c3ncnc4[nH]ccc34)C[C@H]2C1]<br>(3aR,5S,6aS)-isopropyl 5-(methyl(7H-pyrrolo[2,3-d]pyrimidin-4-yl)amino)hexahydrocyclopenta[c]pyrrole-2(1H)-carboxylate |
| 26 | 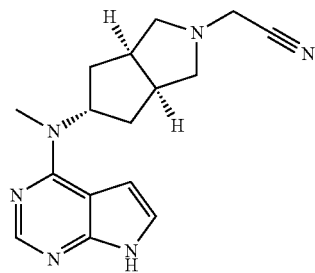 [SMILES: CN(c1ncnc2[nH]ccc12)[C@H]1C[C@@H]2CN(CC#N)C[C@@H]2C1]<br>2-((3aR,5S,6aS)-5-(methyl(7H-pyrrolo[2,3-d]pyrimidin-4-yl)amino)hexahydrocyclopenta[c]pyrrol-2(1H)-yl)acetonitrile |
| 27 | 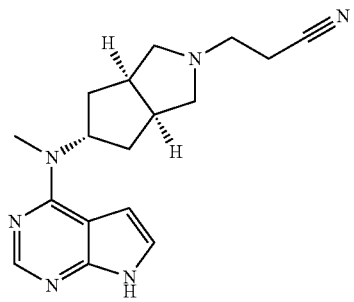<br>3-((3aR,5S,6aS)-5-(methyl(7H-pyrrolo[2,3-d]pyrimidin-4-yl)amino)hexahydrocyclopenta[c]pyrrol-2(1H)-yl)propanenitrile |
| 28 | 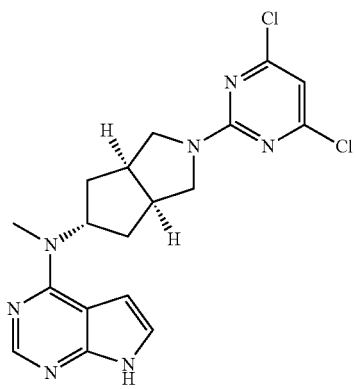 [SMILES: CN(c1ncnc2[nH]ccc12)[C@H]1C[C@@H]2CN(c3nc(Cl)cc(Cl)n3)C[C@@H]2C1]<br>N-((3aR,5S,6aS)-2-(4,6-dichloropyrimidin-2-yl)octahydrocyclopenta[c]pyrrol-5-yl)-N-methyl-7H-pyrrolo[2,3-d]pyrimidin-4-amine |

| Example No. | Structure and Name |
|---|---|
| 29 | 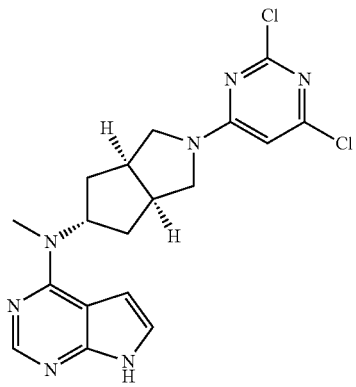 [SMILES: CN(c1ncnc2[nH]ccc12)[C@H]1C[C@@H]2CN(c3cc(Cl)nc(Cl)n3)C[C@@H]2C1]
N-((3aR,5S,6aS)-2-(2,6-dichloropyrimidin-4-yl)octahydrocyclo-penta[c]pyrrol-5-yl)-N-methyl-7H-pyrrolo[2,3-d]pyrimidin-4-amine |
| 30 | 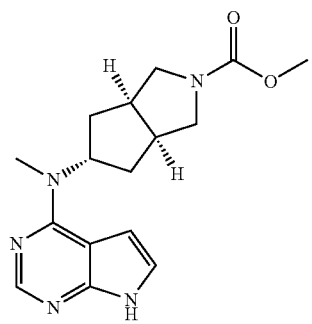 [SMILES: COC(=O)N1C[C@H]2C[C@H](N(C)c3ncnc4[nH]ccc34)C[C@H]2C1]
(3aR,5S,6aS)-methyl 5-(methyl(7H-pyrrolo[2,3-d]pyrimidin-4-yl)amino)hexahydrocyclopenta[c]pyrrole-2(1H)-carboxylate |
| 31 | 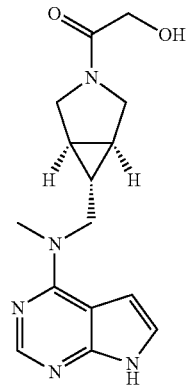 [SMILES: CN(C[C@H]1[C@@H]2CN(C(=O)CO)C[C@@H]21)c1ncnc2[nH]ccc12]
2-hydroxy-1-((1R,5S,6S)-6-((methyl(7H-pyrrolo[2,3-d]pyrimidin-4-yl)amino)methyl)-3-azabicyclo[3.1.0]hexan-3-yl)ethanone |

| Example No. | Structure and Name |
|---|---|
| 32 | 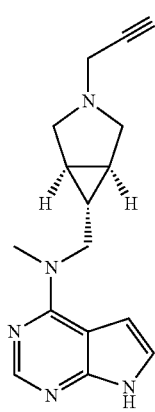<br>2-((1R,5S,6R)-6-((methyl(7H-pyrrolo[2,3-d]pyrimidim-4-yl)amino)methyl)-3-azabicyclo[3.1.0]hexan-3-yl)acetonitrile |
| 33 | 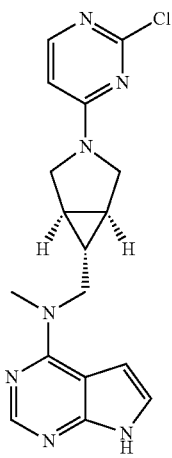 [SMILES: CN(C[C@@H]1[C@H]2CN(c3ccnc(Cl)n3)C[C@@H]12)c1ncnc2[nH]ccc12]<br>N-(((1R,5S,6S)-3-(2-chloropyrimidin-4-yl)-3-azabicyclo[3.1.0]hexan-6-yl)methyl)-N-methyl-7H-pyrrolo[2,3-d]pyrimidin-4-amine |
| 34 | 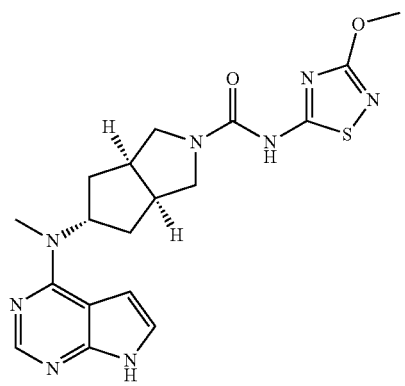 [SMILES: COc1nsc(NC(=O)N2C[C@H]3C[C@H](N(C)c4ncnc5[nH]ccc45)C[C@H]3C2)n1]<br>(3aR,5S,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |

-continued
| Example No. | Structure and Name |
|---|---|
| 35 | 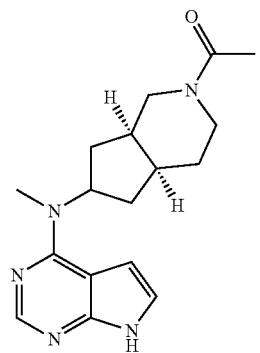 [SMILES: CC(=O)N1CC[C@H]2CC(N(C)c3ncnc4[nH]ccc34)C[C@H]2C1]
1-((4aS,7aR)-6-(methyl(7H-pyrrolo[2,3-d]pyrimidin-4-yl)amino)hexahydro-1H-cyclopenta[c]pyridin-2(3H,4H,4aH,5H,6H,7H,7aH)-yl)ethanone |
| 36 | 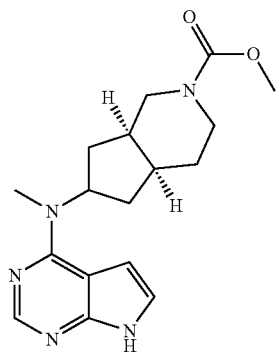 [SMILES: COC(=O)N1CC[C@H]2CC(N(C)c3ncnc4[nH]ccc34)C[C@H]2C1]
(4aS,7aR)-methyl 6-(methyl(7H-pyrrolo[2,3-d]pyrimidin-4-yl)amino)hexahydro-1H-cyclopenta[c]pyridine-2(3H)-carboxylate |
| 37 | 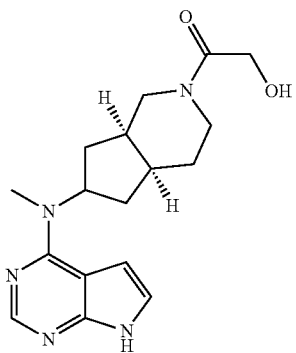
2-hydroxy-1-((4aS,7aR)-6-(methyl(7H-pyrrolo[2,3-d]pyrimidin-4-yl)amino)hexahydro-1H-cyclopenta[c]pyridin-2(3H,4H,4aH,5H,6H,7H,7aH-yl)ethanone |

| Example No. | Structure and Name |
|---|---|
| 38 | 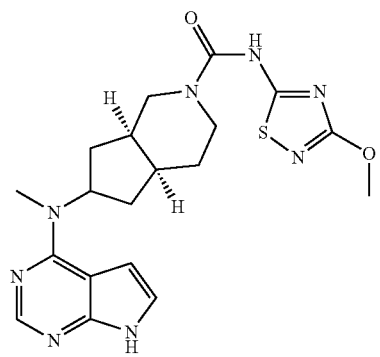 [SMILES: COc1nsc(NC(=O)N2CC[C@H]3CC(N(C)c4ncnc5[nH]ccc45)C[C@H]3C2)n1]<br>(4aS,7aR)-N-(3-methoxy-1,2,4-thiadiazol-5-yl)-6-(methyl(7H-pyrrolo[2,3-d]pyrimidin-4-yl)amino)hexahydro-1H-cyclopenta[c]pyridine-2(3H)-carboxamide |
| 39 | 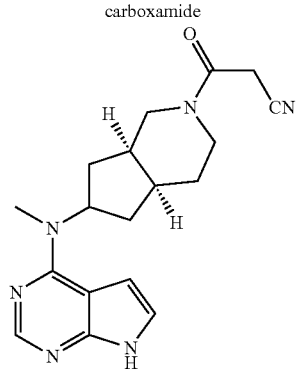<br>3-((4aS,7aR)-6-(methyl(7H-pyrrolo[2,3-d]pyrimidin-4-yl)amino)hexahydro-1H-cyclopenta[c]pyridin-2(3H,4H,4aH,5H,6H,7H,7aH)-yl)-3-oxopropanenitrile |
| 40 | 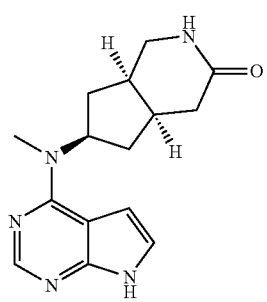 [SMILES: CN(c1ncnc2[nH]ccc12)[C@H]1C[C@H]2CNC(=O)C[C@H]2C1]<br>(4aR,6R,7aR)-6-(methyl(7H-pyrrolo[2,3-d]pyrimidin-4-yl)amino)hexahydro-1H-cyclopenta[c]pyridin-3(2H)-one |
| 41 | 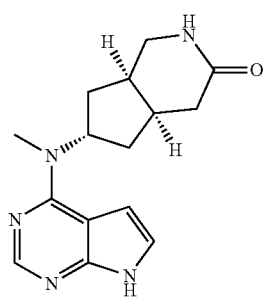 [SMILES: CN(c1ncnc2[nH]ccc12)[C@@H]1C[C@H]2CNC(=O)C[C@H]2C1]<br>(4aR,6S,7aR)-6-(methyl(7H-pyrrolo[2,3-d]pyrimidin-4-yl)amino)hexahydro-1H-cyclopenta[c]pyridin-3(2H)-one |

| Example No. | Structure and Name |
|---|---|
| 42 | 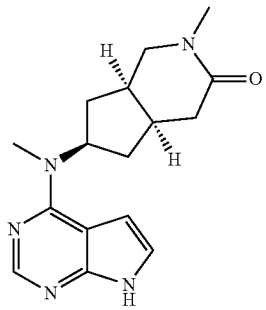 [SMILES: CN1C[C@@H]2C[C@H](N(C)c3ncnc4[nH]ccc34)C[C@@H]2CC1=O]<br>(4aR,6R,7aR)-2-methyl-6-(methyl(7H-pyrrolo[2,3-d]pyrimidin-4-yl)amino)hexahydro-1H-cyclopenta[c]pyridin-3(2H)-one |
| 43 | 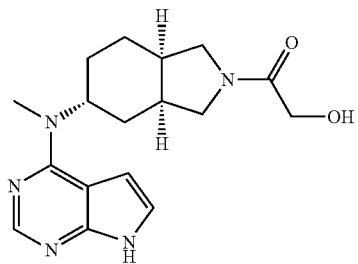<br>2-hydroxy-1-((3aS,5R,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone |
| 44 | 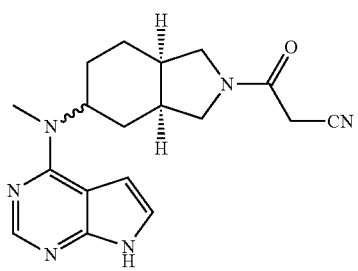 [SMILES: CN(c1ncnc2[nH]ccc12)C1CC[C@H]2CN(C(=O)CC#N)C[C@H]2C1]<br>3-((3aS,7aR)-5-(methyl(7H-pyrrolo[2,3-d]pyrimidin-4-yl)amino)hexahydro-1H-isoindol-2(3H,3aH,4H,5H,6H,7H,7aH)-yl)-3-oxopropanenitrile |
| 45 | 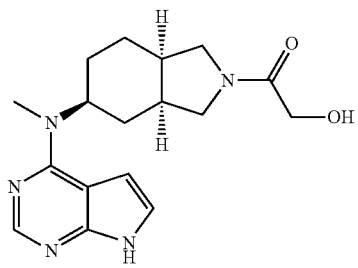 [SMILES: CN(c1ncnc2[nH]ccc12)[C@H]1CC[C@H]2CN(C(=O)CO)C[C@H]2C1]<br>2-hydroxy-1-((3aS,5S,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone |

| Example No. | Structure and Name |
|---|---|
| 46 | 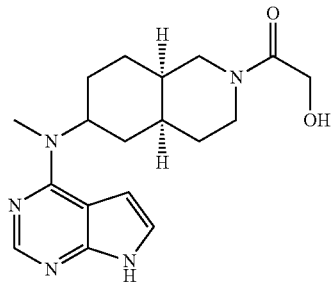 [SMILES: CN(c1ncnc2[nH]ccc12)C1CC[C@H]2CN(C(=O)CO)CC[C@H]2C1]<br>2-hydroxy-1-((4aS,8aR)-6-(methyl(7H-pyrrolo[2,3-d]pyrimidin-4-yl)amino)octahydroisoquinolin-2(1H)-yl)ethanone |
| 47 | 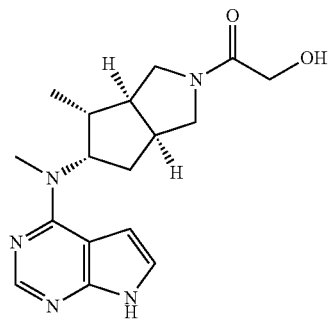 [SMILES: C[C@@H]1[C@H]2CN(C(=O)CO)C[C@H]2C[C@@H]1N(C)c1ncnc2[nH]ccc12]<br>1-((3aS,4R,5S,6aS)-4-methyl-5-(methyl(7H-pyrrolo[2,3-d]pyrimidin-4-yl)amino)-3,3a,4,5,6,6a-hexahydro-1H-cyclopenta[c]pyrrol-2-yl)-2-hydroxy-ethanone |
| 48 | 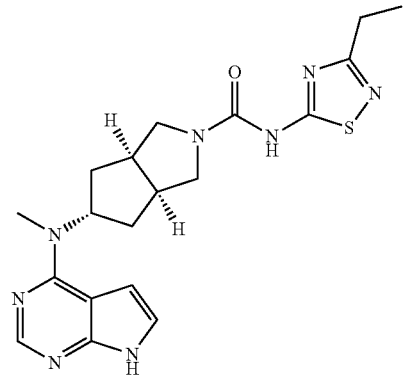<br>(3aR,5S,6aS)-N-(3-ethyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |

| Example No. | Structure and Name |
|---|---|
| 49 | 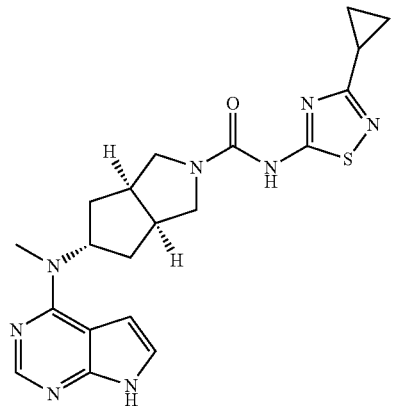 [SMILES: CN(c1ncnc2[nH]ccc12)[C@H]1C[C@@H]2CN(C(=O)Nc3nc(C4CC4)ns3)C[C@@H]2C1]<br>(3aR,5S,6aS)-N-(3-cyclopropyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |
| 50 | 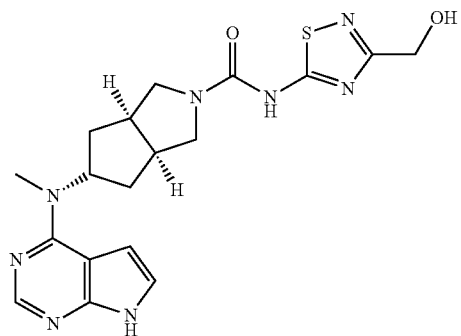<br>(3aR,5S,6aS)-N-(3-(hydroxymethyl)-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |
| 51 | 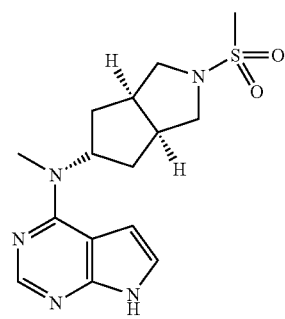<br>N-methyl-N-((3aR,5S,6aS)-2-(methylsulfonyl)octahydrocyclopenta[c]pyrrol-5-yl)-7H-pyrrolo[2,3-d]pyrimidin-4-amine |

| Example No. | Structure and Name |
|---|---|
| 52 | 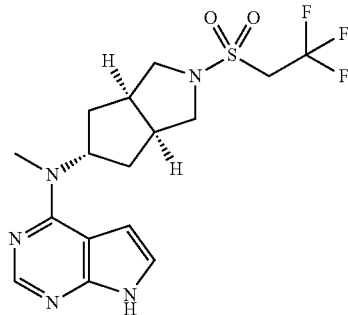 [SMILES: CN(c1ncnc2[nH]ccc12)[C@H]1C[C@@H]2CN(S(=O)(=O)CC(F)(F)F)C[C@@H]2C1]<br>N-methyl-N-((3aR,5S,6aS)-2-((2,2,2-trifluoroethyl)sulfonyl)octahydrocyclopenta[c]pyrrol-5-yl)-7H-pyrrolo[2,3-d]pyrimidin-4-amine |
| 53 | 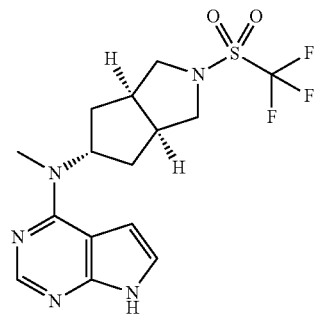 [SMILES: CN(c1ncnc2[nH]ccc12)[C@H]1C[C@@H]2CN(S(=O)(=O)C(F)(F)F)C[C@@H]2C1]<br>N-methyl-N-((3aR,5S,6aS)-2-((trifluoromethyl)sulfonyl)octahydrocyclopenta[c]pyrrol-5-yl)-7H-pyrrolo[2,3-d]pyrimidin-4-amine |
| 54 | 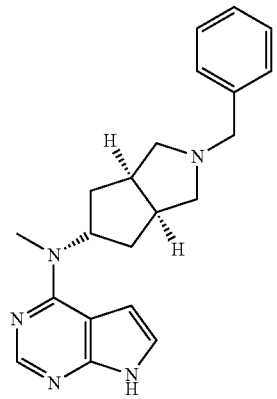<br>N-((3aR,5S,6aS)-2-benzyloctahydrocyclopenta[c]pyrrol-5-yl)-N-methyl-7H-pyrrolo[2,3-d]pyrimidin-4-amine |
| 55 | 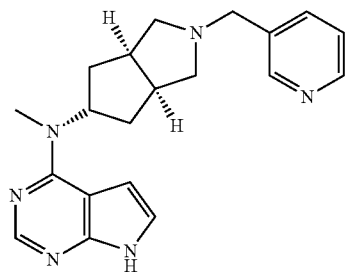<br>N-methyl-N-((3aR,5S,6aS)-2-(pyridin-3-ylmethyl)octahydrocyclopenta[c]pyrrol-5-yl)-7H-pyrrolo[2,3-d]pyrimidin-4-amine |

| Example No. | Structure and Name |
|---|---|
| 56 | 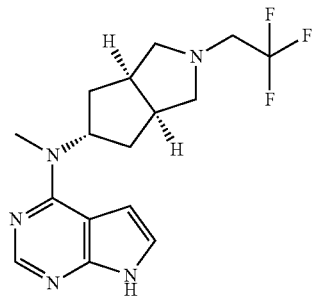 [SMILES: CN(c1ncnc2[nH]ccc12)[C@H]1C[C@@H]2CN(CC(F)(F)F)C[C@@H]2C1]
N-methyl-N-((3aR,5S,6aS)-2-(2,2,2-trifluoroethyl)octahydrocyclopenta[c]pyrrol-5-yl)-7H-pyrrolo[2,3-d]pyrimidin-4-amine |
| 57 | 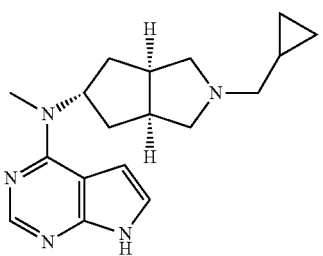 [SMILES: CN(c1ncnc2[nH]ccc12)[C@H]1C[C@@H]2CN(CC3CC3)C[C@@H]2C1]
N-((3aR,5S,6aS)-2-(cyclopropylmethyl)octahydrocyclopenta[c]pyrrol-5-yl)-N-methyl-7H-pyrrolo[2,3-d]pyrimidin-4-amine |
| 58 | 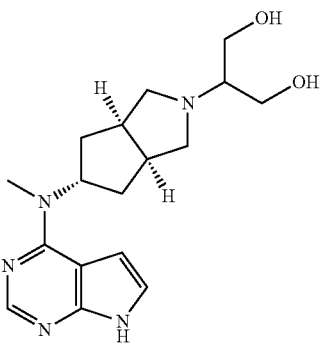 [SMILES: CN(c1ncnc2[nH]ccc12)[C@H]1C[C@@H]2CN(C(CO)CO)C[C@@H]2C1]
2-((3aR,5S,6aS)-5-(methyl(7H-pyrrolo[2,3-d]pyrimidin-4-yl)amino)hexahydrocyclopenta[c]pyrrol-2(1H)-yl)propane-1,3-diol |
| 59 | 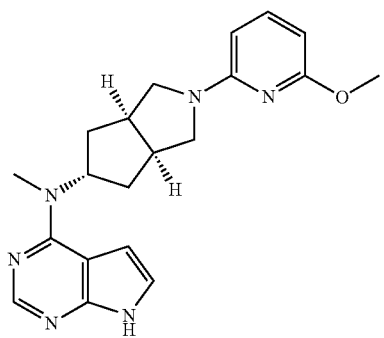
N-((3aR,5S,6aS)-2-(6-methoxypyridin-2-yl)octahydrocyclopenta[c]pyrrol-5-yl)-N-methyl-7H-pyrrolo[2,3-d]pyrimidin-4-amine |

| Example No. | Structure and Name |
|---|---|
| 60 | 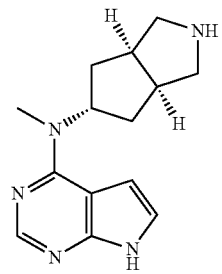<br>N-methyl-N-((3aR,5S,6aS)-octahydrocyclopenta[c]pyrrol-5-yl)-7H-pyrrolo[2,3-d]pyrimidin-4-amine |
| 61 | 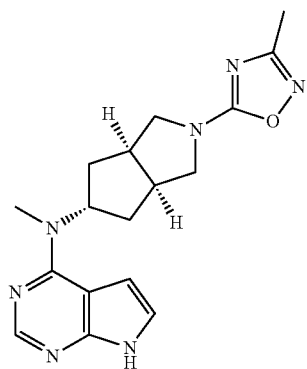 [SMILES: Cc1noc(N2C[C@H]3C[C@H](N(C)c4ncnc5[nH]ccc45)C[C@H]3C2)n1]<br>N-methyl-N-((3aR,5S,6aS)-2-(3-methyl-1,2,4-oxadiazol-5-yl)octa-hydrocyclopenta[c]pyrrol-5-yl)-7H-pyrrolo[2,3-d]pyrimidin-4-amine |
| 62 | 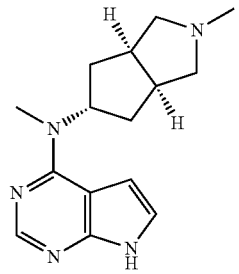<br>N-methyl-N-((3aR,5S,6aS)-2-methyloctahydrocyclopenta[c]pyrrol-5-yl)-7H-pyrrolo[2,3-d]pyrimidin-4-amine |
| 63 | 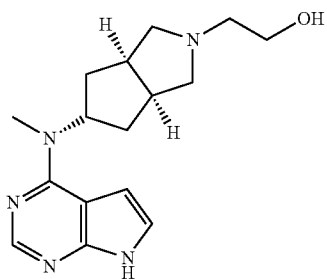<br>2-((3aR,5S,6aS)-5-(methyl(7H-pyrrolo[2,3-d]pyrimidin-4-yl)amino)hexahydrocyclopenta[c]pyrrol-2(1H)-yl)ethanol |

| Example No. | Structure and Name |
|---|---|
| 64 | 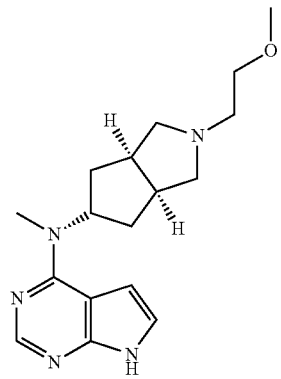<br>N-((3aR,5S,6aS)-2-(2-methoxyethyl)octahydrocyclopenta[c]pyrrol-5-yl)-N-methyl-7H-pyrrolo[2,3-d]pyrimidin-4-amine |
| 65 | 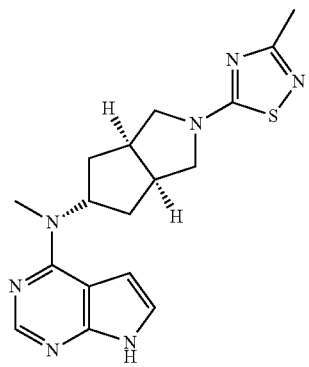<br>N-methyl-N-((3aR,5S,6aS)-2-(3-methyl-1,2,4-thiadiazol-5-yl)octahydrocyclopenta[c]pyrrol-5-yl)-7H-pyrrolo[2,3-d]pyrimidin-4-amine |
| 66 | 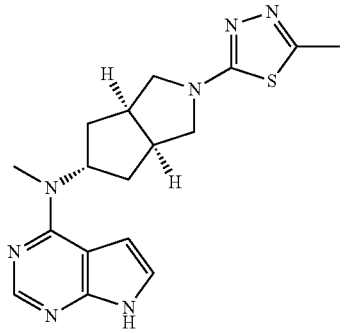<br>N-methyl-N-((3aR,5S,6aS)-2-(5-methyl-1,3,4-thiadiazol-2-yl)octahydrocyclopenta[c]pyrrol-5-yl)-7H-pyrrolo[2,3-d]pyrimidin-4-amine |

| Example No. | Structure and Name |
|---|---|
| 67 | 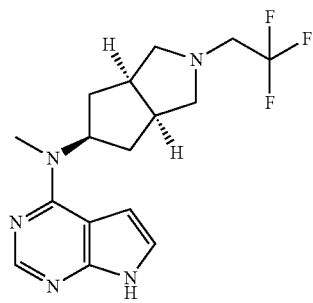 [SMILES: CN(c1ncnc2[nH]ccc12)[C@@H]1C[C@@H]2CN(CC(F)(F)F)C[C@@H]2C1]
N-methyl-N-((3aR,5R,6aS)-2-(2,2,2-trifluoroethyl)octahydrocyclopenta[c]pyrrol-5-yl)-7H-pyrrolo[2,3-d]pyrimidin-4-amine |
| 68 | 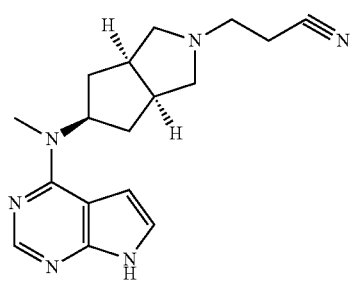 [SMILES: CN(c1ncnc2[nH]ccc12)[C@@H]1C[C@@H]2CN(CCC#N)C[C@@H]2C1]
3-((3aR,5R,6aS)-5-(methyl(7H-pyrrolo[2,3-d]pyrimidin-4-yl)amino)hexahydrocyclopenta[c]pyrrol-2(1H)-yl)propanenitrile |
| 69 | 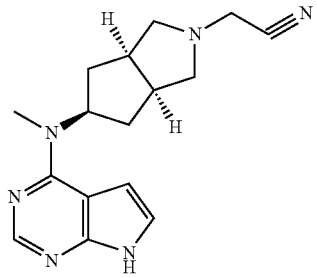 [SMILES: CN(c1ncnc2[nH]ccc12)[C@@H]1C[C@@H]2CN(CC#N)C[C@@H]2C1]
2-((3aR,5R,6aS)-5-(methyl(7H-pyrrolo[2,3-d]pyrimidin-4-yl)amino)hexahydrocyclopenta[c]pyrrol-2(1H)-yl)acetonitrile |
| 70 | 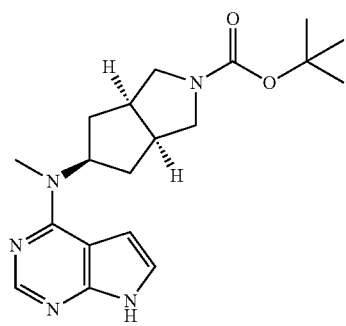 [SMILES: CN(c1ncnc2[nH]ccc12)[C@@H]1C[C@@H]2CN(C(=O)OC(C)(C)C)C[C@@H]2C1]
(3aR,5R,6aS)-tert-butyl 5-(methyl(7H-pyrrolo[2,3-d]pyrimidin-4-yl)amino)hexahydrocyclopenta[c]pyrrole-2(1H)-carboxylate |

| Example No. | Structure and Name |
|---|---|
| 71 | 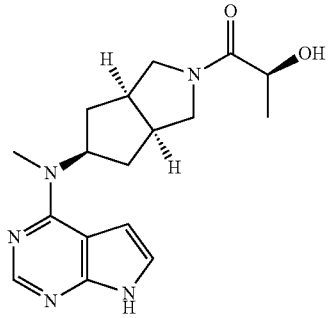<br>(S)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |
| 72 | 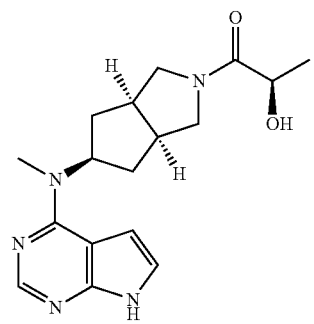 [SMILES: C[C@@H](O)C(=O)N1C[C@H]2C[C@@H](N(C)c3ncnc4[nH]ccc34)C[C@H]2C1]<br>(R)-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)propan-1-one |
| 73 | 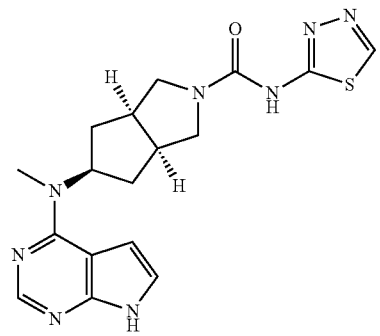 [SMILES: CN(c1ncnc2[nH]ccc12)[C@@H]1C[C@@H]2CN(C(=O)Nc3nncs3)C[C@@H]2C1]<br>(3aR,5R,6aS)-5-(methyl(7H-pyrrolo[2,3-d]pyrimidin-4-yl)amino)-N-(1,3,4-thiadiazol-2-yl)hexahydrocyclopenta[c]pyrrole-2(1H)-carboxamide |

| Example No. | Structure and Name |
|---|---|
| 74 | 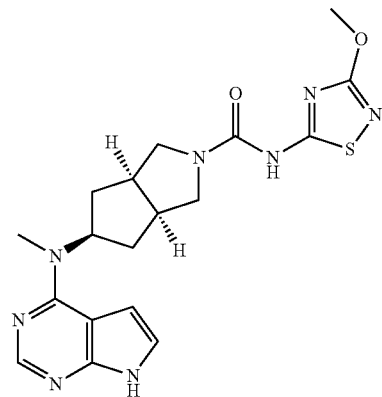 [SMILES: COc1nsc(NC(=O)N2C[C@H]3C[C@@H](N(C)c4ncnc5[nH]ccc45)C[C@H]3C2)n1]<br>(3aR,5R,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |
| 75 | 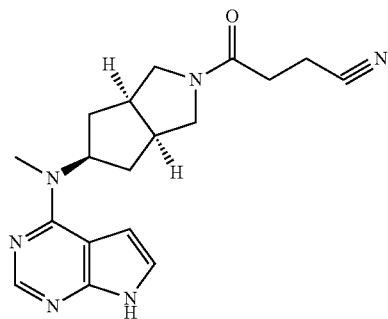 [SMILES: CN(c1ncnc2[nH]ccc12)[C@@H]1C[C@@H]2CN(C(=O)CCC#N)C[C@@H]2C1]<br>4-((3aR,5R,6aS)-5-(methyl(7H-pyrrolo[2,3-d]pyrimidin-4-yl)amino)hexahydrocyclopenta[c]pyrrol-2(1H)-yl)-4-oxobutanenitrile |
| 76 | 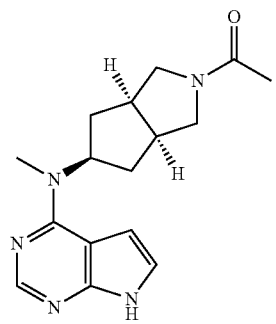 [SMILES: CC(=O)N1C[C@H]2C[C@@H](N(C)c3ncnc4[nH]ccc34)C[C@H]2C1]<br>1-((3aR,5R,6aS)-5-(methyl(7H-pyrrolo[2,3-d]pyrimidin-4-yl)amino)hexahydrocyclopenta[c]pyrrol-2(1H)-yl)ethanone |

-continued

| Example No. | Structure and Name |
|---|---|
| 77 | 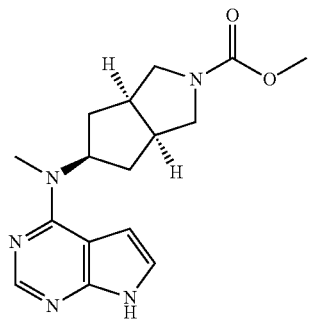 [SMILES: COC(=O)N1C[C@H]2C[C@@H](N(C)c3ncnc4[nH]ccc34)C[C@H]2C1]
(3aR,5R,6aS)-methyl 5-(methyl(7H-pyrrolo[2,3-d]pyrimidin-4-yl)amino)hexahydrocyclopenta[c]pyrrole-2(1H)-carboxylate |
| 78 | 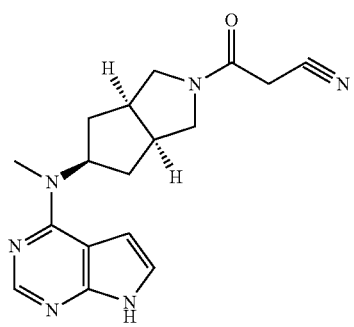 [SMILES: CN(c1ncnc2[nH]ccc12)[C@@H]1C[C@@H]2CN(C(=O)CC#N)C[C@@H]2C1]
3-((3aR,5R,6aS)-5-(methyl(7H-pyrrolo[2,3-d]pyrimidin-4-yl)amino)hexahydrocyclopenta[c]pyrrol-2(1H)-yl)-3-oxopropanenitrile |
| 79 | 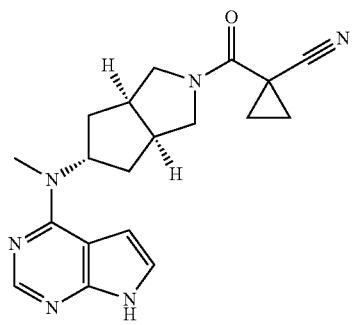 [SMILES: CN(c1ncnc2[nH]ccc12)[C@H]1C[C@@H]2CN(C(=O)C3(C#N)CC3)C[C@@H]2C1]
1-((3aR,5S,6aS)-5-(methyl(7H-pyrrolo[2,3-d]pyrimidin-4-yl)amino)octahydrocyclopenta[c]pyrrol-2-carbonyl)cyclopropanecarbonitrile |
| 80 | 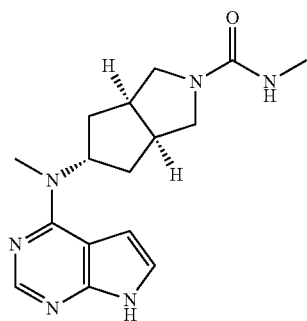 [SMILES: CNC(=O)N1C[C@H]2C[C@H](N(C)c3ncnc4[nH]ccc34)C[C@H]2C1]
(3aR,5S,6aS)-N-methyl-5-(methyl(7H-pyrrolo[2,3-d]pyrimidin-4-yl)amino)hexahydrocyclopenta[c]pyrrole-2(1H)-carboxamide |

-continued

| Example No. | Structure and Name |
|---|---|
| 81 | 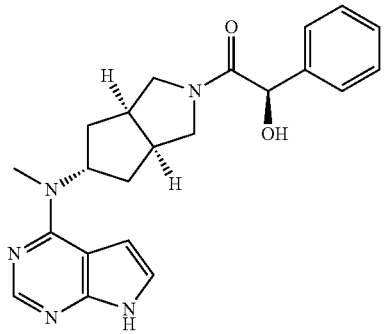 [SMILES: CN(c1ncnc2[nH]ccc12)[C@H]1C[C@@H]2CN(C(=O)[C@H](O)c3ccccc3)C[C@@H]2C1]<br>(R)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)-2-phenylethanone |
| 82 | 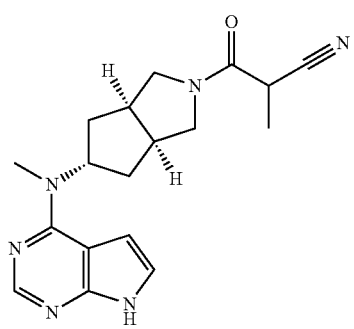 [SMILES: CC(C#N)C(=O)N1C[C@H]2C[C@H](N(C)c3ncnc4[nH]ccc34)C[C@H]2C1]<br>2-methyl-3-((3aR,5S,6aS)-5-(methyl(7H-pyrrolo[2,3-d]pyrimidin-4-yl)amino)hexahydrocyclopenta[c]pyrrol-2(1H)-yl)-3-oxopropanenitrile |
| 83 | 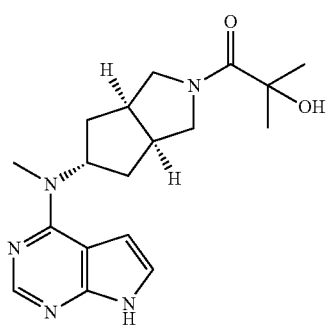 [SMILES: CN(c1ncnc2[nH]ccc12)[C@H]1C[C@@H]2CN(C(=O)C(C)(C)O)C[C@@H]2C1]<br>2-hydroxy-2-methyl-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |
| 84 | 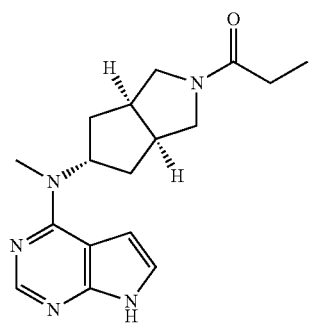 [SMILES: CCC(=O)N1C[C@H]2C[C@H](N(C)c3ncnc4[nH]ccc34)C[C@H]2C1]<br>1-((3aR,5S,6aS)-5-(methyl(7H-pyrrolo[2,3-d]pyrimidin-4-yl)amino)hexahydrocyclopenta[c]pyrrol-2(1H)-yl)propan-1-one |

| Example No. | Structure and Name |
|---|---|
| 85 | 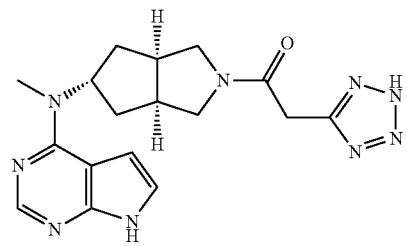 [SMILES: CN(c1ncnc2[nH]ccc12)[C@H]1C[C@@H]2CN(C(=O)Cc3nn[nH]n3)C[C@@H]2C1]<br>1-((3aR,5S,6aS)-5-(methyl(7H-pyrrolo[2,3-d]pyrimidin-4-yl)amino)hexa-hydrocyclopenta[c]pyrrol-2(1H)-yl)-2-(2H-tetrazol-5-yl)ethanone |
| 86 | 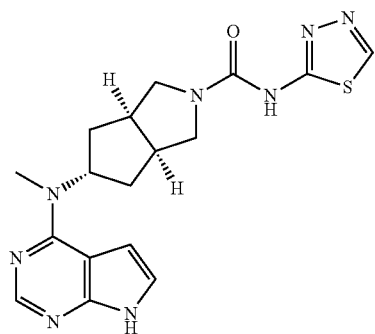 [SMILES: CN(c1ncnc2[nH]ccc12)[C@H]1C[C@@H]2CN(C(=O)Nc3nncs3)C[C@@H]2C1]<br>(3aR,5S,6aS)-5-(methyl(7H-pyrrolo[2,3-d]pyrimidin-4-yl)amino)-N-(1,3,4-thiadiazol-2-yl)hexahydrocyclopenta[c]pyrrole-2(1H)-carboxamide |
| 87 | 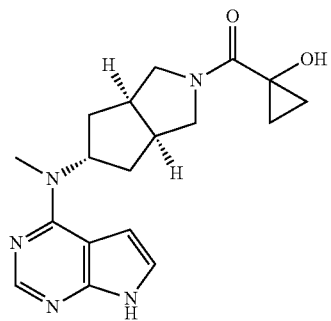 [SMILES: CN(c1ncnc2[nH]ccc12)[C@H]1C[C@@H]2CN(C(=O)C3(O)CC3)C[C@@H]2C1]<br>(1-hydroxycyclopropyl)((3aR,5S,6aS)-5-(methyl(7H-pyrrolo[2,3-d]pyrimidin-4-yl)amino)hexahydrocyclopenta[c]pyrrol-2(1H)-yl)methanone |
| 88 | 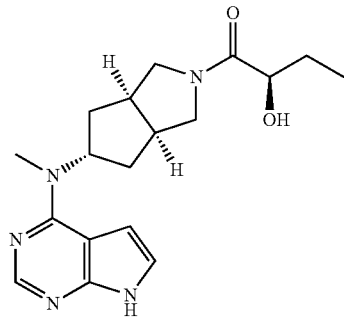 [SMILES: CC[C@@H](O)C(=O)N1C[C@H]2C[C@H](N(C)c3ncnc4[nH]ccc34)C[C@H]2C1]<br>(R)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)butan-1-one |

| Example No. | Structure and Name |
|---|---|
| 89 | 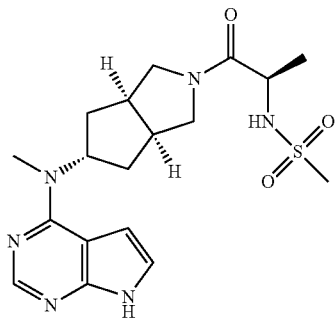 [SMILES: C[C@@H](NS(C)(=O)=O)C(=O)N1C[C@H]2C[C@H](N(C)c3ncnc4[nH]ccc34)C[C@H]2C1]

N-((R)-1-((3aR,5S,6aS)-5-(methyl(7H-pyrrolo[2,3-d]pyrimidin-4-yl)amino)hexahydrocyclopenta[c]pyrrol-2(1H)-yl)-1-oxopropan-2-yl)methanesulfonamide |
| 90 | 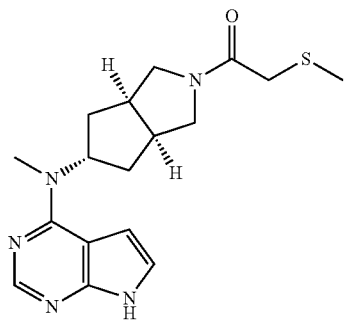 [SMILES: CSCC(=O)N1C[C@H]2C[C@H](N(C)c3ncnc4[nH]ccc34)C[C@H]2C1]

1-((3aR,5S,6aS)-5-(methyl(7H-pyrrolo[2,3-d]pyrimidin-4-yl)amino)hexahydrocyclopenta[c]pyrrol-2(1H)-yl)-2-(methylthio)ethanone |
| 91 | 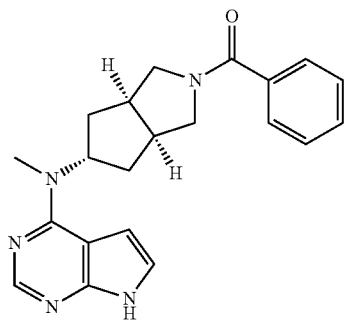 [SMILES: CN(c1ncnc2[nH]ccc12)[C@H]1C[C@@H]2CN(C(=O)c3ccccc3)C[C@@H]2C1]

((3aR,5S,6aS)-5-(methyl(7H-pyrrolo[2,3-d]pyrimidin-4-yl)amino)hexahydrocyclopenta[c]pyrrol-2(1H)-yl)(phenyl)methanone |
| 92 | 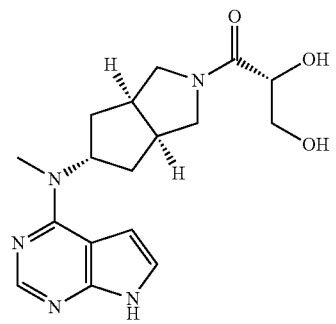 [SMILES: CN(c1ncnc2[nH]ccc12)[C@H]1C[C@@H]2CN(C(=O)[C@H](O)CO)C[C@@H]2C1]

(R)-2,3-dihydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |

| Example No. | Structure and Name |
|---|---|
| 93 | 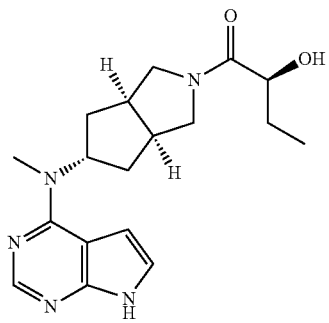 [SMILES: CC[C@H](O)C(=O)N1C[C@H]2C[C@H](N(C)c3ncnc4[nH]ccc34)C[C@H]2C1]

(S)-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)butan-1-one |
| 94 | 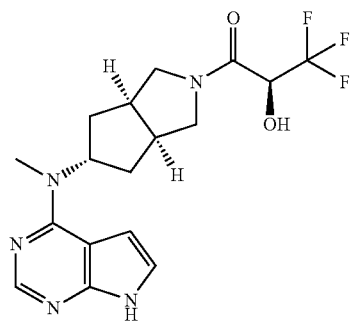 [SMILES: CN(c1ncnc2[nH]ccc12)[C@H]1C[C@@H]2CN(C(=O)[C@H](O)C(F)(F)F)C[C@@H]2C1]

(S)-3,3,3-trifluoro-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)propan-1-one |
| 95 | 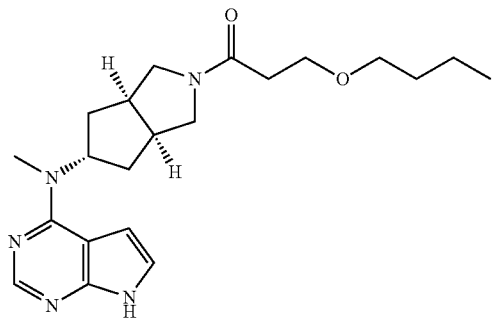 [SMILES: CCCCOCCC(=O)N1C[C@H]2C[C@H](N(C)c3ncnc4[nH]ccc34)C[C@H]2C1]

3-butoxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |
| 96 | 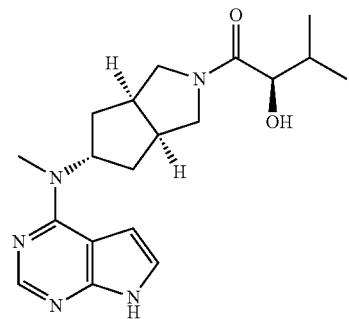 [SMILES: CC(C)[C@@H](O)C(=O)N1C[C@H]2C[C@H](N(C)c3ncnc4[nH]ccc34)C[C@H]2C1]

(R)-2-hydroxy-3-methyl-1-((3aR,5S,6aS)-5-(methyl(7H-pyrrolo[2,3-d]pyrimidin-4-yl)amino)hexahydrocyclopenta[c]pyrrol-2(1H)-yl)butan-1-one |

| Example No. | Structure and Name |
|---|---|
| 97 | 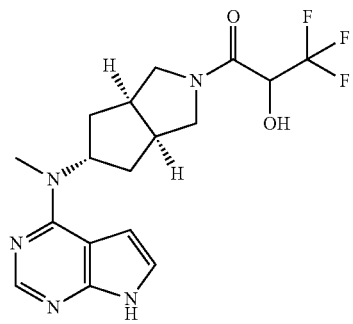 [SMILES: CN(c1ncnc2[nH]ccc12)[C@H]1C[C@@H]2CN(C(=O)C(O)C(F)(F)F)C[C@@H]2C1]<br>3,3,3-trifluoro-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |
| 98 | 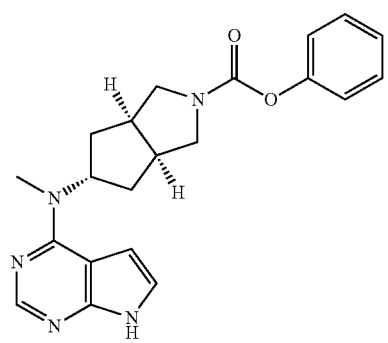 [SMILES: CN(c1ncnc2[nH]ccc12)[C@H]1C[C@@H]2CN(C(=O)Oc3ccccc3)C[C@@H]2C1]<br>(3aR,5S,6aS)-phenyl 5-(methyl(7H-pyrrolo[2,3-d]pyrimidin-4-yl)amino)hexahydrocyclopenta[c]pyrrole-2(1H)-carboxylate |
| 99 | 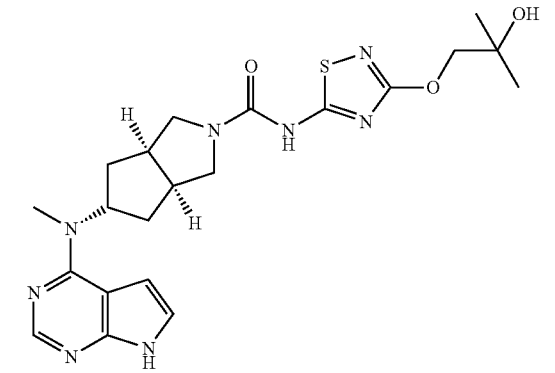<br>(3aR,5S,6aS)-N-(3-(2-hydroxy-2-methylpropoxy)-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |
| 100 | 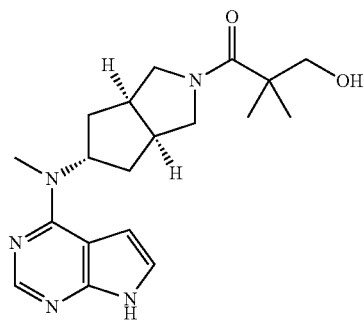 [SMILES: CN(c1ncnc2[nH]ccc12)[C@H]1C[C@@H]2CN(C(=O)C(C)(C)CO)C[C@@H]2C1]<br>3-hydroxy-2,2-dimethyl-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |

-continued

| Example No. | Structure and Name |
|---|---|
| 101 | 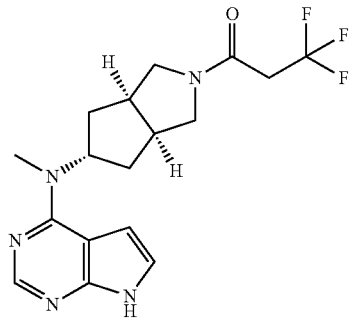 [SMILES: CN(c1ncnc2[nH]ccc12)[C@H]1C[C@@H]2CN(C(=O)CC(F)(F)F)C[C@@H]2C1]<br>3,3,3-trifluoro-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |
| 102 | 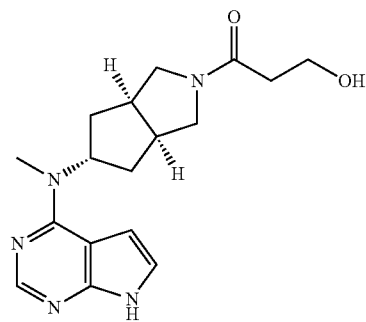 [SMILES: CN(c1ncnc2[nH]ccc12)[C@H]1C[C@@H]2CN(C(=O)CCO)C[C@@H]2C1]<br>3-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one |
| 103 | 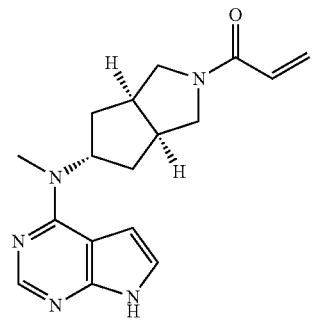 [SMILES: C=CC(=O)N1C[C@H]2C[C@H](N(C)c3ncnc4[nH]ccc34)C[C@H]2C1]<br>1-((3aR,5S,6aS)-5-(methyl(7H-pyrrolo[2,3-d]pyrimidin-4-yl)amino)hexahydrocyclopenta[c]pyrrol-2(1H)-yl)prop-2-en-1-one |
| 104 | 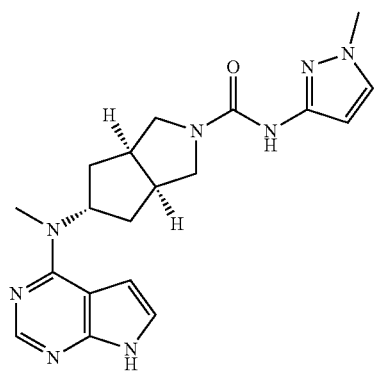 [SMILES: CN(c1ncnc2[nH]ccc12)[C@H]1C[C@@H]2CN(C(=O)Nc3ccn(C)n3)C[C@@H]2C1]<br>(3aR,5S,6aS)-5-(methyl(7H-pyrrolo[2,3-d]pyrimidin-4-yl)amino)-N-(1-methyl-1H-pyrazol-3-yl)hexahydrocyclopenta[c]pyrrole-2(1H)-carboxamide |

| Example No. | Structure and Name |
|---|---|
| 105 | 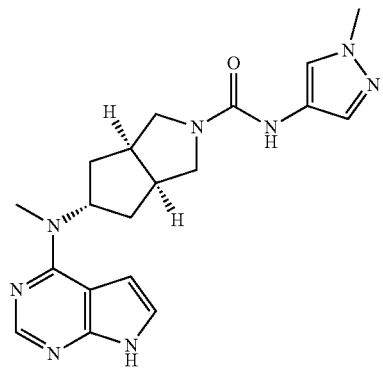 [SMILES: CN(c1ncnc2[nH]ccc12)[C@H]1C[C@@H]2CN(C(=O)Nc3cnn(C)c3)C[C@@H]2C1]
(3aR,5S,6aS)-5-(methyl(7H-pyrrolo[2,3-d]pyrimidin-4-yl)amino)-N-(1-methyl-1H-pyrazol-4-yl)hexahydrocyclopenta[c]pyrrole-2(1H)-carboxamide |
| 106 | 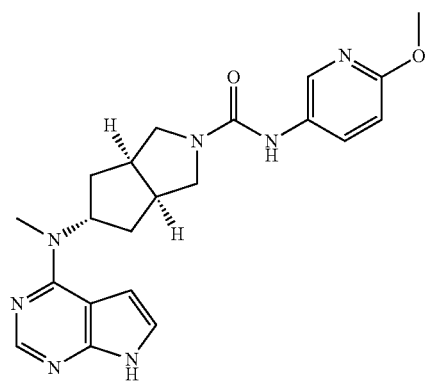 [SMILES: COc1ccc(NC(=O)N2C[C@H]3C[C@H](N(C)c4ncnc5[nH]ccc45)C[C@H]3C2)cn1]
(3aR,5S,6aS)-N-(6-methoxypyridin-3-yl)-5-(methyl(7H-pyrrolo[2,3-d]pyrimidin-4-yl)amino)hexahydrocyclopenta[c]pyrrole-2(1H)-carboxamide |
| 107 | 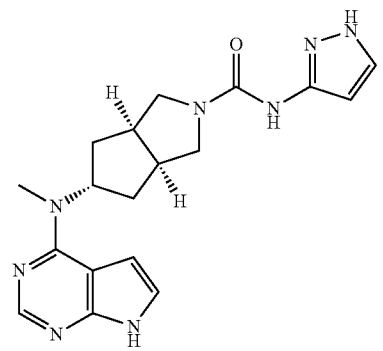 [SMILES: CN(c1ncnc2[nH]ccc12)[C@H]1C[C@@H]2CN(C(=O)Nc3cc[nH]n3)C[C@@H]2C1]
(3aR,5S,6aS)-5-(methyl(7H-pyrrolo[2,3-d]pyrimidin-4-yl)amino)-N-(1H-pyrazol-3-yl)hexahydrocyclopenta[c]pyrrole-2(1H)-carboxamide |

| Example No. | Structure and Name |
|---|---|
| 108 | 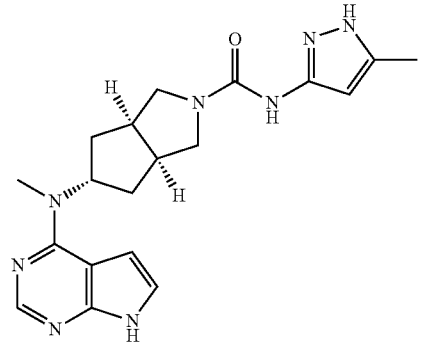 [SMILES: Cc1cc(NC(=O)N2C[C@H]3C[C@H](N(C)c4ncnc5[nH]ccc45)C[C@H]3C2)n[nH]1]<br>(3aR,5S,6aS)-5-(methyl(7H-pyrrolo[2,3-d]pyrimidin-4-yl)amino)-N-(5-methyl-1H-pyrazol-3-yl)hexahydrocyclopenta[c]pyrrole-2(1H)-carboxamide |
| 109 | 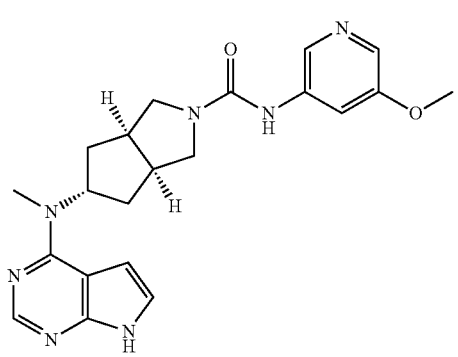 [SMILES: COc1cncc(NC(=O)N2C[C@H]3C[C@H](N(C)c4ncnc5[nH]ccc45)C[C@H]3C2)c1]<br>(3aR,5S,6aS)-N-(5-methoxypyridin-3-yl)-5-(methyl(7H-pyrrolo[2,3-d]pyrimidin-4-yl)amino)hexahydrocyclopenta[c]pyrrole-2(1H)-carboxamide |
| 110 | 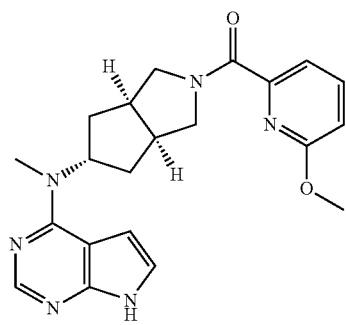 [SMILES: COc1cccc(C(=O)N2C[C@H]3C[C@H](N(C)c4ncnc5[nH]ccc45)C[C@H]3C2)n1]<br>(6-methoxypyridin-2-yl)((3aR,5S,6aS)-5-(methyl(7H-pyrrolo[2,3-d]pyrimidin-4-yl)amino)hexahydrocyclopenta[c]pyrrol-2(1H)-yl)methanone |
| 111 | 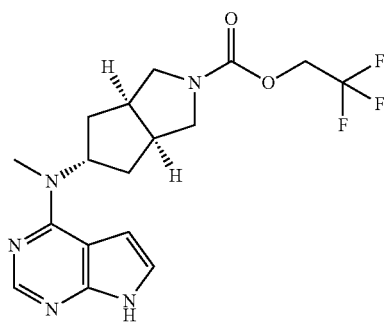 [SMILES: CN(c1ncnc2[nH]ccc12)[C@H]1C[C@@H]2CN(C(=O)OCC(F)(F)F)C[C@@H]2C1]<br>(3aR,5S,6aS)-2,2,2-trifluoroethyl 5-(methyl(7H-pyrrolo[2,3-d]pyrimidin-4-yl)amino)hexahydrocyclopenta[c]pyrrole-2(1H)-carboxylate |

| Example No. | Structure and Name |
|---|---|
| 112 | 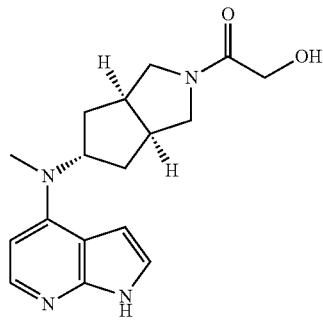 [SMILES: CN(c1ccnc2[nH]ccc12)[C@H]1C[C@@H]2CN(C(=O)CO)C[C@@H]2C1]
2-hydroxy-1-((3aR,5S,6aS)-5-(methyl(1H-pyrrolo[2,3-b]pyridin-4-yl)amino)hexahydrocyclopenta[c]pyrrol-2(1H)-yl)ethanone |
| 113 | 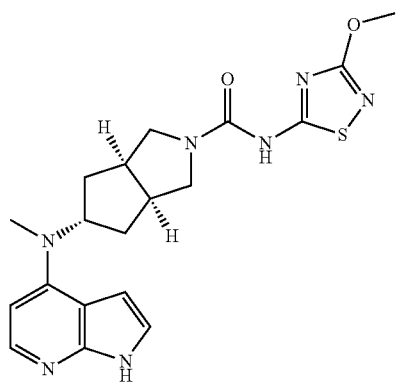 [SMILES: COc1nsc(NC(=O)N2C[C@H]3C[C@H](N(C)c4ccnc5[nH]ccc45)C[C@H]3C2)n1]
(3aR,5S,6aS)-N-(3-methoxy-1,2,4-thiadiazol-5-yl)-5-(methyl(1H-pyrrolo[2,3-b]pyridin-4-yl)amino)hexahydrocyclopenta[c]pyrrole-2(1H)-carboxamide |
| 114 | 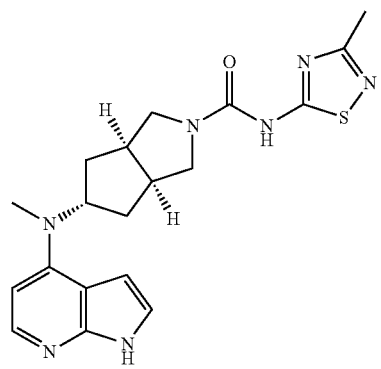 [SMILES: Cc1nsc(NC(=O)N2C[C@H]3C[C@H](N(C)c4ccnc5[nH]ccc45)C[C@H]3C2)n1]
(3aR,5S,6aS)-5-(methyl(1H-pyrrolo[2,3-b]pyridin-4-yl)amino)-N-(3-methyl-1,2,4-thiadiazol-5-yl)hexahydrocyclopenta[c]pyrrole-2(1H)-carboxamide |

| Example No. | Structure and Name |
|---|---|
| 115 | 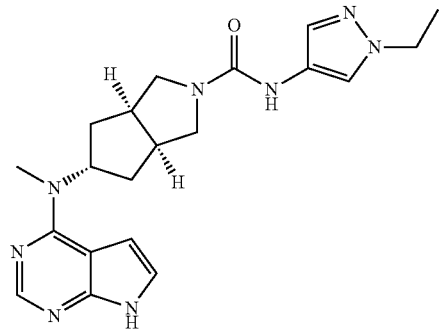 [SMILES: CCn1cc(NC(=O)N2C[C@H]3C[C@H](N(C)c4ncnc5[nH]ccc45)C[C@H]3C2)cn1]<br>(3aR,5S,6aS)-N-(1-ethyl-1H-pyrazol-4-yl)-5-(methyl(7H-pyrrolo[2,3-d]pyrimidin-4-yl)amino)hexahydrocyclopenta[c]pyrrole-2(1H)-carboxamide |
| 116 | 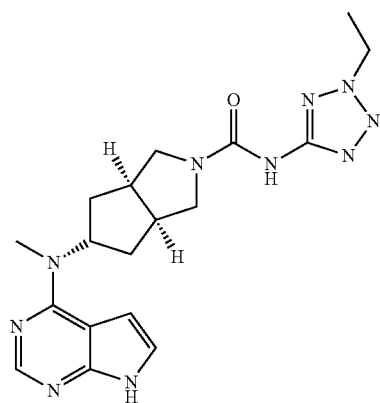<br>(3aR,5S,6aS)-N-(2-ethyl-2H-tetrazol-5-yl)-5-(methyl(7H-pyrrolo[2,3-d]pyrimidin-4-yl)amino)hexahydrocyclopenta[c]pyrrole-2(1H)-carboxamide |
| 117 | 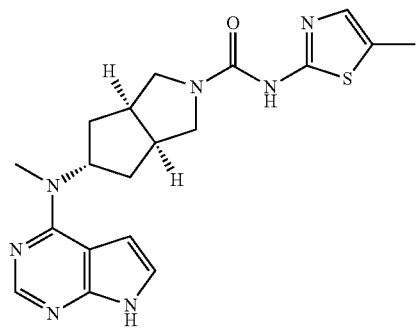 [SMILES: Cc1cnc(NC(=O)N2C[C@H]3C[C@H](N(C)c4ncnc5[nH]ccc45)C[C@H]3C2)s1]<br>(3aR,5S,6aS)-5-(methyl(7H-pyrrolo[2,3-d]pyrimidin-4-yl)amino)-N-(5-methylthiazol-2-yl)hexahydrocyclopenta[c]pyrrole-2(1H)-carboxamide |

-continued

| Example No. | Structure and Name |
|---|---|
| 118 | 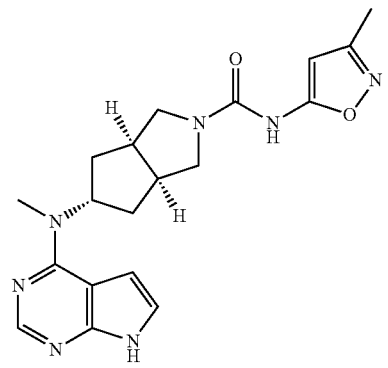 [SMILES: Cc1cc(NC(=O)N2C[C@H]3C[C@H](N(C)c4ncnc5[nH]ccc45)C[C@H]3C2)sn1]

(3aR,5S,6aS)-5-(methyl(7H-pyrrolo[2,3-d]pyrimidin-4-yl)amino)-N-(3-methylisoxazol-5-yl)hexahydrocyclopenta[c]pyrrole-2(1H)-carboxamide |
| 119 | 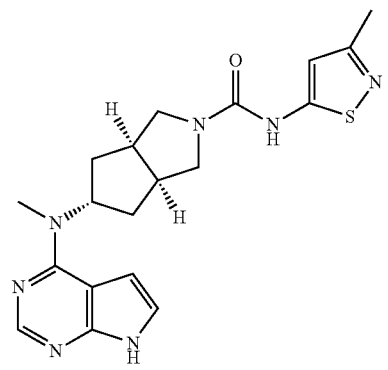

(3aR,5S,6aS)-5-(methyl(7H-pyrrolo[2,3-d]pyrimidin-4-yl)amino)-N-(3-methylisothiazol-5-yl)hexahydrocyclopenta[c]pyrrole-2(1H)-carboxamide |
| 120 | 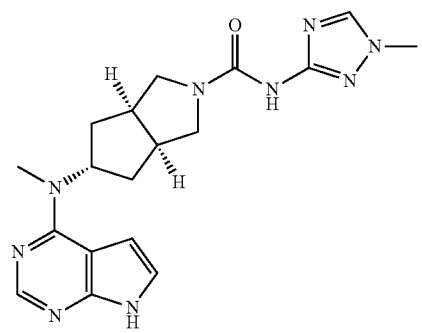 [SMILES: CN(c1ncnc2[nH]ccc12)[C@H]1C[C@@H]2CN(C(=O)Nc3ncn(C)n3)C[C@@H]2C1]

(3aR,5S,6aS)-5-(methyl(7H-pyrrolo[2,3-d]pyrimidin-4-yl)amino)-N-(1-methyl-1H-1,2,4-triazol-3-yl)hexahydrocyclopenta[c]pyrrole-2(1H)-carboxamide |

| Example No. | Structure and Name |
|---|---|
| 121 | 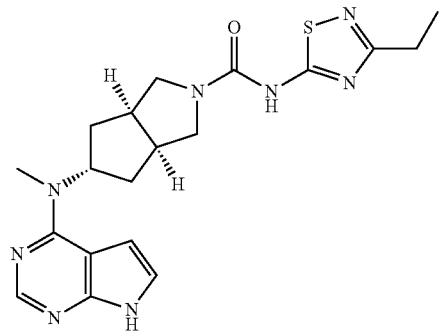 [SMILES: CCc1nsc(NC(=O)N2C[C@H]3C[C@H](N(C)c4ncnc5[nH]ccc45)C[C@H]3C2)n1]<br>(3aR,5S,6aS)-N-(3-ethyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |
| 122 | 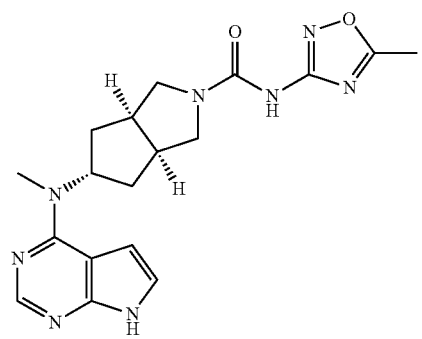 [SMILES: Cc1nc(NC(=O)N2C[C@H]3C[C@H](N(C)c4ncnc5[nH]ccc45)C[C@H]3C2)no1]<br>(3aR,5S,6aS)-5-(methyl(7H-pyrrolo[2,3-d]pyrimidin-4-yl)amino)-N-(5-methyl-1,2,4-oxadiazol-3-yl)hexahydrocyclopenta[c]pyrrole-2(1H)-carboxamide |
| 123 | 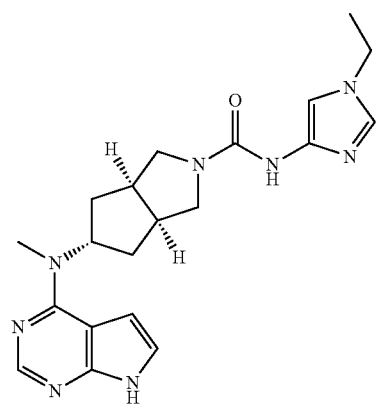 [SMILES: CCn1cnc(NC(=O)N2C[C@H]3C[C@H](N(C)c4ncnc5[nH]ccc45)C[C@H]3C2)c1]<br>(3aR,5S,6aS)-N-(1-ethyl-1H-imidazol-4-yl)-5-(methyl(7H-pyrrolo[2,3-d]pyrimidin-4-yl)amino)hexahydrocyclopenta[c]pyrrole-2(1H)-carboxamide |

| Example No. | Structure and Name |
|---|---|
| 124 | 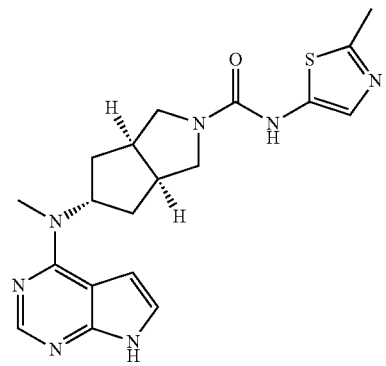 [SMILES: Cc1ncc(NC(=O)N2C[C@H]3C[C@H](N(C)c4ncnc5[nH]ccc45)C[C@H]3C2)s1]

(3aR,5S,6aS)-5-(methyl(7H-pyrrolo[2,3-d]pyrimidin-4-yl)amino)-N-(2-methylthiazol-5-yl)hexahydrocyclopenta[c]pyrrole-2(1H)-carboxamide |
| 125 | 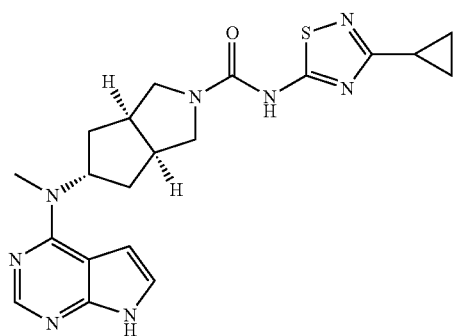 [SMILES: CN(c1ncnc2[nH]ccc12)[C@H]1C[C@@H]2CN(C(=O)Nc3nc(C4CC4)ns3)C[C@@H]2C1]

(3aR,5S,6aS)-N-(3-cyclopropyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide |
| 126 | 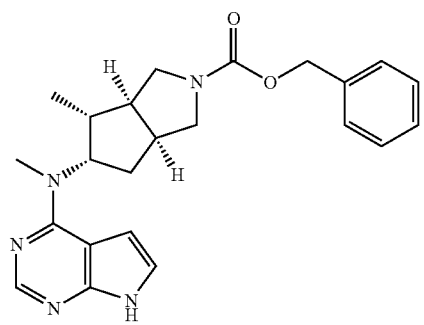 [SMILES: C[C@@H]1[C@H]2CN(C(=O)OCc3ccccc3)C[C@H]2C[C@@H]1N(C)c1ncnc2[nH]ccc12]

(3aS,4R,5S,6aS)-benzyl 4-methyl-5-(methyl(7H-pyrrolo[2,3-d]pyrimidin-4-yl)amino)hexahydrocyclopenta[c]pyrrole-2(1H)-carboxylate |

| Example No. | Structure and Name |
|---|---|
| 127 | 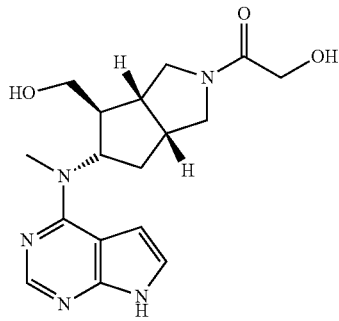<br>2-hydroxy-1-((3aR,4S,5S,6aR)-4-(hydroxymethyl)-5-(methyl(7H-pyrrolo[2,3-d]pyrimidin-4-yl)amino)hexahydrocyclopenta[c]pyrrol-2(1H)-yl)ethanone |
| 128 | 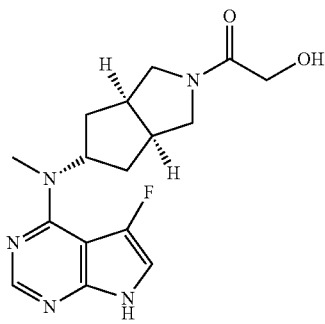<br>1-((3aR,5S,6aS)-5-((5-fluoro-7H-pyrrolo[2,3-d]pyrimidin-4-yl)(methyl)amino)hexahydrocyclopenta[c]pyrrol-2(1H)-yl)-2-hydroxyethanone |
| 129 | 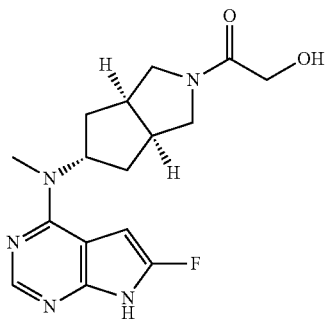 [SMILES: CN(c1ncnc2[nH]c(F)cc12)[C@H]1C[C@@H]2CN(C(=O)CO)C[C@@H]2C1]<br>1-((3aR,5S,6aS)-5-((6-fluoro-7H-pyrrolo[2,3-d]pyrimidin-4-yl)(methyl)amino)hexahydrocyclopenta[c]pyrrol-2(1H)-yl)-2-hydroxyethanone |
| 130 | 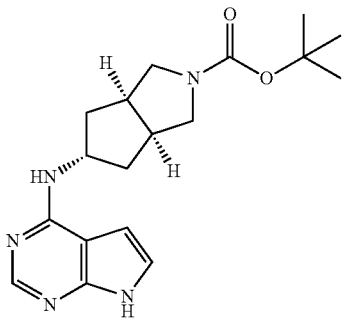 [SMILES: CC(C)(C)OC(=O)N1C[C@H]2C[C@H](Nc3ncnc4[nH]ccc34)C[C@H]2C1]<br>(3aR,5S,6aS)-tert-butyl 5-((7H-pyrrolo[2,3-d]pyrimidin-4-yl)amino)hexahydrocyclopenta[c]pyrrole-2(1H)-carboxylate |

-continued
| Example No. | Structure and Name |
|---|---|
| 131 | 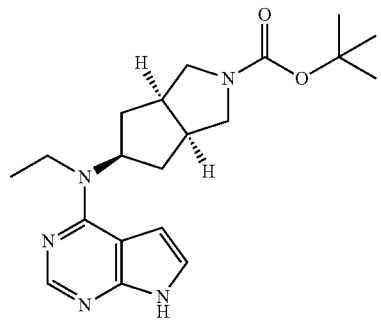 [SMILES: CCN(c1ncnc2[nH]ccc12)[C@@H]1C[C@@H]2CN(C(=O)OC(C)(C)C)C[C@@H]2C1]
(3aR,5R,6aS)-tert-butyl 5-(ethyl(7H-pyrrolo[2,3-d]pyrimidin-4-yl)amino)hexahydrocyclopenta[c]pyrrole-2(1H)-carboxylate |
| 132 | 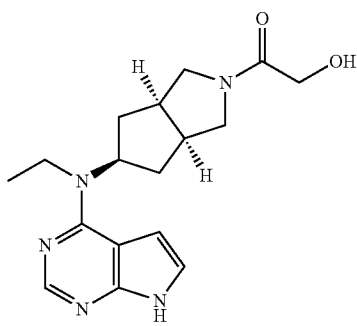 [SMILES: CCN(c1ncnc2[nH]ccc12)[C@@H]1C[C@@H]2CN(C(=O)CO)C[C@@H]2C1]
1-((3aR,5R,6aS)-5-(ethyl(7H-pyrrolo[2,3-d]pyrimidin-4-yl)amino)hexahydrocyclopenta[c]pyrrol-2(1H)-yl)-2-hydroxyethanone |
| 133 | 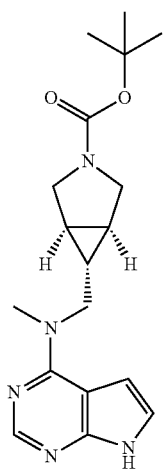 [SMILES: CN(C[C@H]1[C@@H]2CN(C(=O)OC(C)(C)C)C[C@@H]21)c1ncnc2[nH]ccc12]
(1R,5S,6S)-tert-butyl 6-((methyl(7H-pyrrolo[2,3-d]pyrimidin-4-yl)amino)methyl)-3-azabicyclo[3.1.0]hexane-3-carboxylate |

| Example No. | Structure and Name |
|---|---|
| 134 | 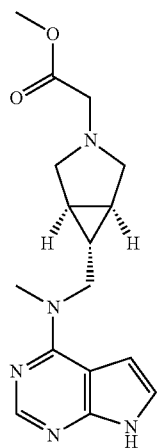 [SMILES: COC(=O)CN1C[C@@H]2[C@H](C1)[C@H]2CN(C)c1ncnc2[nH]ccc12]
methyl 2-((1R,5S,6R)-6-((methyl(7H-pyrrolo[2,3-d]pyrimidin-4-yl)amino)methyl)-3-azabicyclo[3.1.0]hexan-3-yl)acetate |
| 135 | 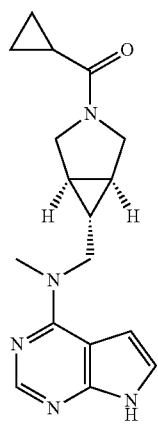 [SMILES: CN(C[C@H]1[C@@H]2CN(C(=O)C3CC3)C[C@@H]21)c1ncnc2[nH]ccc12]
cyclopropyl((1R,5S,6S)-6-((methyl(7H-pyrrolo[2,3-d]pyrimidin-4-yl)amino)methyl)-3-azabicyclo[3.1.0]hexan-3-yl)methanone |
| 136 | 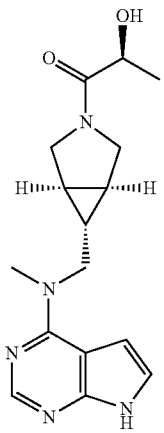 [SMILES: C[C@H](O)C(=O)N1C[C@@H]2[C@H](C1)[C@H]2CN(C)c1ncnc2[nH]ccc12]
(S)-2-hydroxy-1-((1R,5S,6R)-6-((methyl(7H-pyrrolo[2,3-d]pyrimidin-4-yl)amino)methyl)-3-azabicyclo[3.1.0]hexan-3-yl)propan-1-one |

| Example No. | Structure and Name |
|---|---|
| 137 | 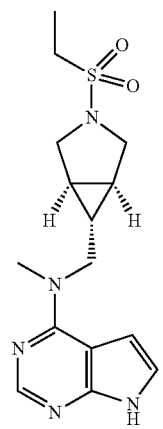 [SMILES: CCS(=O)(=O)N1C[C@@H]2[C@@H](CN(C)c3ncnc4[nH]ccc34)[C@@H]2C1]
N-(((1R,5S,6S)-3-(ethylsulfonyl)-3-azabicyclo[3.1.0]hexan-6-yl)methyl)-N-methyl-7H-pyrrolo[2,3-d]pyrimidin-4-amine |
| 138 | 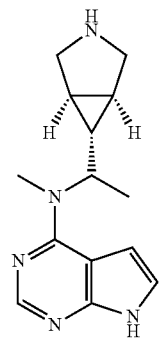 [SMILES: CC([C@H]1[C@@H]2CNC[C@@H]21)N(C)c1ncnc2[nH]ccc12]
N-((R)-1-((1R,5S,6R)-3-azabicyclo[3.1.0]hexan-6-yl)ethyl)-N-methyl-7H-pyrrolo[2,3-d]pyrimidin-4-amine |
| 139 | 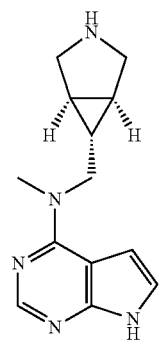
N-((1R,5S,6R)-3-azabicyclo[3.1.0]hexan-6-ylmethyl)-N-methyl-7H-pyrrolo[2,3-d]pyrimidin-4-amine |

| Example No. | Structure and Name |
|---|---|
| 140 | 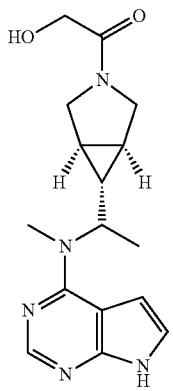 [SMILES: CC([C@H]1[C@@H]2CN(C(=O)CO)C[C@@H]21)N(C)c1ncnc2[nH]ccc12]<br>2-hydroxy-1-((1R,5S,6R)-6-((R)-1-(methyl(7H-pyrrolo[2,3-d]pyrimidin-4-yl)amino)ethyl)-3-azabicyclo[3.1.0]hexan-3-yl)ethanone |
| 141 | 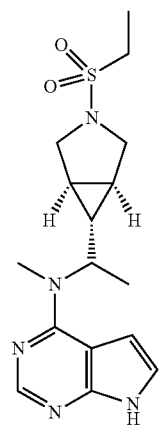<br>N-((R)-1-((1R,5S,6R)-3-(ethylsulfonyl)-3-azabicyclo[3.1.0]hexan-6-yl)ethyl)-N-methyl-7H-pyrrolo[2,3-d]pyrimidin-4-amine |
| 142 | 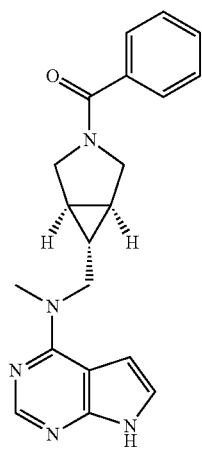 [SMILES: CN(C[C@H]1[C@@H]2CN(C(=O)c3ccccc3)C[C@@H]21)c1ncnc2[nH]ccc12]<br>((1R,5S,6S)-6-((methyl(7H-pyrrolo[2,3-d]pyrimidin-4-yl)amino)methyl)-3-azabicyclo[3.1.0]hexan-3-yl)(phenyl)methanone |

-continued
| Example No. | Structure and Name |
|---|---|
| 143 | 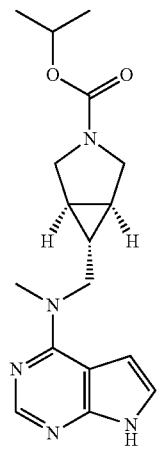 [SMILES: CC(C)OC(=O)N1C[C@@H]2[C@H](C1)[C@H]2CN(C)c1ncnc2[nH]ccc12]<br>(1R,5S,6S)-isopropyl 6-((methyl(7H-pyrrolo[2,3-d]pyrimidin-4-yl)amino)methyl)-3-azabicyclo[3.1.0]hexane-3-carboxylate |
| 144 | 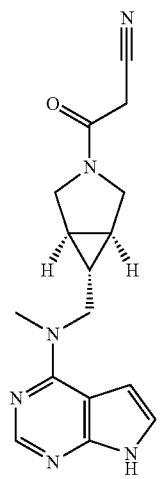<br>3-((1R,5S,6S)-6-((methyl(7H-pyrrolo[2,3-d]pyrimidin-4-yl)amino)methyl)-3-azabicyclo[3.1.0]hexan-3-yl)-3-oxopropanenitrile |
| 145 | 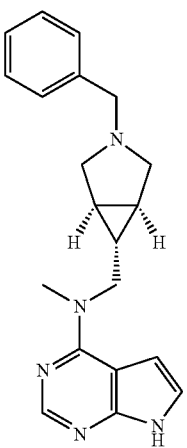 [SMILES: CN(C[C@H]1[C@@H]2CN(Cc3ccccc3)C[C@@H]21)c1ncnc2[nH]ccc12]<br>N-(((1R,5S,6R)-3-benzyl-3-azabicyclo[3.1.0]hexan-6-yl)methyl)-N-methyl-7H-pyrrolo[2,3-d]pyrimidin-4-amine |

| Example No. | Structure and Name |
|---|---|
| 146 | 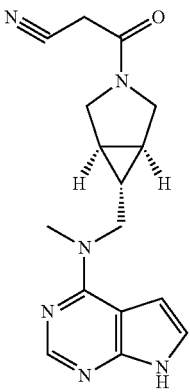 [SMILES: CN(C[C@H]1[C@@H]2CN(C(=O)CC#N)C[C@@H]21)c1ncnc2[nH]ccc12]<br>4-((1R,5S,6S)-6-(((methyl(7H-pyrrolo[2,3-d]pyrimidin-4-yl)amino)methyl)-3-azabicyclo[3.1.0]hexan-3-yl)-4-oxobutanenitrile |
| 147 | 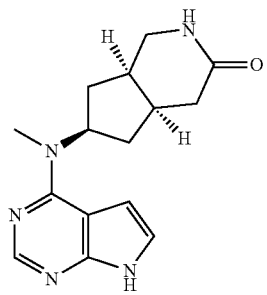 [SMILES: CN(c1ncnc2[nH]ccc12)[C@H]1C[C@H]2CNC(=O)C[C@H]2C1]<br>(4aR,6R,7aR)-6-(methyl(7H-pyrrolo[2,3-d]pyrimidin-4-yl)amino)hexahydro-1H-cyclopenta[c]pyridin-3(2H)-one |
| 148 | 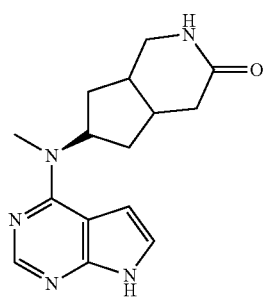<br>(6S)-6-(methyl(7H-pyrrolo[2,3-d]pyrimidin-4-yl)amino)hexahydro-1H-cyclopenta[c]pyridin-3(2H)-one |
| 149 | 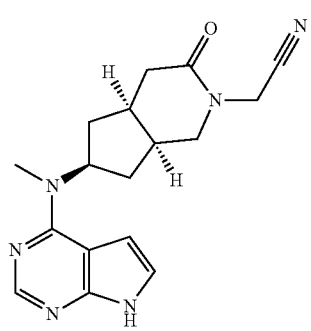 [SMILES: CN(c1ncnc2[nH]ccc12)[C@H]1C[C@H]2CC(=O)N(CC#N)C[C@H]2C1]<br>2-((4aS,6S,7aS)-6-(methyl(7H-pyrrolo[2,3-d]pyrimidin-4-yl)amino)-3-oxohexahydro-1H-cyclopenta[c]pyridin-2(3H)-yl)acetonitrile |

| Example No. | Structure and Name |
|---|---|
| 150 | 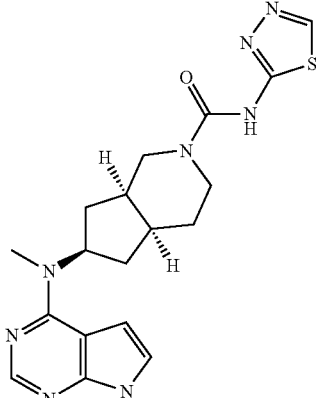<br>(4aS,6R,7aR)-6-(methyl(7H-pyrrolo[2,3-d]pyrimidin-4-yl)amino)-N-(1,3,4-thiadiazol-2-yl)hexahydro-1H-cyclopenta[c]pyridine-2(3H)-carboxamide |
| 151 | 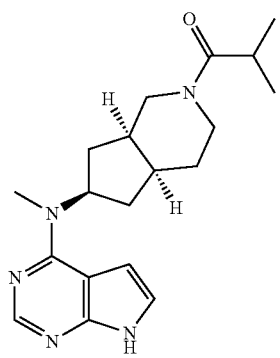<br>2-methyl-1-((4aS,6R,7aR)-6-(methyl(7H-pyrrolo[2,3-d]pyrimidin-4-yl)amino)hexahydro-1H-cyclopenta[c]pyridin-2(3H)-yl)propan-1-one |
| 152 | 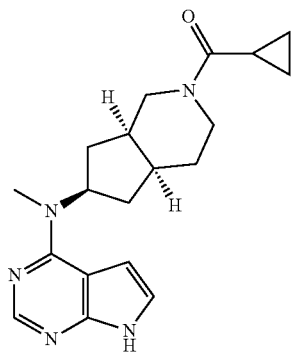<br>cyclopropyl((4aS,6R,7aR)-6-(methyl(7H-pyrrolo[2,3-d]pyrimidin-4-yl)amino)hexahydro-1H-cyclopenta[c]pyridin-2(3H)-yl)methanone |

| Example No. | Structure and Name |
|---|---|
| 153 | 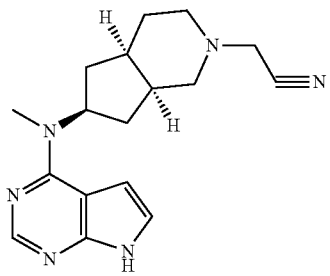
2-((4aR,6S,7aS)-6-(methyl(7H-pyrrolo[2,3-d]pyrimidin-4-yl)amino)hexahydro-1H-cyclopenta[c]pyridin-2(3H)-yl)acetonitrile |
| 154 | 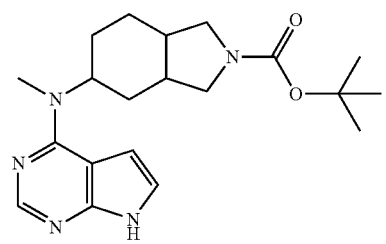
tert-butyl 5-(methyl(7H-pyrrolo[2,3-d]pyrimidin-4-yl)amino)hexahydro-1H-isoindole-2(3H)-carboxylate |
| 155 | 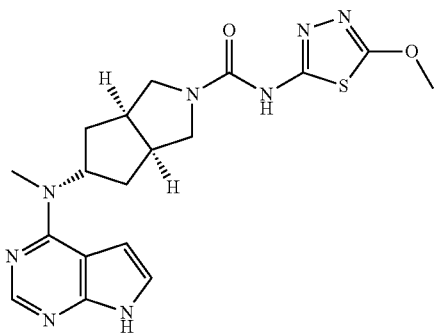
(3aR,5S,6aS)-N-(5-methoxy-1,3,4-thiadiazol-2-yl)-5-(methyl(7H-pyrrolo[2,3-d]pyrimidin-4-yl)amino)hexahydrocyclopenta[c]pyrrole-2(1H)-carboxamide |
| 156 | 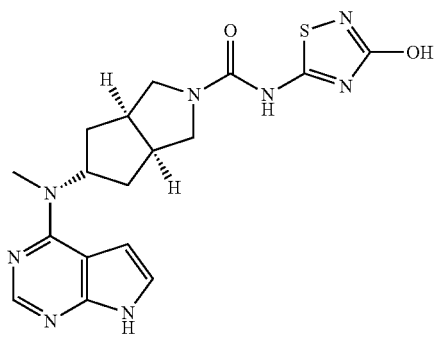
(3aR,5S,6aS)-N-(3-hydroxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide | or a tautomer, mesomer, racemate, enantiomer, diastereomer, or mixture thereof, or a pharmaceutically acceptable salt thereof.

In another aspect, this invention is to provide a compound of formula (IB), or a tautomer, mesomer, racemate, enantiomer, diastereomer, or mixture thereof, used as an intermediate for preparing a compound of formula (I), wherein:

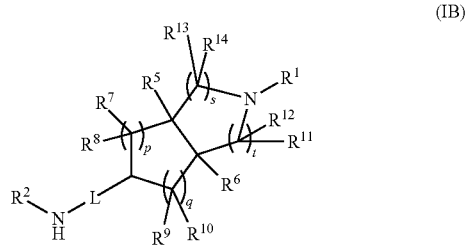

(IB)

L is a bond or alkyl;

$R^1$ is selected from the group consisting of hydrogen, alkyl, cycloalkyl, heterocyclyl, aryl, heteroaryl, —$(CH_2)_nC(O)OR^{15}$, —$OC(O)R^{15}$, —$C(O)R^{15}$, —$C(O)NR^{16}R^{17}$, —$NHC(O)R^{15}$, —$NR^{16}R^{17}$, —$OC(O)NR^{16}R^{17}$, —$NHC(O)NR^{16}R^{17}$, and —$S(O)_mR^{15}$, wherein the alkyl, cycloalkyl, heterocyclyl, aryl or heteroaryl is optionally substituted with one or more groups selected from the group consisting of halogen, hydroxy, cyano, nitro, alkyl, alkoxy, cycloalkyl, heterocyclyl, aryl, heteroaryl, —$(CH_2)_nC(O)OR^{15}$, —$OC(O)R^{15}$, —$C(O)R^{15}$, —$C(O)NR^{16}R^{17}$, —$NHC(O)R^{15}$, —$NR^{16}R^{17}$, —$OC(O)NR^{16}R^{17}$, —$NHC(O)NR^{16}R^{17}$, —$S(O)_mR^{15}$, —$NHC(O)(O)R^{15}$, and —$NHS(O)_mR^{15}$;

$R^2$ is selected from the group consisting of hydrogen and alkyl;

$R^5$ and $R^6$ are each independently selected from the group consisting of hydrogen, alkyl, and aryl, wherein the alkyl or aryl is optionally substituted with one or more groups selected from the group consisting of alkyl and halogen;

each of $R^7$, $R^8$, $R^9$ and $R^{10}$ are independently selected from the group consisting of hydrogen, alkyl, hydroxyalkyl, and halogen; or, $R^7$ and $R^8$, or $R^9$ and $R^{10}$ are taken together to form an oxo group;

each of $R^{11}$, $R^{12}$, $R^{13}$, and $R^{14}$ are each independently selected from the group consisting of hydrogen, alkyl, and halogen; or, $R^{11}$ and $R^{12}$, or $R^{13}$ and $R^{14}$ are taken together to form an oxo group;

$R^{15}$ is selected from the group consisting of hydrogen, alkyl, cycloalkyl, heterocyclyl, alkenyl, alkynyl, aryl, and heteroaryl, wherein the alkyl, cycloalkyl, heterocyclyl, aryl or heteroaryl is optionally substituted with one or more groups selected from the group consisting of alkyl, halogen, hydroxy, cyano, amino, nitro, alkoxy, cycloalkyl, heterocyclyl, aryl, heteroaryl, —$(CH_2)_nC(O)OR^{18}$, —$OC(O)R^{18}$, —$C(O)R^{18}$, —$C(O)NR^{19}R^{20}$, —$NHC(O)R^{18}$, —$NR^{19}R^{20}$, —$OC(O)NR^{19}R^{20}$, —$NHC(O)NR^{19}R^{20}$, —$S(O)_mR^{18}$, —$NHC(O)OR^{18}$, and —$NHS(O)_mR^{18}$;

$R^{16}$ and $R^{17}$ are each independently selected from the group consisting of hydrogen, alkyl, cycloalkyl, heterocyclyl, aryl, and heteroaryl, wherein the alkyl, cycloalkyl, heterocyclyl, aryl, or heteroaryl is optionally substituted with one or more groups selected from the group consisting of alkyl, halogen, hydroxy, cyano, amino, alkoxy, cycloalkyl, heterocyclyl, hydroxyalkyl, alkynyl, aryl, heteroaryl, carboxyl, alkoxycarbonyl, and —$OR^{18}$;

$R^{18}$ is selected from the group consisting of hydrogen, alkyl, cycloalkyl, heterocyclyl, hydroxyalkyl, aryl, and heteroaryl;

$R^{19}$ and $R^{20}$ are each independently selected from the group consisting of hydrogen, alkyl, cycloalkyl, heterocyclyl, aryl, and heteroaryl;

m is 0, 1, or 2;
n is 0, 1, or 2;
p is 0, 1, or 2;
q is 0, 1, or 2;
s is 0, 1, or 2; and
t is 0, 1, or 2;

In another aspect, this invention provides a preparation process of a compound of formula (I), or a tautomer, mesomer, racemate, enantiomer, diastereomer, or mixture thereof, or a pharmaceutically acceptable salt thereof, the preparation process comprising the steps of:

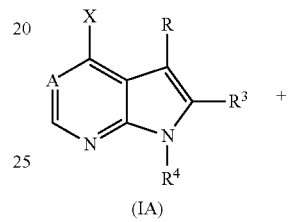

(IA)

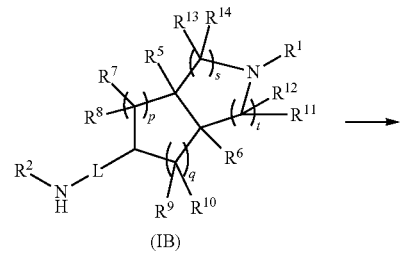

(IB)

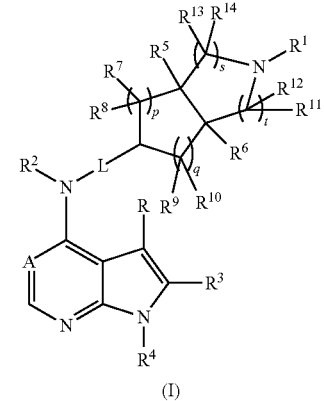

(I)

under alkaline conditions, reacting a compound of formula (IA) with a compound of formula (IB) to obtain a compound of formula (I);

the alkaline conditions are provided by an organic base or inorganic base, wherein said organic base includes, but is not limited to, triethylamine, N,N-diisopropylethylamine, n-butyllithium, tert-butyl potassium alkoxide, tetrabutylammonium bromide, and said inorganic base includes, but is not limited to, sodium hydride, sodium carbonate, sodium bicarbonate, potassium carbonate, potassium bicarbonate or cesium carbonate;

wherein X is a halogen; and A, L, R, $R^1$ to $R^{14}$, p, q, s, and t are as defined in formula (I); preferably, $R_1$ is tert-butoxycarbonyl.

In another aspect, this invention provides a preparation process of a compound of formula (I), or a tautomer, mesomer, racemate, enantiomer, diastereomer, or mixture thereof, or a pharmaceutically acceptable salt thereof, the preparation process comprising the steps of:

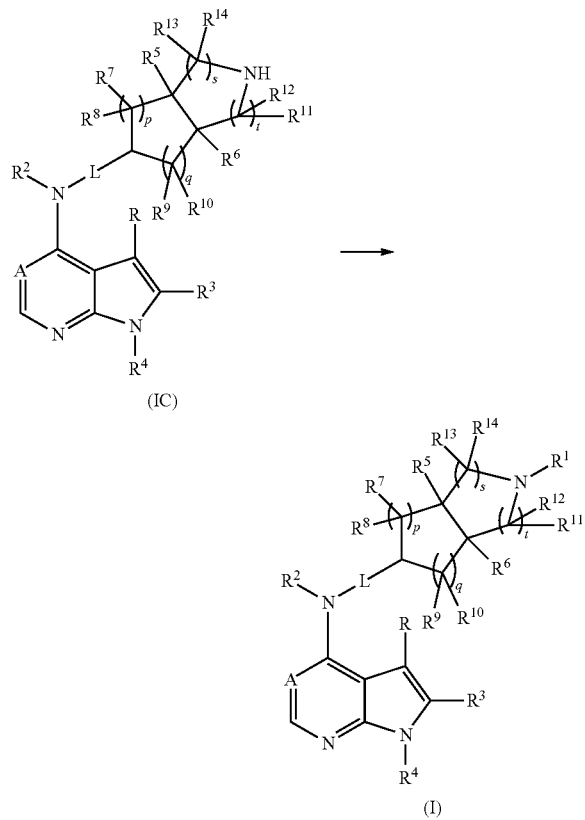

under alkaline conditions, reacting a compound of formula (IC) or a pharmaceutically acceptable salt thereof with a carboxylic acid, acyl chloride, sulfonyl chloride, carboxylic ester, an ethylene oxide derivative, or halide to obtain the compound of formula (I);

wherein: when $R^1$ is t-butoxycarbonyl, t-butoxycarbonyl is further optionally removed from the compound of formula (I) to obtain the compound of formula (IC) or a pharmaceutically acceptable salt thereof;

the reaction solvent includes, but is not limited to, tetrahydrofuran, ethanol, methanol, n-butanol, dichloromethane, 1,4-dioxane or N,N-dimethylformamide;

the alkaline conditions are provided by an organic base or inorganic base, wherein said organic base includes, but is not limited to, triethylamine, N,N-diisopropylethylamine, n-butyllithium, tert-butyl potassium alkoxide, and said inorganic base includes, but is not limited to, sodium hydride, sodium carbonate, sodium bicarbonate, potassium carbonate, potassium bicarbonate or cesium carbonate;

wherein A, L, R, $R^1$ to $R^{14}$, p, q, s, and t are as defined in formula (I).

The present invention also provides a pharmaceutical composition, comprising a therapeutically effective amount of a compound of formula (I), or a tautomer, mesomer, racemate, enantiomer, diastereomer, or mixture thereof, or a pharmaceutically acceptable salt thereof, together with a pharmaceutically acceptable carrier or excipient.

The present invention also relates to use of a compound of formula (I), or a tautomer, mesomer, racemate, enantiomer, diastereomer, or mixture thereof, or a pharmaceutically acceptable salt thereof, or the pharmaceutical composition comprising the same, in the preparation of a medicament for inhibiting JAK kinase; preferably inhibiting JAK1, JAK2, or JAK3.

The present invention also relates to use of a compound of formula (I), or a tautomer, mesomer, racemate, enantiomer, diastereomer, or mixture thereof, or a pharmaceutically acceptable salt thereof, or a pharmaceutical composition comprising the same, in the preparation of a medicament for inhibiting JAK kinase; wherein the medicament optionally contains one or more additional reagents for regulating the mammalian immune system, anti-cancer agents, or anti-inflammatory agents.

The present invention also relates to use of a compound of formula (I), or a tautomer, mesomer, racemate, enantiomer, diastereomer, or mixture thereof, or a pharmaceutically acceptable salt thereof, or a pharmaceutical composition comprising the same, in the preparation of a medicament for inhibiting JAK kinase; wherein the medicament is useful for the treatment or prevention of the following disorders or diseases: diseases of immune system, including, for example, organ transplant rejection (e.g., allograft rejection and graft versus host disease); autoimmune diseases, including, for example, lupus, multiple sclerosis, rheumatoid arthritis, juvenile arthritis, psoriasis, ulcerative colitis, Crohn's disease, autoimmune thyroid disease, etc.; skin diseases, including, for example, psora, rash, atopic dermatitis, etc.; allergic disorders, including, for example, asthma, rhinitis, etc.; viral diseases, including, for example, hepatitis B, hepatitis C, varicella—zoster virus etc.; type I diabetes and diabetic complications; Alzheimer's disease; dry eye; marrow fibrosis; thrombocytosis; polycythemia or leukemia; cancers, including, for example, solid tumors (such as prostate cancer, kidney cancer, liver cancer, pancreatic cancer, stomach cancer, breast cancer, lung cancer, head and neck cancer, thyroid cancer, glioblastoma, melanoma, etc.), blood cancer (such as lymphoma, leukemia, etc.), and skin cancer (such as cutaneous T-cell lymphoma, cutaneous B-cell lymphoma) etc.

The present invention also relates to use of a compound of formula (I), or a tautomer, mesomer, racemate, enantiomer, diastereomer, or mixture thereof, or a pharmaceutically acceptable salt thereof, or a pharmaceutical composition comprising the same, in the preparation of a medicament for inhibiting JAK kinase; wherein the medicament optionally contains one or more additional reagents for regulating mammalian immune system, anti-cancer agents or anti-inflammatory agents, wherein said medicament is for the treatment or prevention of the following disorders or diseases: diseases of immune system, including, for example, organ transplant rejection (e.g., allograft rejection and graft versus host disease); autoimmune diseases, including, for example, lupus, multiple sclerosis, rheumatoid arthritis, juvenile arthritis, psoriasis, ulcerative colitis, Crohn's disease, autoimmune thyroid disease, etc.; skin diseases, including, for example, psora, rash, atopic dermatitis, etc.; allergic disorders, including, for example, asthma, rhinitis, etc.; viral diseases, including, for example, hepatitis B, hepatitis C, varicella—zoster virus etc.; type I diabetes and diabetic complications; Alzheimer's disease; dry eye; marrow fibrosis; thrombocytosis; polycythemia or leukemia; cancers, including, for example, solid tumors (such as prostate cancer, kidney cancer, liver cancer, pancreatic cancer, stomach cancer, breast cancer, lung cancer, head and neck cancer, thyroid cancer, glioblastoma, melanoma, etc.), blood cancer (such as lymphoma, leukemia, etc.), and skin cancer (such as cutaneous T-cell lymphoma, cutaneous B-cell lymphoma), etc., wherein said mammal is human.

The present invention further relates to a compound of formula (I), or a tautomer, mesomer, racemate, enantiomer, diastereomer, or mixture thereof, or a pharmaceutically acceptable salt thereof, or a pharmaceutical composition comprising the same, for use as a medicament for inhibiting JAK kinase. Said JAK kinase is preferably selected from the group consisting of JAK1, JAK2, and JAK3.

The present invention further relates to use of a compound of formula (I), or a tautomer, mesomer, racemate, enantiomer, diastereomer, or mixture thereof, or a pharmaceutically acceptable salt thereof, or a pharmaceutical composition comprising the same, for use as a medicament combined with one or more additional reagents for regulating mammalian immune system, anti-cancer agents, or anti-inflammatory agents.

The present invention also relates to a compound of formula (I), or a tautomer, mesomer, racemate, enantiomer, diastereomer, or mixture thereof, or a pharmaceutically acceptable salt thereof, or a pharmaceutical composition comprising the same, for use as a medicament for the treatment or prevention of the following disorders or diseases: diseases of immune system, including, for example, organ transplant rejection (e.g., allograft rejection and graft versus host disease); autoimmune diseases, including, for example, lupus, multiple sclerosis, rheumatoid arthritis, juvenile arthritis, psoriasis, ulcerative colitis, Crohn's disease, autoimmune thyroid disease, etc.; skin diseases, including, for example, psora, rash, atopic dermatitis, etc.; allergic disorders, including, for example, asthma, rhinitis, etc.; viral diseases, including, for example, hepatitis B, hepatitis C, varicella—zoster virus etc.; type I diabetes and diabetic complications; Alzheimer's disease; dry eye; marrow fibrosis; thrombocytosis; polycythemia or leukemia; cancers, including, for example, solid tumors (such as prostate cancer, kidney cancer, liver cancer, pancreatic cancer, stomach cancer, breast cancer, lung cancer, head and neck cancer, thyroid cancer, glioblastoma, melanoma, etc.), blood cancer (such as lymphoma, leukemia, etc.), and skin cancer (such as cutaneous T-cell lymphoma, cutaneous B-cell lymphoma) etc.

The present invention also relates to a compound of formula (I), or a tautomer, mesomer, racemate, enantiomer, diastereomer, or mixture thereof, or a pharmaceutically acceptable salt thereof, or a pharmaceutical composition comprising the same, further combined with one or more reagents for regulating a mammalian immune system, anti-cancer agents, or anti-inflammatory agents, for use as a medicament for the treatment or prevention of the following disorders or disease: diseases of immune system, including, for example, organ transplant rejection (e.g., allograft rejection and graft versus host disease); autoimmune diseases, including, for example, lupus, multiple sclerosis, rheumatoid arthritis, juvenile arthritis, psoriasis, ulcerative colitis, Crohn's disease, autoimmune thyroid disease, etc.; skin diseases, including, for example, psora, rash, atopic dermatitis, etc.; allergic disorders, including, for example, asthma, rhinitis, etc.; viral diseases, including, for example, hepatitis B, hepatitis C, varicella—zoster virus etc.; type I diabetes and diabetic complications; Alzheimer's disease; dry eye; marrow fibrosis; thrombocytosis; polycythemia or leukemia; cancers, including, for example, solid tumors (such as prostate cancer, kidney cancer, liver cancer, pancreatic cancer, stomach cancer, breast cancer, lung cancer, head and neck cancer, thyroid cancer, glioblastoma, melanoma, etc.), blood cancer (such as lymphoma, leukemia, etc.), and skin cancer (such as cutaneous T-cell lymphoma, cutaneous B-cell lymphoma) etc.

In other words, the present invention relates to a method for inhibiting JAK kinase, comprising a step of administering to a subject in need thereof a therapeutically effective amount of a compound of formula (I), or a tautomer, racemate, enantiomer, diastereoisomer, or mixture thereof, or a pharmaceutically acceptable salt thereof, or a pharmaceutical composition containing the same. Furthermore, the compounds of formula (I) or tautomers, racemates, enantiomers, diastereoisomers, and mixtures thereof, or pharmaceutically acceptable salts thereof, or pharmaceutical composition containing the same, can be combined with one or more additional reagents for regulating a mammalian immune system, anti-cancer agents, or anti-inflammatory agents.

The present invention relates to a method for the treatment or prevention of disorders or diseases of immune system, comprising a step of administering to a subject in need thereof a therapeutically effective amount of a compound of formula (I), or a tautomer, mesomer, racemate, enantiomer, diastereomer, or mixture thereof, or a pharmaceutically acceptable salt thereof, or a pharmaceutical composition comprising the same; wherein said disorders or diseases of the immune system include, for example, organ transplant rejection (e.g., allograft rejection and graft versus host disease); autoimmune diseases, including, for example, lupus, multiple sclerosis, rheumatoid arthritis, juvenile arthritis, psoriasis, ulcerative colitis, Crohn's disease, autoimmune thyroid disease, etc.; skin diseases, including, for example, psora, rash, atopic dermatitis, etc.; allergic disorders, including, for example, asthma, rhinitis, etc.; viral diseases, including, for example, hepatitis B, hepatitis C, varicella—zoster virus etc.; type I diabetes and diabetic complications; Alzheimer's disease; dry eye; marrow fibrosis; thrombocytosis; polycythemia or leukemia; cancers, including, for example, solid tumors (such as prostate cancer, kidney cancer, liver cancer, pancreatic cancer, stomach cancer, breast cancer, lung cancer, head and neck cancer, thyroid cancer, glioblastoma, melanoma, etc.), blood cancer (such as lymphoma, leukemia, etc.), and skin cancer (such as cutaneous T-cell lymphoma, cutaneous B-cell lymphoma) etc.

The present invention also relates to a method for the treatment or prevention of disorders or diseases of immune system, comprising a step of administering to a subject in need thereof a therapeutically effective amount of a compound of formula (I), or a tautomer, mesomer, racemate, enantiomer, diastereomer, or mixture thereof, or a pharmaceutically acceptable salt thereof, or a pharmaceutical composition comprising the same, and one or more additional reagents for regulating a mammalian immune system, anti-cancer agents, or anti-inflammatory agents, wherein said disorders or diseases of immune system include, for example, organ transplant rejection (e.g., allograft rejection and graft versus host disease); autoimmune diseases, including, for example, lupus, multiple sclerosis, rheumatoid arthritis, juvenile arthritis, psoriasis, ulcerative colitis, Crohn's disease, autoimmune thyroid disease, etc.; skin diseases, including, for example, psora, rash, atopic dermatitis, etc.; allergic disorders, including, for example, asthma, rhinitis, etc.; viral diseases, including, for example, hepatitis B, hepatitis C, varicella—zoster virus etc.; type I diabetes and diabetic complications; Alzheimer's disease; dry eye; marrow fibrosis; thrombocytosis; polycythemia or leukemia;

cancers, including, for example, solid tumors (such as prostate cancer, kidney cancer, liver cancer, pancreatic cancer, stomach cancer, breast cancer, lung cancer, head and neck cancer, thyroid cancer, glioblastoma, melanoma, etc.), blood cancer (such as lymphoma, leukemia, etc.), and skin cancer (such as cutaneous T-cell lymphoma, cutaneous B-cell lymphoma) etc.

The compositions of this invention can be formulated by conventional methods using one or more pharmaceutically acceptable carriers. Thus, the active compounds of this invention can be formulated as various dosage forms for oral, buccal, intranasal, parenteral (e.g., intravenous, intramuscular or subcutaneous) or rectal administration, or inhalation or insufflation administration. The compounds of this invention can also be formulated as sustained release dosage forms.

For oral administration, the pharmaceutical compositions, for example, can be formulated as tablets or capsules with pharmaceutically acceptable excipients by conventional means, wherein the excipients include, for example, binding agents (e.g., starch, gelatin, polyvinyl-pyrrolidone or acacia) and fillers (e.g. lactose, microcrystalline cellulose or calcium phosphate), lubricants (e.g. magnesium stearate, talc or silica), disintegrants (e.g., potato starch or sodium starch glycollate) or wetting agents (such as sodium lauryl sulphate). The tablets can be coated by methods well known in the field. Liquid preparations for oral administration can be solutions, syrups or suspensions, or may be a dry product for reconstitution with water or other suitable carrier before use. Such liquid preparations can be prepared by conventional means with pharmaceutically acceptable additives such as suspending agents (e.g. sorbitol syrup, methyl cellulose or hydrogenated edible fats), emulsifying agents (e.g. lecithin or acacia), non-aqueous vehicles (e.g. almond oil, oily esters or ethanol) and preservatives (e.g. methyl or propyl p-hydroxy benzoate).

For buccal administration, the compositions can be formulated as tablets or lozenges by conventional means.

The active compounds of this invention can be formulated for parenteral administration by injection, including using conventional catheterization techniques or infusion. Injection can be presented in unit dosage form, e.g., in ampoules or in multi-capacity containers, with an added preservative. The compositions can be suspensions, solutions or emulsions in oily or aqueous carriers, and can contain formulating agents such as suspending, stabilizing and/or dispersing agents. Alternatively, the active ingredient can be in powder form for reconstitution with a suitable carrier, e.g., sterile pyrogen-free water, before use.

The active compounds of this invention can also be formulated as rectal compositions, such as suppositories or retention enemas, e.g., containing conventional suppository bases such as cocoa butter or other glycerides.

For intranasal administration or administration by inhalation, the active compounds of the present invention are conveniently delivered in the form of a solution or suspension released from a pump spray container that is squeezed or pumped by the patient, or as an aerosol spray released from a pressurized container or nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. The pressurized container or nebulizer can contain a solution or suspension of the active compound. Capsules or cartridges (for example, made from gelatin) for use in an inhaler or insufflator can be formulated containing a powder mix of the present invention and a suitable powder base such as lactose or starch.

The compounds of this invention can be administered in a pharmaceutically acceptable dosage form either alone, or in combination with one or more agents for regulating mammalian immune system or anti-inflammatory agents. These agents can include, but are not limited, to cyclosporin A (such as Sandimmune® or Neroal®), rapamycin, FK-506 (tacrolimus), leflunomide, deoxyspergualin, mycophenolate salts (e.g. Cellcept®), azathioprine (e.g. Imuran®), daclizumab (e.g. Zenapax®), OKT3 (e.g. Orthoclone®), AcGam, aspirin, acetaminophen, ibuprofen, naproxen, meloxicam pyrrole and anti-inflammatory steroids (such as prednisone or dexamethasone). These agents can be administered as part of the same or separate dosage forms, via the same or different route of administration, according to standard pharmaceutical practice based on the same or different administration schedules.

DETAILED DESCRIPTION OF THE INVENTION

Unless otherwise stated, the terms used in the specification and claims have the meanings described below.

"Alkyl" refers to a saturated aliphatic hydrocarbon group including C1-C20 straight chain and branched chain groups. Preferably an alkyl group is an alkyl having 1 to 12 carbon atoms. Representative examples include, but are not limited to methyl, ethyl, n-propyl, isopropyl, n-butyl, isobutyl, tert-butyl, sec-butyl, n-pentyl, 1,1-dimethyl propyl, 1,2-dimethyl propyl, 2,2-dimethyl propyl, 1-ethyl propyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and the isomers of branched chain thereof. More preferably an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, preferably the substituent group(s) is one or more groups independently selected from the group consisting of alkyl, alkenyl, alkynyl, alkyloxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocylic alkylthio, oxo group, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Alkenyl" refers to an alkyl defined as above that has at least two carbon atoms and at least one carbon-carbon double bond, for example, vinyl, 1-propenyl, 2-propenyl, 1-, 2-, or 3-butenyl, etc. The alkenyl group can be substituted or unsubstituted. When substituted, the substituent group(s) is preferably one or more group(s) independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Alkynyl" refers to an alkyl defined as above that has at least two carbon atoms and at least one carbon-carbon triple bond, for example, ethynyl, 1-propynyl, 2-propynyl, 1-, 2-, or 3-butynyl etc., preferably C2-10 alkynyl, more preferably C2-6 alkynyl, and most preferably C2-4 alkynyl. The alkynyl group can be substituted or unsubstituted. When substituted, the substituent group(s) is preferably one or more group(s) independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Cycloalkyl" refers to a saturated and/or partially unsaturated monocyclic or polycyclic hydrocarbon group having 3 to 20 carbon atoms, preferably 3 to 12 carbon atoms, more preferably 3 to 10 carbon atoms, and most preferably 3 to 8 carbon atoms or 3 to 6 carbon atoms. Representative examples of monocyclic cycloalkyls include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. Polycyclic cycloalkyl includes a cycloalkyl having a spiro ring, fused ring or bridged ring.

"Spiro Cycloalkyl" refers to a 5 to 20 membered polycyclic group with rings connected through one common carbon atom (called a spiro atom), wherein one or more rings can contain one or more double bonds, but none of the rings has a completely conjugated pi-electron system. Preferably a spiro cycloalkyl is 6 to 14 membered, and more preferably 7 to 10 membered. According to the number of common spiro atoms, a spiro cycloalkyl is divided into mono-spiro cycloalkyl, di-spiro cycloalkyl, or poly-spiro cycloalkyl, and preferably refers to a mono-spiro cycloalkyl or di-spiro cycloalkyl, more preferably 4-membered/4-membered, 4-membered/5-membered, 4-membered/6-membered, 5-membered/5-membered, or 5-membered/6-membered mono-spiro cycloalkyl. Representative examples of spiro cycloalkyl include, but are not limited to the following groups:

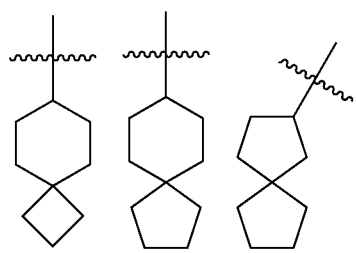

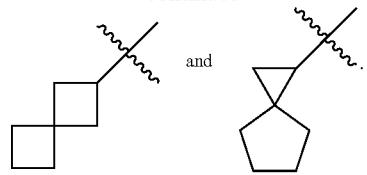

"Fused Cycloalkyl" refers to a 5 to 20 membered polycyclic hydrocarbon group, wherein each ring in the system shares an adjacent pair of carbon atoms with another ring, wherein one or more rings can contain one or more double bonds, but none of the rings has a completely conjugated pi-electron system. Preferably, a fused cycloalkyl group is 6 to 14 membered, more preferably 7 to 10 membered. According to the number of membered rings, fused cycloalkyl is divided into bicyclic, tricyclic, tetracyclic or polycyclic fused cycloalkyl, and preferably refers to a bicyclic or tricyclic fused cycloalkyl, more preferably 5-membered/5-membered, or 5-membered/6-membered bicyclic fused cycloalkyl. Representative examples of fused cycloalkyls include, but are not limited to, the following groups:

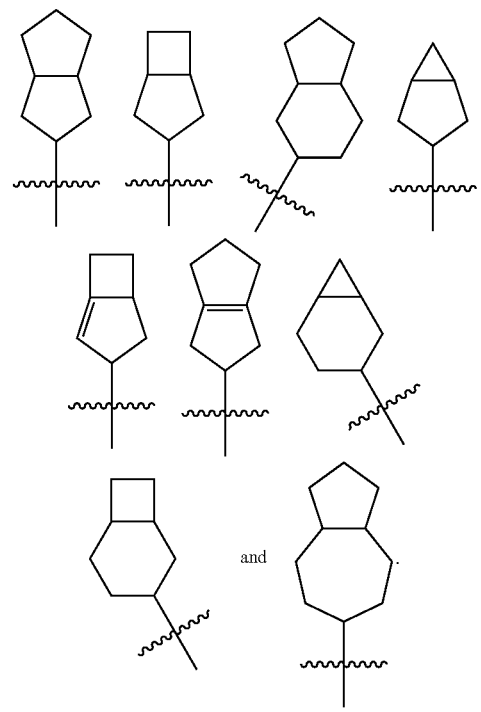

"Bridged Cycloalkyl" refers to a 5 to 20 membered polycyclic hydrocarbon group, wherein every two rings in the system share two disconnected carbon atoms. The rings can have one or more double bonds, but have no completely conjugated pi-electron system. Preferably, a bridged cycloalkyl is 6 to 14 membered, and more preferably 7 to 10 membered. According to the number of membered rings, bridged cycloalkyl is divided into bicyclic, tricyclic, tetracyclic or polycyclic bridged cycloalkyl, and preferably refers to a bicyclic, tricyclic or tetracyclic bridged cycloalkyl, more preferably a bicyclic or tricyclic bridged cycloalkyl. Representative examples of bridged cycloalkyls include, but are not limited to, the following groups:

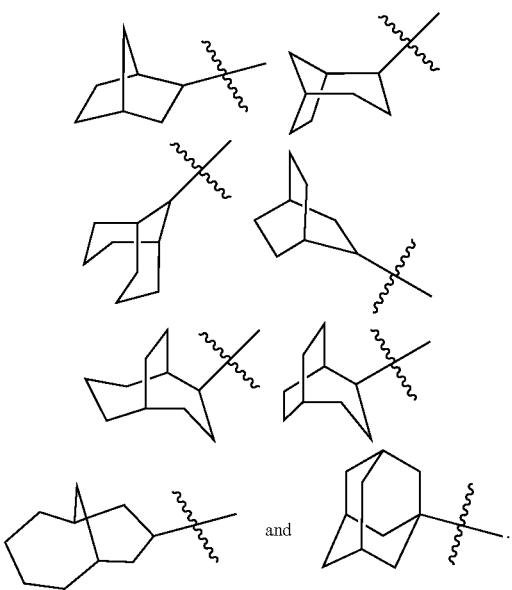

The cycloalkyl can be fused to the ring of an aryl, heteroaryl or heterocyclic alkyl, wherein the ring bound to the parent structure is cycloalkyl. Representative examples include, but are not limited to indanylacetic, tetrahydronaphthalene, benzocycloheptyl and so on. The cycloalkyl is optionally substituted or unsubstituted. When substituted, the substituent group(s) is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, oxo group, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Heterocyclyl" refers to a 3 to 20 membered saturated and/or partially unsaturated monocyclic or polycyclic hydrocarbon group having one or more heteroatoms selected from the group consisting of N, O, and S(O)m (wherein m is 0, 1, or 2) as ring atoms, but excluding —O—O—, —O—S— or —S—S— in the ring, the remaining ring atoms being C. Preferably, heterocyclyl is a 3 to 12 membered having 1 to 4 heteroatoms; more preferably a 3 to 10 membered having 1 to 3 heteroatoms; most preferably a 5 to 6 membered having 1 to 2 heteroatoms. Representative examples of monocyclic heterocyclyls include, but are not limited to, pyrrolidyl, piperidyl, piperazinyl, morpholinyl, sulfo-morpholinyl, homopiperazinyl, and so on. Polycyclic heterocyclyl includes the heterocyclyl having a spiro ring, fused ring or bridged ring.

"Spiro heterocyclyl" refers to a 5 to 20 membered polycyclic heterocyclyl with rings connected through one common carbon atom (called a spiro atom), wherein said rings have one or more heteroatoms selected from the group consisting of N, O, and S(O)m (wherein m is 0, 1 or 2) as ring atoms, the remaining ring atoms being C, wherein one or more rings can contain one or more double bonds, but none of the rings has a completely conjugated pi-electron system. Preferably a spiro heterocyclyl is 6 to 14 membered, and more preferably 7 to 10 membered. According to the number of common spiro atoms, spiro heterocyclyl is divided into mono-spiro heterocyclyl, di-spiro heterocyclyl, or poly-spiro heterocyclyl, and preferably refers to mono-spiro heterocyclyl or di-spiro heterocyclyl, more preferably 4-membered/4-membered, 4-membered/5-membered, 4-membered/6-membered, 5-membered/5-membered, or 5-membered/6-membered mono-spiro heterocyclyl. Representative examples of spiro heterocyclyl include, but are not limited to the following groups:

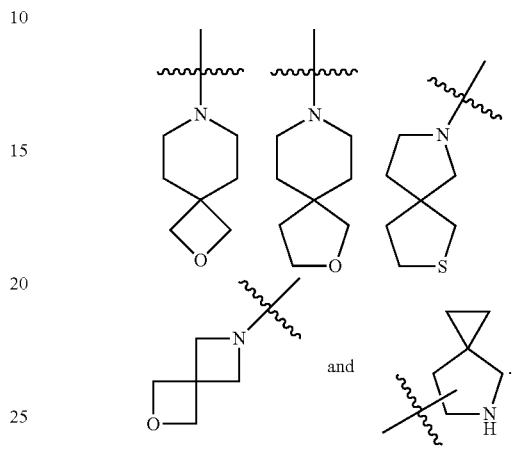

"Fused Heterocyclyl" refers to a 5 to 20 membered polycyclic heterocyclyl group, wherein each ring in the system shares an adjacent pair of carbon atoms with the other ring, wherein one or more rings can contain one or more double bonds, but none of the rings has a completely conjugated pi-electron system, and wherein said rings have one or more heteroatoms selected from the group consisting of N, O, and S(O)p (wherein p is 0, 1, or 2) as ring atoms, the remaining ring atoms being C. Preferably a fused heterocyclyl is 6 to 14 membered, and more preferably 7 to 10 membered. According to the number of membered rings, fused heterocyclyl is divided into bicyclic, tricyclic, tetracyclic or polycyclic fused heterocyclyl, preferably refers to bicyclic or tricyclic fused heterocyclyl, more preferably 5-membered/5-membered, or 5-membered/6-membered bicyclic fused heterocyclyl. Representative examples of fused heterocyclyl include, but are not limited to, the following groups:

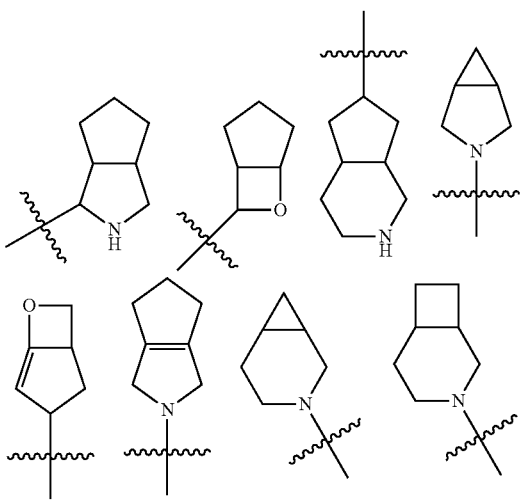

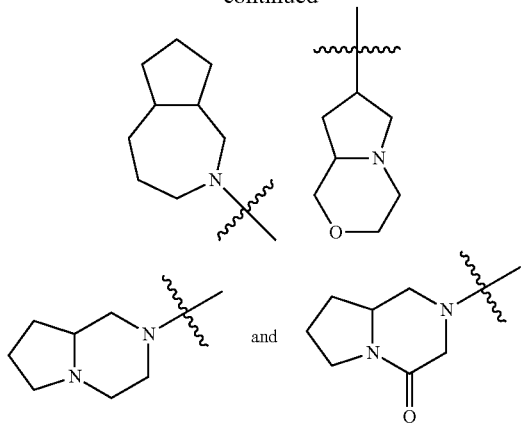

"Bridged Heterocyclyl" refers to a 5 to 14 membered polycyclic heterocyclic alkyl group, wherein every two rings in the system share two disconnected atoms, the rings can have one or more double bonds, but have no completely conjugated pi-electron system, and the rings have one or more heteroatoms selected from the group consisting of N, O, and S(O)m (wherein m is 0, 1, or 2) as ring atoms, the remaining ring atoms being C. Preferably a bridged heterocyclyl is 6 to 14 membered, and more preferably 7 to 10 membered. According to the number of membered rings, bridged heterocyclyl is divided into bicyclic, tricyclic, tetracyclic or polycyclic bridged heterocyclyl, and preferably refers to bicyclic, tricyclic or tetracyclic bridged heterocyclyl, more preferably bicyclic or tricyclic bridged heterocyclyl. Representative examples of bridged heterocyclyl include, but are not limited to, the following groups:

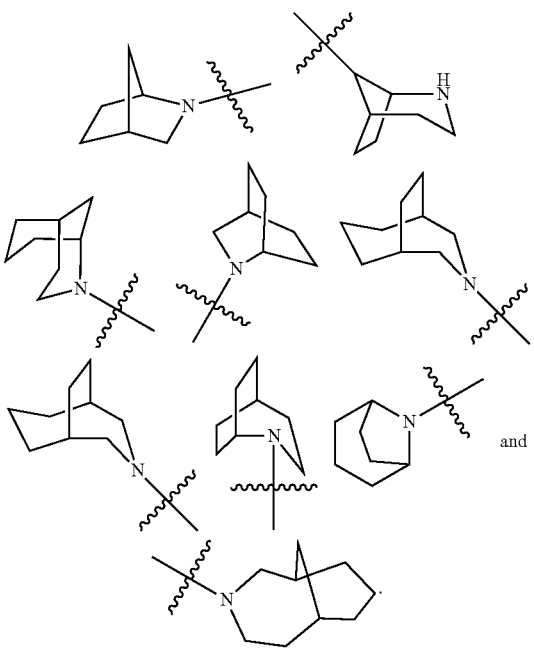

The ring of said heterocyclyl can be fused to the ring of an aryl, heteroaryl or cycloalkyl, wherein the ring bound to the parent structure is heterocyclyl. Representative examples include, but are not limited to the following groups:

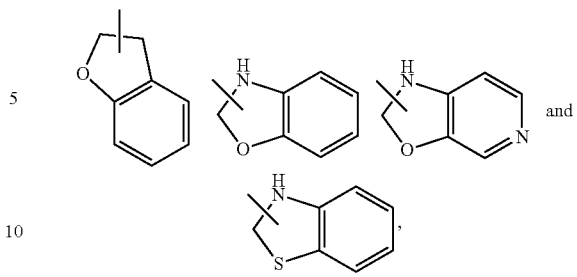

etc.

The heterocyclyl is optionally substituted or unsubstituted. When substituted, the substituent group(s) is preferably one or more group(s) independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, oxo group, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Aryl" refers to a 6 to 14 membered all-carbon monocyclic ring or a polycyclic fused ring (a "fused" ring system means that each ring in the system shares an adjacent pair of carbon atoms with another ring in the system) group, and has a completely conjugated pi-electron system. Preferably aryl is 6 to 10 membered, such as phenyl and naphthyl, most preferably phenyl. The aryl can be fused to the ring of heteroaryl, heterocyclyl or cycloalkyl, wherein the ring bound to parent structure is aryl. Representative examples include, but are not limited to, the following groups:

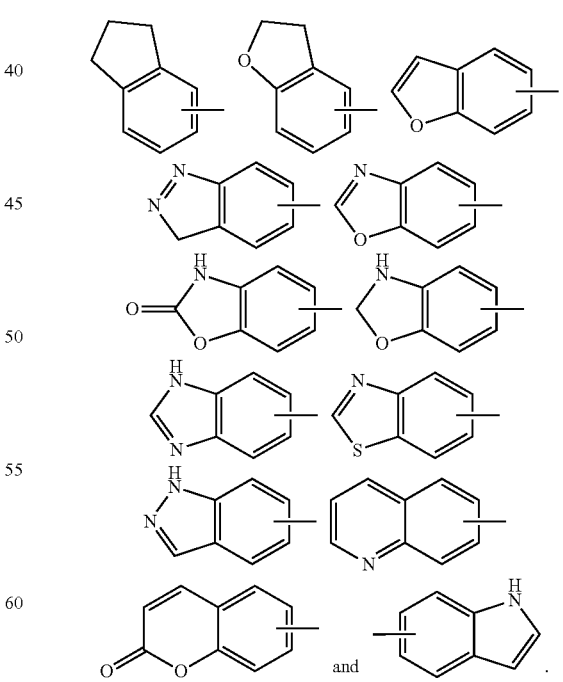

The aryl group can be substituted or unsubstituted. When substituted, the substituent group(s) is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Heteroaryl" refers to an aryl system having 1 to 4 heteroatoms selected from the group consisting of O, S and N as ring atoms and having 5 to 14 annular atoms. Preferably a heteroaryl is 5- to 10-membered, more preferably 5- or 6-membered, for example, thiadiazolyl, pyrazolyl, oxazolyl, oxadiazolyl, imidazolyl, triazolyl, thiazolyl, furyl, thienyl, pyridyl, pyrrolyl, N-alkyl pyrrolyl, pyrimidinyl, pyrazinyl, imidazolyl, tetrazolyl, and the like. The heteroaryl can be fused with the ring of an aryl, heterocyclyl or cycloalkyl, wherein the ring bound to parent structure is heteroaryl. Representative examples include, but are not limited to, the following groups:

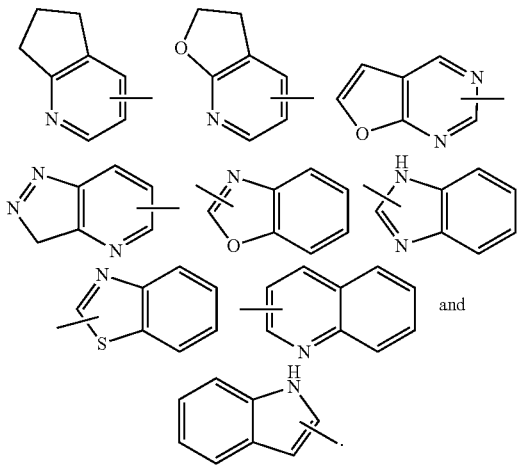

and

The heteroaryl group can be substituted or unsubstituted. When substituted, the substituent group(s) is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocylic alkoxyl, cycloalkylthio, heterocylic alkylthio, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Alkoxyl" refers to both an —O-(alkyl) and an —O-(unsubstituted cycloalkyl) group, wherein the alkyl is defined as above. Representative examples include, but are not limited to, methoxy, ethoxy, propoxy, butoxy, cyclopropyloxy, cyclobutyloxy, cyclopentyloxy, cyclohexyloxy, and the like. The alkoxyl can be substituted or unsubstituted. When substituted, the substituent is preferably one or more groups independently selected from the group consisting of alkyl, alkenyl, alkynyl, alkoxyl, alkylsulfo, alkylamino, halogen, thiol, hydroxyl, nitro, cyano, cycloalkyl, heterocyclic alkyl, aryl, heteroaryl, cycloalkoxyl, heterocyclic alkoxyl, cycloalkylthio, heterocyclic alkylthio, —(CH2)nC(O)OR15, —OC(O)R15, —C(O)R15, —C(O)NR16R17, —NHC(O)R15, —NR16R17, —OC(O)NR16R17, —NHC(O)NR16R17, —S(O)mR15, —NHC(O)OR15 and —NHS(O)mR15.

"Bond" refers to a covalent bond using a sign of "—".

"Hydroxyl alkyl" refers to an alkyl group substituted by a hydroxyl group, wherein alkyl is as defined above.

"Hydroxy" refers to an —OH group.

"Halogen" refers to fluoro, chloro, bromo or iodo atoms.

"Amino" refers to a —NH2 group.

"Cyano" refers to a —CN group.

"Nitro" refers to a —NO2 group.

"Oxo group" refers to a =O group.

"Carboxyl" refers to a —C(O)OH group.

"Alkoxycarbonyl" refers to a —C(O)O(alkyl) or (cycloalkyl) group, wherein the alkyl and cycloalkyl are defined as above.

"Optional" or "optionally" means that the event or circumstance described subsequently can, but need not, occur, and the description includes the instances in which the event or circumstance may or may not occur. For example, "the heterocyclic group optionally substituted by an alkyl" means that an alkyl group can be, but need not be, present, and the description includes the case of the heterocyclic group being substituted with an alkyl and the heterocyclic group being not substituted with an alkyl.

"Substituted" refers to one or more hydrogen atoms in the group, preferably up to 5, more preferably 1 to 3 hydrogen atoms, independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxyl group having free hydrogen and carbon atoms having unsaturated bonds (such as olefinic) may be unstable.

A "pharmaceutical composition" refers to a mixture of one or more of the compounds described in the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient and thus displaying biological activity.

"Pharmaceutically acceptable salts" refer to salts of the compounds of the invention, such salts being safe and effective when used in a mammal and have corresponding biological activity.

N, m and R15 to R17 are as defined in the compound of formula (I).

Synthesis Method of the Compound of the Present Invention

In order to complete the purpose of the invention, the present invention applies, but is not limited to, the following technical solution:

A preparation process of a compound of formula (I) of the invention or a pharmaceutically acceptable salt thereof, comprising the following steps of:

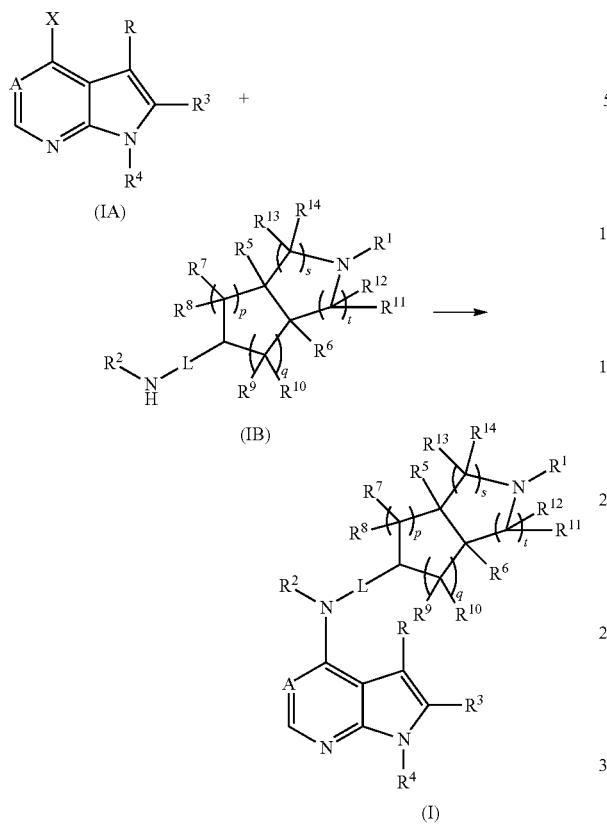

reacting a compound of formula (IA) with a compound of formula (IB) under alkaline conditions to obtain the compound of formula (I);

the alkaline conditions are provided by an organic base or inorganic base, wherein said organic base includes, but is not limited to, triethylamine, N,N-diisopropylethylamine, n-butyllithium, tert-butyl potassium alkoxide, and said inorganic base includes, but is not limited to, sodium hydride, sodium carbonate, sodium bicarbonate, potassium carbonate, potassium bicarbonate, or cesium carbonate;

wherein X is halogen, A, R, L, R1 to R14, p, q, s, and t are as defined in formula (I); preferably, R1 is tert-butoxycarbonyl; and preferably L is a bond.

A preparation process of a compound or a salt of formula (I) of the invention, comprising the following steps of:

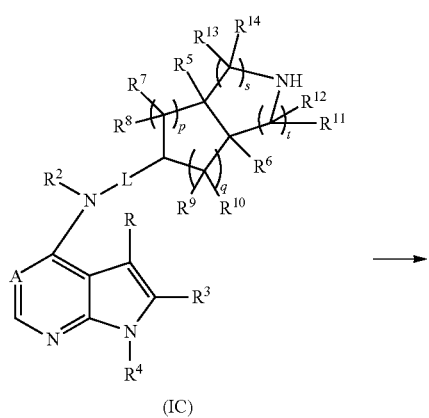

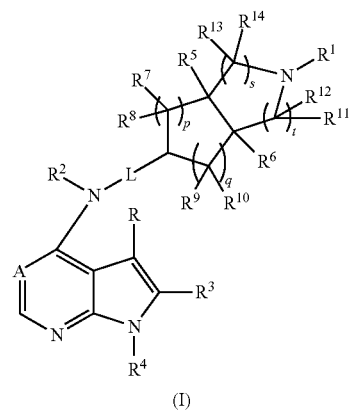

when R1 is t-butoxycarbonyl, t-butoxycarbonyl is further optionally removed from the compound of formula (I) to obtain the compound of formula (IC) or pharmaceutically acceptable salt thereof; reacting the compound of formula (IC) or a pharmaceutically acceptable salt thereof with a carboxylic acid, acyl chloride, sulfonyl chloride, carboxylic ester, an ethylene oxide derivative or halide under alkaline condition to obtain the compound of formula (I);

the reaction solvent includes, but is not limited to, tetrahydrofuran, ethanol, methanol, n-butanol, dichloromethane, 1,4-dioxane, or N,N-dimethylformamide;

the alkaline condition is provided by an organic base or inorganic base, wherein said organic base includes, but is not limited to, triethylamine, N,N-diisopropylethylamine, n-butyllithium, tert-butyl potassium alkoxide, tetrabutylammonium bromide, and said inorganic base includes, but is not limited to, sodium hydride, sodium carbonate, sodium bicarbonate, potassium carbonate, potassium bicarbonate or cesium carbonate;

wherein A, R, L, R1 to R14, p, q, s and t are as defined in formula (I); and preferably L is a bond.

PREFERRED EMBODIMENTS

The following examples serve to illustrate the invention, but the examples should not be considered as limiting the scope of the invention. If specific conditions for the experimental method are not specified in the examples of the present invention, they are generally in accordance with conventional conditions or recommended conditions of the raw materials and the product manufacturer. The reagents without a specific source indicated are commercially available, conventional reagents.

The structure of each compound was identified by nuclear magnetic resonance (NMR) and/or mass spectrometry (MS). NMR chemical shifts (δ) were given in 10-6 (ppm). NMR was determined by a Bruker AVANCE-400 machine. The solvents were deuterated-dimethyl sulfoxide (DMSO-d6), deuterated-chloroform (CDCl3) and deuterated-methanol (CD3OD), with tetramethylsilane (TMS) as an internal standard.

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average rates of kinase inhibition, and the IC50 values were determined by Microplate reader (BMG company, Germany).

The thin-layer silica gel plates used in thin-layer chromatography were Yantai Huanghai HSGF254 or Qingdao GF254 silica gel plate. The dimension of the plates used in TLC was 0.15 mm to 0.2 mm, and the dimension of the plates used in thin-layer chromatography for product purification was 0.4 mm to 0.5 mm.

Column chromatography generally used Yantai Huanghai 200 to 300 mesh silica gel as carrier.

The known starting material of the invention can be prepared by the conventional synthesis method in the prior art, or can be purchased from ABCR GmbH & Co. KG, Acros Organics, Aldrich Chemical Company, Accela ChemBio Inc or Dari chemical Company, etc.

Unless otherwise stated in the examples, the following reactions were placed under argon atmosphere or nitrogen atmosphere.

The term "argon atmosphere" or "nitrogen atmosphere" means that a reaction flask was equipped with a balloon having 1 L of argon or nitrogen.

The term "hydrogen atmosphere" means that a reaction flask was equipped with a balloon having 1 L of hydrogen.

High pressure hydrogenation reactions were performed with a Parr 3916EKX hydrogenation apparatus and clear blue QL-500 hydrogen generator or HC2-SS hydrogenation apparatus.

In hydrogenation reactions, the reaction system was generally vacuumed and filled with hydrogen, and the above operation was repeated three times.

Microwave reactions were performed with a CEM Discover-S 908860 microwave reactor.

Unless otherwise stated in the examples, the solution used in following reactions refers to an aqueous solution.

Unless otherwise stated in the examples, the reaction temperature in the following reactions was room temperature.

Room temperature was the most proper reaction temperature, which was 20° C. to 30° C.

The reaction process was monitored by thin layer chromatography (TLC), the system of developing solvent included: (A) dichloromethane and methanol system, (B) n-hexane and ethyl acetate system, (C) petroleum ether and ethyl acetate system, (D) acetone. The ratio of the volume of the solvent was adjusted according to the polarity of the compounds.

The elution system for purification the of compounds by column chromatography and thin layer chromatography included: (A) dichloromethane and methanol system, (B) n-hexane and ethyl acetate system, (C) dichloromethane and acetone system. The ratio of the volume of the solvent was adjusted according to the polarity of the compounds, and sometimes a little alkaline reagent such as triethylamine or an acidic reagent such as acetic acid was also added.

Example 1

(3aR,5R,6aS/3aS,5S,6aR)-tert-butyl-3a-methyl-5-(methyl(7H-pyrrolo[2,3-d]pyrimidin-4-yl)amino)hexahydro cyclopenta[c]pyrrole-2(1H)-carboxylate

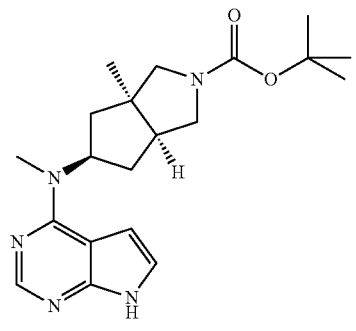

and enantiomer thereof

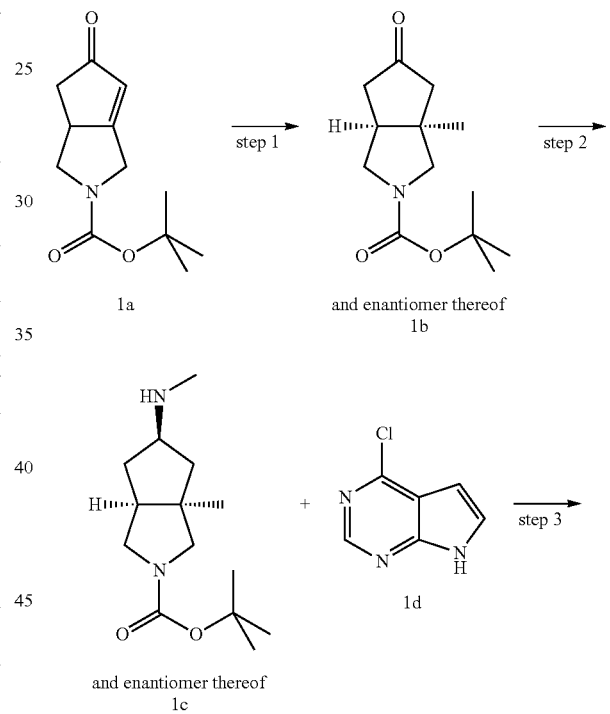

and enantiomer thereof
1c

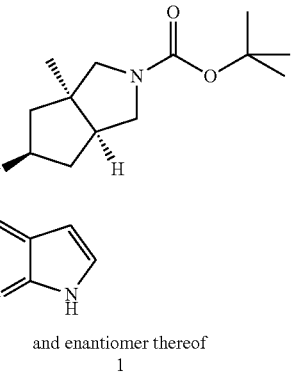

and enantiomer thereof
1

Step 1

(3aR,6aS/3aS,6aR)-tert-Butyl 3a-methyl-5-oxohexahydrocyclopenta[c]pyrrole-2(1H)-carboxylate Cuprous iodide (770 mg, 4 mmol) was dissolved in 10 mL of tetrahydrofuran. After cooling to −78° C., a 3 M solution of methylmagnesium bromide in diethyl ether (30 mL, 6.7 mmol) was added into the reaction mixture. After reacting for 30 minutes, the reaction mixture was warmed up to −35° C., followed by dropwise addition of 10 mL of a solution of tert-butyl 5-oxo-3,3a,4,5-tetrahydrocyclopenta[c]pyrrol-2 (1H)-carboxylate 1a (500 mg, 2.24 mmol) in tetrahydrofuran. After reacting for 30 minutes, the reaction mixture was warmed to room temperature, followed by addition of 10 mL of a saturated ammonium chloride solution to quench the reaction. The reaction mixture was extracted with ethyl acetate (20 mL×3). The organic phases were combined, dried over anhydrous magnesium sulfate, and filtered. The filtrate was concentrated under reduced pressure to obtain the crude title product (3aR,6aS/3aS,6aR)-tert-butyl 3a-methyl-5-oxohexahydrocyclopenta[c]pyrrole-2(1H)-carboxylate 1b (500 mg, brown grease), which was used directly in the next step without further purification.

Step 2

(3aR,5R,6aS/3aS,5S,6aR)-tert-Butyl 3a-methyl-5-(methylamino)hexahydrocyclopenta[c]pyrrole-2 (1H)-carboxylate The crude product of (3aR,6aS/3aS,6aR)-tert-butyl 3a-methyl-5-oxohexahydrocyclopenta[c]pyrrole-2(1H)-carboxylate 1b (200 mg, 0.84 mmol) was dissolved in 5 mL of methanol, followed by addition of 2 mL of 37% methyl amine—ethanol solution and sodium triacetoxyborohydride (532 mg, 2.5 mmol). After reacting for 16 hours, 10 mL of saturated ammonium chloride solution was added to the reaction mixture to quench the reaction. The reaction mixture was extracted with ethyl acetate (20 mL×3). The organic phases were combined, dried over anhydrous magnesium sulfate, and filtered. The filtrate was concentrated under reduced pressure to obtain the title product (3aR,5R,6aS/3aS,5S,6aR)-tert-butyl 3a-methyl-5-(methylamino) hexahydrocyclopenta[c]pyrrole-2(1H)-carboxylate 1c (130 mg, yield 61.0%) as a brown grease.

MS m/z (ESI): 255.2 [M+1]

Step 3

(3aR,5R,6aS/3aS,5S,6aR)-tert-Butyl-3a-methyl-5-(methyl(7H-pyrrolo[2,3-d]pyrimidin-4-yl)amino) hexahydro cyclopenta[c]pyrrol-2(1H)-carboxylate 4-Chloro-7H-pyrrolo[2,3-d]pyrimidine 1d (60 mg, 0.39 mmol) was dissolved in 5 mL of H$_2$O, followed by addition of (3aR,5R,6aS/3aS,5S,6aR)-tert-butyl 3a-methyl-5-(methylamino)hexahydrocyclopenta[c]pyrrole-2(1H)-carboxylate 1c (100 mg, 0.39 mmol) and potassium carbonate (322 mg, 2.34 mmol). After reacting for 16 hours at 100° C., the reaction mixture was extracted with ethyl acetate (10 mL×3). The organic phases were combined, dried over anhydrous magnesium sulfate, and filtered. The filtrate was concentrated under reduced pressure and the resulting residue was purified by thin layer chromatography with elution system A to obtain the title product (3aR,5R,6aS/3aS,5S, 6aR)-tert-butyl-3a-methyl-5-(methyl(7H-pyrrolo[2,3-d]pyrimidin-4-yl)amino)hexahydro cyclopenta[c]pyrrole-2(1H)-carboxylate 1 (40 mg, yield 28.8%) as a white solid.

MS m/z (ESI): 372.5[M+1]

$^1$H NMR (400 MHz, CDCl$_3$): δ 10.38 (s, 1H), 8.30 (s, 1H), 7.05-7.04 (m, 1H), 6.57-6.56 (m, 1H), 5.57-5.52 (m, 1H), 3.56-3.49 (m, 3H), 3.37 (s, 3H), 3.27-3.25 (m, 1H), 2.25-2.21 (m, 2H), 1.89-1.87 (m, 2H), 1.67-1.65 (m, 2H), 1.49 (s, 9H), 0.88-0.86 (m, 2H)

Example 2

N-((3aR,5R,6aS/3aS,5S,6aR)-2-(Ethylsulfonyl)-3a-methyl octahydro cyclopenta[c]pyrrol-5-yl)-N-methyl-7H-pyrrolo[2,3-d]pyrimidin-4-amine

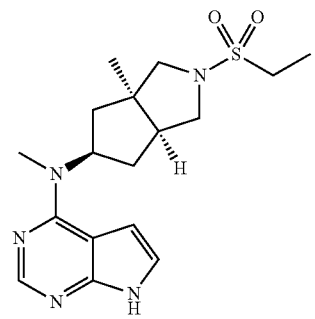

and enantiomer thereof

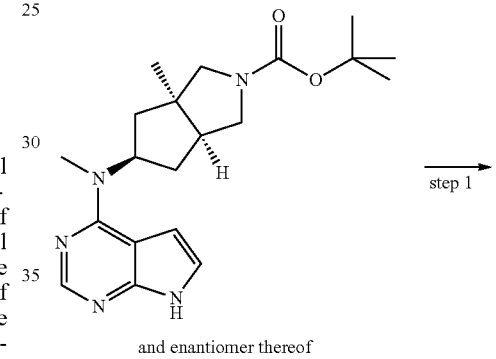

and enantiomer thereof
1

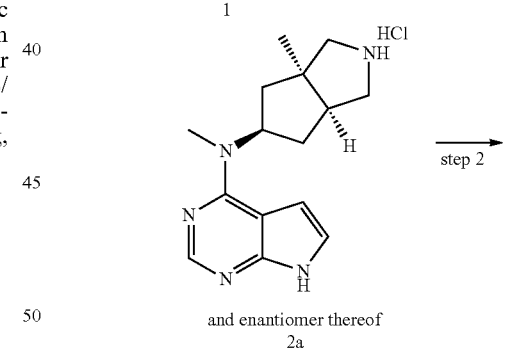

and enantiomer thereof
2a

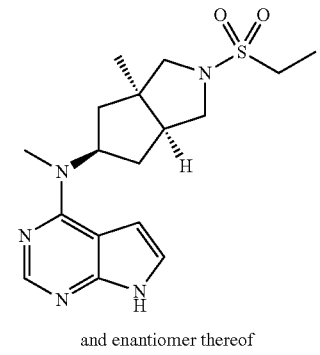

and enantiomer thereof
2

Step 1

N-Methyl-N-((3aR,5R,6aS)-3a-methyloctahydrocyclopenta[c]pyrrol-5-yl)-7H-pyrrolo[2,3-d]pyrimidin-4-amine hydrochloride (3aR,5R,6aS/3aS,5S,6aR)-tert-Butyl-3a-methyl-5-(methyl(7H-pyrrolo[2,3-d]pyrimidin-4-yl)amino)hexahydro cyclopenta[c]pyrrole-2(1H)-carboxylate 1 (1 g, 2.7 mmol) was dissolved in 15 mL of a solution of 6 M hydrogen chloride in methanol. After reacting for 12 hours, the reaction mixture was concentrated under reduced pressure to obtain the crude title product N-methyl-N-((3aR,5R,6aS)-3a-methyloctahydrocyclopenta[c]pyrrol-5-yl)-7H-pyrrolo[2,3-d]pyrimidin-4-amine hydrochloride 2a (1.2 g, white solid), which was used directly in the next step without further purification.

MS m/z (ESI): 272.2 [M+1]

Step 2

N-((3aR,5R,6aS/3aS,5S,6aR)-2-(Ethylsulfonyl)-3a-methyl octahydro cyclopenta[c]pyrrol-5-yl)-N-methyl-7H-pyrrolo[2,3-d]pyrimidin-4-amine N-Methyl-N-((3aR,5R,6aS/3aS,5S,6aR)-3a-methyloctahydrocyclopenta[c]pyrrol-5-yl)-7H-pyrrolo[2,3-d]pyrimidin-4-amine hydrochloride 2a (100 mg, 0.37 mmol) and triethylamine (112 mg, 1.11 mmol) were dissolved in 5 mL of tetrahydrofuran, followed by dropwise addition of ethyl sulfonyl chloride (95 mg, 0.74 mmol). After reacting for 16 hours, the reaction mixture was mixed with 20 mL of H₂O, and extracted with ethyl acetate (20 mL×3). The organic phases were combined, dried over anhydrous magnesium sulfate, and filtered. The filtrate was concentrated under reduced pressure, and the resulting residue was purified by thin layer chromatography with elution system A to obtain the title product N-((3aR,5R,6aS/3aS,5S,6aR)-2-(ethylsulfonyl)-3a-methyl octahydro cyclopenta[c]pyrrol-5-yl)-N-methyl-7H-pyrrolo[2,3-d]pyrimidin-4-amine 2 (28 mg, yield 21.5%) as a white solid.

MS m/z (ESI): 364.2 [M+1]

$^1$H NMR (400 MHz, DMSO-d$_6$): δ 12.56 (s, 1H), 8.25-8.23 (m, 1H), 7.95-7.93 (m, 1H), 7.21-7.20 (m, 1H), 5.51-5.49 (m, 1H), 4.02 (m, 2H), 3.75-3.58 (m, 6H), 3.38 (s, 3H), 3.22-3.16 (m, 2H), 2.06 (s, 3H), 1.97-1.95 (m, 1H), 1.43-1.41 (m, 3H)

Example 3

3-((3aR,5R,6aS/3aS,5S,6aR)-3a-Methyl-5-(methyl(7H-pyrrolo[2,3-d]pyrimidin-4-yl)amino)hexahydro cyclopenta[c]pyrrol-2(1H)-yl)-3-oxopropanenitrile

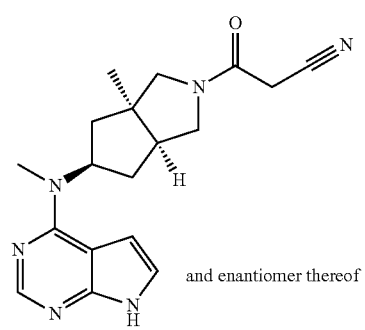

and enantiomer thereof

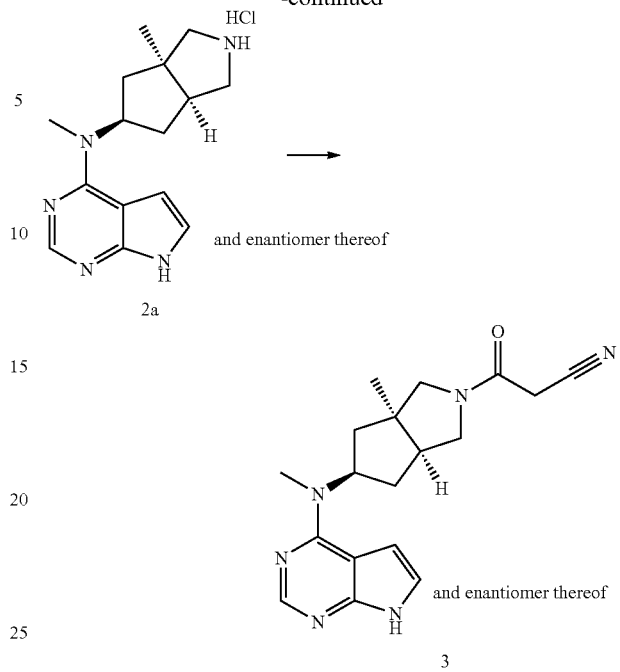

N-Methyl-N-((3aR,5R,6aS/3aS,5S,6aR)-3a-methyloctahydrocyclopenta[c]pyrrol-5-yl)-7H-pyrrolo[2,3-d]pyrimidin-4-amine hydrochloride 2a (50 mg, 0.18 mmol) and ethyl 2-cyanoacetate (49 mg, 0.36 mmol) were dissolved in 3 mL of ethanol, followed by dropwise addition of 1,4-diazabicyclo octane (56 mg, 0.36 mmol). After reacting for 16 hours at 40° C., the reaction mixture was mixed with 20 mL of H2O and extracted with ethyl acetate (20 mL×3). The organic phases were combined, dried over anhydrous magnesium sulfate, and filtered. The filtrate was concentrated under reduced pressure, and the resulting residue was purified by thin layer chromatography with elution system A to obtain the title product 3-((3aR,5R,6aS/3aS,5S,6aR)-3a-methyl-5-(methyl(7H-pyrrolo[2,3-d]pyrimidin-4-yl)amino) hexahydro cyclopenta[c]pyrrol-2(1H)-yl)-3-oxopropanenitrile 3 (46 mg, yield 56.8%) as a white solid.

MS m/z (ESI): 339.1 [M+1]

$^1$H NMR (400 MHz, DMSO-d$_6$): δ 12.58 (s, 1H), 8.27-8.25 (m, 1H), 7.97-7.95 (m, 1H), 7.26-7.24 (m, 1H), 5.58-5.53 (m, 1H), 4.33 (s, 2H), 3.75-3.58 (m, 6H), 3.39 (s, 3H), 3.22-3.16 (m, 2H), 2.08 (s, 3H), 1.99-1.97 (m, 1H)

Example 4

2-((3aR,5R,6aS/3aS,5S,6aR)-3a-Methyl-5-(methyl(7H-pyrrolo[2,3-d]pyrimidin-4-yl)amino)hexahydro cyclopenta[c]pyrrol-2(1H)-yl)acetonitrile

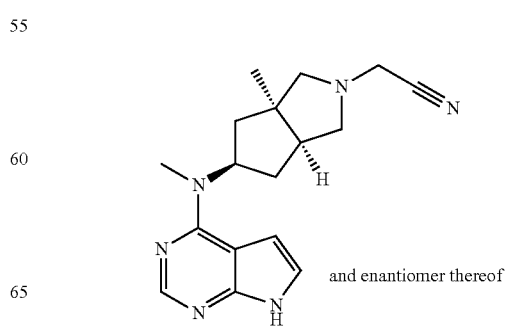

and enantiomer thereof

-continued

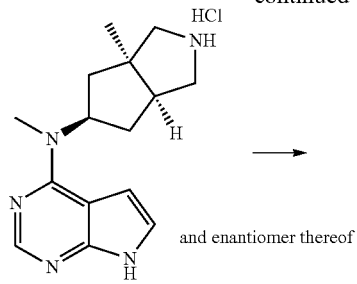

and enantiomer thereof

2a

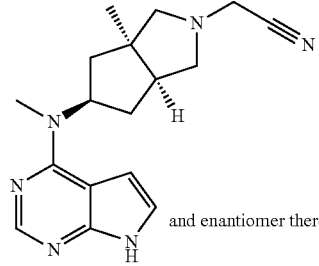

and enantiomer thereof

4

N-Methyl-N-((3aR,5R,6aS/3aS,5S,6aR)-3a-methyloctahydrocyclopenta[c]pyrrol-5-yl)-7H-pyrrolo[2,3-d]pyrimidin-4-amine hydrochloride 2a (50 mg, 0.18 mmol) was dissolved in 5 mL of acetonitrile, followed by addition of potassium carbonate (75 mg, 0.54 mmol), bromoacetonitrile1 (24 mg, 0.2 mmol), and 5 mL of dichloromethane. After reacting for 16 hours, the reaction mixture was mixed with a small amount of H$_2$O to quench the reaction. The aqueous phase and organic phase were separated. The aqueous phase was extracted with dichloromethane (10 mL×3). The organic phases were combined, washed with water (5 mL), saturated sodium chloride solution (5 mL) successively, dried over anhydrous magnesium sulfate, and filtered. The filtrate was concentrated under reduced pressure, and the resulting residue was purified by thin layer chromatography with elution system A to obtain the title product 2-((3aR,5R,6aS/3aS,5S,6aR)-3a-methyl-5-(methyl(7H-pyrrolo[2,3-d]pyrimidin-4-yl)amino)hexahydro cyclopenta[c]pyrrol-2(1H)-yl)acetonitrile 4 (20 mg, yield 35.1%) as a white solid.

MS m/z (ESI): 311.5 [M+1]

$^1$H NMR (400 MHz, DMSO-d$_6$): δ 11.64 (s, 1H), 8.12-8.10 (m, 1H), 7.14 (s, 1H), 6.54 (s, 1H), 3.86-3.85 (m, 2H), 3.14-3.13 (m, 3H), 2.77-2.75 (m, 1H), 2.62-2.60 (m, 1H), 2.08-2.06 (m, 3H), 1.86-1.80 (m, 1H), 1.70-1.69 (m, 1H), 1.58-1.55 (m, 1H), 1.30-1.18 (m, 2H), 0.86 (s, 3H)

Example 5

(3aR,5S,6aS)-tert-Butyl-(methyl((7H-pyrrolo[2,3-d]pyrimidin-4-yl)amino)hexahydro cyclopenta[c]pyrrole-2(1H)-carboxylate

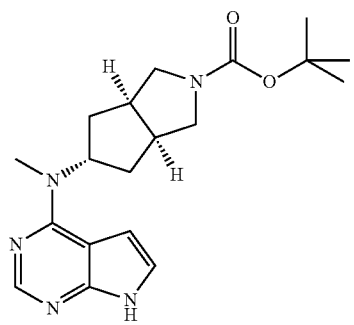

-continued

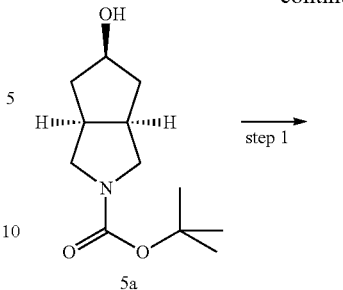

5a

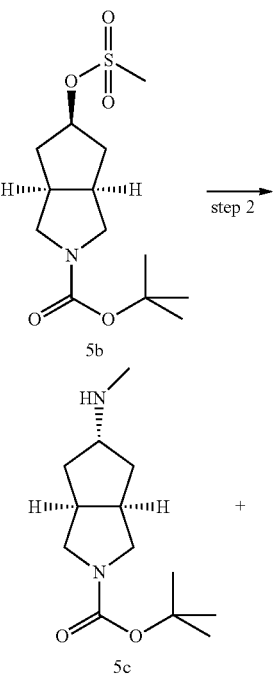

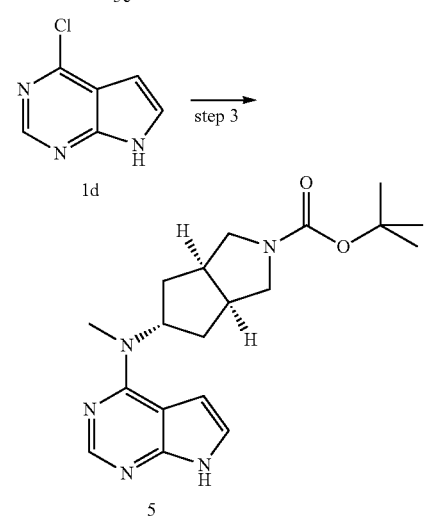

5

Step 1

(3aR,5R,6aS)-tert-Butyl 5-((methylsulfonyl)oxy)hexahydrocyclopenta[c]pyrrole-2(1H)-carboxylate (3aR,5R,6aS)-tert-Butyl 5-hydroxyhexahydrocyclopenta[c]pyrrole-2(1H)-carboxylate 5a (9 g, 40 mmol) was dissolved in 150 mL of dichloromethane, followed by addition of methylsulfonyl chloride (4.70 mL, 60 mmol) and triethylamine (11.20 mL, 80 mmol) at 0° C. After reacting for 2 hours at room temperature, 200 mL of saturated sodium bicarbonate solution was added to the reaction mixture. The aqueous phase and organic phase were separated. The organic phase was washed with saturated sodium chloride solution (200 mL), dried over anhydrous magnesium sulfate, and filtered. The filtrate was concentrated under reduced pressure to obtain the title product (3aR,5R,6aS)-tert-butyl 5-((methylsulfonyl)oxy)hexahydrocyclopenta[c]pyrrole-2 (1H)-carboxylate 5b (12.00 g, yield 98.4%) as a yellow liquid.

Step 2

(3aR,5S,6aS)-tert-Butyl 5-(methyl amino) hexa-hydro cyclopenta[c]pyrrole-2(1H)-carboxylate (3aR,5R,6aS)-tert-Butyl 5-((methylsulfonyl)oxy)hexahydrocyclopenta[c]pyrrole-2(1H)-carboxylate 5b (60 mg, 0.2 mmol) was dissolved in 10 mL of methanol, followed by addition of 5 mL of methylamine. After reacting for 16 hours at 40° C., the reaction mixture was concentrated under reduced pressure to obtain the crude title product (3aR,5S,6aS)-tert-butyl 5-(methylamino)hexahydrocyclopenta[c]pyrrole-2(1H)-carboxylate 5c (60 mg, brown grease), which was used directly in the next step without further purification.

MS m/z (ESI): 241.5 [M+1]

Step 3

(3aR,5S,6aS)-tert-Butyl 5-(methyl(7H-pyrrolo[2,3-d]pyrimidin-4-yl)amino)hexahydro cyclopenta[c]pyrrole-2(1H)-carboxylate (3aR,5S,6aS)-tert-Butyl 5-(methylamino)hexahydrocyclopenta[c]pyrrole-2(1H)-carboxylate 5c (200 mg, 0.8 mmol) and 4-chloro-7H-pyrrolo[2,3-d]pyrimidine 1d (127 mg, 0.8 mmol) were dissolved in 5 mL of n-butanol, followed by addition of triethylamine (168 mg, 1.6 mmol). After reacting for 48 hours at 100° C., the reaction mixture was concentrated under reduced pressure, followed by addition of 10 mL of H$_2$O and 10 mL of ethyl acetate. The aqueous phase and organic phase were separated. The organic phases were combined, dried over anhydrous sodium sulfate, and filtered. The filtrate was concentrated under reduced pressure, and purified by preparative HPLC to obtain the title product (3aR,5S,6aS)-tert-butyl 5-(methyl (7H-pyrrolo[2,3-d]pyrimidin-4-yl)amino)hexahydro cyclopenta[c]pyrrole-2(1H)-carboxylate 5 (5 mg, yield 5.0%) as a white solid.

MS m/z (ESI): 358.5[M+1]

$^1$H NMR (400 MHz, CDCl$_3$): δ 10.07 (s, 1H), 8.31 (s, 1H), 7.50 (s, 1H), 6.55 (s, 1H), 5.58-5.54 (m, 1H), 3.65-3.62 (m, 2H), 3.27-3.23 (m, 5H), 2.86-2.81 (m, 2H), 2.06-2.02 (m, 2H), 1.93-1.91 (m, 2H), 1.49 (s, 6H)

Example 6

2-Hydroxy-1-((3aR,5S,6aS)-5-(methyl(7H-pyrrolo[2,3-d]pyrimidin-4-yl)amino)hexahydrocyclopenta[c]pyrrol-2(1H)-yl)ethanone

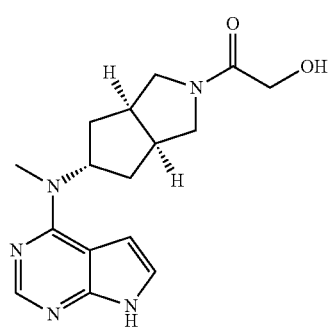

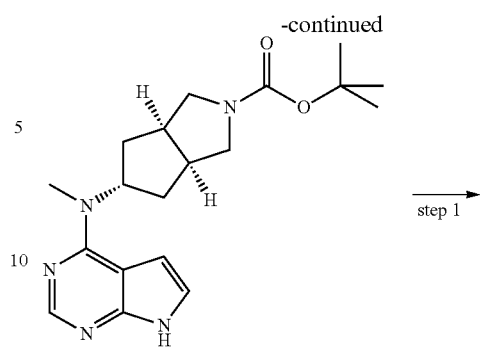

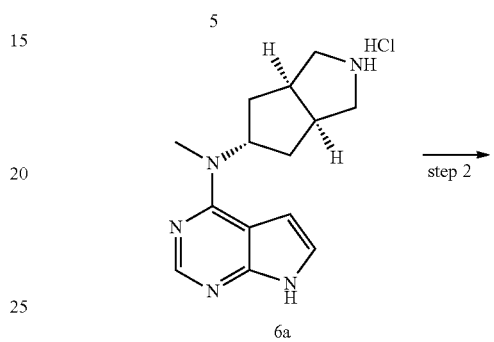

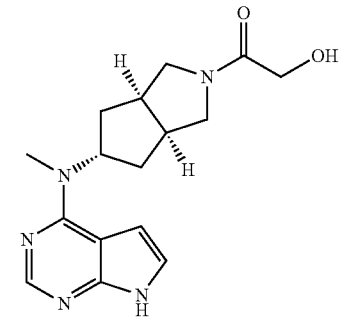

Step 1

N-Methyl-N-((3aR,5S,6aS)-octahydrocyclopenta[c]pyrrol-5-yl)-7H-pyrrolo[2,3-d]pyrimidin-4-amine hydrochloride (3aR,5S,6aS)-tert-Butyl 5-(methyl(7H-pyrrolo[2,3-d]pyrimidin-4-yl)amino) hexahydro cyclopenta[c]pyrrole-2 (1H)-carboxylate 5 (1.5 g, 4.2 mmol) was dissolved in 20 mL of a solution of 1 M hydrogen chloride in methanol. After reacting for 16 hours, the reaction mixture was concentrated under reduced pressure to obtain the crude title product N-methyl-N-((3aR,5S,6aS)-octahydrocyclopenta[c]pyrrol-5-yl)-7H-pyrrolo[2,3-d]pyrimidin-4-amine hydrochloride 6a (1.5 g, brown solid), which was used directly in the next step without further purification.

MS m/z (ESI): 258.1 [M+1]

Step 2

2-Hydroxy-1-((3aR,5S,6aS)-5-(methyl(7H-pyrrolo[2,3-d]pyrimidin-4-yl)amino)hexahydrocyclopenta[c]pyrrol-2(1H)-yl)ethanone N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.3 mmol) was dissolved in 5 mL of dichloromethane, followed by addition of 2-glycolic acid (26 mg, 0.3 mmol), triethylamine (103 mg, 1.02 mmol) and O-(7-azabenzotriazol-1-yl)-N,N,N',N'-tetramethyluronium hexafluorophosphate (194 mg, 0.45 mmol). After reacting for 16 hours, the reaction mixture was mixed with 10 mL of H$_2$O. The aqueous phase and organic phase were separated. The organic phases were combined, dried over anhydrous sodium sulfate, and filtered. The filtrate was concentrated under reduced pressure and purified by preparative HPLC to obtain the title product 2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)ethanone 6 (10 mg, yield 9.7%) as a white solid.

MS m/z (ESI): 316.2 [M+1]

$^1$H NMR (400 MHz, DMSO-d$_6$): δ 11.60 (s, 1H), 8.09 (s, 1H), 7.11 (s, 1H), 6.53 (s, 1H), 5.47-5.44 (m, 1H), 4.52-4.49 (m, 1H), 4.03-3.99 (m, 2H), 3.60-3.57 (m, 2H), 3.24-3.22 (m, 2H), 3.15 (s, 3H), 2.80-2.75 (m, 2H), 2.02-1.94 (m, 2H), 1.78-1.75 (m, 2H)

Example 7

2-Methyl-1-((3aR,5S,6aS)-5-(methyl(7H-pyrrolo[2,3-d]pyrimidin-4-yl)amino)hexahydrocyclopenta[c]pyrrol-2(1H)-yl)propan-2-ol

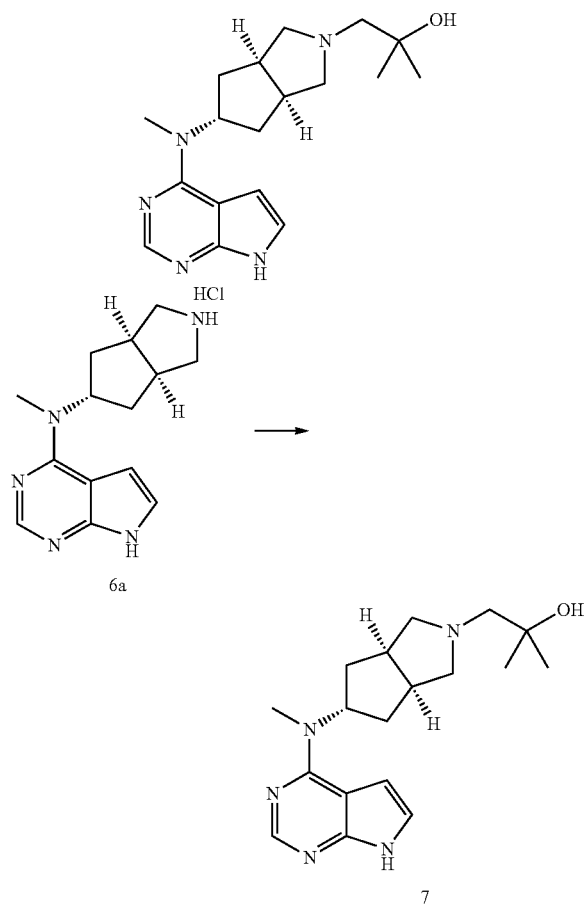

methanol, followed by addition of 2,2-dimethyl epoxy ethane (42 mg, 0.58 mmol). After reacting for 16 hours, the reaction mixture was concentrated under reduced pressure, and the resulting residue was purified by thin layer chromatography with elution system A to obtain the title product 2-methyl-1-((3aR,5S,6aS)-5-(methyl(7H-pyrrolo[2,3-d]pyrimidin-4-yl)amino)hexahydrocyclopenta[c]pyrrol-2(1H)-yl)propan-2-ol 7 (50 mg, yield 39.1%) as a right yellow solid.

MS m/z (ESI): 330.2 [M+1]

$^1$H NMR (400 MHz, DMSO-d$_6$): δ 11.68 (s, 1H), 8.11 (s, 1H), 7.14-713 (m, 1H), 6.60 (s, 1H), 5.46 (s, 1H), 5.12 (s, 1H), 3.86 (m, 2H), 3.18 (s, 4H), 3.07-3.01 (m, 3H), 2.84 (d, 2H), 1.95-1.91 (m, 2H), 1.68 (s, 2H), 1.33-1.18 (m, 6H)

Example 8

3-((3aR,5S,6aS)-5-(Methyl(7H-pyrrolo[2,3-d]pyrimidin-4-yl)amino) hexahydrocyclopenta[c]pyrrol-2(1H)-yl)-3-oxopropanenitrile

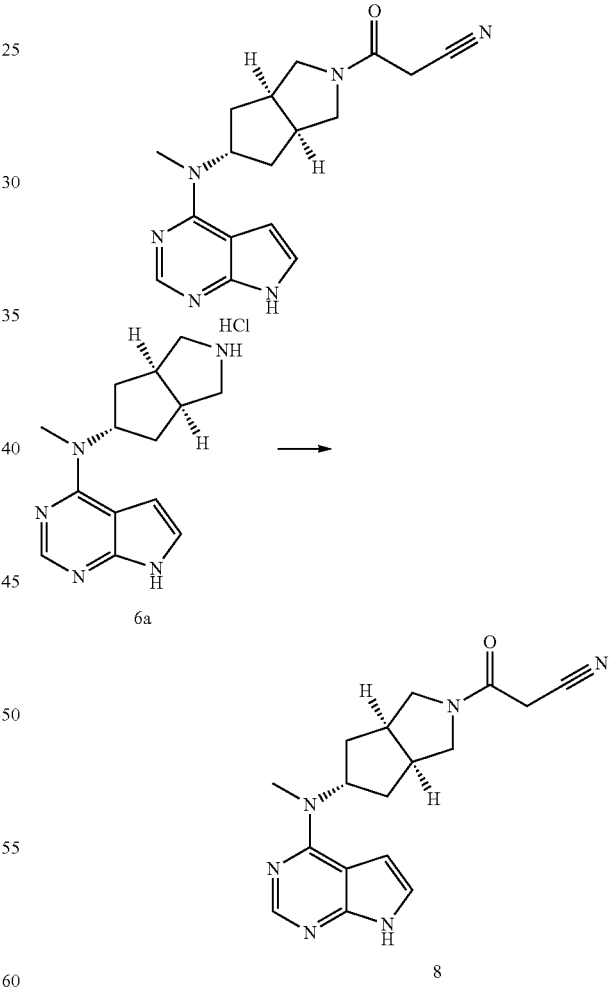

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of n-butanol, followed by addition of 2-ethyl cyanoacetate (77 mg, 0.68 mmol) and DBU (103 mg, 0.68 mmol). After reacting for 15 hours at 40° C., the reaction mixture was concentrated under reduced pressure. The residue was mixed with 50 mL of ethyl acetate and washed with saturated sodium chloride solution (15 mL×2). The organic phases were combined, dried over anhydrous sodium sulfate, and filtered. The filtrate was concentrated under reduced pressure, and purified by preparative HPLC to obtain the title product 3-((3aR,5S,6aS)-5-(methyl(7H-pyrrolo[2,3-d]pyrimidin-4-yl)amino)hexahydrocyclopenta[c]pyrrol-2(1H)-yl)-3-oxopropanenitrile 8 (15 mg, yield 13.6%) as a right yellow solid.

MS m/z (ESI): 325.1 [M+1]

$^1$H NMR (400 MHz, CDCl$_3$): δ 9.79 (s, 1H), 8.28 (s, 1H), 7.06-7.05 (m, 1H), 6.55-6.54 (m, 1H), 5.68-5.64 (m, 1H), 3.85-3.79 (m, 2H), 3.49 (s, 2H), 3.47-3.37 (m, 2H), 3.27 (s, 3H), 3.08-2.91 (m, 2H), 2.09-2.05 (m, 2H), 1.96-1.94 (m, 2H)

Example 9

(3aR,5S,6aS)—N-Isopropyl-5-(methyl(7H-pyrrolo[2,3-d]pyrimidin-4-yl)amino) hexahydrocyclopenta[c]pyrrole-2(1H)-carboxamide triethylamine (39 mg, 0.39 mmol). After reacting for 30 minutes, the reaction mixture was mixed with isocyanatopropane (33 mg, 0.39 mmol). After reacting for 16 hours, the reaction mixture was mixed with 10 mL of H$_2$O and 10 mL of ethyl acetate. The aqueous phase and organic phase were separated. The organic phases were combined, dried over anhydrous sodium sulfate, and filtered. The filtrate was concentrated under reduced pressure, and purified by preparative HPLC to obtain the title product (3aR,5S,6aS)—N-isopropyl-5-(methyl(7H-pyrrolo[2,3-d]pyrimidin-4-yl)amino)hexahydrocyclopenta[c]pyrrole-2(1H)-carboxamide 9 (15 mg, yield 11.3%) as a white solid.

MS m/z (ESI): 343.3 [M+1]

$^1$H NMR (400 MHz, CDCl$_3$): δ 11.18 (s, 1H), 8.31 (s, 1H), 7.06 (s, 1H), 6.54 (s, 1H), 5.63-5.58 (m, 1H), 4.06-4.01 (m, 2H), 3.63-3.58 (m, 2H), 3.26-3.21 (m, 5H), 2.92-2.88 (m, 2H), 2.04-2.01 (m, 2H), 1.94-1.89 (m, 2H), 1.89-1.74 (m, 6H)

Example 10

(3aR,5S,6aS/3aS,5R,6aR)-tert-Butyl 3a-methyl-5-(methyl(7H-pyrrolo[2,3-d]pyrimidin-4-yl)amino)hexahydrocyclopenta[c]pyrrole-2(1H)-carboxylate

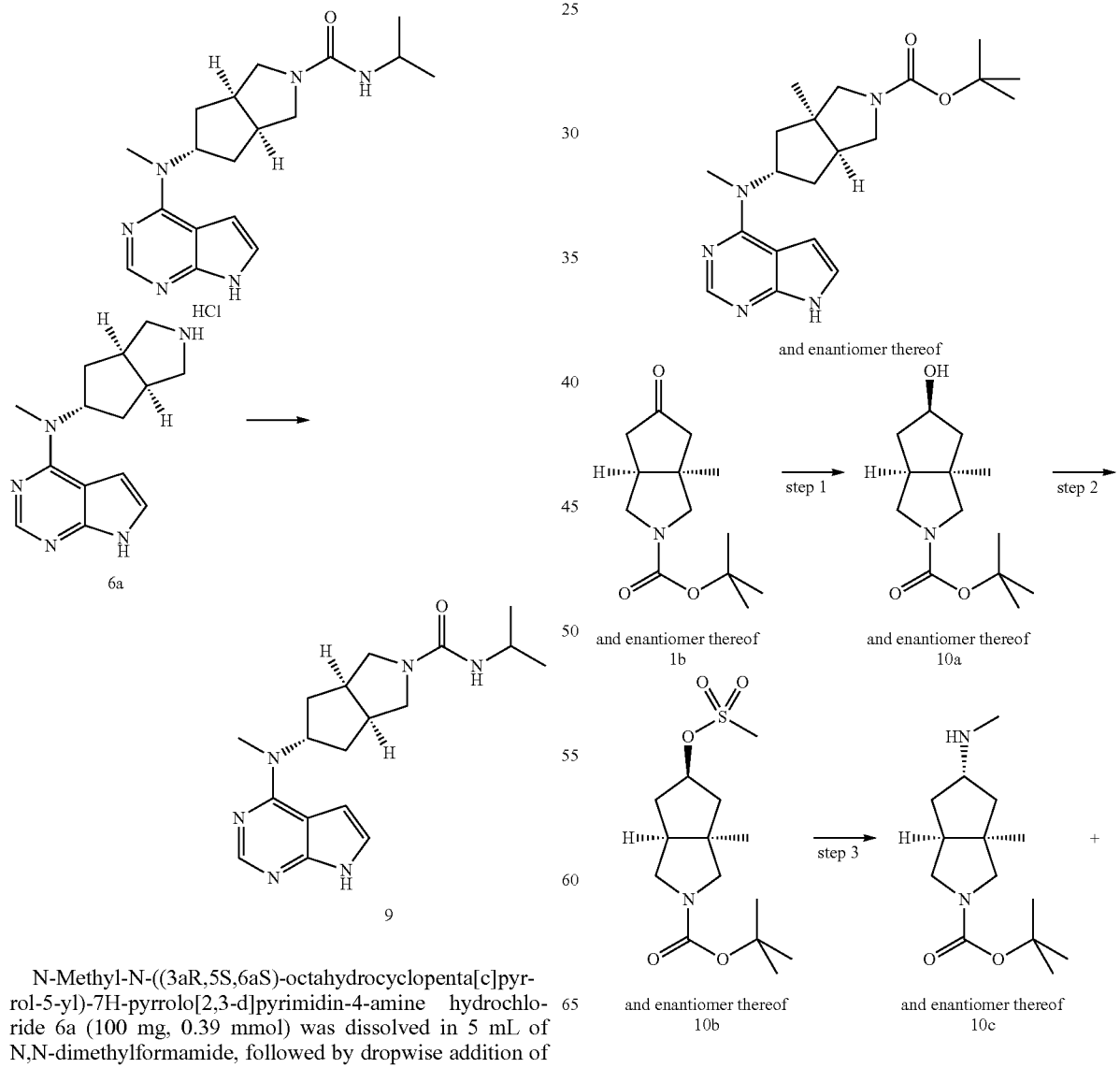

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.39 mmol) was dissolved in 5 mL of N,N-dimethylformamide, followed by dropwise addition of -continued

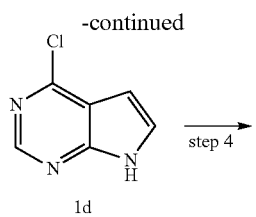

1d

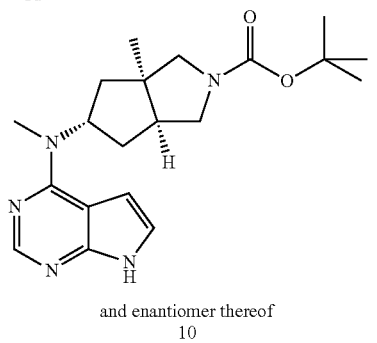

and enantiomer thereof
10

Step 1

(3aR,5S,6aS/3aS,5R,6aR)-tert-Butyl 5-hydroxy-3a-methylhexahydrocyclopenta[c]pyrrole-2(1H)-carboxylate Crude product (3aR,6aS/3aS,6aR)-tert-butyl 3a-methyl-5-oxohexahydro cyclopenta[c]pyrrole-2(1H)-carboxylate 1b (1 g, 4.2 mmol) was dissolved in 10 mL of methanol, followed by addition of sodium borohydride (320 mg, 8.4 mmol). After reacting for 1 hour, the reaction mixture was poured into 50 mL of saturated ammonium chloride solution and extracted with ethyl acetate (20 mL×3). The organic phases were combined, washed with $H_2O$ (5 mL×3) and saturated sodium chloride solution (5 mL×3) successively, dried over anhydrous sodium sulfate, and filtered. The filtrate was concentrated under reduced pressure to obtain the crude title product (3aR,5S,6aS/3aS,5R,6aR)-tert-butyl 5-hydroxy-3a-methylhexahydrocyclopenta[c]pyrrole-2 (1H)-carboxylate 10a (900 mg, colourless grease), which was used directly in the next step without further purification.

Step 2

(3aR,5R,6aS/3aS,5S,6aR)-tert-Butyl 3a-methyl-5-((methylsulfonyl)oxy) hexahydrocyclopenta[c]pyrrole-2(1H)-carboxylate Crude product (3aR,5R,6aS/3aS,5S,6aR)-tert-butyl 5-hydroxy-3a-methylhexahydro cyclopenta[c]pyrrole-2(1H)-carboxylate 10a (1 g, 4.2 mmol) was dissolved in 10 mL of dichloromethane, followed by addition of triethylamine (1.27 g, 12.6 mmol). A 5 mL solution of methylsulfonyl chloride in dichloromethane (700 mg, 6.2 mmol) was added dropwise to the reaction mixture at 0° C. After reacting for 16 hours, the reaction mixture was poured into 10 mL of $H_2O$. The aqueous phase and organic phase were separated. The organic phases were combined and washed with saturated sodium bicarbonate (10 mL×3) and saturated sodium chloride solution (10 mL×3) successively, dried over anhydrous sodium sulfate, and filtered. The filtrate was concentrated under reduced pressure to obtain the title product (3aR,5R,6aS/3aS,5S,6aR)-tert-butyl 3a-methyl-5-((methylsulfonyl)oxy)hexahydrocyclopenta[c]pyrrole-2(1H)-carboxylate 10b (1.2 g, yield 92.3%) as a light yellow grease.

Step 3

(3aR,5S,6aS/3aS,5R,6aR)-tert-Butyl 3a-methyl-5-(methylamino) hexahydrocyclopenta[c]pyrrole-2 (1H)-carboxylate (3aR,5R,6aS/3aS,5S,6aR)-tert-butyl 3a-Methyl-5-((methylsulfonyl)oxy) hexahydrocyclopenta[c]pyrrole-2(1H)-carboxylate 10b (500 mg, 1.6 mmol) was dissolved in 10 mL of a solution of 1M methylamine in methanol. After reacting for 16 hours at 40° C., the reaction mixture was concentrated under reduced pressure at 40° C. to obtain the crude title product (3aR,5S,6aS/3aS,5R,6aR)-tert-butyl 3a-methyl-5-(methylamino)hexahydrocyclopenta[c]pyrrole-2(1H)-carboxylate 10c (350 mg, light yellow grease), which was used directly in the next step without further purification.

Step 4

(3aR,5S,6aS/3aS,5R,6aR)-tert-Butyl 3a-methyl-5-(methyl(7H-pyrrolo[2,3-d]pyrimidin-4-yl)amino) hexahydrocyclopenta[c]pyrrole-2(1H)-carboxylate Crude product (3aR,5S,6aS/3aS,5R,6aR)-tert-butyl 3a-methyl-5-(methylamino) hexahydrocyclopenta[c]pyrrole-2(1H)-carboxylate 10c (350 mg, 1.37 mmol) was dissolved in 10 mL of n-butanol, followed by addition of 4-chloro-7H-pyrrolo[2,3-d]pyrimidine 1d (320 mg, 2.06 mmol) and triethylamine (410 mg, 4.13 mmol). After reacting for 16 hours at 100° C., the reaction mixture was cooled to room temperature and poured into 50 mL of $H_2O$, followed by addition of 20 mL of ethyl acetate. The aqueous phase and organic phase were separated. The aqueous phase was extracted with ethyl acetate (10 mL). The organic phases were combined, washed with $H_2O$ (5 mL×3) and saturated sodium chloride solution (5 mL×3) successively, dried over anhydrous sodium sulfate, and filtered. The filtrate was concentrated under reduced pressure, and the resulting residue was purified by thin layer chromatography with elution system A to obtain the title product (3aR,5S,6aS/3aS,5R,6aR)-tert-butyl 3a-methyl-5-(methyl(7H-pyrrolo[2,3-d]pyrimidin-4-yl)amino)hexahydrocyclopenta[c]pyrrole-2(1H)-carboxylate 10 (20 mg, yield 3.9%) as a light yellow grease.

MS m/z (ESI): 372.2 [M+1]

$^1$H NMR (400 MHz, DMSO-$d_6$): δ 11.61 (s, 1H), 8.09 (s, 1H), 7.10 (s, 1H), 6.53 (s, 1H), 5.47-5.44 (m, 1H), 3.52 (t, 1H), 3.44 (m, 1H), 3.28 (d, 1H), 3.20 (d, 1H), 3.17 (s, 3H), 2.33-2.30 (m, 1H), 2.13-2.07 (m, 1H), 1.96-1.91 (m, 1H), 1.73-1.67 (m, 2H), 1.42 (s, 9H), 1.22 (s, 3H)

Example 11

1-((3aR,5S,6aS)-5-(Methyl(7H-pyrrolo[2,3-d]pyrimidin-4-yl)amino) hexahydrocyclopenta[c]pyrrol-2(1H)-yl)ethanone

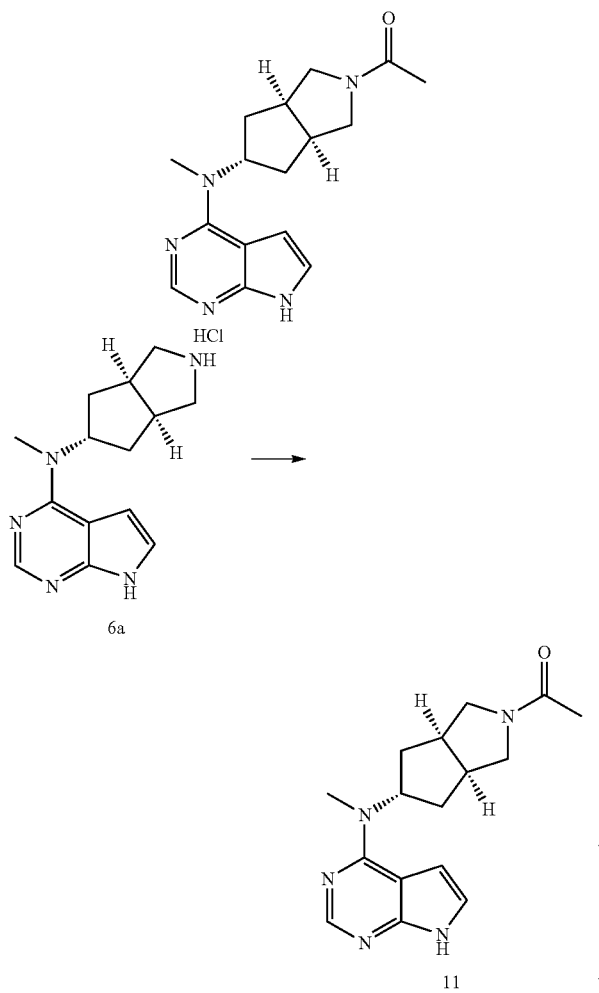

6a

11

N-Methyl-N-((3aR,5S,6aS)-octahydrocyclopenta[c]pyrrol-5-yl)-7H-pyrrolo[2,3-d]pyrimidin-4-amine hydrochloride 6a (200 mg, 0.68 mmol) was dissolved in 20 mL of dichloromethane, followed by addition of triethylamine (206 mg, 2.04 mmol). After reacting for 0.5 hour, the reaction mixture was mixed dropwise with acetylchloride (53 mg, 0.68 mmol). After reacting for 16 hours, the reaction mixture was mixed with 10 mL of $H_2O$. The aqueous phase and organic phase were separated. The organic phases were combined, dried over anhydrous sodium sulfate, and filtered. The filtrate was concentrated under reduced pressure and purified by preparative HPLC to obtain the title product 1-((3aR,5S,6aS)-5-(methyl(7H-pyrrolo[2,3-d]pyrimidin-4-yl)amino) hexahydrocyclopenta[c]pyrrol-2(1H)-yl)ethanone 11 (20 mg, yield 9.8%) as a white solid.

MS m/z (ESI): 300.3 [M+1]

$^1$H NMR (400 MHz, $CDCl_3$): δ 11.32 (s, 1H), 8.30 (s, 1H), 7.08 (s, 1H), 6.52 (s, 1H), 5.66-5.61 (m, 1H), 3.77-3.71 (m, 2H), 3.43-3.40 (m, 2H), 3.33 (s, 3H), 3.87-2.95 (m, 2H), 2.02-2.00 (m, 2H), 1.94-1.89 (m, 2H)

Example 12

Ethyl 2-((3aR,5S,6aS)-5-(methyl(7H-pyrrolo[2,3-d]pyrimidin-4-yl)amino)hexahydrocyclopenta[c]pyrrol-2(1H)-yl)acetate

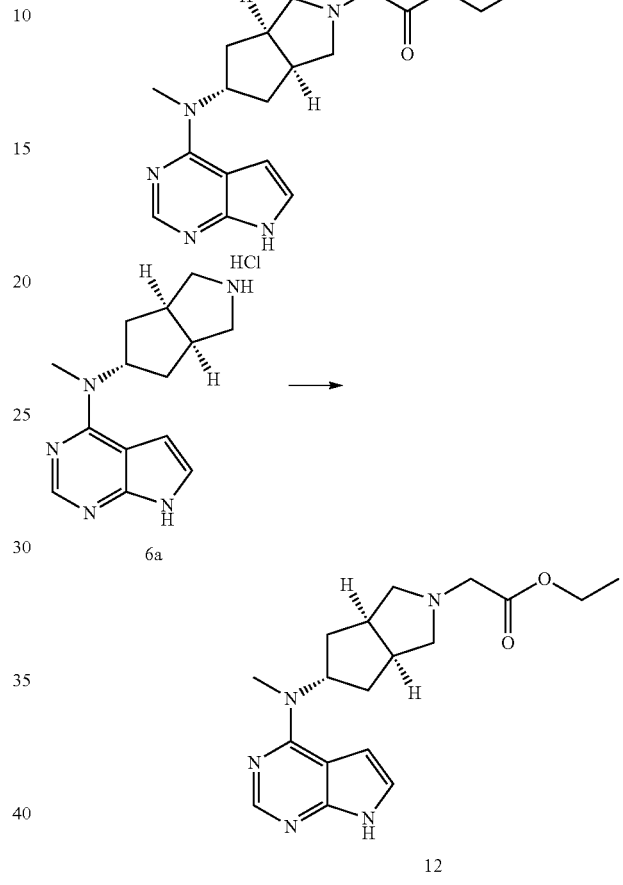

6a

12

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) and potassium carbonate (94 mg, 0.68 mmol) was dissolved in 5 mL of 1,4-dioxane. After reacting for 0.5 hour, the reaction mixture was mixed dropwise with 2-ethyl bromoacetate (56 mg, 0.34 mmol). After reacting for 4 hours, 50 mL of dichloromethane were added to the reaction mixture to dissolve the residue. The reaction mixture was washed with saturated sodium chloride solution (15 mL). The organic phases were combined, dried over anhydrous sodium sulfate, and filtered. The filtrate was concentrated under reduced pressure and the resulting residue was purified by thin layer chromatography with elution system A to obtain the title product ethyl 2-((3aR,5S,6aS)-5-(methyl(7H-pyrrolo[2,3-d]pyrimidin-4-yl)amino)hexahydrocyclopenta[c]pyrrol-2(1H)-yl)acetate 12 (24 mg, yield 21.4%) as a white solid.

MS m/z (ESI): 344.4[M+1]

$^1$H NMR (400 MHz, DMSO-$d_6$): δ 11.54 (s, 1H), 8.09 (s, 1H), 7.07-7.06 (m, 1H), 6.76-6.75 (m, 1H), 5.36-5.34 (m, 1H), 4.11 (q, 2H), 3.28 (s, 2H), 3.08 (s, 3H), 2.67-2.65 (m, 4H), 1.95-1.93 (m, 2H), 1.63-1.58 (m, 2H), 1.25-1.18 (m, 5H)

Example 13

Cyclopropyl((3aR,5S,6aS)-5-(methyl(7H-pyrrolo[2,3-d]pyrimidin-4-yl)amino) hexahydrocyclopenta[c]pyrrol-2(1H)-yl)methanone

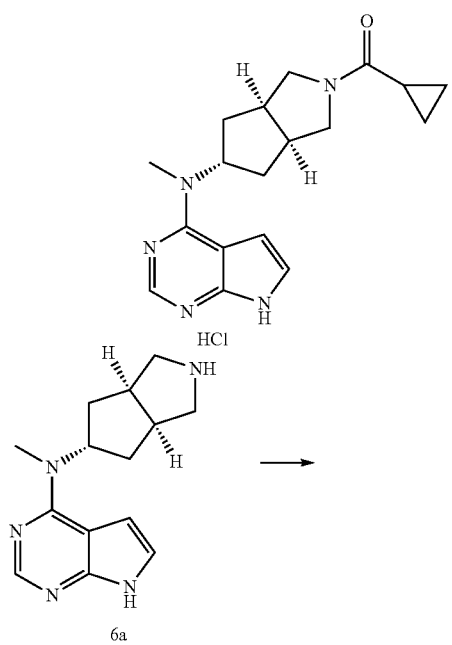

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by dropwise addition of triethylamine (69 mg, 0.68 mmol). After reacting for 0.5 hour, the reaction mixture was mixed with cyclopropyl formyl chloride (39 mg, 0.37 mmol). After reacting for 3 hours, 50 mL of dichloromethane was added into the reaction mixture to dissolve the residue. The reaction mixture was washed with saturated sodium chloride solution (15 mL). The organic phases were combined, dried over anhydrous sodium sulfate, and filtered. The filtrate was concentrated under reduced pressure, and the resulting residue was purified by thin layer chromatography with elution system A to obtain the title product cyclopropyl ((3aR,5S,6aS)-5-(methyl(7H-pyrrolo[2,3-d]pyrimidin-4-yl)amino)hexahydrocyclopenta[c]pyrrol-2(1H)-yl)methanone 13 (26 mg, yield 23.6%) as a white solid.

MS m/z (ESI): 326.1 [M+1]

$^1$H NMR (400 MHz, DMSO-$d_6$): δ 11.60 (s, 1H), 8.09 (s, 1H), 7.11-7.10 (m, 1H), 6.52-6.51 (m, 1H), 5.48-5.44 (m, 1H), 3.85-3.83 (m, 1H), 3.55-3.49 (m, 2H), 3.24-3.21 (m, 1H), 3.15 (s, 3H), 2.93-2.91 (m, 1H), 2.81-2.79 (m, 1H), 2.03-1.98 (m, 2H), 1.83-1.78 (m, 3H), 0.78-0.71 (m, 4H)

Example 14

2-Hydroxy-1-((3aS,5R,6aR/3aS,5R,6aR)-3a-methyl-5-(methyl(7H-pyrrolo[2,3-d]pyrimidin-4-yl)amino)hexahydrocyclopenta[c]pyrrol-2(1H-yl)ethanone

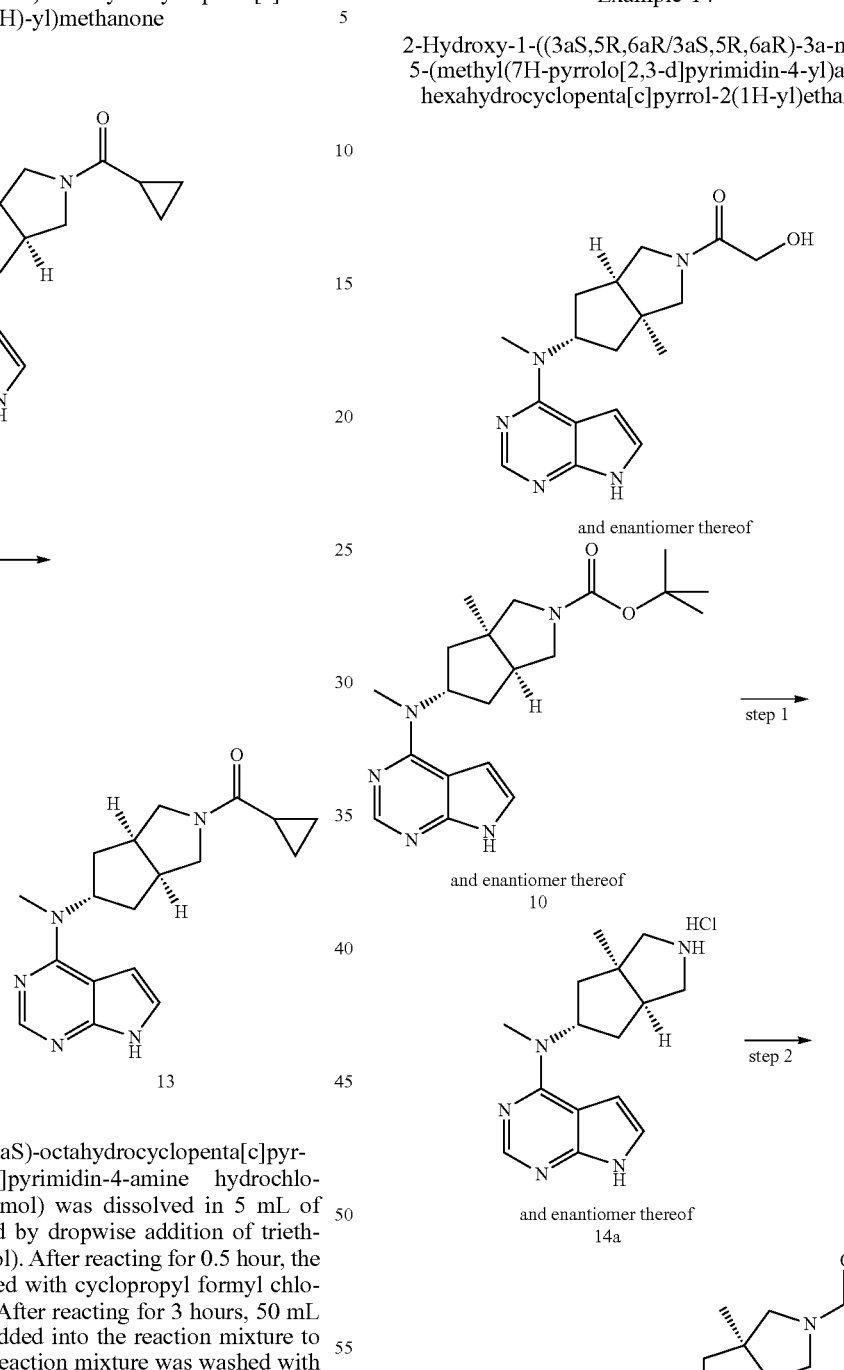

Step 1

N-Methyl-N-((3aR,5S,6aS/3aS,5R,6aR)-3a-methyl octahydro cyclopenta[c]pyrrol-5-yl)-7H-pyrrolo[2,3-d]pyrimidin-4-amine hydrochloride

(3aR,5S,6aS/3aS,5R,6aR)-tert-Butyl 3a-methyl-5-(methyl(7H-pyrrolo[2,3-d]pyrimidin-4-yl)amino)hexahydrocyclopenta[c]pyrrole-2(1H)-carboxylate 10 (1.56 g, 4.2 mmol) was dissolved in 20 mL of a solution of 1 M hydrogen chloride in methanol. After reacting for 16 hours, the reaction mixture was concentrated under reduced pressure to obtain the crude title product N-methyl-N-((3aR,5S,6aS/3aS,5R,6aR)-3a-methyloctahydrocyclopenta[c]pyrrol-5-yl)-7H-pyrrolo[2,3-d]pyrimidin-4-amine hydrochloride 14a (1.5 g, brown solid), which was used directly in the next step without further purification.

Step 2

2-Hydroxy-1-((3aS,5R,6aR/3aS,5R,6aR)-3a-methyl-5-(methyl(7H-pyrrolo[2,3-d]pyrimidin-4-yl)amino) hexahydrocyclopenta[c]pyrrol-2(1H)-yl)ethanone

N-Methyl-N-((3aR,5S,6aS/3aS,5R,6aR)-3a-methyl octahydro cyclopenta[c]pyrrol-5-yl)-7H-pyrrolo[2,3-d]pyrimidin-4-amine hydrochloride 14a (70 mg, 0.22 mmol) was dissolved in 5 mL of dichloromethane, followed by addition of triethylamine (67 mg, 0.66 mmol). After reacting for 0.5 hour, the reaction mixture was mixed with 2-glycolic acid (25 mg, 0.33 mmol) and O-(7-azabenzotriazol-1-yl)-N,N,N',N'-tetramethylformamidinium hexafluorophosphate (210 mg, 0.33 mmol). After reacting for 16 hours, the reaction mixture was concentrated under reduced pressure, and purified by preparative HPLC to obtain the title product 2-hydroxy-1-((3aS,5R,6aR/3aS,5R,6aR)-3a-methyl-5-(methyl(7H-pyrrolo[2,3-d]pyrimidin-4-yl)amino) hexahydrocyclopenta[c]pyrrol-2(1H)-yl)ethanone 14 (11 mg, yield 13.9%) as a light yellow solid.

MS m/z (ESI): 330.4[M+1]

$^1$H NMR (400 MHz, DMSO-$d_6$): δ 11.62 (s, 1H), 8.09 (s, 1H), 7.12 (s, 1H), 6.54 (s, 1H), 5.51 (s, 1H), 4.56 (s, 1H), 4.01-3.66 (m, 2H), 3.64-3.58 (m, 1H), 3.23 (s, 3H), 2.11 (d, 1H), 2.10-2.08 (m, 1H), 1.99-1.97 (m, 1H), 1.76-1.70 (m, 2H), 1.30-1.19 (m, 5H)

Example 15

N-((3aR,5S,6aS)-2-(Cyclopropylsulfonyl)octahydrocyclopenta[c]pyrrol-5-yl)-N-methyl-7H-pyrrolo[2,3-d]pyrimidin-4-amine

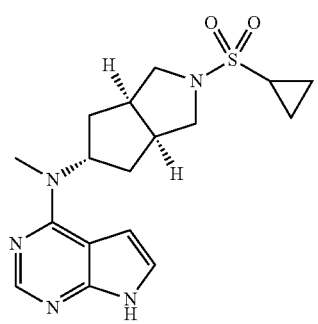

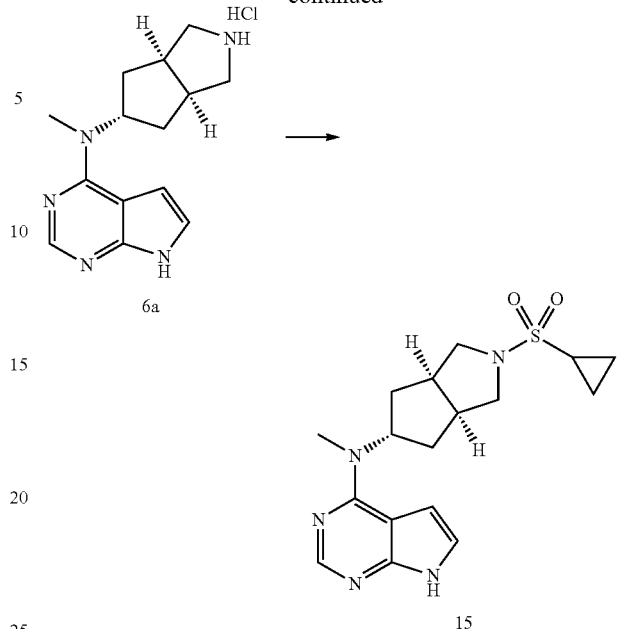

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (78 mg, 0.7 mmol). After reacting for 0.5 hour, the reaction mixture was mixed dropwise with cyclopropyl sulfonyl chloride (54 mg, 0.4 mmol). After reacting for 16 hours, the reaction mixture was mixed with 10 mL of H$_2$O. The aqueous phase and organic phase were separated. The organic phases were combined, dried over anhydrous sodium sulfate, and filtered. The filtrate was concentrated under reduced pressure, and purified by preparative HPLC to obtain the title product N-((3aR,5S,6aS)-2-(cyclopropylsulfonyl)octahydrocyclopenta[c]pyrrol-5-yl)-N-methyl-7H-pyrrolo[2,3-d]pyrimidin-4-amine 15 (20 mg, yield 14.3%) as a white solid.

MS m/z (ESI): 362.3 [M+1]

$^1$H NMR (400 MHz, CDCl$_3$): δ 10.11 (s, 1H), 8.31 (s, 1H), 7.08 (s, 1H), 6.70 (s, 1H), 5.52 (s, 1H), 3.57 (s, 2H), 3.31-3.25 (m, 4H), 2.95-2.93 (m, 2H), 2.39-2.27 (m, 2H), 1.25-1.20 (m, 4H), 1.04-1.03 (m, 2H), 0.87-0.86 (m, 2H)

Example 16 tert-Butyl (2-((3aR,5S,6aS)-5-(methyl(7H-pyrrolo[2,3-d]pyrimidin-4-yl)amino) hexahydrocyclopenta[c]pyrrol-2(1H)-yl)-2-oxoethyl)carbamate

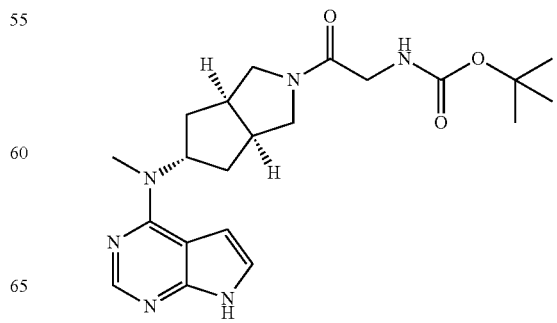

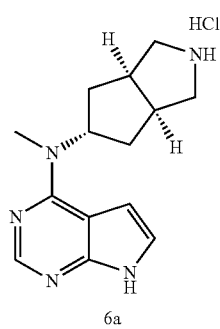

6a

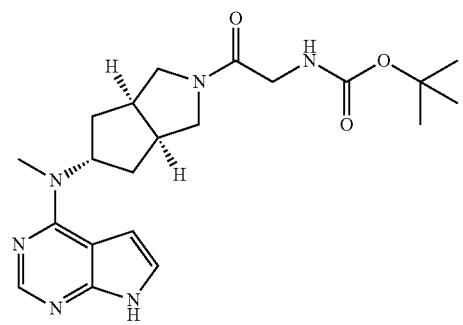

16

N-Methyl-N-((3aR,5S,6aS)-octahydrocyclopenta[c]pyrrol-5-yl)-7H-pyrrolo[2,3-d]pyrimidin-4-amine hydrochloride 6a (500 mg, 1.7 mmol) was dissolved in 20 mL of dichloromethane, followed by addition of triethylamine (0.47 mL, 3.4 mmol). After reacting for 1 hour, the reaction mixture was added with 2-(tert-butoxy formamide) acetic acid (0.36 g, 2.04 mmol) and O-(7-azabenzotriazol-1-yl)-N,N,N',N'-tetramethylformamidinium hexafluorophosphate (0.76 g, 2.04 mmol). After reacting for 11 hours, the reaction mixture was mixed with 100 mL of dichloromethane. The reaction mixture was washed with saturated sodium chloride solution (20 mL×2). The organic phases were combined, dried over anhydrous sodium sulfate, and filtered. The filtrate was concentrated under reduced pressure, and the resulting residue was purified by thin layer chromatography with elution system A to obtain the title product tert-butyl (2-((3aR,5S,6aS)-5-(methyl(7H-pyrrolo[2,3-d]pyrimidin-4-yl)amino)hexahydrocyclopenta[c]pyrrol-2(1H)-yl)-2-oxoethyl)carbamate 16 (320 mg, yield 45.5%) as a light yellow solid.

MS m/z (ESI): 415.4 [M+1]

$^1$H NMR (400 MHz, DMSO-$d_6$): δ 11.60 (s, 1H), 8.10 (s, 1H), 7.13-7.12 (m, 1H), 6.76-6.75 (m, 1H), 6.54 (s, 1H), 5.49-5.47 (m, 1H), 3.73-3.59 (m, 4H), 3.28-3.20 (m, 2H), 3.16 (s, 3H), 2.91-2.90 (m, 1H), 2.79-2.78 (m, 1H), 2.02-1.95 (m, 2H), 1.81-1.76 (m, 2H), 1.39 (s, 9H)

Example 17

(S)-2-Hydroxy-1-((3aR,5R,6aS)-5-(methyl(7H-pyrrolo[2,3-d]pyrimidin-4-yl)amino)hexahydrocyclopenta[c]pyrrol-2(1H)-yl)propan-1-one

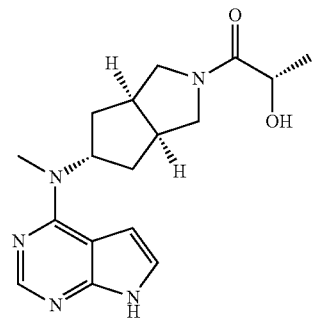

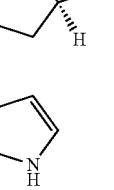

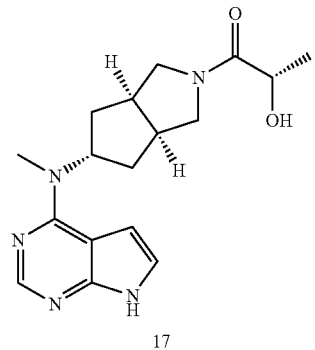

17

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (101 mg, 1 mmol), (S)-2-hydracrylic acid (46 mg, 0.5 mmol), and O-(7-azabenzotriazol-1-yl)-N,N,N',N'-tetramethylformamidinium hexafluorophosphate (190 mg, 0.5 mmol). After reacting for 16 hours, the reaction mixture was concentrated under reduced pressure, and the resulting residue was purified by thin layer chromatography with elution system A to obtain the title product (S)-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)propan-1-one 17 (13 mg, yield 11.6%) as a light yellow solid.

MS m/z (ESI): 330.3 [M+I]

$^1$H NMR (400 MHz, DMSO-$d_6$): 11.61 (s, 1H), 8.09-8.07 (m, 1H), 7.12-7.10 (m, 1H), 6.53 (s, 1H), 5.46-5.44 (m, 1H), 4.88-4.83 (m, 1H), 4.32-4.28 (m, 1H), 3.65-3.60 (m, 3H), 3.32-3.23 (m, 2H), 3.22-3.15 (m, 2H), 2.88-2.79 (m, 2H), 2.01-1.95 (m, 2H), 1.77-1.74 (m, 2H), 1.23-1.17 (m, 3H)

Example 18

2-Methoxy-1-((3aR,5S,6aS)-5-(methyl(7H-pyrrolo[2,3-d]pyrimidin-4-yl)amino) hexahydrocyclopenta[c]pyrrol-2(1H)-yl)ethanone

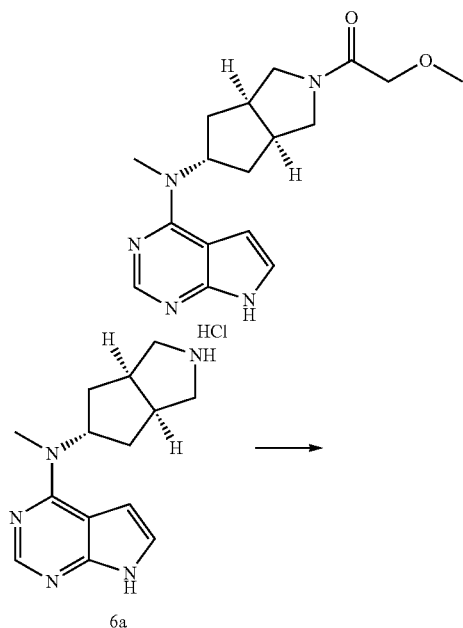

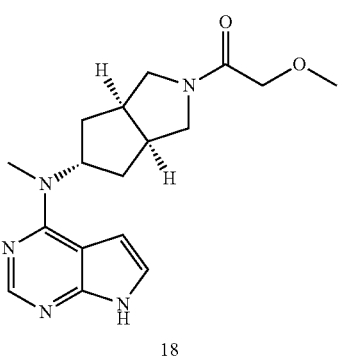

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (101 mg, 1.02 mmol). After reacting for 0.5 hour, the reaction mixture was mixed dropwise with 2-methoxyacetic acid (30 mg, 0.33 mmol). After reacting for 16 hours, the reaction mixture was mixed with 10 mL of H₂O. The aqueous phase and organic phase were separated. The organic phases were combined, dried over anhydrous sodium sulfate, and filtered. The filtrate was concentrated under reduced pressure, and purified by preparative HPLC to obtain the title product 2-methoxy-1-((3aR,5S,6aS)-5-(methyl(7H-pyrrolo[2,3-d]pyrimidin-4-yl)amino)hexahydrocyclopenta[c]pyrrol-2(1H)-yl)ethanone 18 (20 mg, yield 17.9%) as a white solid.

MS m/z (ESI): 330.3 [M+1]

$^1$H NMR (400 MHz, CDCl$_3$): δ 10.51 (s, 1H), 8.30 (s, 1H), 7.06 (s, 1H), 6.54 (s, 1H), 5.66-5.58 (m, 1H), 4.07 (s, 2H), 3.84-3.72 (m, 2H), 3.50-3.46 (m, 4H), 3.45-3.36 (m, 1H), 3.26 (s, 3H), 2.97-2.86 (m, 2H), 2.08-2.04 (m, 2H), 1.95-1.93 (m, 2H)

Example 19

(R)-2-Hydroxy-1-((3aR,5S,6aS)-5-(methyl(7H-pyrrolo[2,3-d]pyrimidin-4-yl)amino) hexahydrocyclopenta[c]pyrrol-2(1H)-yl)propan-1-one

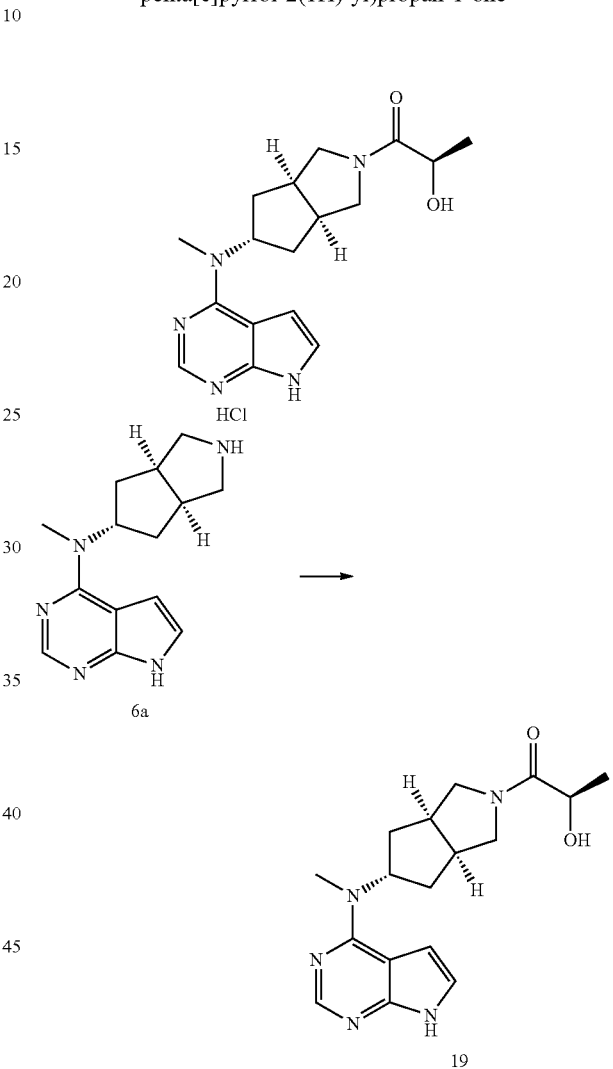

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of (R)-2-hydracrylic acid (46 mg, 0.5 mmol) and O-(7-azabenzotriazol-1-yl)-N,N,N',N'-tetramethylformamidinium hexafluorophosphate (190 mg, 0.5 mmol). After reacting for 16 hours, the reaction mixture was concentrated under reduced pressure, and the resulting residue was purified by thin layer chromatography with elution system A to obtain the title product (R)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one 19 (6 mg, yield 5.4%) as a yellow solid.

MS m/z (ESI): 330.4[M+1]

$^1$H NMR (400 MHz, DMSO-d$_6$): δ 11.61 (s, 1H), 8.09-8.08 (m, 1H), 7.12-7.11 (m, 1H), 6.53 (s, 1H), 5.47-5.45 (m,

1H), 4.87-4.82 (m, 1H), 4.31-4.27 (m, 1H), 3.67-3.60 (m, 3H), 3.32-3.24 (m, 1H), 3.22-3.15 (m, 3H), 2.89-2.79 (m, 2H), 2.03-1.95 (m, 2H), 1.79-1.74 (m, 2H), 1.23-1.17 (m, 3H)

Example 20

2-Amino-1-((3aR,5S,6aS)-5-(methyl(7H-pyrrolo[2,3-d]pyrimidin-4-yl)amino) hexahydrocyclopenta[c]pyrrol-2(1H)-yl)ethanone

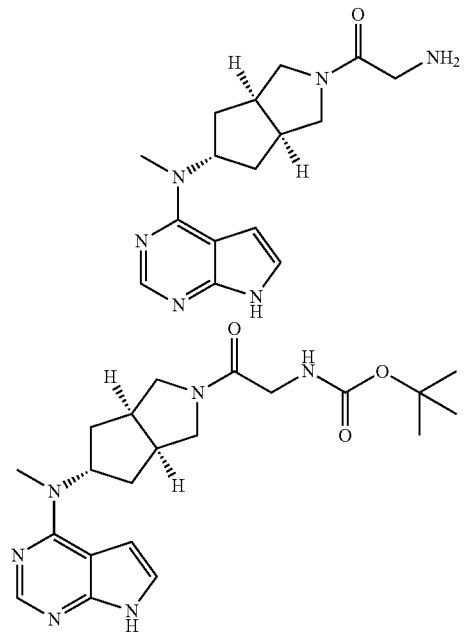

16

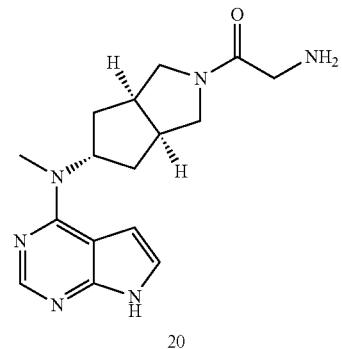

20 tert-Butyl (2-((3aR,5S,6aS)-5-(methyl(7H-pyrrolo[2,3-d]pyrimidin-4-yl)amino) hexahydrocyclopenta[c]pyrrol-2(1H)-yl)-2-oxoethyl)carbamate 16 (261 mg, 0.63 mmol) was dissolved in 8 mL of dichloromethane, followed by dropwise addition of 2 mL of trifluoroacetic acid. After reacting for 1 hour, the reaction mixture was mixed with 10 mL of H₂O and extracted with dichloromethane (20 mL×2). 1 M sodium hydroxide solution was added to the aqueous phase to increase the pH value up to 9, and extracted with dichloromethane (30 mL×5). The organic phases were combined, washed with saturated sodium chloride solution (15 mL), dried over anhydrous sodium sulfate and filtered. The filtrate was concentrated under reduced pressure, and the resulting residue was purified by thin layer chromatography with elution system A to obtain the title product 2-amino-1-((3aR,5S,6aS)-5-(methyl(7H-pyrrolo[2,3-d]pyrimidin-4-yl)amino)hexahydrocyclopenta[c]pyrrol-2(1H)-yl)ethanone 20 (145 mg, yield 73.2%) as a light yellow solid.

MS m/z (ESI): 315.5 [M+1]

¹H NMR (400 MHz, DMSO-d₆): δ 11.93 (s, 1H), 8.30 (s, 2H), 8.13 (s, 1H), 7.21-7.20 (m, 1H), 6.63-6.62 (m, 1H), 5.49-5.45 (m, 1H), 3.83-3.65 (m, 4H), 3.40-3.35 (m, 2H), 3.20 (s, 3H), 2.93-2.83 (m, 2H), 2.03-1.97 (m, 2H), 1.83-1.81 (m, 2H)

Example 21

N-(2-((3aR,5S,6aS)-5-(Methyl(7H-pyrrolo[2,3-d]pyrimidin-4-yl)amino) hexahydrocyclopenta[c]pyrrol-2(1H)-yl)-2-oxoethyl)methanesulfonamide

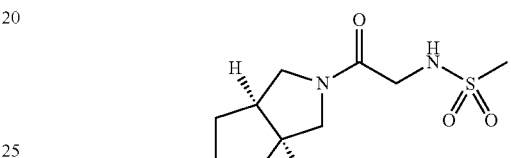

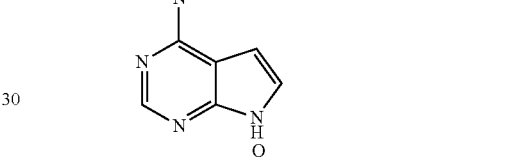

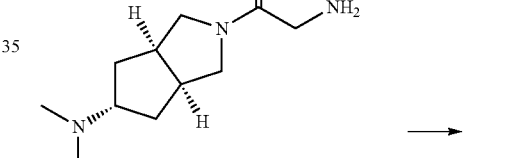

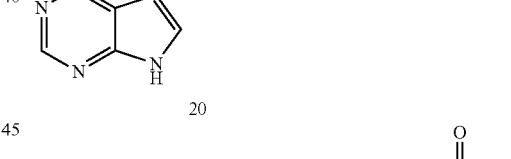

20

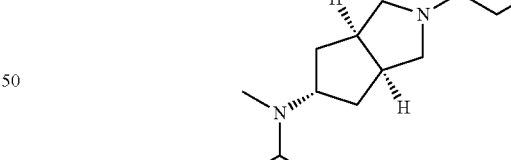

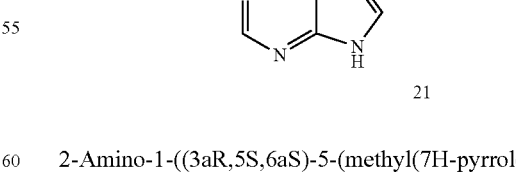

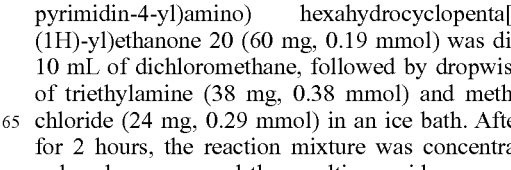

21

2-Amino-1-((3aR,5S,6aS)-5-(methyl(7H-pyrrolo[2,3-d]pyrimidin-4-yl)amino) hexahydrocyclopenta[c]pyrrol-2(1H)-yl)ethanone 20 (60 mg, 0.19 mmol) was dissolved in 10 mL of dichloromethane, followed by dropwise addition of triethylamine (38 mg, 0.38 mmol) and methylsulfonyl chloride (24 mg, 0.29 mmol) in an ice bath. After reacting for 2 hours, the reaction mixture was concentrated under reduced pressure and the resulting residue was purified by thin layer chromatography with elution system A to obtain the title product N-(2-((3aR,5S,6aS)-5-(methyl(7H-pyrrolo[2,3-d]pyrimidin-4-yl)amino)hexahydrocyclopenta[c]pyrrol-2(1H)-yl)-2-oxoethyl)methanesulfonamide 21 (8 mg, yield 11.3%) as a light yellow solid.

MS m/z (ESI): 393.3 [M+1]

$^1$H NMR (400 MHz, DMSO-$d_6$): δ 11.60 (s, 1H), 8.09 (s, 1H), 7.13-7.10 (m, 2H), 6.55-6.53 (m, 1H), 5.50-5.46 (m, 1H), 3.88-3.82 (m, 2H), 3.65-3.60 (m, 2H), 3.32-3.25 (m, 2H), 3.15 (s, 3H), 2.96 (s, 3H), 2.93-2.73 (m, 2H), 1.99-1.94 (m, 2H), 1.78-1.75 (m, 2H)

Example 22

4-((3aR,5S,6aS)-5-(Methyl(7H-pyrrolo[2,3-d]pyrimidin-4-yl)amino) hexahydrocyclopenta[c]pyrrol-2(1H)-yl)-4-oxobutanenitrile

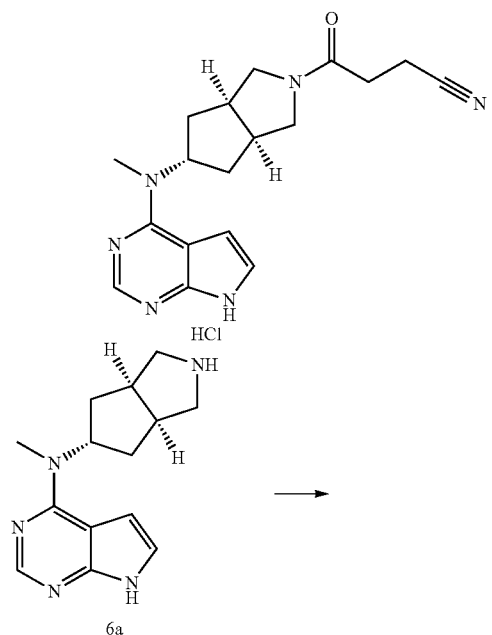

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (101 mg, 1 mmol), 3-cyano propionic acid (37 mg, 0.37 mmol), and O-(7-azabenzotriazol-1-yl)-N,N,N',N'-tetramethylformamidinium hexafluorophosphate (194 mg, 0.5 mmol). After reacting for 24 hours, the reaction mixture was added with 10 mL of saturated ammonium chloride to quench the reaction. The aqueous phase and the organic phase were separated. The aqueous phase was extracted with dichloromethane (15 mL×2). The organic phases were combined, washed with saturated sodium chloride solution (15 mL), dried over anhydrous magnesium sulfate, and filtered. The filtrate was concentrated under reduced pressure, and the resulting residue was purified by thin layer chromatography with elution system A to obtain the title product 4-((3aR,5S,6aS)-5-(methyl(7H-pyrrolo[2,3-d]pyrimidin-4-yl)amino)hexahydrocyclopenta[c]pyrrol-2(1H)-yl)-4-oxobutanenitrile 22 (6 mg, yield 5.2%) as a white solid.

MS m/z (ESI): 339.4[M+1]

$^1$H NMR (400 MHz, DMSO-$d_6$): δ 11.61 (s, 1H), 8.10-8.09 (m, 1H), 7.12-7.11 (m, 1H), 6.54-6.53 (m, 1H), 3.69-3.57 (m, 2H), 3.36-3.35 (m, 6H), 3.24-3.21 (m, 1H), 3.16-3.15 (m, 3H), 2.65-2.64 (m, 3H), 1.25-1.24 (m, 3H)

Example 23

2-Hydroxy-1-((3aR,5R,6aS)-5-(methyl(7H-pyrrolo[2,3-d]pyrimidin-4-yl)amino) hexahydrocyclopenta[c]pyrrol-2(1H)-yl)ethanone

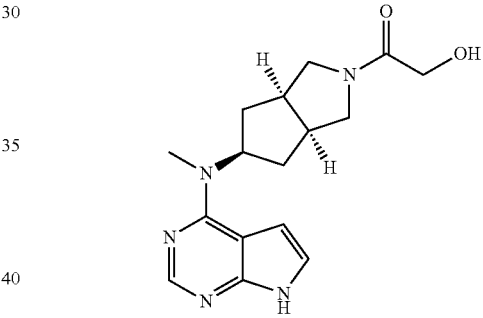

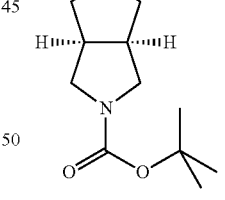

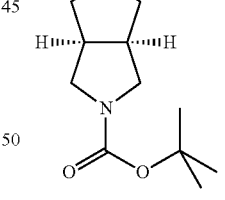

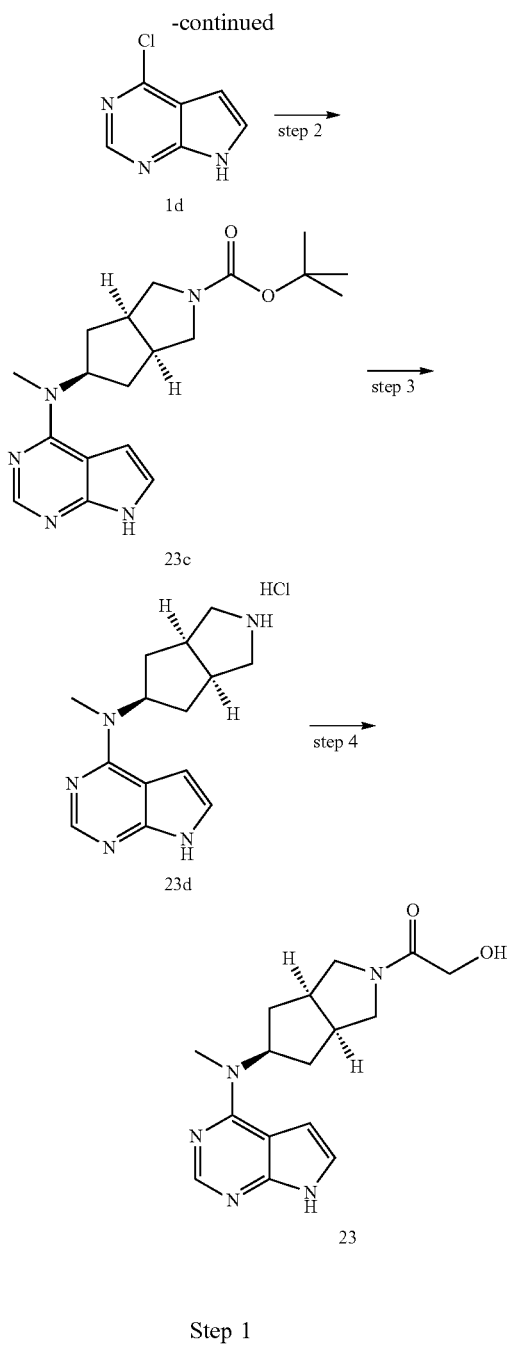

5-(methylamino)hexahydrocyclopenta[c]pyrrole-2(1H)-carboxylate 23b (1.23 g, yellow grease), which was used directly in the next step without further purification.

MS m/z (ESI): 241.3 [M+1]

Step 2

(3aR,5R,6aS)-tert-Butyl 5-(methyl(7H-pyrrolo[2,3-d]pyrimidin-4-yl)amino) hexahydrocyclopenta[c]pyrrole-2(1H)-carboxylate (3aR,5R,6aS)-tert-Butyl 5-(methylamino)hexahydrocyclopenta[c]pyrrole-2(1H)-carboxylate 23b (1.06 g, 4.41 mmol) was dissolved in 20 mL of n-butanol, followed by addition of 4-chlorine-7H-pyrrolo[2,3-d]pyrimidine (670 mg, 4.41 mmol) and potassium carbonate (1.22 g, 8.82 mmol). After reacting for 24 hours at 110° C., the reaction mixture was concentrated under reduced pressure, and the resulting residue was purified by silica gel column chromatography with elution system A to obtain the title product (3aR,5R,6aS)-tert-butyl 5-(methyl(7H-pyrrolo[2,3-d]pyrimidin-4-yl)amino)hexahydrocyclopenta[c]pyrrole-2(1H)-carboxylate 23c (830 mg, yield 52.9%) as a light yellow solid.

MS m/z (ESI): 358.2 [M+1]

Step 3

N-Methyl-N-((3aR,5R,6aS)-octahydrocyclopenta[c]pyrrol-5-yl)-7H-pyrrolo[2,3-d]pyrimidin-4-amine hydrochloride (3aR,5R,6aS)-tert-Butyl 5-(methyl(7H-pyrrolo[2,3-d]pyrimidin-4-yl)amino) hexahydrocyclopenta[c]pyrrole-2(1H)-carboxylate 23c (830 mg, 2.32 mmol) was dissolved in 10 mL of a solution of 6 M hydrogen chloride in methanol. After reacting for 16 hours, the reaction mixture was concentrated under reduced pressure, washed with anhydrous diethyl ether (20 mL), and dried in vacuo to obtain the title product N-methyl-N-((3aR,5R,6aS)-octahydrocyclopenta[c]pyrrol-5-yl)-7H-pyrrolo[2,3-d]pyrimidin-4-amine hydrochloride 23d (630 mg, yield 92.6%) as a gray solid.

Step 4

2-Hydroxy-1-((3aR,5R,6aS)-5-(methyl(7H-pyrrolo[2,3-d]pyrimidin-4-yl)amino) hexahydrocyclopenta[c]pyrrol-2(1H)-yl)ethanone N-Methyl-N-((3aR,5R,6aS)-octahydrocyclopenta[c]pyrrol-5-yl)-7H-pyrrolo[2,3-d]pyrimidin-4-amine hydrochloride 23d (100 mg, 0.34 mmol) was dissolved in 5 mL of n-butanol, followed by addition of 2-hydroxy methyl acetate (61 mg, 0.68 mmol) and 1,8-diazabicyclo-bicyclo[5,4,0]-7-hendecene (103 mg, 0.68 mmol). After reacting for 10 hours at 60° C., the reaction mixture was warmed up to 60° C. for 10 hours. The reaction mixture was concentrated under reduced pressure, and the resulting residue was purified by thin layer chromatography with elution system A to obtain the title product 2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)ethanone 23 (8 mg, yield 7.5%) as a gray solid.

MS m/z (ESI): 316.2 [M+1]

$^1$H NMR (400 MHz, DMSO-$d_6$): δ 11.61 (s, 1H), 8.09 (s, 1H), 7.12 (s, 1H), 6.58 (s, 1H), 5.32-5.30 (m, 1H), 4.52-4.49

Step 1

(3aR,5R,6aS)-tert-Butyl 5-(methylamino)hexahydrocyclopenta[c]pyrrole-2(1H)-carboxylate (3aR,6aS)-tert-Butyl 5-oxohexahydrocyclopenta[c]pyrrole-2(1H)-carboxylate 23a (1.0 g, 4.44 mmol) was dissolved in 20 mL of 2 M methylamine. After reacting for 1 hour, the reaction mixture was mixed with sodium cyanoborohydride (420 mg, 6.66 mmol) in batches. After reacting for 1 hour, the reaction mixture was concentrated under reduced pressure, followed by addition of 50 mL of dichloromethane to dissolve the residue, then washed with saturated sodium chloride solution (20 mL). The organic phases were combined, dried over anhydrous sodium sulfate and filtered. The filtrate was concentrated under reduced pressure to obtain the crude title product (3aR,5R,6aS)-tert-butyl (m, 1H), 4.08-3.99 (m, 2H), 3.54-3.51 (m, 2H), 3.42-3.37 (m, 2H), 3.16 (s, 3H), 2.75-2.63 (m, 2H), 2.02-1.99 (m, 2H), 1.57-1.52 (m, 2H)

Example 24

Methyl 2-((3aR,5S,6aS)-5-(methyl(7H-pyrrolo[2,3-d]pyrimidin-4-yl)amino)hexahydrocyclopenta[c]pyrrol-2(1H)-ylacetate

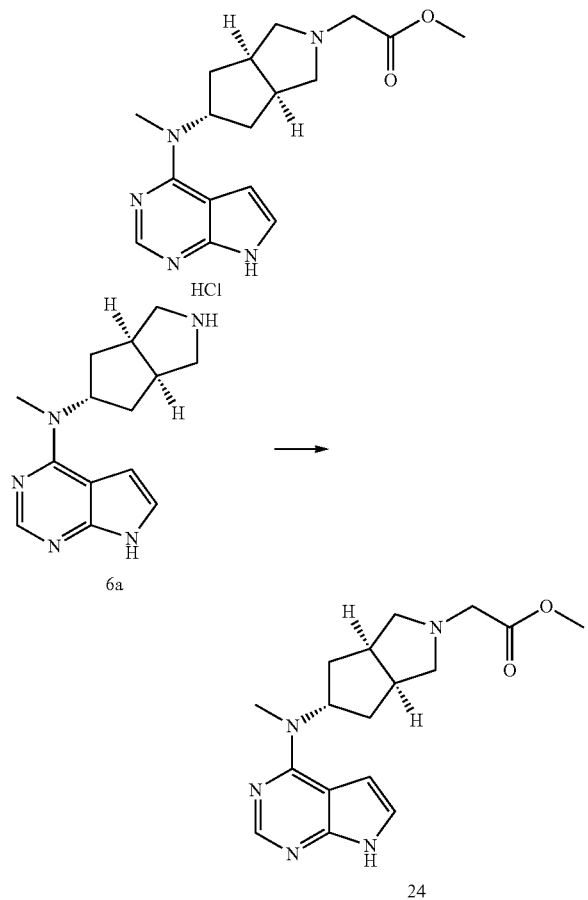

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (101 mg, 1 mmol) and 2-methyl bromoacetate (54 mg, 0.35 mmol). After reacting for 16 hours, the reaction mixture was mixed with 15 mL of saturated ammonium chloride to quench the reaction. The aqueous phase and the organic phase were separated. The aqueous phase was extracted with dichloromethane (15 mL×2). The organic phases were combined, washed with saturated sodium chloride solution (25 mL), dried over anhydrous magnesium sulfate, and filtered. The filtrate was concentrated under reduced pressure, and the resulting residue was purified by thin layer chromatography with elution system A to obtain the title product methyl 2-((3aR,5S,6aS)-5-(methyl(7H-pyrrolo[2,3-d]pyrimidin-4-yl)amino) hexahydrocyclopenta[c]pyrrol-2(1H)-yl)acetate 24 (6 mg, yield 5.4%) as a white solid.

MS m/z (ESI): 330.4[M+1]

¹H NMR (400 MHz, CDCl₃): δ 10.61 (s, 1H), 8.27-8.26 (m, 1H), 7.10-7.09 (m, 1H), 6.91 (s, 1H), 5.49-5.46 (m, 1H), 3.78 (s, 3H), 3.40-3.33 (m, 2H), 3.23 (s, 3H), 2.90-2.83 (m, 4H), 2.57-2.55 (m, 1H), 2.02-1.94 (m, 2H), 1.83-1.78 (m, 2H), 1.47-1.46 (m, 1H)

Example 25

(3aR,5S,6aS)-Isopropyl 5-(methyl(7H-pyrrolo[2,3-d]pyrimidin-4-yl)amino) hexahydrocyclopenta[c]pyrrole-2(1H)-carboxylate

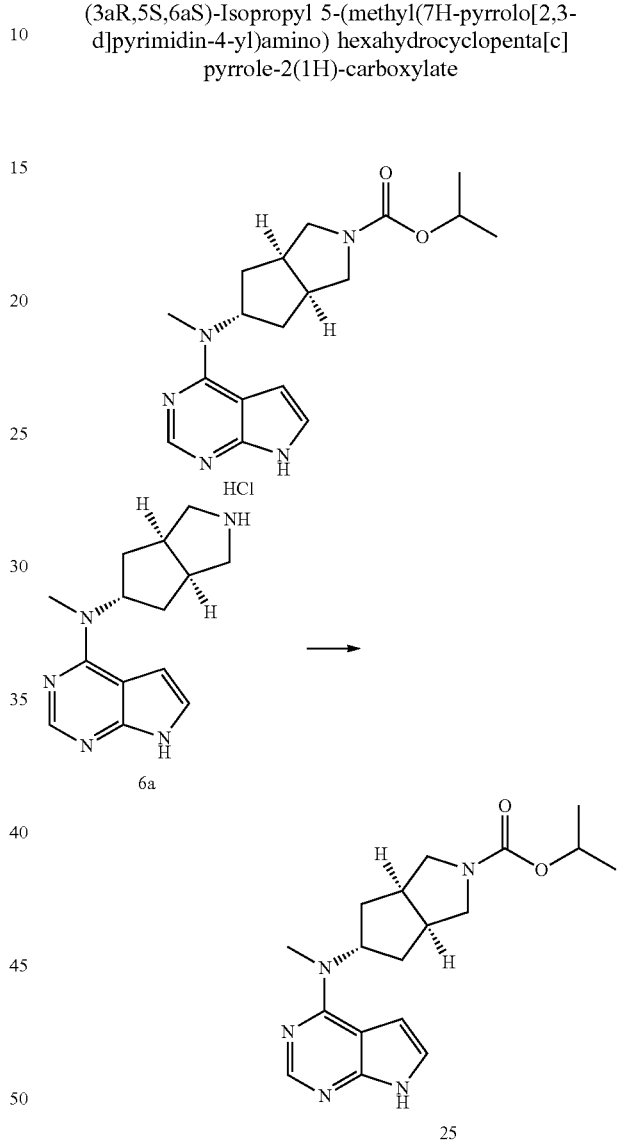

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (101 mg, 1 mmol) and isopropyl chloroformate (46 mg, 0.37 mmol). After reacting for 16 hours, the reaction mixture was mixed with 15 mL of saturated ammonium chloride to quench the reaction. The aqueous phase and the organic phase were separated. The aqueous phase was extracted with dichloromethane (15 mL×2). The organic phases were combined, washed with saturated sodium chloride solution (15 mL), dried over anhydrous magnesium sulfate and filtered. The filtrate was concentrated under reduced pressure, and the resulting residue was purified by thin layer chromatography with elution system A to obtain the title product (3aR,5S,6aS)-isopropyl 5-(methyl(7H-pyrrolo[2,3-d]pyrimidin-4-yl)amino)hexahydrocyclopenta[c]pyrrole-2(1H)-carboxylate 25 (6 mg, yield 5.1%) as a white solid.

MS m/z (ESI): 344.4[M+1]

$^1$H NMR (400 MHz, CDCl$_3$): δ 10.61 (s, 1H), 8.34 (s, 1H), 7.10-7.09 (m, 1H), 6.60-6.59 (m, 1H), 5.64-5.60 (m, 1H), 5.01-4.95 (m, 1H), 3.32-3.30 (m, 4H), 2.91-2.90 (m, 1H), 2.11-2.03 (m, 2H), 1.98-1.93 (m, 2H), 1.31-1.30 (m, 10H)

Example 26

2-((3aR,5S,6aS)-5-(Methyl(7H-pyrrolo[2,3-d]pyrimidin-4-yl)amino)hexahydrocyclopenta[c]pyrrol-2(1H)-yl)acetonitrile reduced pressure, and the resulting residue was purified by thin layer chromatography with elution system A to obtain the title product 2-((3aR,5S,6aS)-5-(methyl(7H-pyrrolo[2,3-d]pyrimidin-4-yl)amino) hexahydrocyclopenta[c]pyrrol-2(1H)-yl)acetonitrile 26 (10 mg, yield 9.9%) as a white solid.

MS m/z (ESI): 297.2 [M+1]

$^1$H NMR (400 MHz, CDCl$_3$): δ 10.43 (s, 1H), 8.33-8.32 (m, 1H), 7.10-7.09 (m, 1H), 6.72-6.71 (m, 1H), 5.50-5.43 (m, 1H), 3.22 (s, 3H), 2.87-2.86 (m, 4H), 2.73-2.66 (m, 2H), 2.09-2.04 (m, 2H), 1.85-1.80 (m, 4H)

Example 27

3-((3aR,5S,6aS)-5-(Methyl(7H-pyrrolo[2,3-d]pyrimidin-4-yl)amino)hexahydrocyclopenta[c]pyrrol-2(1H)-yl)propanenitrile

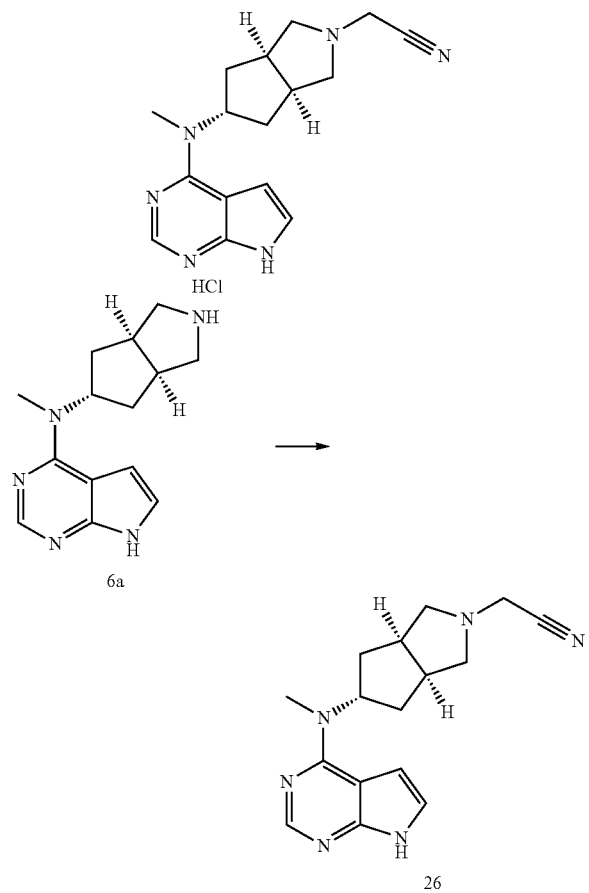

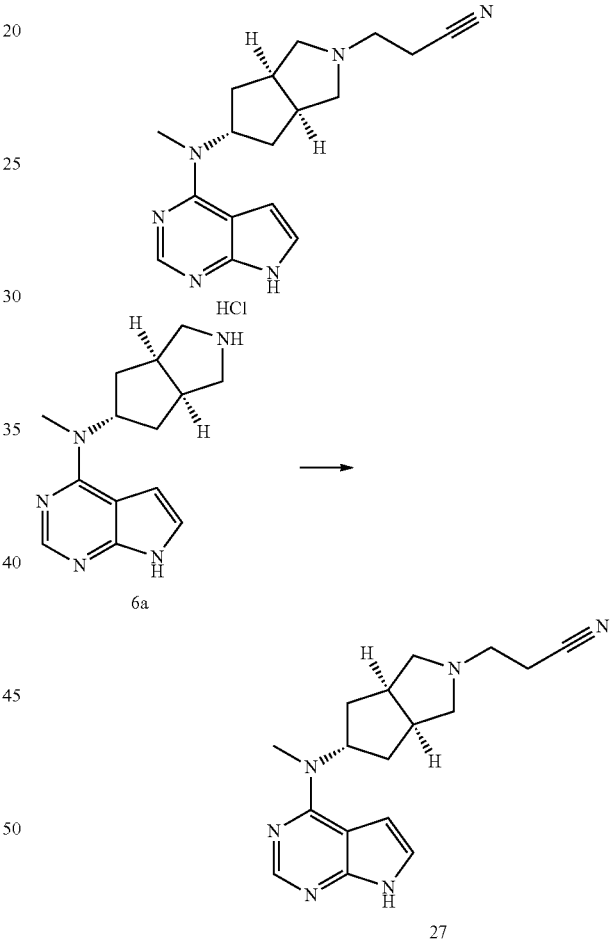

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (101 mg, 1 mmol) and bromoacetonitrile (41 mg, 0.34 mmol). After reacting for 24 hours, the reaction mixture was mixed with a small amount of saturated ammonium chloride solution to quench the reaction. The aqueous phase and the organic phase were separated. The aqueous phase was extracted with dichloromethane (10 mL×3). The organic phases were combined, washed with saturated ammonium chloride solution (10 mL) and saturated sodium chloride solution (10 mL) successively, dried over anhydrous sodium sulfate, and filtered. The filtrate was concentrated under N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 5 mL of dichloromethane, followed by addition of triethylamine (101 mg, 1 mmol) and 3-bromo propionitrile (46 mg, 0.34 mmol). After reacting for 24 hours, the reaction mixture was mixed with a small amount of saturated ammonium chloride solution to quench the reaction. The aqueous phase and the organic phase were separated. The aqueous phase was extracted with dichloromethane (10 mL×3). The organic phases were combined, washed with saturated ammonium chloride solution (10 mL) and saturated sodium chloride solution (10 mL) successively, dried over anhydrous sodium sulfate, and filtered. The filtrate was concentrated under reduced pressure, and the resulting residue was purified by thin layer chromatography with elution system A to obtain the title product 3-((3aR,5S,6aS)-5-(methyl(7H-pyrrolo[2,3-d]pyrimidin-4-yl)amino) hexahydrocyclopenta[c]pyrrol-2(1H)-yl)propanenitrile 27 (10 mg, yield 9.4%) as a white solid.

MS m/z (ESI): 311.3 [M+1]

$^1$H NMR (400 MHz, CDCl$_3$): δ 10.77 (s, 1H), 8.35-8.34 (m, 1H), 7.12-7.11 (m, 1H), 6.75-6.74 (m, 1H), 5.50-5.41 (m, 1H), 3.22 (s, 3H), 2.83-2.80 (m, 4H), 2.63-2.59 (m, 4H), 1.98-1.81 (m, 4H), 1.81-1.78 (m, 2H)

Examples 28 and 29

N-((3aR,5S,6aS)-2-(4,6-Dichloropyrimidin-2-yl)octahydrocyclopenta[c]pyrrol-5-yl)-N-methyl-7H-pyrrolo[2,3-d]pyrimidin-4-amine N-((3aR,5S,6aS)-2-(2,6-Dichloropyrimidin-4-yl)octahydrocyclopenta[c]pyrrol-5-yl)-N-methyl-7H-pyrrolo[2,3-d]pyrimidin-4-amine

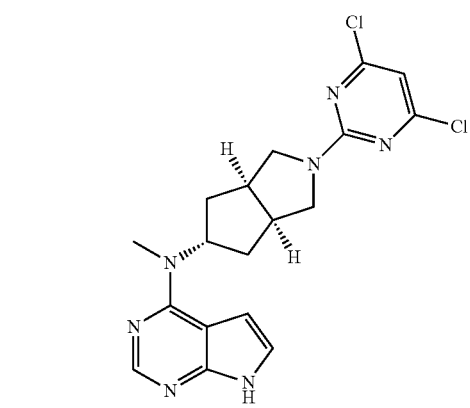

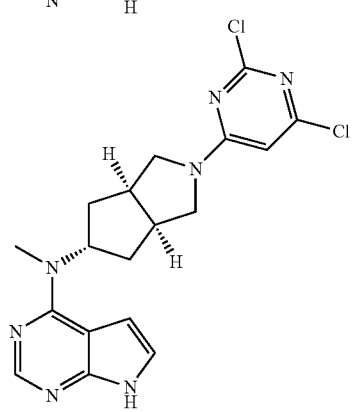

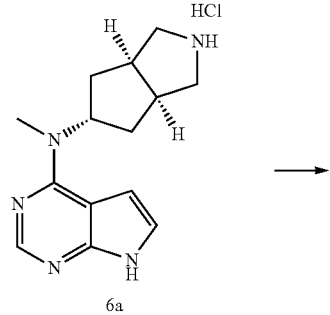

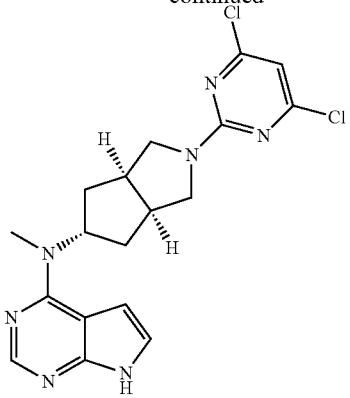

28

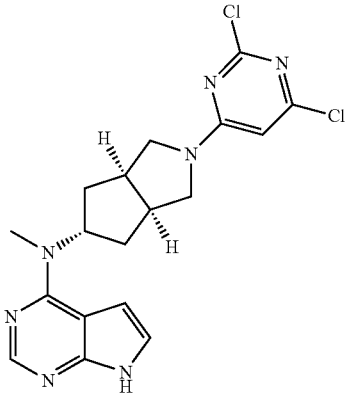

29

N-Methyl-N-((3aR,5S,6aS)-octahydrocyclopenta[c]pyrrol-5-yl)-7H-pyrrolo[2,3-d]pyrimidin-4-amine hydrochloride 6a (55 mg, 0.2 mmol) was dissolved in 5 mL of ethanol, followed by addition of triethylamine (52 mg, 0.5 mmol). After reacting for 0.5 hour, the reaction mixture was mixed with 2,4,6-trichloropyrimidine (32 mg, 0.2 mmol). After reacting for 16 hours, the reaction mixture was concentrated under reduced pressure, and the resulting residue was purified by thin layer chromatography with elution system A to obtain the title products N-((3aR,5S,6aS)-2-(4,6-dichloropyrimidin-2-yl)octahydrocyclopenta[c]pyrrol-5-yl)-N-methyl-7H-pyrrolo[2,3-d]pyrimidin-4-amine 28 (10 mg, yield 20.0%) as a white solid) and N-((3aR,5S,6aS)-2-(2,6-dichloropyrimidin-4-yl)octahydrocyclopenta[c]pyrrol-5-yl)-N-methyl-7H-pyrrolo[2,3-d]pyrimidin-4-amine 29 (20 mg, yield 40.0%) as a white solid.

MS m/z (ESI): 404.3 [M+1]

$^1$H NMR (400 MHz, CDCl$_3$): δ 9.81 (s, 1H), 8.28 (s, 1H), 7.01 (s, 1H), 6.57 (s, 1H), 6.50 (d, 1H), 5.64-5.60 (m, 1H), 3.90-3.85 (m, 2H), 3.59-3.56 (m, 2H), 3.25 (s, 3H), 3.04-2.96 (m, 2H), 2.13-2.05 (m, 2H), 1.99-1.95 (m, 2H)

$^1$H NMR (400 MHz, CDCl$_3$): δ 9.97 (s, 1H), 8.28 (s, 1H), 7.04 (s, 1H), 6.52 (d, 1H), 6.26 (d, 1H), 5.69-5.65 (m, 1H), 3.96-3.92 (m, 1H), 3.68-3.64 (m, 2H), 3.28-3.24 (m, 4H), 3.06-3.01 (m, 2H), 2.09-2.00 (m, 2H), 1.98-1.95 (m, 2H)

Example 30

(3aR,5S,6aS)-Methyl 5-(methyl(7H-pyrrolo[2,3-d]pyrimidin-4-yl)amino) hexahydro cyclopenta[c]pyrrole-2(1H)-carboxylate

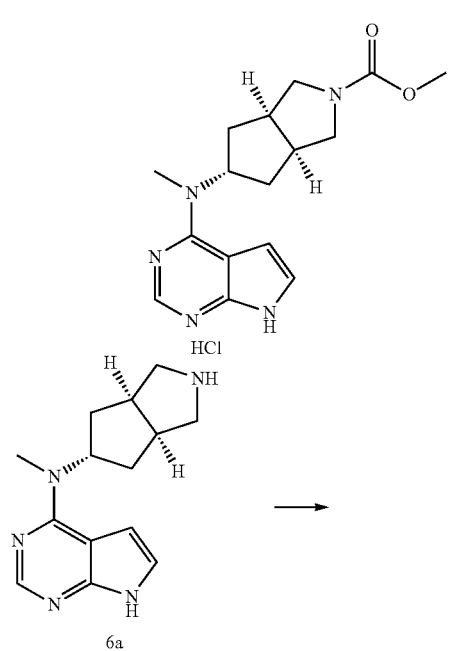

N-Methyl-N-((3aR,5S,6aS)-octahydrocyclopenta[c]pyrrol-5-yl)-7H-pyrrolo[2,3-d]pyrimidin-4-amine hydrochloride 6a (100 mg, 0.34 mmol) was dissolved in 15 mL of dichloromethane, followed by addition of methylchloroformate (44 mg, 0.47 mmol) and 3-triethylamine (59 mg, 0.58 mmol) in an ice bath. After reacting for 16 h, the reaction mixture was mixed with a small amount of saturated sodium bicarbonate solution and extracted with dichloromethane (20 mL×3). The organic phases were combined, dried over anhydrous sodium sulfate, and filtered. The filtrate was concentrated under reduced pressure, and the resulting residue was purified by thin layer chromatography with elution system A to obtain the title product (3aR,5S,6aS)-methyl 5-(methyl(7H-pyrrolo[2,3-d]pyrimidin-4-yl)amino)hexahydro cyclopenta[c]pyrrole-2(1H)-carboxylate 30 (50 mg, yield 41.0%) as a white solid.

MS m/z (ESI): 316.3 [M+1]

$^1$H NMR (400 MHz, CDCl$_3$): δ 10.60 (s, 1H), 8.26 (s, 1H), 7.06-7.05 (m, 1H), 6.54-6.53 (m, 1H), 5.60-5.56 (m, 1H), 3.72 (s, 3H), 3.70-3.65 (m, 2H), 3.32-3.25 (m, 2H), 3.24 (s, 3H), 2.91-2.85 (m, 2H), 2.06-2.00 (m, 2H), 1.92-1.82 (m, 2H)

Example 31

2-Hydroxy-1-((1R,5S,6S)-6-((methyl(7H-pyrrolo[2,3-d]pyrimidin-4-yl)amino)methyl)-3-azabicyclo[3.1.0]hexan-3-yl)ethanone

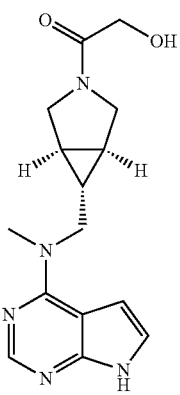

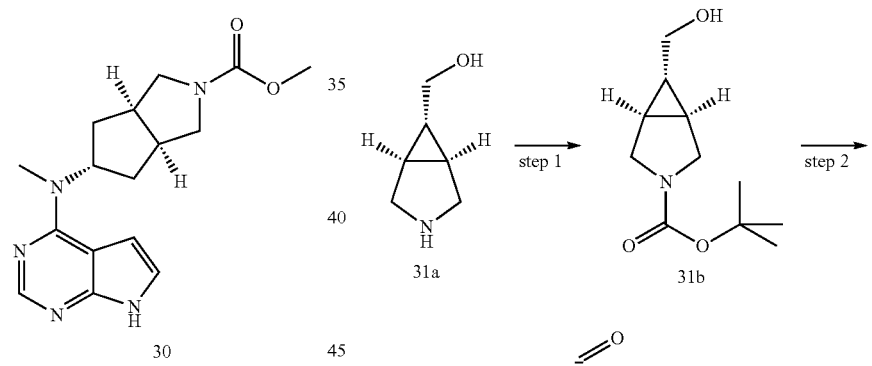

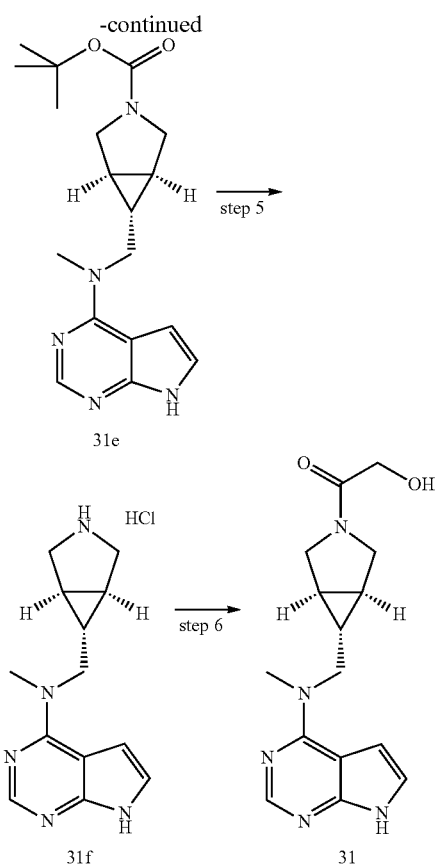

31e

31f → step 6 → 31

Step 1

(1R,5S,6R)-tert-Butyl 6-(hydroxymethyl)-3-azabicyclo[3.1.0]hexane-3-carboxylate (1R,5S,6R)-3-Azabicyclo[3.1.0]hexan-6-ylmethanol 31a (10 g, 88.4 mmol) was dissolved in a mixed solvent of dioxane and $H_2O$ (V/V=3/2), followed by addition of sodium hydroxide (4.2 g, 106 mmol) and di-tert-butyl dicarbonate (28.9 g, 132.6 mmol). After reacting for 10 hours, 50 mL of $H_2O$ was added to the reaction mixture. The reaction mixture was extracted with ethyl acetate (150 mL×3). The organic phases were combined, washed with saturated sodium chloride solution (50 mL×2), dried over anhydrous sodium sulfate, and filtered. The filtrate was concentrated under reduced pressure, and the resulting residue was purified by silica gel column chromatography with elution system C to obtain the title product (1R,5S,6R)-tert-butyl 6-(hydroxymethyl)-3-azabicyclo[3.1.0]hexane-3-carboxylate 31b (16.9 g, yield 89.9%) as a light yellow liquid.

Step 2

(1R,5S)-tert-Butyl 6-formyl-3-azabicyclo[3.1.0]hexane-3-carboxylate

Oxalyl chloride (2.41 mL, 28.1 mmol) was dissolved in 100 mL of dichloromethane, followed by dropwise addition of dimethyl sulfoxide (4.32 mL, 60.8 mmol) at −78° C. After reacting for 30 minutes, (1R,5S,6R)-tert-butyl 6-(hydroxymethyl)-3-azabicyclo[3.1.0]hexane-3-carboxylate 31b (5.0 g, 23.4 mmol) was added into the reaction mixture. After reacting for 1 hour, triethylamine (16.23 mL, 117 mmol) was added to the reaction mixture. After reacting for 30 minutes at room temperature, 200 mL dichloromethane, 50 mL of $H_2O$, 50 mL of 1 M hydrochloric acid, and 50 mL of saturated sodium bicarbonate solution were added into the reaction mixture. The aqueous phase and organic phase were separated, the organic phase was washed with saturated sodium chloride solution (50 mL), dried over anhydrous sodium sulfate, and filtered. The filtrate was concentrated under reduced pressure and the resulting residue was purified by silica gel column chromatography with elution system C to obtain the title product (1R,5S)-tert-butyl 6-formyl-3-azabicyclo[3.1.0]hexane-3-carboxylate 31c (4.12 g, yield 82.4%) as a light yellow liquid.

Step 3

(1R,5S,6S)-tert-Butyl 6-((methylamino)methyl)-3-azabicyclo[3.1.0]hexane-3-carboxylate (1R,5S)-tert-Butyl 6-formyl-3-azabicyclo[3.1.0]hexane-3-carboxylate 31c (3.05 g, 14.4 mmol) was dissolved in 20 mL of a solution of methylamine in methanol. After reacting for 24 hours, sodium cyanoborohydride (1.09 g, 17.3 mmol) was added into the reaction mixture in an ice bath in batches. After reacting for 2 hours at room temperature, 15 mL of saturated sodium chloride solution and 15 mL of $H_2O$ were added to the reaction mixture. The reaction mixture was extracted with ethyl acetate (30 mL×5). The organic phases were combined, washed with saturated sodium chloride solution (15 mL), dried over anhydrous sodium sulfate, and filtered. The filtrate was concentrated under reduced pressure to obtain the title product (1R,5S,6S)-tert-butyl 6-((methylamino)methyl)-3-azabicyclo[3.1.0]hexane-3-carboxylate 31d (3.95 g) as a colourless grease, which was used directly in the next step without further purification.

MS m/z (ESI): 227.46 [M+1]

Step 4

(1R,5S,6S)-tert-Butyl 6-((methyl(7H-pyrrolo[2,3-d]pyrimidin-4-yl)amino)methyl)-3-azabicyclo[3.1.0]hexane-3-carboxylate 4-Chloro-7H-pyrrolo[2,3-d]pyrimidine 1d (2.21 g, 14.4 mmol) was dissolved in 320 mL of n-butanol, followed by addition of (1R,5S,6S)-tert-butyl 6-((methylamino)methyl)-3-azabicyclo[3.1.0]hexane-3-carboxylate 31d (3.25 g, 14.4 mmol) and potassium carbonate (3.97 g, 28.8 mmol). After reacting for 24 hours at 120° C., 150 mL of ethyl acetate and 20 mL of $H_2O$ were added to the reaction mixture. The aqueous phase and organic phase were separated, the organic phase was washed with saturated sodium chloride solution (20 mL), dried over anhydrous sodium sulfate, and filtered. The filtrate was concentrated under reduced pressure, and the resulting residue was purified by silica gel column chromatography with elution system A to obtain the title product (1R,5S,6S)-tert-butyl 6-((methyl(7H-pyrrolo[2, 3-d]pyrimidin-4-yl)amino)methyl)-3-azabicyclo[3.1.0]
hexane-3-carboxylate 31e (1.82 g, yield 36.8%) as a white
solid.

MS m/z (ESI): 344.2 [M+1]

Step 5

N-((1R,5S,6R)-3-Azabicyclo[3.1.0]hexan-6-ylmethyl)-N-methyl-7H-pyrrolo[2,3-d]pyrimidin-4-amine hydrochloride (1R,5S,6S)-tert-Butyl 6-((methyl(7H-pyrrolo[2,3-d]pyrimidin-4-yl)amino) methyl)-3-azabicyclo[3.1.0]hexane-3-carboxylate 31e (1.72 g, 5.01 mmol) was dissolved in 20 mL of a solution of 1 M hydrogen chloride in methanol. After reacting for 14 hours, the reaction mixture was concentrated under reduced pressure, and the resulting residue was washed with a mixed solvent of dichloromethane and diethyl ether (V/V=1/1), dried under vacuum to obtain the title product N-((1R,5S,6R)-3-azabicyclo[3.1.0]hexan-6-ylmethyl)-N-methyl-7H-pyrrolo[2,3-d]pyrimidin-4-amine hydrochloride 31f (1.17 g, yield 95.9%) as a gray solid.

MS m/z (ESI): 244.46 [M+1]

Step 6

2-Hydroxy-1-((1R,5S,6S)-6-((methyl(7H-pyrrolo[2,3-d]pyrimidin-4-yl)amino)methyl)-3-azabicyclo[3.1.0]hexan-3-yl)ethanone N-((1R,5S,6R)-3-Azabicyclo[3.1.0]hexan-6-ylmethyl)-N-methyl-7H-pyrrolo[2,3-d]pyrimidin-4-amine hydrochloride 31f (100 mg, 0.36 mmol) was dissolved in 5 mL of tetrahydrofuran, followed by addition of triethylamine (111 mg, 1.1 mmol) and O-(7-azabenzotriazol-1-yl)-N,N,N',N'-tetramethylformamidinium hexafluorophosphate (204 mg, 0.54 mmol). After reacting for 30 minutes, 2-glycolic acid (30 mg, 0.39 mmol) was added to the reaction mixture. After reacting for 16 hours, a small amount of saturated ammonium chloride solution was added to the reaction mixture to quench the reaction. The aqueous phase and organic phase were separated. The aqueous phase was extracted with dichloromethane (10 mL×3). The organic phases were combined, dried over anhydrous sodium sulfate, and filtered. The filtrate was concentrated under reduced pressure, and the resulting residue was purified by thin layer chromatography with elution system A to obtain the title product 2-hydroxy-1-((1R,5S,6S)-6-((methyl(7H-pyrrolo[2,3-d]pyrimidin-4-yl)amino)methyl)-3-azabicyclo[3.1.0]hexan-3-yl)ethanone 31 (5 mg, yield 4.7%) as a yellow solid.

MS m/z (ESI): 300.45 [M−1]

$^1$H NMR (400 MHz, CDCl$_3$): δ 10.64 (s, 1H), 8.27 (s, 1H), 7.12-7.11 (m, 1H), 6.61-6.60 (m, 1H), 5.34-5.33 (m, 1H), 4.09-4.04 (m, 2H), 3.83-3.81 (m, 2H), 3.49 (s, 3H), 1.79-1.72 (m, 2H), 1.53-1.45 (m, 2H), 1.31-1.28 (m, 1H), 1.00-0.89 (m, 2H)

Example 32

2-((1R,5S,6R)-6-((Methyl(7H-pyrrolo[2,3-d]pyrimidin-4-yl)amino)methyl)-3-azabicyclo[3.1.0]hexan-3-yl acetonitrile

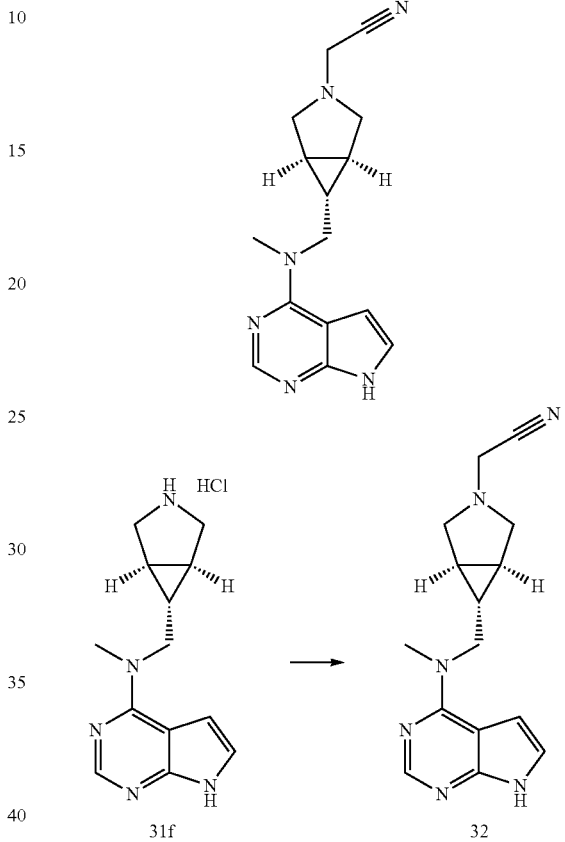

N-((1R,5S,6R)-3-Azabicyclo[3.1.0]hexan-6-ylmethyl)-N-methyl-7H-pyrrolo[2,3-d]pyrimidin-4-amine hydrochloride 31f (100 mg, 0.36 mmol) was dissolved in 5 mL acetonitrile, followed by addition of triethylamine (109 mg, 1.1 mmol) and bromoacetonitrile (47.5 mg, 0.4 mmol). After reacting for 16 hours, a small amount of saturated ammonium chloride solution was added to the reaction mixture to quench the reaction. The aqueous phase and organic phase were separated. The aqueous phase was extracted with dichloromethane (10 mL×3). The organic phases were combined, washed with saturated sodium chloride solution (10 mL), dried over anhydrous sodium sulfate, and filtered. The filtrate was concentrated under reduced pressure, and the resulting residue was purified by thin layer chromatography with elution system A to obtain the title product 2-((1R,5S,6R)-6-((methyl(7H-pyrrolo[2,3-d]pyrimidin-4-yl)amino)methyl)-3-azabicyclo[3.1.0]hexan-3-yl)acetonitrile 32 (15 mg, yield 14.9%) as a white solid.

MS m/z (ESI): 283.2 [M+1]

$^1$H NMR (400 MHz, CDCl$_3$): δ 10.64 (s, 1H), 8.31 (s, 1H), 7.09-7.08 (m, 1H), 6.64-6.63 (m, 1H), 3.76-3.74 (m, 2H), 3.63 (s, 2H), 3.47 (s, 3H), 3.00-2.98 (m, 2H), 2.75-2.73 (m, 2H), 1.57-1.53 (m, 2H), 1.33-1.30 (m, 1H)

Example 33

N-(((1R,5S,6S)-3-(2-Chloropyrimidin-4-yl)-3-azabicyclo[3.1.0]hexan-6-yl)methyl)-N-methyl-7H-pyrrolo[2,3-d]pyrimidin-4-amine

Example 34

(3aR,5S,6aS)—N-(3-Methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide

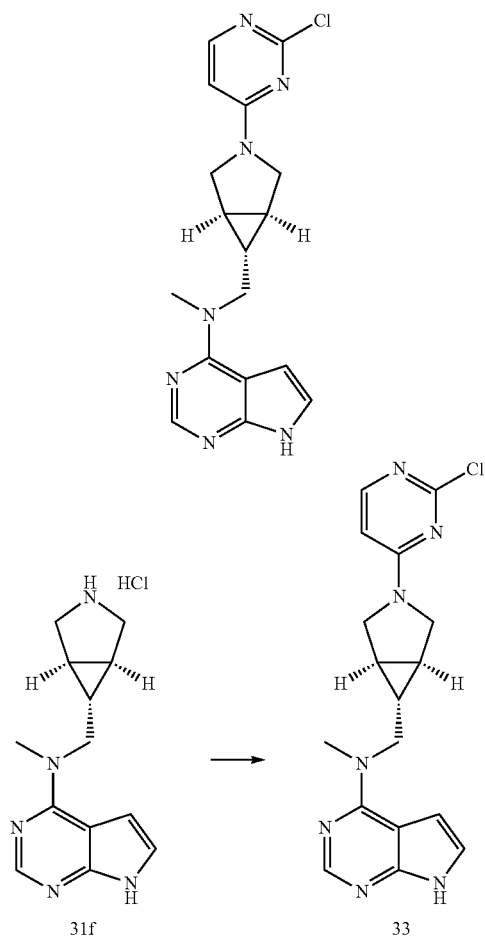

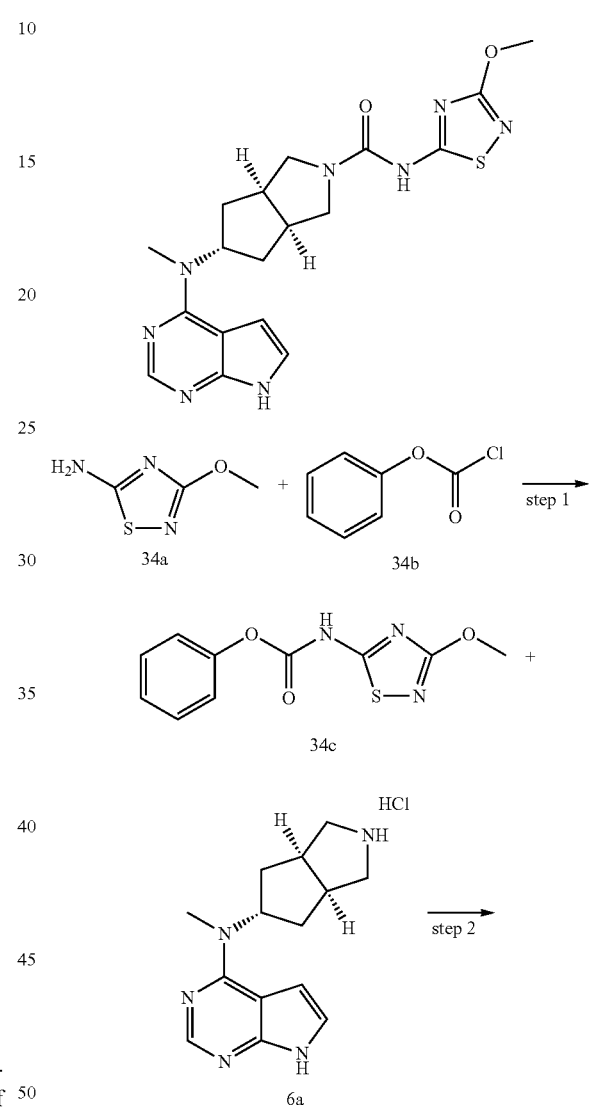

N-((1R,5S,6R)-3-Azabicyclo[3.1.0]hexan-6-ylmethyl)-N-methyl-7H-pyrrolo[2,3-d]pyrimidin-4-amine hydrochloride 31f (100 mg, 0.36 mmol) was dissolved in 5 mL of ethanol, followed by addition of triethylamine (108 mg, 1.07 mmol) and 4,6-dichloropyrimidine (26.6 mg, 0.17 mmol). After reacting for 16 hours, the reaction mixture was concentrated under reduced pressure, and the resulting residue was purified by thin layer chromatography with elution system A to obtain the title product N-((((1R,5S,6S)-3-(2-chloropyrimidin-4-yl)-3-azabicyclo[3.1.0]hexan-6-yl)methyl)-N-methyl-7H-pyrrolo[2,3-d]pyrimidin-4-amine 33 (5 mg, yield 7.9%) as a white solid.

MS m/z (ESI): 356.1 [M+1]

$^1$H NMR (400 MHz, CDCl$_3$): δ 10.46 (s, 1H), 8.25 (s, 1H), 7.97 (s, 1H), 7.07 (s, 1H), 6.59 (s, 1H), 6.13 (s, 1H), 4.03-4.01 (m, 1H), 3.84-3.81 (m, 2H), 3.49-3.47 (m, 3H), 3.42 (s, 3H), 1.96-1.94 (m, 2H), 1.07-1.05 (m, 1H)

Step 1

Phenyl(3-methoxy-1,2,4-thiadiazol-5-yl)carbamate

3-Methoxy-1,2,4-thiadiazol-5-amine 34a (500 mg, 3.82 mmol) and phenyl carbonochloridate 34b (600 mg, 3.82 mmol) were dissolved in 20 mL of dichloromethane, followed by addition of triethylamine (0.8 mL, 5.73 mmol). After reacting for 16 hours, 30 mL of H₂O were added to the reaction mixture to dilute the solution. The aqueous phase and organic phase were separated, the aqueous phase was extracted with dichloromethane (20 mL×2), and the organic phases were combined, dried over anhydrous sodium sulfate, and filtered. The filtrate was concentrated under reduced pressure, and the resulting residue was purified by silica gel column chromatography with elution system A to obtain the title product phenyl(3-methoxy-1,2,4-thiadiazol-5-yl)carbamate 34c (200 mg, yield 20.8%) as a white solid.
MS m/z (ESI): 252.0 [M+1]

Step 2

(3aR,5S,6aS)—N-(3-Methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide N-Methyl-N-((3aR,5S,6aS)-octahydrocyclopenta[c]pyrrol-5-yl)-7H-pyrrolo[2,3-d]pyrimidin-4-amine hydrochloride 6a (120 mg, 0.47 mmol) was dissolved in 15 mL of tetrahydrofuran, followed by addition of phenyl(3-methoxy-1,2,4-thiadiazol-5-yl)carbamate 34c (117 mg, 0.47 mmol) and triethylamine (0.13 mL, 0.94 mmol). After reacting for 5 hour at 60° C., the reaction mixture was mixed with 30 mL of H₂O and extracted with dichloromethane (50 mL×3). The organic phase was combined, washed with saturated sodium chloride solution (50×2 mL), dried over anhydrous sodium sulfate, and filtered. The filtrate was concentrated under reduced pressure, and the resulting residue was purified by silica gel column chromatography with elution system A to obtain the title product (3aR,5S,6aS)—N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide 34 (50 mg, yield 25.9%) as a white solid.
MS m/z (ESI): 412.9 [M−1]
¹H NMR (400 MHz, DMSO-d₆): δ 11.60 (m, 2H), 8.08 (s, 1H), 7.06-7.05 (m, 1H), 6.53-6.51 (m, 1H), 5.48-5.44 (m, 1H), 3.90 (s, 3H), 3.69-3.65 (m, 2H), 3.37-3.32 (m, 2H), 3.16 (s, 3H), 2.90-2.88 (m, 2H), 2.02-1.99 (m, 2H), 1.80-1.77 (m, 2H)

Example 35

1-((4aS,7aR)-6-(Methyl(7H-pyrrolo[2,3-d]pyrimidin-4-yl)amino)hexahydro-1H-cyclopenta[c]pyridin-2(3H,4H,4aH,5H,6H,7H,7aH)-yl)ethanone

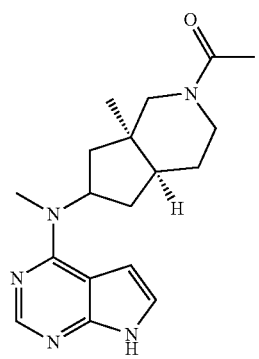

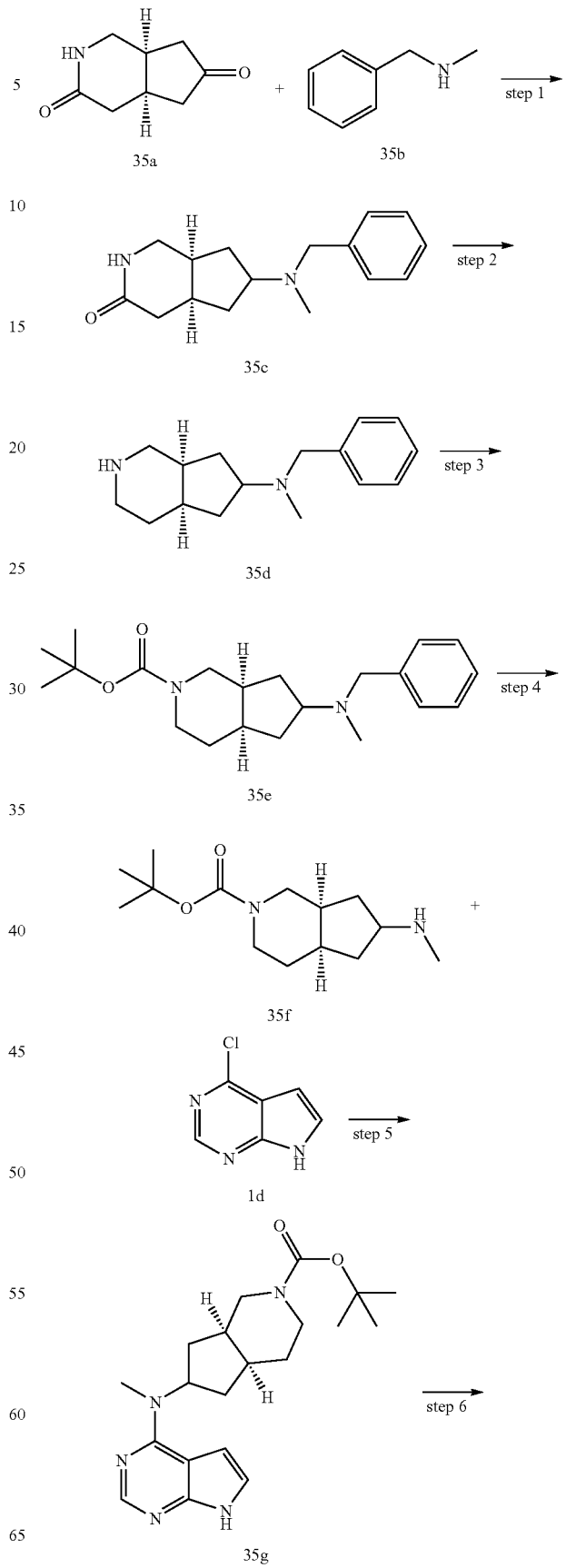

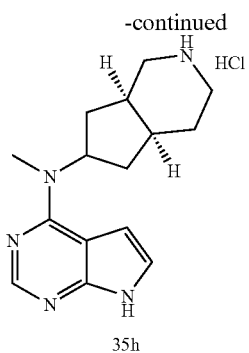

35h

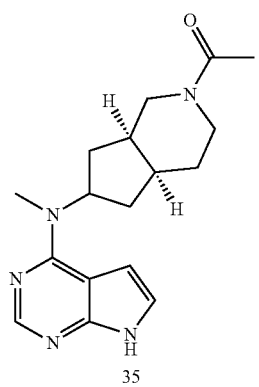

35

Step 1

(4aS,7aS)-6-(Benzyl(methyl)amino)hexahydro-1H-cyclopenta[c]pyridin-3(2H)-one (4aS,7aS)-Tetrahydro-1H-cyclopenta[c]pyridin-3,6(2H,4H)-dione 35a (3 g, 19.60 mmol, prepared from a well known method "Tetrahedron: Asymmetry, 1997, 8 (17), 2893-2904") and N-methyl-1-phenylmethanamine 35b (2.37 g, 19.60 mmol) were dissolved in 5 mL of methanol, followed by addition of two drops of acetic acid. After stirring and reacting for 3 hours, sodium cyanoborohydride (1.80 g, 29.40 mmol) was added to the reaction mixture. After reacting for 12 hours, the reaction mixture was filtered, and concentrated under reduced pressure. The resulting residue was purified by silica gel column chromatography with elution system A to obtain the title product (4aS,7aS)-6-(Benzyl(methyl)amino)hexahydro-1H-cyclopenta[c]pyridin-3(2H)-one 35c (1.99 g, yield 39.8%) as a yellow solid.
MS m/z (ESI): 259.2 [M+1]

Step 2

(4aR,7aS)—N-Benzyl-N-methyloctahydro-1H-cyclopenta[c]pyridin-6-amine (4aS,7aS)-6-(Benzyl(methyl)amino)hexahydro-1H-cyclopenta[c]pyridin-3(2H)-one 35c (3.90 g, 15.11 mmol) was dissolved in 150 mL of tetrahydrofuran, followed by addition of lithium aluminum hydride (3 g, 78.60 mmol) in batches in an ice bath. After stirring for 48 hours, 10 mL of ice water was added to the reaction mixture. The reaction mixture was filtered, washed with dichloromethane (50 mL), and concentrated under reduced pressure to obtain the crude title product (4aR,7aS)—N-benzyl-N-methyloctahydro-1H-cyclopenta[c]pyridin-6-amine 35d (3.69 g, white solid), which was used directly in the next step without further purification.
MS m/z (ESI): 245.2 [M+1]

Step 3

(4aR,7aS)-tert-Butyl 6-(benzyl(methyl)amino)hexahydro-1H-cyclopenta[c]pyridine-2(3H)-carboxylate (4aR,7aS)—N-Benzyl-N-methyloctahydro-1H-cyclopenta[c]pyridin-6-amine 35d (3.69 g, 15.11 mmol) was dissolved in 50 mL of dichloromethane, followed by addition of di-tert-butyl dicarbonate (4.94 g, 22.60 mmol), and ethylamine (3.81 g, 37.75 mmol). After stirring for 12 hours, the reaction mixture was mixed with 20 mL of H₂O, and extracted with dichloromethane (30 mL×2). The organic phases were combined, dried over anhydrous sodium sulfate and filtered. The filtrate was concentrated under reduced pressure, and the resulting residue was purified by silica gel column chromatography with elution system A to obtain the title product (4aR,7aS)-tert-butyl 6-(benzyl(methyl)amino)hexahydro-1H-cyclopenta[c]pyridine-2(3H)-carboxylate 35e (3.28 g, yield 63%) as a light yellow solid.
MS m/z (ESI): 345.3 [M+1]

Step 4

(4aR,7aS)-tert-Butyl 6-(methylamino)hexahydro-1H-cyclopenta[c]pyridine-2(3H)-carboxylate (4aR,7aS)-tert-Butyl 6-(benzyl(methyl)amino)hexahydro-1H-cyclopenta[c]pyridine-2(3H)-carboxylate 35e (2 g, 5.81 mmol) was dissolved in 150 mL of methanol, followed by addition of palladium hydroxide on carbon (500 mg, 25%). After the reactor was purged with hydrogen three times, the reaction mixture was stirred for 72 hours, and then filtered, washed with methanol (20 mL), and concentrated under reduced pressure to obtain the crude title product (4aR,7aS)-tert-butyl 6-(methylamino)hexahydro-1H-cyclopenta[c]pyridine-2(3H)-carboxylate 35f (1.72 g) as a colorless, viscous liquid, which was used directly in the next step without further purification.
MS m/z (ESI): 255.2 [M+1]

Step 5

(4aS,7aR)-tert-Butyl 6-(methyl(7H-pyrrolo[2,3-d]pyrimidin-4-yl)amino) hexahydro-1H-cyclopenta[c]pyridine-2(3H)-carboxylate 4-Chloro-7H-pyrrolo[2,3-d]pyrimidine 1d (1.78 g, 11.65 mmol) was dissolved in 50 mL of 1,4-dioxane, followed by addition of (4aR,7aS)-tert-butyl 6-(methylamino)hexahydro-1H-cyclopenta[c]pyridine-2(3H)-carboxylate 35f (2.96 g, 11.65 mmol) and potassium carbonate (3.22 g, 23.30 mmol). After reacting for 48 hours at 110° C., the reaction mixture was concentrated under reduced pressure, followed by addition of 50 mL of H₂O, and extracted with ethyl acetate (30 mL×3). The organic phases were combined, dried over anhydrous sodium sulfate, and filtered. The filtrate was concentrated under reduced pressure and the resulting residue was purified by silica gel column chromatography with elution system A to obtain the title product (4aS,7aR)-tert-butyl 6-(methyl(7H-pyrrolo[2,3-d]pyrimidin-4-yl)amino)hexahydro-1H-cyclopenta[c]pyridine-2(3H)-carboxylate 35g (1.34 g, yield 31%) as a white solid.
MS m/z (ESI): 372.2 [M+1]

Step 6

N-Methyl-N-((4aS,7aR)-octahydro-1H-cyclopenta[c]pyridin-6-yl)-7H-pyrrolo[2,3-d]pyrimidin-4-amine hydrochloride (4aS,7aR)-tert-Butyl 6-(methyl(7H-pyrrolo[2,3-d]pyrimidin-4-yl)amino) hexahydro-1H-cyclopenta[c]pyridine-2

(3H)-carboxylate 35g (1.34 g, 3.61 mmol) was dissolved in 15 mL of a solution of 6 M hydrogen chloride in methanol solution. After reacting for 12 hours, the reaction mixture was concentrated under reduced pressure, followed by addition of 20 mL of H$_2$O and 10% sodium hydroxide solution until the pH of the reaction mixture was between 9 and 10. The reaction mixture was extracted with dichloromethane (20 mL×2). The organic phases were combined, dried over anhydrous sodium sulfate, and filtered. The filtrate was concentrated under reduced pressure to obtain the crude title product N-methyl-N-((4aS,7aR)-octahydro-1H-cyclopenta [c]pyridin-6-yl)-7H-pyrrolo[2,3-d]pyrimidin-4-amine hydrochloride 35h (1 g, white solid), which was used directly in the next step without further purification.

MS m/z (ESI): 272.2 [M+1]

Step 7

1-((4aS,7aR)-6-(Methyl(7H-pyrrolo[2,3-d]pyrimidin-4-yl)amino)hexahydro-1H-cyclopenta[c]pyridin-2(3H,4H,4aH,5H,6H,7H,7aH)-yl)ethanone N-Methyl-N-((4aS,7aR)-octahydro-1H-cyclopenta[c] pyridin-6-yl)-7H-pyrrolo[2,3-d]pyrimidin-4-amine hydrochloride 35h (100 mg, 0.37 mmol) was dissolved in 5 mL of N,N-dimethylformamide, followed by addition of anhydrous acetic acid (22 mg, 0.37 mmol), triethylamine (112 mg, 1.10 mmol), 1-ethyl-3-(3-dimethylaminopropyl) carbodiimide hydrochloride (106 mg, 0.55 mmol), and 1-hydroxybenzotriazole (74 mg, 0.55 mmol). After reacting for 12 hours, 10 mL of H$_2$O were added to the reaction mixture. The reaction mixture was extracted with dichloromethane (20 mL×2). The organic phases were combined, dried over anhydrous sodium sulfate, and filtered. The filtrate was concentrated under reduced pressure, and purified by preparative HPLC to obtain the title product 1-((4aS,7aR)-6-(methyl(7H-pyrrolo[2,3-d]pyrimidin-4-yl)amino) hexahydro-1H-cyclopenta[c]pyridin-2(3H,4H,4aH,5H,6H,7H, 7aH)-yl)ethanone 35 (7 mg, yield 5%) as a white solid.

MS m/z (ESI): 314.2 [M+1]

$^1$H NMR (400 MHz, CDCl$_3$): δ 11.34 (s, 1H), 8.32 (s, 1H), 7.08 (s, 1H), 6.56 (s, 1H), 5.43-5.45 (m, 1H), 3.88-3.91 (m, 1H), 3.27-3.55 (m, 6H), 2.28-2.30 (m, 2H), 1.91-1.96 (m, 6H), 1.58-1.60 (m, 3H)

Example 36

(4aS,7aR)-Methyl 6-(methyl(7H-pyrrolo[2,3-d]pyrimidin-4-yl)amino) hexahydro-1H-cyclopenta[c] pyridine-2(3H)-carboxylate

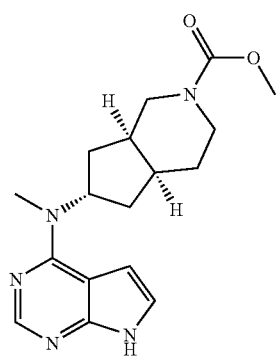

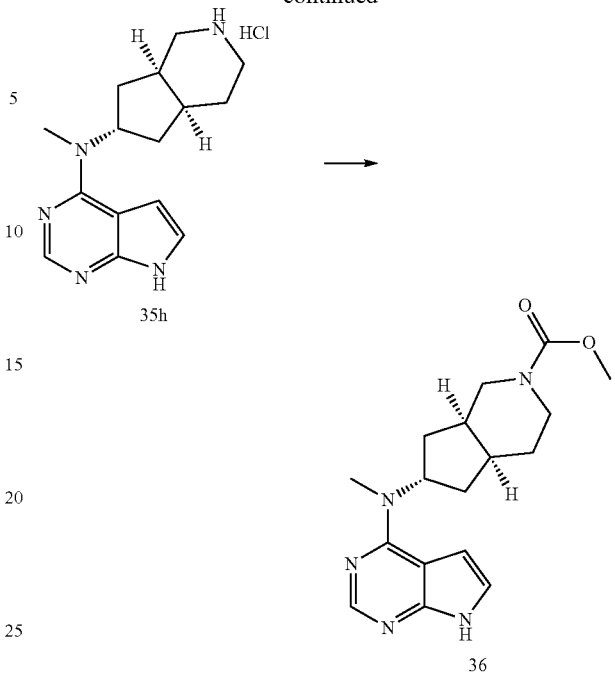

N-Methyl-N-((4aS,7aR)-octahydro-1H-cyclopenta[c] pyridin-6-yl)-7H-pyrrolo[2,3-d]pyrimidin-4-amine hydrochloride 35h (100 mg, 0.37 mmol) was dissolved in 10 mL of dichloromethane, followed by addition of methyl chloroformate (35 mg, 0.37 mmol) and triethylamine (56 mg, 0.55 mmol) in an ice bath. After reacting for 12 hours, 10 mL of H$_2$O were added to the reaction mixture. The reaction mixture was extracted with dichloromethane (10 mL×2). The organic phases were combined, dried over anhydrous sodium sulfate, and filtered. The filtrate was concentrated under reduced pressure and the resulting residue was purified by thin layer chromatography with elution system A to obtain the title product (4aS,7aR)-methyl 6-(methyl(7H-pyrrolo[2,3-d]pyrimidin-4-yl)amino)hexahydro-1H-cyclopenta[c]pyridine-2(3H)-carboxylate 36 (20 mg, yield 16.5%) as a white solid.

MS m/z (ESI): 330.3 [M+1]

$^1$H NMR (400 MHz, CDCl$_3$): δ 10.57 (s, 1H), 8.24 (s, 1H), 7.05 (s, 1H), 6.56 (s, 1H), 5.38-5.39 (m, 1H), 3.70 (s, 3H), 3.61-3.62 (m, 2H), 3.39-3.40 (m, 1H), 3.23-3.27 (m, 4H), 2.20-2.23 (m, 2H), 2.05-2.09 (m, 1H), 1.83-1.84 (m, 2H), 1.52-1.57 (m, 3H)

Example 37

2-Hydroxy-1-((4aS,7aR)-6-(methyl(7H-pyrrolo[2,3-d]pyrimidin-4-yl)amino) hexahydro-1H-cyclopenta [c]pyridin-2(3H,4H,4aH,5H,6H,7H,7aH)-yl)ethanone

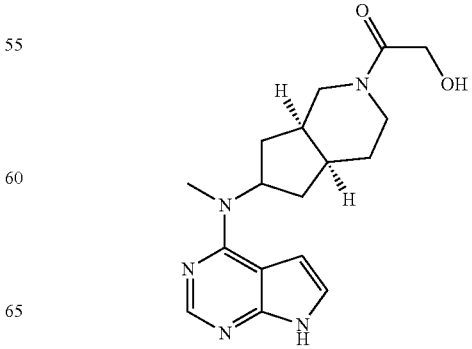

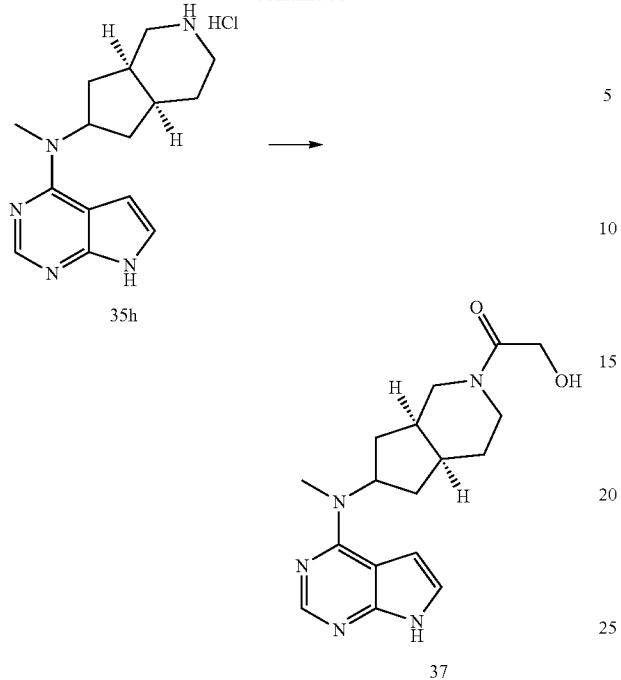

35h

37

N-Methyl-N-((4aS,7aR)-octahydro-1H-cyclopenta[c]pyridin-6-yl)-7H-pyrrolo[2,3-d]pyrimidin-4-amine hydrochloride 35h (80 mg, 0.30 mmol) was dissolved in 5 mL of N,N-dimethylformamide, followed by addition of 2-glycolic acid (22 mg, 0.30 mmol), triethylamine (89 mg, 0.89 mmol), 1-ethyl-3-(3-dimethylaminopropyl) carbodiimide hydrochloride (84 mg, 0.44 mmol), and 1-hydroxybenzotriazole (60 mg, 0.44 mmol). After reacting for 12 hours, the reaction mixture was concentrated under reduced pressure and purified by preparative HPLC to obtain the title product 2-hydroxy-1-((4aS,7aR)-6-(methyl(7H-pyrrolo[2,3-d]pyrimidin-4-yl)amino)hexahydro-1H-cyclopenta[c]pyridin-2(3H,4H,4aH,5H,6H,7H,7aH)-yl)ethanone 37 (8 mg, yield 8.2%) as a white solid.

MS m/z (ESI): 330.2 [M+1]

$^1$H NMR (400 MHz, CDCl$_3$): δ 11.57 (s, 1H), 8.30 (s, 1H), 7.07 (s, 1H), 6.56 (s, 1H), 5.40-5.44 (m, 1H), 4.14-4.18 (m, 1H), 3.34-3.39 (m, 2H), 3.27 (s, 3H), 3.18-3.22 (m, 1H), 2.30-2.32 (m, 2H), 1.95-2.13 (m, 3H), 1.66-1.68 (m, 1H), 1.52-1.57 (m, 2H)

Example 38

(4aS,7aR)—N-(3-Methoxy-1,2,4-thiadiazol-5-yl)-6-(methyl(7H-pyrrolo[2,3-d]pyrimidin-4-yl)amino)hexahydro-1H-cyclopenta[c]pyridine-2(3H)-carboxamide

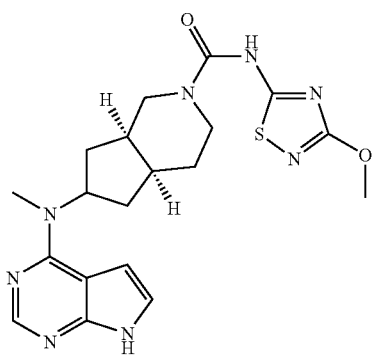

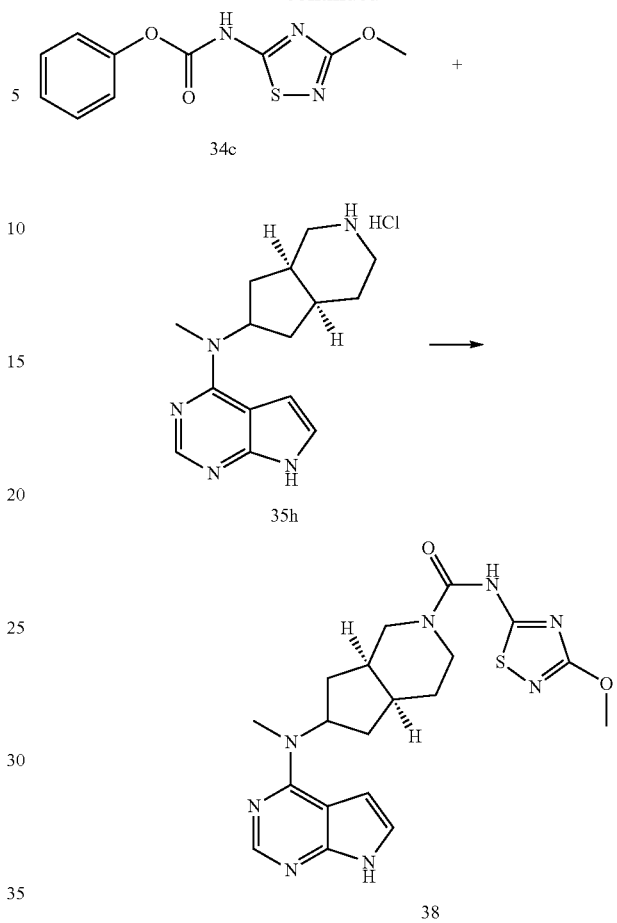

34c

35h

38

N-Methyl-N-((4aS,7aR)-octahydro-1H-cyclopenta[c]pyridin-6-yl)-7H-pyrrolo[2,3-d]pyrimidin-4-amine hydrochloride 35h (80 mg, 0.30 mmol) was dissolved in 20 mL of tetrahydrofuran, followed by addition of phenyl(3-methoxy-1,2,4-thiadiazol-5-yl)carbamate 34c (75 mg, 0.30 mmol) and triethylamine (0.06 mL, 0.44 mmol). After reacting for 3 hours at 60° C., 30 mL of H$_2$O were added to the reaction mixture. The reaction mixture was extracted with dichloromethane (30 mL×2). The organic phases were combined, washed with saturated sodium chloride solution (20 mL×2), dried over anhydrous sodium sulfate, and filtered. The filtrate was concentrated under reduced pressure and purified by silica gel column chromatography with elution system A to obtain the title product (4aS,7aR)—N-(3-methoxy-1,2,4-thiadiazol-5-yl)-6-(methyl(7H-pyrrolo[2,3-d]pyrimidin-4-yl)amino)hexahydro-1H-cyclopenta[c]pyridine-2(3H)-carboxamide 38 (30 mg, yield 23.8%) as a white solid.

MS m/z (ESI): 429.3 [M+1]

$^1$H NMR (400 MHz, DMSO-d$_6$): δ 11.63 (s, 1H), 11.61 (s, 1H), 8.08 (s, 1H), 7.12 (d, 1H), 6.58 (d, 1H), 5.26-4.30 (m, 1H), 3.84 (s, 3H), 3.69-3.73 (m, 1H), 3.59-3.64 (m, 1H), 3.38-3.40 (m, 2H), 3.17 (s, 3H), 2.20-2.23 (m, 2H), 1.82-1.92 (m, 3H), 1.60-1.65 (m, 2H), 1.40-1.48 (m, 1H)

Example 39

3-((4aS,7aR)-6-(Methyl(7H-pyrrolo[2,3-d]pyrimidin-4-yl)amino)hexahydro-1H-cyclopenta[c]pyridin-2(3H,4H,4aH,5H,6H,7H,7aH)-yl)-3-oxopropanenitrile

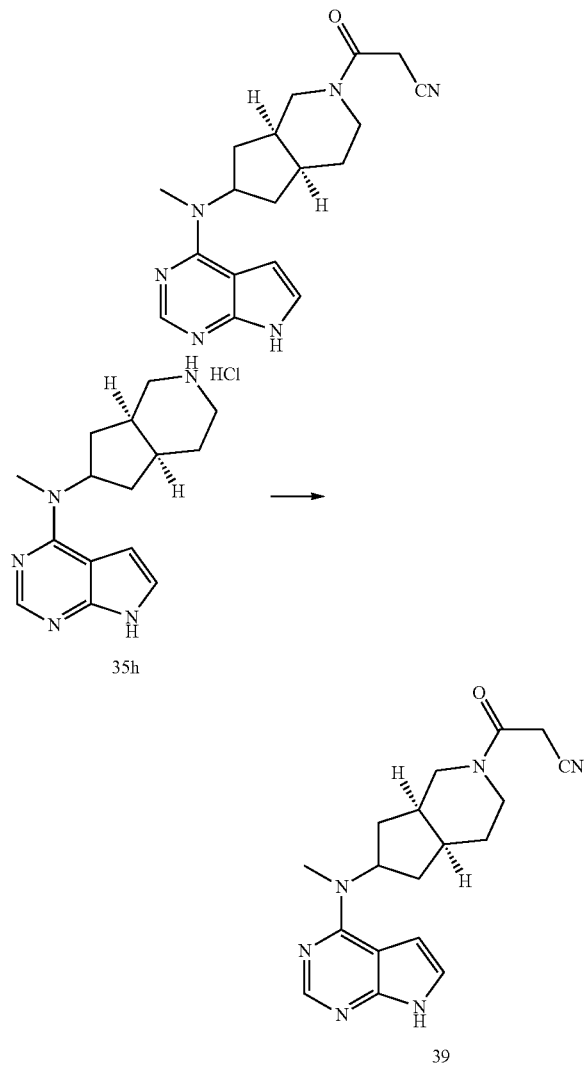

N-Methyl-N-((4aS,7aR)-octahydro-1H-cyclopenta[c]pyridin-6-yl)-7H-pyrrolo[2,3-d]pyrimidin-4-amine hydrochloride 35h (100 mg, 0.37 mmol) was dissolved in 5 mL of n-butanol, followed by addition of 2-ethyl cyanoacetate (83 mg, 0.74 mmol) and DBU (113 mg, 0.74 mmol). After reacting for 15 hours at 50° C., the reaction mixture was concentrated under reduced pressure, extracted with ethyl acetate (20 mL×2), and washed with saturated sodium chloride solution (15 mL×2). The organic phases were combined, dried over anhydrous sodium sulfate, and filtered. The filtrate was concentrated under reduced pressure, and purified by preparative HPLC to obtain the title product 3-((4aS,7aR)-6-(methyl(7H-pyrrolo[2,3-d]pyrimidin-4-yl)amino) hexahydro-1H-cyclopenta[c]pyridin-2(3H,4H,4aH, 5H,6H,7H,7aH)-yl)-3-oxopropanenitrile 39 (35 mg, yield 28.0%) as a light pink solid.

MS m/z (ESI): 339.3 [M+1]

$^1$H NMR (400 MHz, DMSO-d$_6$): δ 11.6 (s, 1H), 8.09 (s, 1H), 7.13 (s, 1H), 6.58 (s, 1H), 5.27-5.29 (m, 1H), 4.01-4.09 (m, 2H), 3.60-3.63 (m, 1H), 3.43-3.48 (m, 2H), 3.18 (s, 3H), 2.08-2.10 (m, 2H), 1.81-1.88 (m, 3H), 1.23-1.43 (m, 4H)

Examples 40 and 41

(4aR,6R,7aR)-6-(Methyl(7H-pyrrolo[2,3-d]pyrimidin-4-yl)amino) hexahydro-1H-cyclopenta[c]pyridin-3(2H)-one (4aR,6S,7aR)-6-(Methyl(7H-pyrrolo[2,3-d]pyrimidin-4-yl)amino) hexahydro-1H-cyclopenta[c]pyridin-3(2H)-one

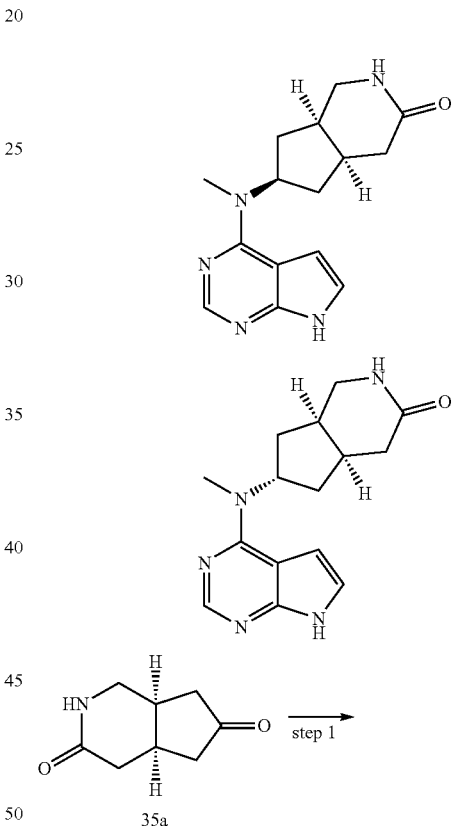

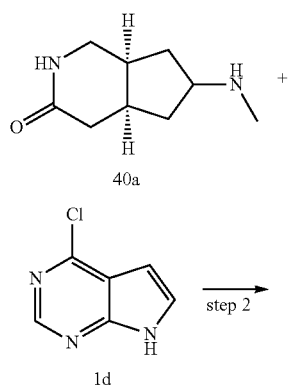

-continued

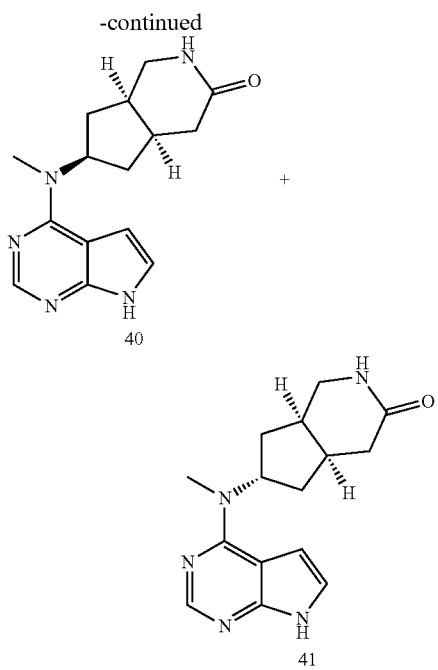

Step 1

(4aS,7aS)-6-(Methylamino)hexahydro-1H-cyclopenta[c]pyridin-3(2H)-one (4aS,7aS)-Tetrahydro-1H-cyclopenta[c]pyridin-3,6(2H,4H)-dione 35a (1 g, 6.54 mmol, prepared by well known methods (Tetrahedron: Asymmetry, 1997, 8 (17), 2893-2904) and methylamine hydrochloride (200 mg, 6.54 mmol) were dissolved in 20 mL of methanol, followed by addition of two drops of acetic acid. After stirring and reacting for 1 hour, sodium cyanoborohydride (600 mg, 9.68 mmol) was added to the reaction mixture. After reacting for 12 hours, the reaction mixture was filtered, and concentrated under reduced pressure to obtain the title product (4aS,7aS)-6-(methylamino)hexahydro-1H-cyclopenta[c]pyridin-3(2H)-one 40a (1 g) as a brown grease, which was used directly in the next step without further purification.

MS m/z (ESI): 169.2 [M+1]

Step 2

(4aR,6R,7aR)-6-(Methyl(7H-pyrrolo[2,3-d]pyrimidin-4-yl)amino) hexahydro-1H-cyclopenta[c]pyridin-3(2H)-one (4aR,6S,7aR)-6-(Methyl(7H-pyrrolo[2,3-d]pyrimidin-4-yl)amino) hexahydro-1H-cyclopenta[c]pyridin-3(2H)-one 4-Chloro-7H-pyrrolo[2,3-d]pyrimidine 1d (910 g, 5.95 mmol) was dissolved in 30 mL of $H_2O$, followed by addition of (4aS,7aS)-6-(methylamino)hexahydro-1H-cyclopenta[c]pyridin-3(2H)-one 40a (1 g, 5.95 mmol) and potassium carbonate (1.6 g, 11.59 mmol). After reacting for 12 hours at 100° C., the reaction mixture was concentrated under reduced pressure, mixed with 50 mL of $H_2O$, and extracted with ethyl acetate (30 mL×3). The organic phases were combined, dried over anhydrous sodium sulfate, and filtered. The filtrate was concentrated under reduced pressure, and purified by chiral preparative HPLC to obtain the title products (4aR,6R,7aR)-6-(methyl (7H-pyrrolo[2,3-d]pyrimidin-4-yl)amino)hexahydro-1H-cyclopenta[c]pyridin-3(2H)-one 40 (15 mg, yield 0.9%) as a white solid and (4aR,6S,7aR)-6-(methyl(7H-pyrrolo[2,3-d]pyrimidin-4-yl)amino)hexahydro-1H-cyclopenta[c]pyridin-3(2H)-one 41 (15 mg, yield 0.9%) as a white solid.

MS m/z (ESI): 286.4 [M+1]

$^1$H NMR (400 MHz, CDCl$_3$): δ 11.37 (s, 1H), 8.28 (s, 1H), 7.06 (s, 1H), 6.98 (s, 1H), 6.53 (s, 1H), 5.24-5.27 (m, 1H), 3.41-3.44 (m, 1H), 3.21 (s, 3H), 3.10-3.13 (m, 1H), 2.56-2.58 (m, 1H), 2.50-2.52 (m, 2H), 2.30-2.31 (m, 1H), 2.07-2.09 (m, 2H), 1.50-1.64 (m, 2H)

$^1$H NMR (400 MHz, CDCl$_3$): δ 11.37 (s, 1H), 8.28 (s, 1H), 7.06 (s, 1H), 6.98 (s, 1H), 6.53 (s, 1H), 5.24-5.27 (m, 1H), 3.41-3.44 (m, 1H), 3.21 (s, 3H), 3.10-3.13 (m, 1H), 2.56-2.58 (m, 1H), 2.50-2.52 (m, 2H), 2.30-2.31 (m, 1H), 2.07-2.09 (m, 2H), 1.50-1.64 (m, 2H)

Example 42

(4aR,6R,7aR)-2-Methyl-6-(methyl(7H-pyrrolo[2,3-d]pyrimidin-4-yl)amino)hexahydro-1H-cyclopenta[c]pyridin-3(2H)-one

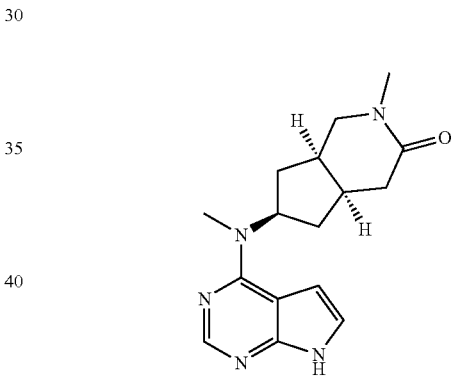

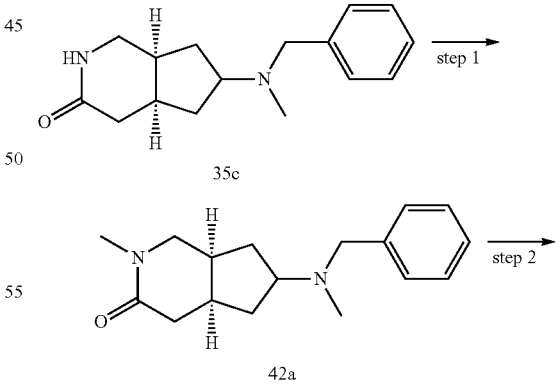

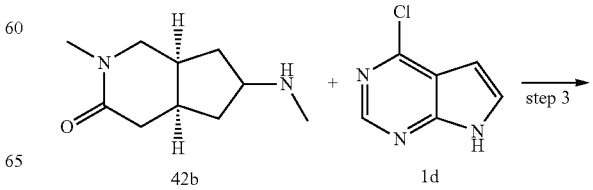

-continued

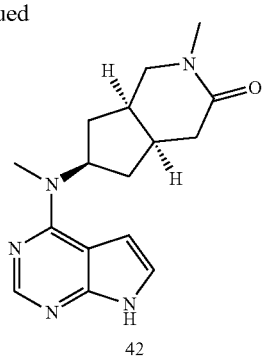

42

Step 1

(4aS,7aS)-6-(Benzyl(methyl)amino)-2-methylhexahydro-1H-cyclopenta[c]pyridin-3(2H)-one In an ice bath, (4aS,7aS)-6-(benzyl(methyl)amino)hexahydro-1H-cyclopenta[c]pyridin-3(2H)-one 35c (400 mg, 1.55 mmol) was dissolved in 10 mL of tetrahydrofuran, followed by addition of sodium hydride (56 mg, 2.33 mmol). After stirring for 30 minutes, the reaction mixture was mixed with methyl iodide (241 mg, 1.71 mmol). After reacting for 12 hours, the reaction mixture was mixed with 50 mL of $H_2O$ and extracted with ethyl acetate (20 mL×2). The organic phases were combined, dried over anhydrous sodium sulfate, and filtered. The filtrate was concentrated under reduced pressure to obtain the crude title product (4aS,7aS)-6-(benzyl(methyl)amino)-2-methylhexahydro-1H-cyclopenta[c]pyridin-3(2H)-one 42a (500 mg) as a colourless liquid, which was used directly in the next step without further purification.

MS m/z (ESI): 273.2 [M+1]

Step 2

(4aS,7aS)-2-Methyl-6-(methylamino)hexahydro-1H-cyclopenta[c]pyridin-3(2H)-one (4aS,7aS)-6-(Benzyl(methyl)amino)-2-methylhexahydro-1H-cyclopenta[c]pyridin-3(2H)-one 42a (500 g, 1.84 mmol) was dissolved in 10 mL of methanol, followed by addition of palladium hydroxide on carbon (125 mg, 25%). After the reactor was purged with hydrogen for three times, the reaction mixture was stirred for 6 hours, and then filtered, washed with methanol (10 mL), and concentrated under reduced pressure to obtain the crude title product (4aS,7aS)-2-methyl-6-(methylamino)hexahydro-1H-cyclopenta[c]pyridin-3(2H)-one 42b (300 mg) as a colourless grease, which was used directly in the next step without further purification.

MS m/z (ESI): 183.2 [M+1]

Step 3

(4aR,6R,7aR)-2-Methyl-6-(methyl(7H-pyrrolo[2,3-d]pyrimidin-4-yl)amino)hexahydro-1 H-cyclopenta[c]pyridin-3(2H)-one 4-Chloro-7H-pyrrolo[2,3-d]pyrimidine 1d (168 mg, 1.10 mmol) was dissolved in 20 mL of $H_2O$, followed by addition of (4aS,7aS)-2-methyl-6-(methylamino)hexahydro-1H-cyclopenta[c]pyridin-3(2H)-one 42b (200 mg, 1.10 mmol) and potassium carbonate (303 mg, 2.20 mmol). After reacting for 48 hours at 100° C., the reaction mixture was mixed with 30 mL of $H_2O$, and extracted with ethyl acetate (20 mL×3). The organic phases were combined, dried over anhydrous sodium sulfate, and filtered. The filtrate was concentrated under reduced pressure and purified by preparative HPLC to obtain the title product (4aR,6R,7aR)-2-methyl-6-(methyl(7H-pyrrolo[2,3-d]pyrimidin-4-yl)amino)hexahydro-1H-cyclopenta[c]pyridin-3(2H)-one 42 (8 mg, yield 5%) as a white solid.

MS m/z (ESI): 300.3 [M+1]

$^1$H NMR (400 MHz, CDCl$_3$): δ 11.61 (s, 1H), 8.09 (s, 1H), 7.12 (s, 1H), 6.56 (s, 1H), 5.10-5.15 (m, 1H), 3.40-3.44 (m, 1H), 3.15-3.16 (m, 1H), 3.11 (s, 3H), 2.89 (s, 3H), 2.40-2.44 (m, 3H), 2.14-2.16 (m, 1H), 1.90-1.92 (m, 2H), 1.35-1.47 (m, 2H)

Examples 43 and 45

2-Hydroxy-1-((3aS,5R,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone 2-Hydroxy-1-((3aS,5S,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone

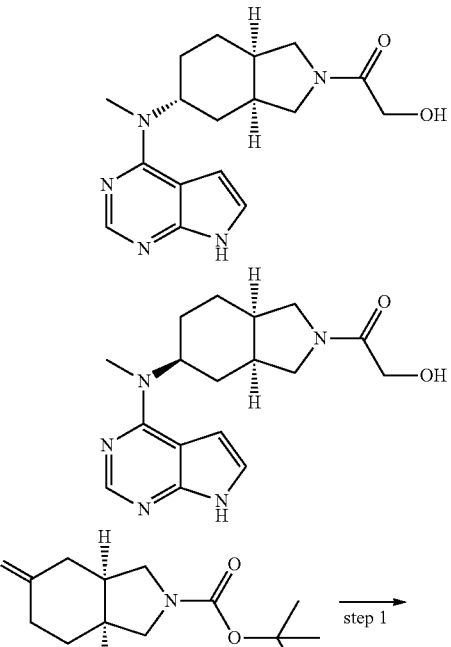

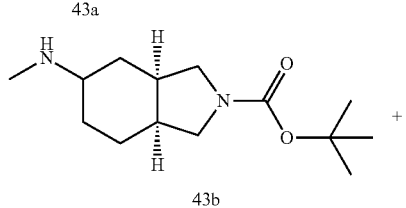

43a

43b

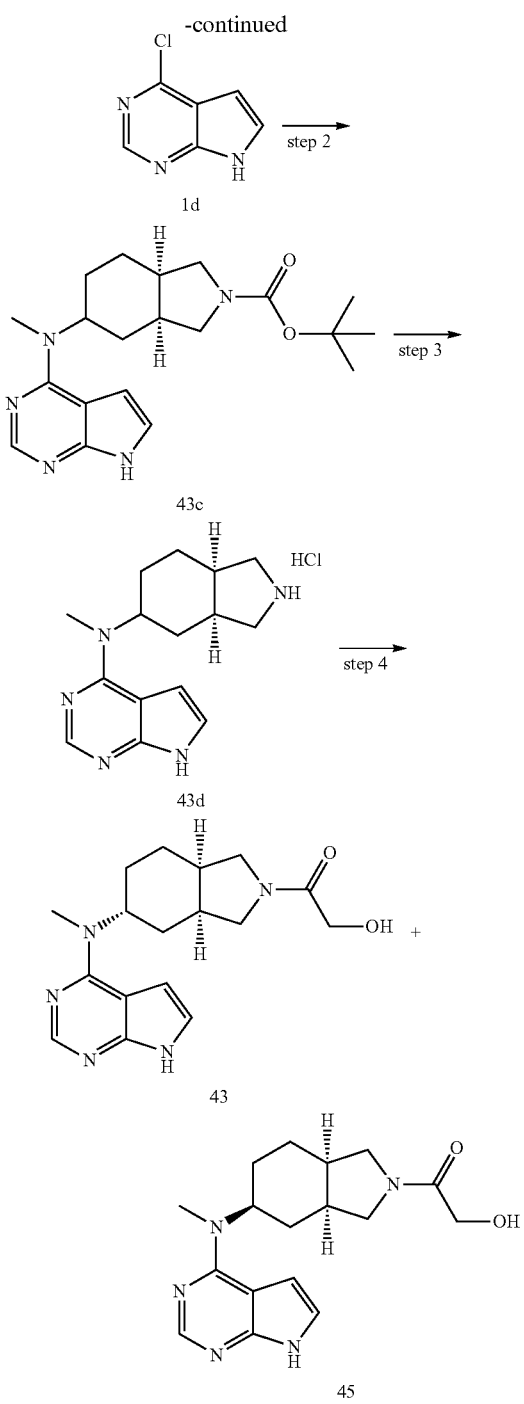

reaction mixture. After reacting for 1 hour at 70° C., the reaction mixture was mixed with 100 mL of H₂O and extracted with dichloromethane (30 mL×3). The organic phases were combined, dried over anhydrous sodium sulfate, and filtered. The filtrate was concentrated under reduced pressure to obtain the title product (3aR,7aS)-tert-butyl 5-(methylamino)hexahydro-1H-isoindole-2(3H)-carboxylate 43b (3.2 g, brown grease), which was used directly in the next step without further purification.

MS m/z (ESI): 255.2 [M+1]

Step 2

(3aS,7aR)-tert-Butyl 5-(methyl(7H-pyrrolo[2,3-d]pyrimidin-4-yl)amino)hexahydro-1H-isoindole-2(3H)-carboxylate 4-Chloro-7H-pyrrolo[2,3-d]pyrimidine 1d (1.93 g, 12.58 mmol) was dissolved in 50 mL of n-butanol, followed by addition of (3aR,7aS)-tert-butyl 5-(methylamino)hexahydro-1H-isoindole-2(3H)-carboxylate 43b (3.20 g, 12.58 mmol) and potassium carbonate (3.47 g, 25.16 mmol). After reacting for 12 hours at 110° C., the reaction mixture was mixed with 100 mL of H₂O, and extracted with ethyl acetate (100 mL×2). The organic phases were combined, dried over anhydrous sodium sulfate, and filtered. The filtrate was concentrated under reduced pressure, and purified by silica gel column chromatography with elution system A to obtain the title product (3aS,7aR)-tert-butyl 5-(methyl(7H-pyrrolo[2,3-d]pyrimidin-4-yl)amino)hexahydro-1H-isoindole-2(3H)-carboxylate 43c (2.5 g, yield 53.2%) as a white solid.

MS m/z (ESI): 372.2 [M+1]

Step 3

N-Methyl-N-((3aS,7aR)-octahydro-1H-isoindol-5-yl)-7H-pyrrolo[2,3-d]pyrimidin-4-amine hydrochloride (3aS,7aR)-tert-Butyl 5-(methyl(7H-pyrrolo[2,3-d]pyrimidin-4-yl)amino) hexahydro-1H-isoindole-2(3H)-carboxylate 43c (2 g, 5.38 mmol) was dissolved in 15 mL of a solution of 6 M hydrogen chloride in methanol. After reacting for 12 hours, the reaction mixture was concentrated under reduced pressure to obtain the title product N-methyl-N-((3aS,7aR)-octahydro-1H-isoindol-5-yl)-7H-pyrrolo[2,3-d]pyrimidin-4-amine hydrochloride 43d (1.1 g, white solid), which was used directly in the next step without further purification.

MS m/z (ESI): 272.3 [M+1]

Step 4

2-Hydroxy-1-((3aS,5R,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone
2-Hydroxy-1-((3aS,5S,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone N-Methyl-N-((3aS,7aR)-octahydro-1H-isoindol-5-yl)-7H-pyrrolo[2,3-d]pyrimidin-4-amine hydrochloride 43d (100 mg, 0.37 mmol) was dissolved in 10 mL of N,N-dimethylformamide, followed by addition of 2-glycolic acid (33 mg, 0.44 mmol), triethylamine (120 mg, 1.11 mmol) and O-(7-azabenzotriazol-1-yl)-N,N,N',N'-tetramethylformamidinium hexafluorophosphate (0.21 g, 0.55 mmol). After Step 1

(3aR,7aS)-tert-Butyl 5-(methylamino)hexahydro-1H-isoindole-2(3H)-carboxylate (3aR,7aS)-tert-Butyl 5-oxohexahydro-1H-isoindole-2(3H)-carboxylate 43a (3.77 g, 15.75 mmol, prepared by a well known method (*Journal of the American Chemical Society*, 2000, 122(44), 10743-10753) and methylamine alcohol solution (0.73 g, 23.63 mmol) were dissolved in 50 mL of methanol. After stirring for 2 hours at 70° C., sodium cyanoborohydride (2 g, 31.51 mmol) was added to the reacting for 12 hours, the reaction mixture was added with 30 mL of H₂O, and extracted with ethyl acetate (20 mL×3). The organic phases were combined, dried over anhydrous sodium sulfate, and filtered. The filtrate was concentrated under reduced pressure, and purified by silica gel column chromatography with elution system A to obtain the title products 2-hydroxy-1-((3aS,5R,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone 43 (10 mg, yield 8.3%) as a white solid and 2-hydroxy-1-((3aS,5S,7aR)-5-(methyl(7H-pyrrolo[2,3-d]pyrimidin-4-yl)amino)hexahydro-1H-isoindol-2(3H,3aH,4H,5H,6H,7H,7aH)-yl)ethanone 45 (5 mg, yield 4.2%) as a white solid.

MS m/z (ESI): 330.3 [M+1]

¹H NMR (400 MHz, CD₃OD-d₄): δ 8.12 (s, 1H), 7.06 (d, 1H), 6.58 (d, 1H), 4.96-4.99 (m, 1H), 4.60-4.64 (m, 1H), 4.18-4.24 (m, 2H), 3.52-3.57 (m, 1H), 3.48 (s, 3H), 3.26 (d, 2H), 2.72-2.74 (m, 1H), 2.16-2.26 (m, 1H), 1.96-1.98 (m, 1H), 1.83-1.87 (m, 2H), 1.69-1.72 (m, 1H), 1.44-1.52 (m, 1H), 1.23-1.33 (m, 3H)

¹H NMR (400 MHz, CD₃OD-d₄): δ 8.10 (s, 1H), 7.11 (d, 1H), 6.66 (d, 1H), 4.71-4.75 (m, 1H), 4.58-4.62 (m, 1H), 4.10-4.22 (m, 2H), 3.43-3.57 (m, 1H), 3.48 (s, 3H), 3.26 (d, 2H), 2.50-2.54 (m, 1H), 2.44-2.48 (m, 1H), 1.96-1.98 (m, 2H), 1.58-1.68 (m, 2H), 1.28-1.33 (m, 4H)

Example 44

3-((3aS,7aR)-5-(Methyl(7H-pyrrolo[2,3-d]pyrimidin-4-yl)amino)hexahydro-1H-isoindol-2(3H,3aH,4H,5H,6H,7H,7aH)-yl-3-oxopropanenitrile N-Methyl-N-((3aS,7aR)-octahydro-1H-isoindol-5-yl)-7H-pyrrolo[2,3-d]pyrimidin-4-amine hydrochloride 43d (110 mg, 0.41 mmol) was dissolved in 15 mL of N,N-dimethylformamide, followed by addition of 2-cyanoacetic acid (42 mg, 0.49 mmol), triethylamine (82 mg, 0.82 mmol) and O-(7-azabenzotriazol-1-yl)-N,N,N',N'-tetramethylformamidinium hexafluorophosphate (231 mg, 0.61 mmol). After stirring for 12 hours, the reaction mixture was mixed with 15 mL of H₂O, and extracted with ethyl acetate (20 mL×3). The organic phases were combined, dried over anhydrous sodium sulfate, and filtered. The filtrate was concentrated under reduced pressure, and purified by silica gel column chromatography with elution system A to obtain the title product 3-((3aS,7aR)-5-(methyl(7H-pyrrolo[2,3-d]pyrimidin-4-yl)amino)hexahydro-1H-isoindol-2(3H,3aH,4H,5H,6H,7H,7aH)-yl)-3-oxopropanenitrile 44 (13 mg, yield 9.5%) as a white solid.

MS m/z (ESI): 339.3 [M+1]

¹H NMR (400 MHz, DMSO-d₆): δ 10.68 (s, 1H), 9.01 (s, 1H), 7.79 (d, 1H), 7.30 (d, 1H), 5.65-4.69 (m, 1H), 4.17-4.43 (m, 6H), 4.02 (s, 3H), 3.31-3.34 (m, 1H), 3.25-3.28 (m, 1H), 2.61-2.71 (m, 2H), 2.24-2.32 (m, 2H), 1.98-2.05 (m, 2H)

Example 46

2-Hydroxy-1-((4aS,8aR)-6-(methyl(7H-pyrrolo[2,3-d]pyrimidin-4-yl)amino)octahydroisoquinolin-2(1H)-yl)ethanone

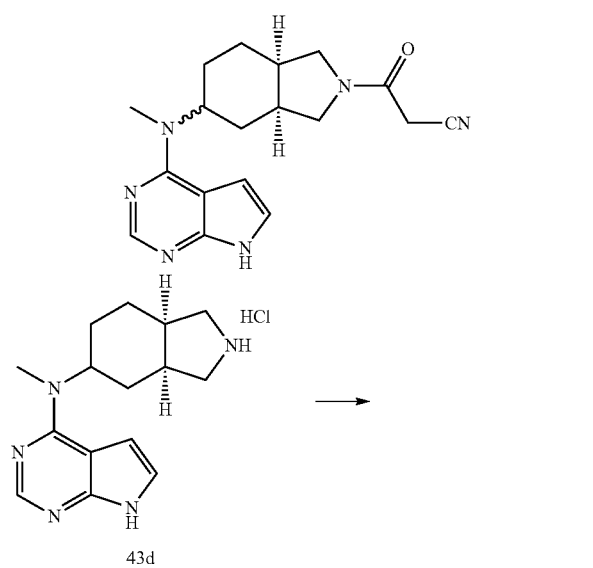

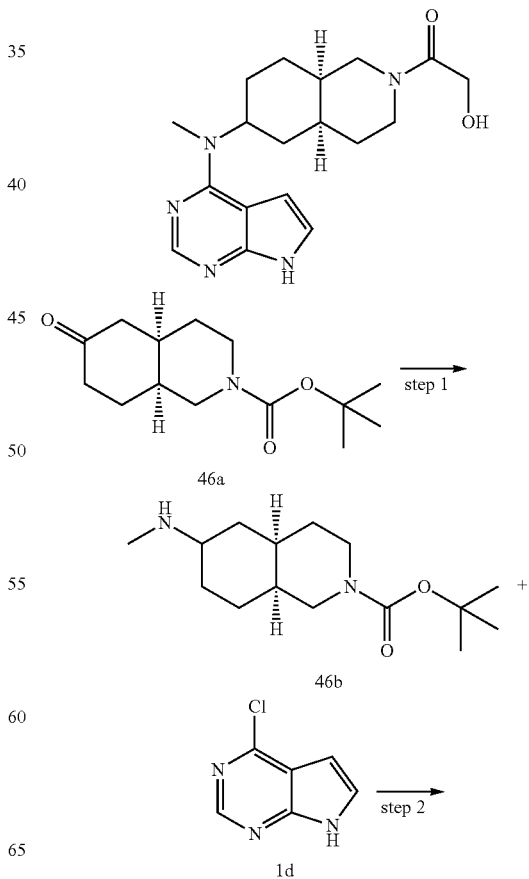

-continued

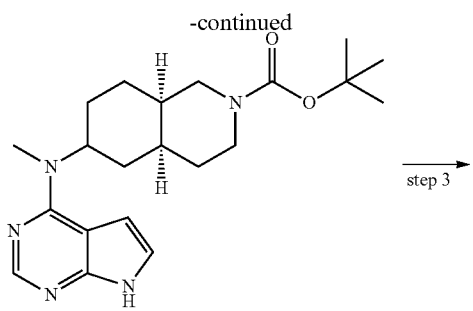

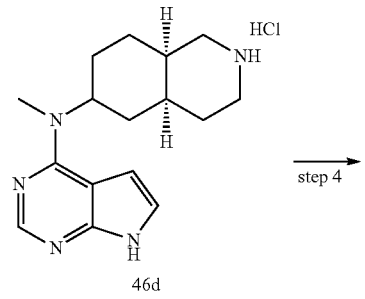

46d

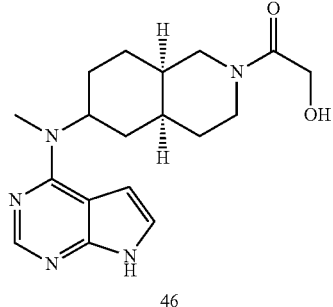

46

Step 1

(4aR,8aS)-tert-Butyl 6-(methylamino)octahydroisoquinoline-2(1H)-carboxylate (4aR,8aS)-tert-Butyl 6-oxooctahydroisoquinoline-2(1H)-carboxylate 46a (2.50 g, 9.87 mmol, prepared by a well known method (*Journal of the American Chemical Society, Perkin Transactions 1: Organic and Bio-Organic Chemistry* (1972-1999), 1995, 20, 2535-2542) and methylamine alcohol solution (0.92 g, 29.61 mmol) were dissolved in 50 mL of methanol. After stirring for 2 hours at 70° C., sodium cyanoborohydride (1.24 g, 19.74 mmol) was added to the reaction mixture. After reacting for 2 hours at 70° C., the reaction mixture was mixed with 50 mL of H$_2$O, and extracted with dichloromethane (50 mL×3). The organic phases were combined, dried over anhydrous sodium sulfate, and filtered. The filtrate was concentrated under reduced pressure to obtain the crude title product (4aR,8aS)-tert-butyl 6-(methylamino)octahydroisoquinoline-2(1H)-carboxylate 46b (2 g, brown grease), which was used directly in the next step without further purification.

Step 2

(4aS,8aR)-tert-Butyl 6-(methyl(7H-pyrrolo[2,3-d]pyrimidin-4-yl)amino) octahydroisoquinoline-2(1H)-carboxylate 4-Chloro-7H-pyrrolo[2,3-d]pyrimidine 1d (1.14 g, 7.45 mmol) was dissolved in 50 mL of 1,4-dioxane, followed by addition of (4aR,8aS)-tert-butyl 6-(methylamino)octahydroisoquinoline-2(1H)-carboxylate 46b (2 g, 7.45 mmol) and potassium carbonate (2 g, 14.90 mmol). After reacting for 24 hours at 100° C., the reaction mixture was mixed with 100 mL of H$_2$O and extracted with ethyl acetate (100 mL×3). The organic phases were combined, dried over anhydrous sodium sulfate, and filtered. The filtrate was concentrated under reduced pressure, and purified by silica gel column chromatography with elution system A to obtain the title product (4aS,8aR)-tert-butyl 6-(methyl(7H-pyrrolo[2,3-d]pyrimidin-4-yl)amino) octahydroisoquinoline-2(1H)-carboxylate 46c (1.4 g, yield 48.3%) as an off-white solid.

MS m/z (ESI): 386.0 [M+1]

Step 3

(4aS,8aR)—N-Methyl-N-(7H-pyrrolo[2,3-d]pyrimidin-4-yl) decahydroisoquinolin-6-amine hydrochloride (4aS,8aR)-tert-Butyl 6-(methyl(7H-pyrrolo[2,3-d]pyrimidin-4-yl)amino) octahydroisoquinoline-2(1H)-carboxylate 46c (300 mg, 0.78 mmol) was dissolved in 15 mL of a solution of 6 M hydrogen chloride in methanol. After reacting for 12 hours, the reaction mixture was concentrated under reduced pressure to obtain the crude title product (4aS,8aR)—N-methyl-N-(7H-pyrrolo[2,3-d]pyrimidin-4-yl) decahydroisoquinolin-6-amine hydrochloride 46d (220 mg, off-white solid), which was used directly in the next step without further purification.

MS m/z (ESI): 286.2 [M+1]

Step 4

2-Hydroxy-1-((4aS,8aR)-6-(methyl(7H-pyrrolo[2,3-d]pyrimidin-4-yl)amino)octahydroisoquinolin-2(1H)-yl)ethanone ((4aS,8aR)—N-Methyl-N-(7H-pyrrolo[2,3-d]pyrimidin-4-yl)decahydroisoquinolin-6-amine hydrochloride 46d (100 mg, 0.35 mmol) was dissolved in 10 mL of dichloromethane, followed by addition of glycolic acid (32 mg, 0.42 mmol), triethylamine (106 mg, 1.05 mmol), 1-ethyl-3-(3-dimethylaminopropyl)carbodiimide hydrochloride (100 mg, 0.53 mmol), and 1-hydroxybenzotrizole (69 mg, 0.53 mmol). After reacting for 12 hours, the reaction mixture was mixed with 30 mL of H$_2$O, and extracted with dichloromethane (30 mL×2). The organic phases were combined, dried over anhydrous sodium sulfate, and filtered. The filtrate was concentrated under reduced pressure, and purified by thin layer chromatography with elution system A to obtain the title product 2-hydroxy-1-((4aS,8aR)-6-(methyl(7H-pyrrolo[2,3-d]pyrimidin-4-yl)amino)octahydroisoquinolin-2(1H)-yl)ethanone 46 (15 mg, yield 12.5%) as a white solid.

MS m/z (ESI): 344.2 [M+1]

$^1$H NMR (400 MHz, CDCl$_3$): δ 10.87 (s, 1H), 8.28 (s, 1H), 7.06 (d, 1H), 6.55 (d, 1H), 4.90-4.95 (m, 1H), 4.18 (s, 2H), 3.48-3.51 (m, 1H), 3.30 (s, 3H), 3.12-3.32 (m, 4H), 1.82-1.85 (m, 2H), 1.70-1.80 (m, 2H), 1.58-1.61 (m, 2H), 1.21-1.29 (m, 4H)

Example 47

1-((3aS,4R,5S,6aS)-4-Methyl-5-(methyl(7H-pyrrolo[2,3-d]pyrimidin-4-yl)amino)-3,3a,4,5,6,6a-hexahydro-1H-cyclopenta[c]pyrrol-2-yl)-2-hydroxy-ethanone

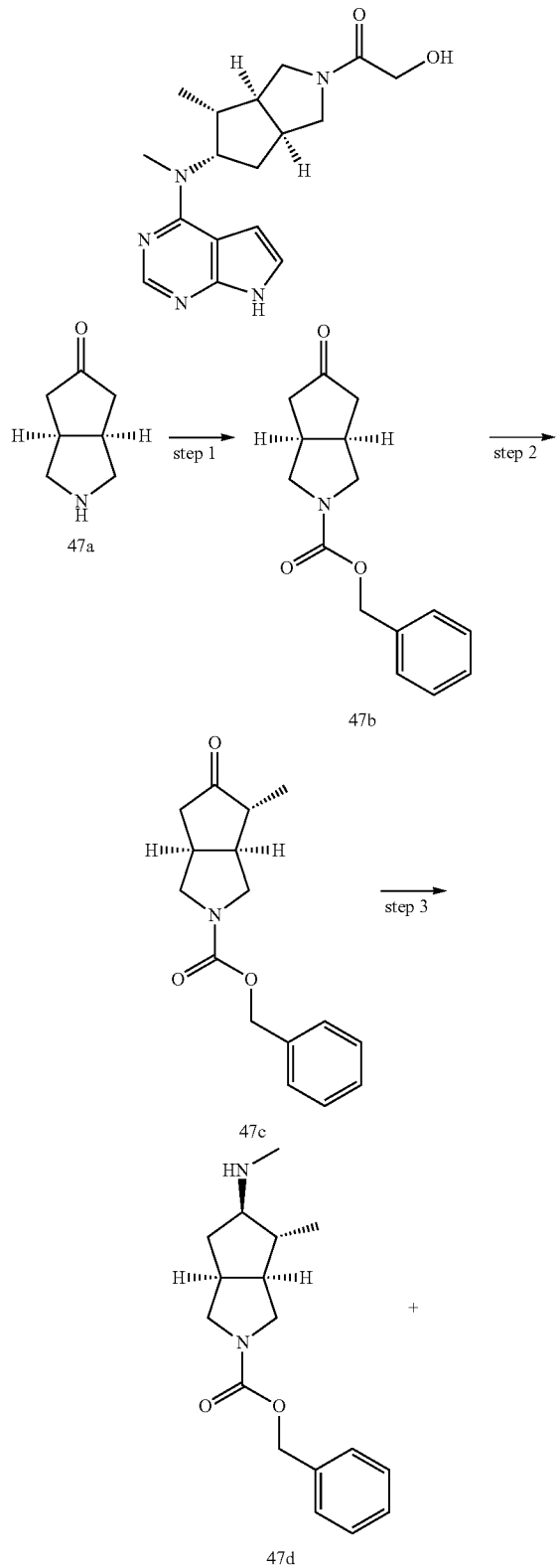

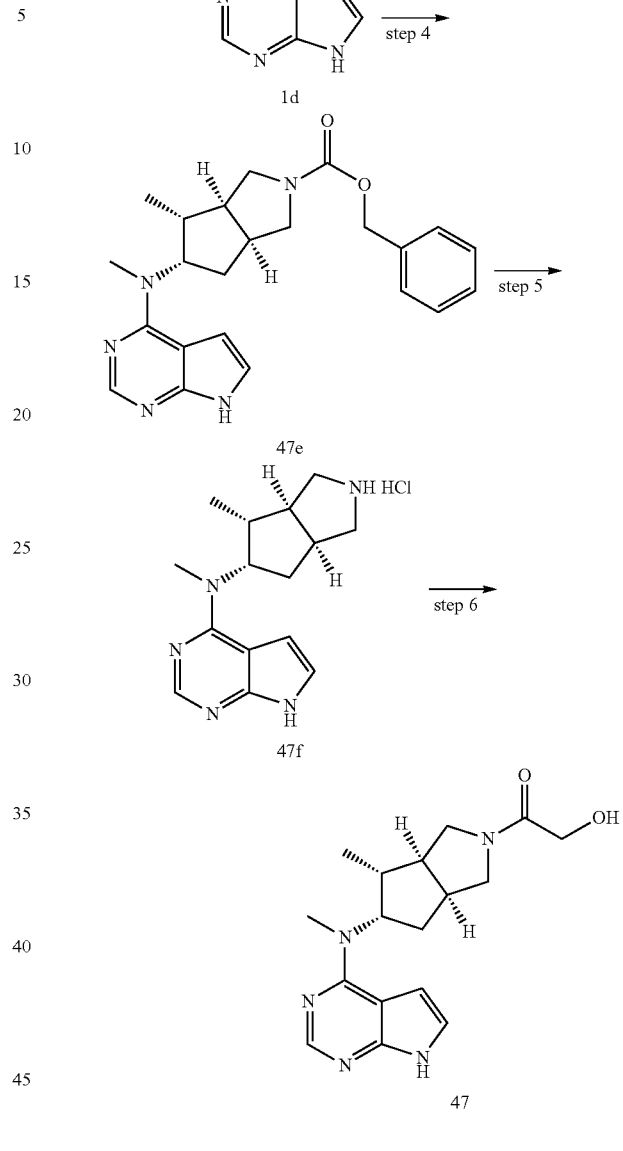

Step 1

(3aR,6aS)-Benzyl 5-oxohexahydrocyclopenta[c]pyrrole-2(1H)-carboxylate (3aR,6aS)-Hexahydrocyclopenta[c]pyrrol-5(1H)-one 47a (16.80 g, 0.13 mol, prepared by a well known method, see European Patent EP2246347) was dissolved in 200 mL of dichloromethane in an ice bath, followed by addition of triethylamine (16.2 mL, 0.16 mol) and dropwise addition of benzyl chloroformate (25.22 g, 0.15 mol). The reaction mixture was warmed up to room temperature. After reacting for 3 hours, the reaction mixture was mixed with 200 mL of H₂O, and extracted with dichloromethane (100 mL×2). The organic phases were combined, washed with saturated sodium bicarbonate (50 mL), saturated sodium chloride solution (50 mL), dried over anhydrous sodium sulfate, and filtered. The filtrate was concentrated under reduced pressure, and purified by silica gel column chromatography with elution system B to obtain the title product (3aR,6aS)-benzyl 5-oxohexahydrocyclopenta[c]pyrrole-2(1H)-carboxylate 47b (18.5 g, yield 54.9%) as a white solid.

MS m/z (ESI): 260.1 [M+1]

Step 2

(3aS,4R,6aS)-Benzyl 4-methyl-5-oxohexahydrocyclopenta[c]pyrrole-2(1H)-carboxylate (3aR,6aS)-Benzyl 5-oxohexahydrocyclopenta[c]pyrrole-2(1H)-carboxylate 47b (5 g, 19.28 mmol) was dissolved in 70 mL of tetrahydrofuran at −78° C., followed by dropwise addition of lithium bis(trimethylsilyl)amide (19.7 mL, 19.67 mmol). After stirring for 1 hour at −78° C., the reaction mixture was mixed with methyl iodide (3.01 g, 21.21 mmol). The reaction mixture was warmed up to room temperature. After reacting for 2 hours, the reaction mixture was mixed with 20 mL of saturated ammonium chloride, and extracted with ethyl acetate (50 mL×2). The organic phases were combined, washed with saturated sodium chloride solution (20 mL×2), dried over anhydrous sodium sulfate, and filtered. The filtrate was concentrated under reduced pressure, and purified by silica gel column chromatography with elution system B to obtain the title product (3aS,4R,6aS)-benzyl 4-methyl-5-oxohexahydrocyclopenta[c]pyrrole-2(1H)-carboxylate 47c (1.08 g, yield 20.5%) as a bright yellow slime.

MS m/z (ESI): 274.1 [M+1]

Step 3

(3aS,4R,5R,6aS)-Benzyl 4-methyl-5-(methylamino) hexahydrocyclopenta[c]pyrrole-2(1H)-carboxylate (3aS,4R,6aS)-Benzyl 4-methyl-5-oxohexahydrocyclopenta[c]pyrrole-2(1H)-carboxylate 47c (1.08 g, 3.95 mmol) was dissolved in 30 mL of methylamine alcohol solution. After stirring for 24 hours at 50° C., sodium cyanoborohydride (500 mg, 7.90 mmol) was added to the reaction mixture in batches. After reacting for 24 hours at 50° C., the reaction mixture was concentrated under reduced pressure, followed by addition of 50 mL of H$_2$O, and extracted with dichloromethane (50 mL×2). The organic phases were combined, washed with saturated sodium chloride solution (20 mL×2), dried over anhydrous sodium sulfate, and filtered. The filtrate was concentrated under reduced pressure to obtain the crude title product (3aS,4R,5R,6aS)-benzyl 4-methyl-5-(methylamino)hexahydrocyclopenta[c]pyrrole-2(1H)-carboxylate 47d (0.95 g, pale yellow solid), which was used directly in the next step without further purification.

MS m/z (ESI): 289.2 [M+1]

Step 4

(3aS,4R,5S,6aS)-Benzyl 4-methyl-5-(methyl(7H-pyrrolo[2,3-d]pyrimidin-4-yl)amino) hexahydrocyclopenta[c]pyrrole-2(1H)-carboxylate 4-Chloro-7H-pyrrolo[2,3-d]pyrimidine 1d (176 mg, 1.14 mmol) was dissolved in 15 mL of H$_2$O, followed by addition of (3aS,4R,5R,6aS)-benzyl 4-methyl-5-(methylamino)hexahydrocyclopenta[c]pyrrole-2(1H)-carboxylate 47d (300 mg, 1.04 mmol) and potassium carbonate (287 mg, 2.08 mmol). After reacting for 24 hours at 100° C., the reaction mixture was mixed with 10 mL of H$_2$O and extracted with dichloromethane (20 mL×2). The organic phases were combined, washed with saturated sodium chloride solution (10 mL×2), dried over anhydrous sodium sulfate, and filtered. The filtrate was concentrated under reduced pressure and purified by silica gel column chromatography with elution system A to obtain the title product (3aS,4R,5S,6aS)-benzyl 4-methyl-5-(methyl(7H-pyrrolo[2,3-d]pyrimidin-4-yl)amino) hexahydrocyclopenta[c]pyrrole-2(1H)-carboxylate 47e (0.21 g, yield 49.9%) as a bright yellow solid.

MS m/z (ESI): 406.3 [M+1]

Step 5

N-Methyl-N-((3aS,4R,5S,6aS)-4-methyloctahydrocyclopenta[c]pyrrol-5-yl)-7H-pyrrolo[2,3-d]pyrimidin-4-amine hydrochloride (3aS,4R,5S,6aS)-Benzyl 4-methyl-5-(methyl(7H-pyrrolo[2,3-d]pyrimidin-4-yl)amino)hexahydrocyclopenta[c]pyrrole-2(1H)-carboxylate 47e (280 mg, 0.69 mmol) was dissolved in 20 mL of methanol, followed by addition of palladium hydroxide on carbon (10 mg, 4%). After the reactor was purged with hydrogen three times, the reaction mixture was stirred for 2 hours, and then filtered, washed with methanol (10 mL), and concentrated under reduced pressure to obtain the crude title product N-methyl-N-((3aS, 4R,5S,6aS)-4-methyloctahydrocyclopenta[c]pyrrol-5-yl)-7H-pyrrolo[2,3-d]pyrimidin-4-amine hydrochloride 47f (160 mg, right yellow solid), which was used directly in the next step without further purification.

MS m/z (ESI): 272.3 [M+1]

Step 6

1-((3aS,4R,5S,6aS)-4-Methyl-5-(methyl(7H-pyrrolo[2,3-d]pyrimidin-4-yl)amino)-3,3a,4,5,6,6a-hexahydro-1H-cyclopenta[c]pyrrol-2-yl)-2-hydroxy-ethanone N-methyl-N-((3aS,4R,5S,6aS)-4-methyloctahydrocyclopenta[c]pyrrol-5-yl)-7H-pyrrolo[2,3-d]pyrimidin-4-amine hydrochloride 47f (160 mg, 0.59 mmol) was dissolved in 10 mL of N,N-dimethylformamide, followed by addition of 2-glycolic acid (54 mg, 0.71 mmol), triethylamine (119 mg, 1.18 mmol), 1-ethyl-3-(3-dimethylamino propyl) carbodiimide hydrochloride (169 mg, 0.88 mmol) and 1-hydroxybenzotriazole (119 mg, 0.88 mmol). After reacting for 15 hours, the reaction mixture was concentrated under reduced pressure, added with 20 mL water, and then extracted with dichloromethane (30 mL×2). The organic phases were combined, washed with saturated sodium chloride solution (10 mL×2), dried over anhydrous sodium sulfate, and filtered. The filtrate was concentrated under reduced pressure, and purified by chiral preparative HPLC to obtain the title product 21-((3aS,4R,5S,6aS)-4-methyl-5-(methyl(7H-pyrrolo[2,3-d]pyrimidin-4-yl)amino)-3,3a,4,5,6,6a-hexahydro-1H-cyclopenta[c]pyrrol-2-yl)-2-hydroxy-ethanone 47 (32 mg, yield 16.5%) as a white solid.

MS m/z (ESI): 330.2 [M+1]

$^1$H NMR (400 MHz, DMSO-d$_6$): δ 11.6 (s, 1H), 8.08 (s, 1H), 7.13 (s, 1H), 6.61 (s, 1H), 4.94-4.96 (m, 1H), 4.47-4.50 (m, 1H), 4.00-4.07 (m, 2H), 3.61-3.63 (m, 1H), 3.41-3.51 (m, 2H), 3.37-3.39 (m, 1H), 3.13 (s, 3H), 2.60-2.70 (m, 1H), 2.08-2.18 (m, 3H), 1.50-1.51 (m, 1H), 1.47-1.49 (m, 1H), 0.86-0.89 (m, 3H)

Example 48

(3aR,5S,6aS)—N-(3-Ethyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide

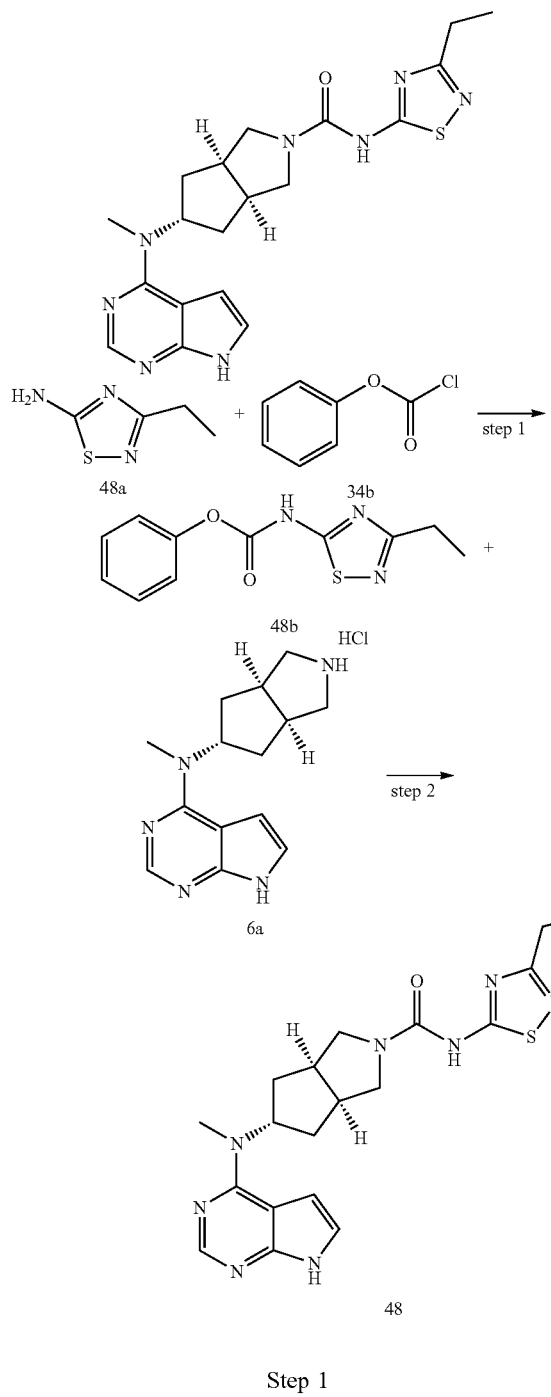

Step 1

Phenyl(3-ethyl-1,2,4-thiadiazol-5-yl)carbamate

3-Ethyl-1,2,4-thiadiazol-5-amine 48a (1.29 g, 9.98 mmol, prepared by a well known method, see *Collection of Czechoslovak Chemical Communications*, 1971, 36, 4091-4098) was dissolved in 50 mL of tetrahydrofuran in an ice bath, followed by addition of anhydrous potassium carbonate (1.79 g, 12.80 mmol), and dropwise addition of phenyl carbonochloridate 34b (1.72 g, 10.98 mmol). The reaction mixture was warmed up to room temperature. After reacting for 12 hours, the reaction mixture was filtered and concentrated under reduced pressure to obtain the crude title product phenyl (3-ethyl-1,2,4-thiadiazol-5-yl)carbamate 48b (2.14 g, yellow solid), which was used directly in the next step without further purification.

MS m/z (ESI): 250.2 [M+1]

Step 2

(3aR,5S,6aS)—N-(3-Ethyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide N-Methyl-N-((3aR,5S,6aS)-octahydrocyclopenta[c]pyrrol-5-yl)-7H-pyrrolo[2,3-d]pyrimidin-4-amine hydrochloride 6a (120 mg, 0.47 mmol) was dissolved in 50 mL of tetrahydrofuran, followed by addition of phenyl(3-ethyl-1,2,4-thiadiazol-5-yl)carbamate 48b (2.14 g, 8.58 mmol) and dropwise addition of triethylamine (2.4 mL, 17.17 mmol). After reacting for 12 hours at 60° C., the reaction mixture was mixed with 30 mL of H$_2$O and extracted with dichloromethane (50 mL×3). The organic phases were combined, washed with saturated sodium chloride solution (50×2 mL), dried over anhydrous sodium sulfate and filtered. The filtrate was concentrated under reduced pressure, and the resulting residue was purified by silica gel column chromatography with elution system A to obtain the title product (3aR,5S,6aS)—N-(3-ethyl-1,2,4-thiadiazol-5-yl)-5-(methyl(7H-pyrrolo[2,3-d]pyrimidin-4-yl)amino) hexahydrocyclopenta[c]pyrrole-2(1H)-carboxamide 48 (1.25 g, yield 81.7%) as a white solid.

MS m/z (ESI): 413.4 [M+1]

$^1$H NMR (400 MHz, DMSO-d$_6$): δ 11.60 (s, 1H), 11.52 (s, 1H), 8.08 (s, 1H), 7.07-7.02 (m, 1H), 6.55-6.5 (m, 1H), 5.56-5.38 (m, 1H), 3.78-3.60 (m, 2H), 3.48-3.36 (m, 2H), 3.16 (s, 3H), 2.90 (m, 2H), 2.74 (q, 2H), 2.10-1.94 (m, 2H), 1.8-1.7 (m, 2H), 1.25 (t, 3H)

Example 49

(3aR,5S,6aS)—N-(3-Cyclopropyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide

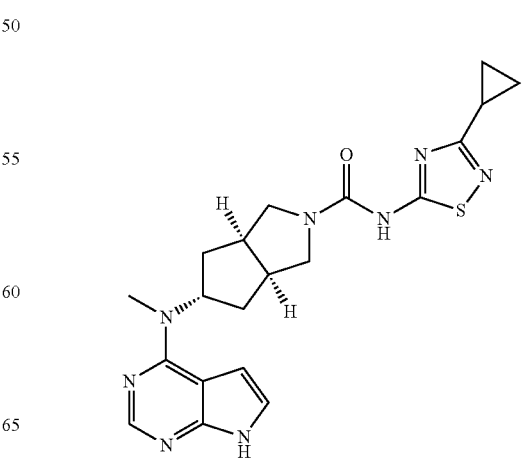

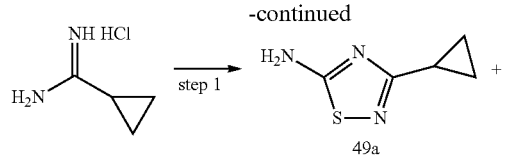

49a

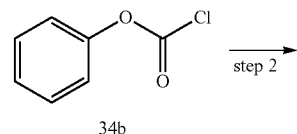

34b

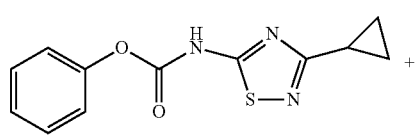

49b

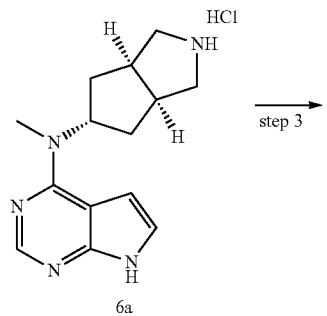

6a

49

Step 1

3-Cyclopropyl-1,2,4-thiadiazol-5-amine

Sodium thiocyanate (527 mg, 6.50 mmol) was dissolved in 20 mL of methanol and placed at −20° C., followed by addition of cyclopropylcarbamidine hydrochloride (603 mg, 5 mmol) and triethylamine (0.8 mL, 5.74 mmol). After stirring for 45 minutes, triethylamine (0.7 mL, 5.02 mmol) and 8% sodium hypochlorite solution (4.2 mL, 5 mmol) were added dropwise to the reaction mixture. After reacting for 2 hours at −20° C., the reaction mixture was warmed up to room temperature. After reacting for 12 hours, the reaction mixture was concentrated under reduced pressure, followed by addition of 35 mL of $H_2O$ and extracted with ethyl acetate (30 mL×3). The organic phases were combined, washed with saturated sodium chloride solution (50 mL), dried over anhydrous sodium sulfate, and filtered. The filtrate was concentrated under reduced pressure to obtain the crude title product 3-cyclopropyl-1,2,4-thiadiazol-5-amine 49a (243 mg, white solid), which was used directly in the next step without further purification.

MS m/z (ESI): 142.2 [M+1]

Step 2

Phenyl(3-cyclopropyl-1,2,4-thiadiazol-5-yl)carbamate

3-Cyclopropyl-1,2,4-thiadiazol-5-amine 49a (212 mg, 1.50 mmol) was dissolved in 5 mL of tetrahydrofuran in an ice bath, followed by addition of anhydrous potassium carbonate (270 mg, 1.95 mmol) and dropwise addition of phenyl carbonochloridate 34b (246 mg, 1.58 mmol), then the reaction mixture was warmed up to room temperature. After reacting for 12 hours, the reaction mixture was filtered, and concentrated under reduced pressure to obtain the crude title product phenyl(3-cyclopropyl-1,2,4-thiadiazol-5-yl)carbamate 49b (350 mg, colourless grease), which was used directly in the next step without further purification.

MS m/z (ESI): 262.3 [M+1]

Step 3

(3aR,5S,6aS)—N-(3-Cyclopropyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide N-Methyl-N-((3aR,5S,6aS)-octahydrocyclopenta[c]pyrrol-5-yl)-7H-pyrrolo[2,3-d]pyrimidin-4-amine hydrochloride 6a (344 mg, 1.34 mmol) was dissolved in 6 mL of tetrahydrofuran, followed by addition of phenyl(3-cyclopropyl-1,2,4-thiadiazol-5-yl)carbamate 49b (350 mg, 1.34 mmol) and dropwise addition of triethylamine (0.6 mL, 4.02 mmol). After reacting for 12 hours at 50° C., the reaction mixture was mixed with 20 mL of $H_2O$, and extracted with dichloromethane (20 mL×3). The organic phases were combined, washed with saturated sodium chloride solution (20×2 mL), dried over anhydrous sodium sulfate, and filtered. The filtrate was concentrated under reduced pressure, and the resulting residue was purified by thin layer chromatography with elution system A to obtain the title product (3aR,5S,6aS)—N-(3-cyclopropyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide 49 (120 mg, yield 21.1%) as a bright yellow solid.

MS m/z (ESI): 425.4 [M+1]

$^1$H NMR (400 MHz, DMSO-$d_6$): δ 11.53 (d, 2H), 8.07 (s, 1H), 7.05-7.03 (m, 1H), 6.53-6.52 (m, 1H), 5.47-5.43 (m, 1H), 3.70-3.65 (m, 2H), 3.37-3.32 (m, 2H), 3.15 (s, 3H), 2.90-2.89 (m, 2H), 2.12-2.07 (m, 1H), 2.05-1.98 (m, 2H), 1.80-1.74 (m, 2H), 0.97-0.93 (m, 4H)

Example 50

(3aR,5S,6aS)—N-(3-(Hydroxymethyl)-1,2,4-thiadiazol-5-yl)-5-(methyl(7H-pyrrolo[2,3-d]pyrimidin-4-yl)amino)hexahydrocyclopenta[c]pyrrole-2(1H)-carboxamide

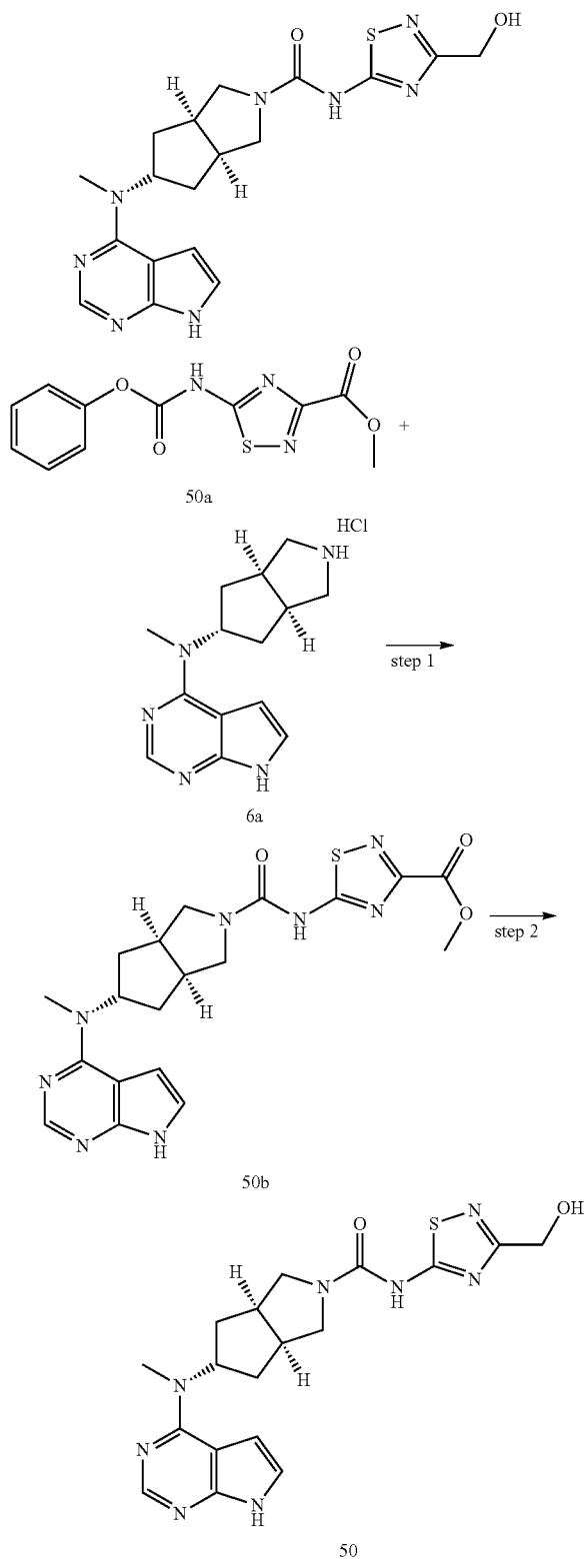

Step 1

Methyl 5-((3aR,5S,6aS)-5-(methyl(7H-pyrrolo[2,3-d]pyrimidin-4-yl)amino) octahydrocyclopenta[c]pyrrol-2-carboxamido)-1,2,4-thiadiazole-3-carboxylate N-Methyl-N-((3aR,5S,6aS)-octahydrocyclopenta[c]pyrrol-5-yl)-7H-pyrrolo[2,3-d]pyrimidin-4-amine hydrochloride 6a (90 mg, 0.35 mmol) was dissolved in 2 mL of N,N-dimethylformamide, followed by addition of methyl 5-((phenoxycarbonyl)amino)-1,2,4-thiadiazole-3-carboxylate 50a (97 mg, 0.35 mmol, prepared by a well known method, see PCT Patent Application Publication WO2004103980) and dropwise addition of triethylamine (105 mg, 1.04 mmol). After reacting for 12 hours at 100° C., 10 mL of H$_2$O were added to the reaction mixture, and the reaction mixture was extracted with dichloromethane (10 mL×3). The organic phases were combined, washed with saturated sodium chloride solution (10×2 mL), dried over anhydrous sodium sulfate, and filtered. The filtrate was concentrated under reduced pressure, and the resulting residue was purified by silica gel column chromatography with elution system A to obtain the title product methyl 5-((3aR,5S,6aS)-5-(methyl(7H-pyrrolo[2,3-d]pyrimidin-4-yl)amino)octahydrocyclopenta[c]pyrrol-2-carboxamido)-1,2,4-thiadiazole-3-carboxylate 50b (99.5 mg, yield 65.0%) as a white solid.

MS m/z (ESI): 443.4 [M+1]

Step 2

(3aR,5S,6aS)—N-(3-(Hydroxymethyl)-1,2,4-thiadiazol-5-yl)-5-(methyl(7H-pyrrolo[2,3-d]pyrimidin-4-yl)amino)hexahydrocyclopenta[c]pyrrole-2(1H)-carboxamide Methyl 5-((3aR,5S,6aS)-5-(methyl(7H-pyrrolo[2,3-d]pyrimidin-4-yl)amino) octahydrocyclopenta[c]pyrrol-2-carboxamido)-1,2,4-thiadiazole-3-carboxylate 50b (95 mg, 0.21 mmol) was dissolved in 3 mL of ethanol, followed by addition of sodium borohydride (49 mg, 1.29 mmol) in batches. After reacting for 2 hours, the reaction mixture was concentrated under reduced pressure, followed by addition of 10 mL of H$_2$O, and extracted with dichloromethane (10 mL×2). The organic phases were combined, washed with saturated sodium chloride solution (10×2 mL), dried over anhydrous sodium sulfate, and filtered. The filtrate was concentrated under reduced pressure, and the resulting residue was purified by thin layer chromatography with elution system A to obtain the title product (3aR,5S,6aS)—N-(3-(hydroxymethyl)-1,2,4-thiadiazol-5-yl)-5-(methyl(7H-pyrrolo[2,3-d]pyrimidin-4-yl)amino)hexahydrocyclopenta[c]pyrrole-2(1H)— carboxamide 50 (10 mg, yield 11.2%) as a white solid.

MS m/z (ESI): 415.4 [M+1]

$^1$H NMR (400 MHz, DMSO-d$_6$): δ 11.56 (s, 1H), 8.08 (s, 1H), 6.99-7.04 (m, 1H), 6.50-6.54 (m, 1H), 5.37-5.50 (m, 1H), 4.70 (br. s, 1H), 4.26-4.34 (m, 2H), 3.55-3.66 (m, 2H), 3.21-3.29 (m, 2H), 3.14 (s, 3H), 2.74-2.85 (m, 2H), 1.92-2.05 (m, 2H), 1.67-1.76 (m, 2H)

The compounds of Examples 51 to 156 were synthesized by reference to the procedures of Example 1 and Example 2, using appropriate reactants according to the synthetic method of the compounds of the present invention.

Their Example numbers, structures, and characteristic data are provided as follows:

| No | Structure | Properties | MS | ¹H NMR |
|---|---|---|---|---|
| 51 | 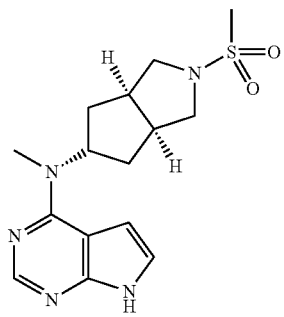<br>N-methyl-N-((3aR,5S,6aS)-2-(methylsulfonyl)octahydro-cyclopenta[c]pyrrol-5-yl)-7H-pyrrolo[2,3-d]pyrimidin-4-amine | white solid | 336.3 [M + 1] | ¹H NMR (400 MHz, CDCl₃) δ 9.48 (s, 1H), 8.28 (s, 1H), 7.05 (s, 1H), 6.64 (s, 1H), 5.50-5.54 (m, 1H), 3.52-3.56 (m, 2H), 3.17-3.21 (m, 5H), 2.80-2.95 (m, 5H), 1.88-1.90 (m, 2H), 1.85-1.87 (m, 2H) |
| 52 | 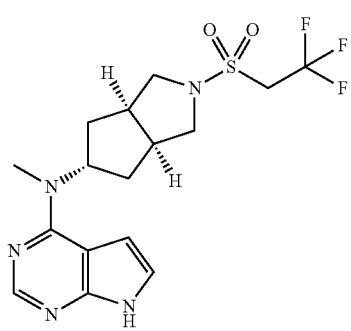<br>N-methyl-N-((3aR,5S,6aS)-2-((2,2,2-trifluoroethyl)sulfonyl)octa-hydrocyclopenta[c]pyrrol-5-yl)-7H-pyrrolo[2,3-d]pyrimidin-4-amine | white solid | 404.2 [M + 1] | ¹H NMR (400 MHz, CDCl₃) δ 10.48 (s, 1H), 8.23 (s, 1H), 7.08 (s, 1H), 6.61 (s, 1H), 5.56-5.60 (m, 1H), 3.80-3.85 (m, 2H), 3.69-3.72 (m, 2H), 3.29 (s, 3H), 2.97-3.00 (m, 2H), 2.02-2.05 (m, 2H), 1.86-1.91 (m, 4H) |
| 53 | 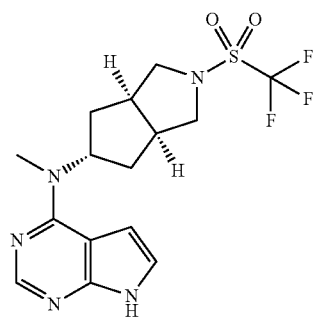<br>N-methyl-N-((3aR,5S,6aS)-2-((trifluoromethyl)sulfonyl)octa-hydrocyclopenta[c]pyrrol-5-yl)-7H-pyrrolo[2,3-d]pyrimidin-4-amine | white solid | 389.9 [M + 1] | ¹H NMR (400 MHz, CDCl₃) δ 10.53 (s, 1H), 8.25 (s, 1H), 7.09 (s, 1H), 6.58 (s, 1H), 5.62-5.64 (m, 1H), 3.85-3.86 (m, 2H), 3.69-3.72 (m, 2H), 3.27 (s, 3H), 2.80-2.82 (m, 2H), 2.06-2.07 (m, 2H), 1.91-1.93 (m, 2H) |

-continued

| No | Structure | Properties | MS | ¹H NMR |
|---|---|---|---|---|
| 54 | 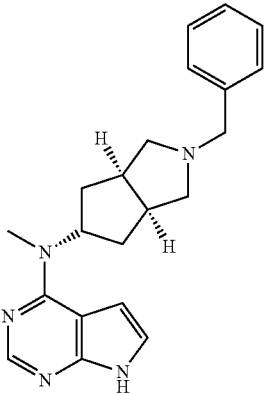<br>N-((3aR,5S,6aS)-2-benzyl-octahydrocyclopenta[c]pyrrol-5-yl)-N-methyl-7H-pyrrolo[2,3-d]pyrimidin-4-amine | gray solid | 348 [M + 1] | ¹H NMR (400 MHz, DMSO-$d_6$) δ 11.66 (s, 1H), 8.14 (s, 1H), 7.33-7.65 (m, 5H), 7.13-7.14 (m, 1H), 6.61-6.62 (m, 1H), 5.48-5.50 (m, 1H), 3.28-3.40 (m, 4H), 3.14 (s, 3H), 2.70-2.89 (m, 4H), 1.90-2.02 (m, 2H), 1.58-1.72 (m, 2H) |
| 55 | 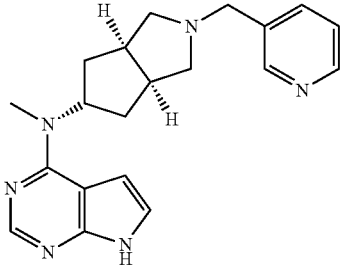<br>N-methyl-N-((3aR,5S,6aS)-2-(pyridin-3-ylmethyl)octahydro-cyclopenta[c]pyrrol-5-yl)-7H-pyrrolo[2,3-d]pyrimidin-4-amine | white solid | 349 [M + 1] | ¹H NMR (400 MHz, DMSO-$d_6$) δ 11.61 (s, 1H), 8.53-8.61 (m, 1H), 8.48-8.50 (m, 1H), 8.13 (s, 1H), 7.72-7.80 (m, 1H), 7.30-7.41 (m, 1H), 7.08-7.13 (m, 1H), 6.58-6.63 (m, 1H), 5.31-5.42 (m, 1H), 3.50-3.65 (m, 2H), 3.29-3.40 (m, 4H), 3.07 (s, 3H), 2.60-2.71 (m, 2H), 1.85-2.01 (m, 2H), 1.52-1.62 (m, 2H) |
| 56 | 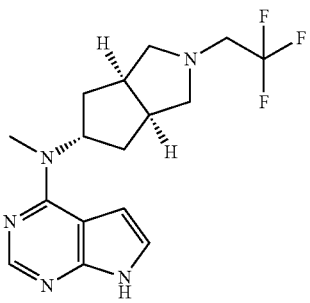<br>N-methyl-N-((3aR,5S,6aS)-2-(2,2,2-trifluoroethyl)octahydro-cyclopenta[c]pyrrol-5-yl)-7H-pyrrolo[2,3-d]pyrimidin-4-amine | white solid | 340.3 [M + 1] | ¹H NMR (400 MHz, DMSO-$d_6$) δ 11.60 (s, 1H), 8.09 (s, 1H), 7.11-7.13 (m, 1H), 6.55-6.56 (m, 1H), 5.06-5.12 (m, 1H), 3.34 (s, 3H), 3.21-3.28 (m, 2H), 3.14 (s, 2H), 2.70-2.72 (m, 2H), 2.54-2.58 (m, 2H), 1.94-2.01 (m, 2H), 1.46-1.53 (m, 2H) |

-continued

| No | Structure | Properties | MS | ¹H NMR |
|---|---|---|---|---|
| 57 | 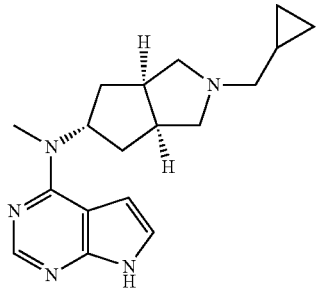<br>N-((3aR,5S,6aS)-2-(cyclopropylmethyl)octahydro-cyclopenta[c]pyrrol-5-yl)-N-methyl-7H-pyrrolo[2,3-d]pyrimidin-4-amine | white solid | 312.2 [M + 1] | ¹H NMR (400 MHz, DMSO-d$_6$) δ 11.66 (s, 1H), 8.14 (s, 1H), 7.16 (s, 1H), 6.61 (s, 1H), 5.50-5.53 (m, 1H), 3.40-3.48 (m, 1H), 3.36-3.38 (m, 2H), 3.26 (s, 3H), 3.10-3.19 (m, 2H), 2.75-2.88 (m, 2H), 1.96-1.98 (m, 2H), 1.70-1.72 (m, 2H), 1.24-1.28 (m, 1H), 1.08-1.10 (m, 4H) |
| 58 | 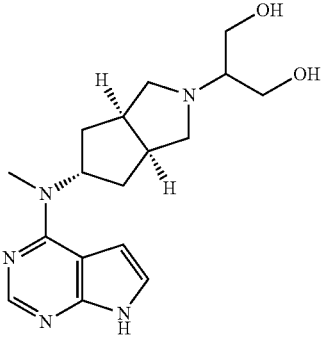<br>2-((3aR,5S,6aS)-5-(methyl(7H-pyrrolo[2,3-d]pyrimidin-4-yl)amino)hexahydrocyclo-penta[c]pyrrol-2(1H)-yl)propane-1,3-diol | white solid | 332.3 [M + 1] | ¹H NMR (400 MHz, DMSO-d$_6$) δ 11.54 (s, 1H), 8.08 (s, 1H), 7.07 (s, 1H), 6.76 (s, 1H), 5.29-5.31 (m, 1H), 4.33-4.35 (m, 2H), 3.58-3.60 (m, 4H), 3.51 (s, 3H), 2.66-2.71 (m, 2H), 2.13-2.15 (m, 1H), 1.92-1.93 (m, 2H), 1.57-1.60 (m, 2H) |
| 59 | 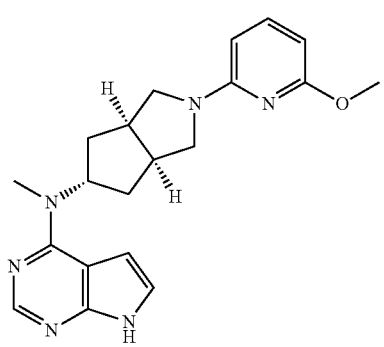<br>N-((3aR,5S,6aS)-2-(6-methoxy-pyridin-2-yl)octahydro-cyclopenta[c]pyrrol-5-yl)-N-methyl-7H-pyrrolo[2,3-d]pyrimidin-4-amine | white solid | 365.3 [M + 1] | ¹H NMR (400 MHz, CDCl$_3$) δ 9.98 (s, 1H), 8.28 (s, 1H), 7.42 (s, 1H), 6.96 (s, 1H), 6.53 (s, 1H), 5.98-6.05 (m, 2H), 5.55-5.58 (m, 1H), 3.90 (s, 3H), 3.71-3.73 (m, 2H), 3.39-3.41 (m, 2H), 3.26 (s, 3H), 2.98-3.00 (m, 2H), 2.10-2.17 (m, 2H), 1.98-2.00 (m, 2H) |

-continued

| No | Structure | Properties | MS | ¹H NMR |
|---|---|---|---|---|
| 60 | 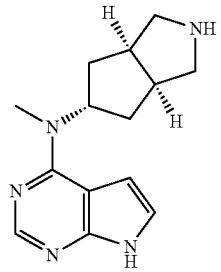<br>N-methyl-N-((3aR,5S,6aS)-octahydrocyclopenta[c]pyrrol-5-yl)-7H-pyrrolo[2,3-d]pyrimidin-4-amine | white solid | 258.2 [M + 1] | ¹H NMR (400 MHz, DMSO-$d_6$) δ 11.63 (s, 1H), 8.10 (s, 1H), 7.13 (s, 1H), 6.59 (s, 1H), 5.38-5.41 (m, 1H), 3.34-3.39 (m, 2H), 3.16 (s, 3H), 2.69-2.77 (m, 4H), 1.91-1.98 (m, 2H), 1.67-1.72 (m, 2H) |
| 61 | 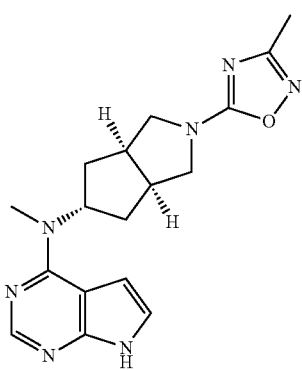<br>N-methyl-N-((3aR,5S,6aS)-2-(3-methyl-1,2,4-oxadiazol-5-yl)octahydrocyclopenta[c]pyrrol-5-yl)-7H-pyrrolo[2,3-d]pyrimidin-4-amine | white solid | 340.2 [M + 1] | ¹H NMR (400 MHz, CDCl$_3$) δ 11.00 (s, 1H), 8.23 (s, 1H), 7.05 (s, 1H), 6.51 (s, 1H), 5.59-5.63 (m, 1H), 3.81-3.86 (m, 2H), 3.46-3.49 (m, 2H), 3.27 (s, 3H), 3.02-3.03 (m, 2H), 2.08 (s, 3H), 2.03-2.04 (m, 2H), 1.92-1.95 (m, 2H) |
| 62 | 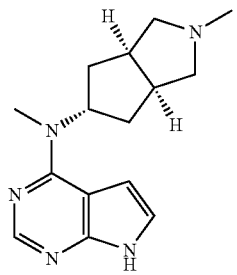<br>N-methyl-N-((3aR,5S,6aS)-2-methyloctahydrocyclopenta[c]pyrrol-5-yl)-7H-pyrrolo[2,3-d]pyrimidin-4-amine | white solid | 272.3 [M + 1] | ¹H NMR (400 MHz, DMSO-$d_6$) δ 11.63 (s, 1H), 8.12 (s, 1H), 7.14 (s, 1H), 6.60 (s, 1H), 5.46-5.50 (m, 1H), 3.48-3.50 (m, 2H), 3.17 (s, 3H), 2.88-2.90 (m, 4H), 2.76 (s, 3H), 1.92-1.96 (m, 2H), 1.72-1.74 (m, 2H) |

-continued

| No | Structure | Properties | MS | ¹H NMR |
|---|---|---|---|---|
| 63 | 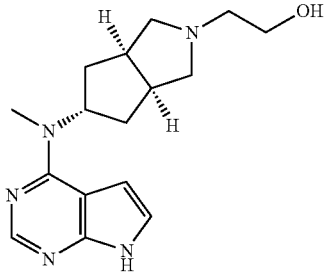<br>2-((3aR,5S,6aS)-5-(methyl(7H-pyrrolo[2,3-d]pyrimidin-4-yl)amino)hexahydrocyclopenta[c]pyrrol-2(1H)-yl)ethanol | white solid | 302.4 [M + 1] | ¹H NMR (400 MHz, CDCl₃) δ 10.31 (s, 1H), 8.31 (s, 1H), 7.05 (s, 1H), 6.66 (s, 1H), 5.53-5.56 (m, 1H), 3.68-3.71 (m, 2H), 3.19 (s, 3H), 2.70-2.75 (m, 2H), 2.64-2.68 (m, 4H), 2.58-2.60 (m, 2H), 1.94-2.00 (m, 2H), 1.72-1.77 (m, 2H) |
| 64 | 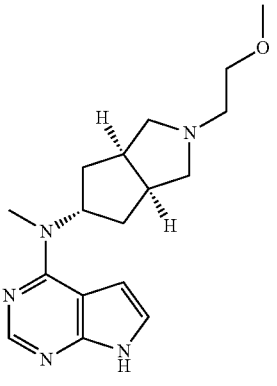<br>N-((3aR,5S,6aS)-2-(2-methoxyethyl)octahydrocyclopenta[c]pyrrol-5-yl)-N-methyl-7H-pyrrolo[2,3-d]pyrimidin-4-amine | white solid | 316.3 [M + 1] | ¹H NMR (400 MHz, CDCl₃) δ 10.53 (s, 1H), 8.27 (s, 1H), 7.05 (s, 1H), 6.64 (s, 1H), 5.52-5.60 (m, 1H), 3.78-3.81 (m, 2H), 3.60-3.62 (m, 2H), 3.40 (s, 3H), 3.26 (s, 3H), 3.08-3.11 (m, 4H), 2.65-2.68 (m, 2H), 1.89-1.94 (m, 2H), 1.76-1.81 (m, 2H) |
| 65 | 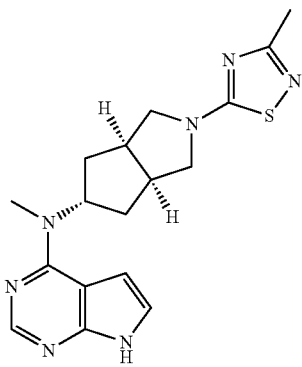<br>N-methyl-N-((3aR,5S,6aS)-2-(3-methyl-1,2,4-thiadiazol-5-yl)octahydrocyclopenta[c]pyrrol-5-yl)-7H-pyrrolo[2,3-d]pyrimidin-4-amine | white solid | 356.2 [M + 1] | ¹H NMR (400 MHz, CDCl₃) δ 10.84 (s, 1H), 8.22 (s, 1H), 7.03 (s, 1H), 6.51 (s, 1H), 5.59-5.63 (m, 1H), 3.74-3.76 (m, 2H), 3.36-3.38 (m, 2H), 3.27 (s, 3H), 3.06-3.09 (m, 2H), 2.45 (s, 3H), 2.06-2.08 (m, 2H), 1.95-1.97 (m, 2H) |

| No | Structure | Properties | MS | ¹H NMR |
|---|---|---|---|---|
| 66 | N-methyl-N-((3aR,5S,6aS)-2-(5-methyl-1,3,4-thiadiazol-5-yl)octahydrocyclopenta[c]pyrrol-5-yl)-7H-pyrrolo[2,3-d]pyrimidin-4-amine | white solid | 356.2 [M + 1] | ¹H NMR (400 MHz, DMSO-$d_6$) δ 11.59 (s, 1H), 8.08 (s, 1H), 7.08 (s, 1H), 6.51 (s, 1H), 5.44-5.46 (m, 1H), 3.60-3.64 (m, 2H), 3.31 (s, 3H), 3.24-3.26 (m, 2H), 3.16 (s, 3H), 2.97-2.99 (m, 2H), 2.01-2.03 (m, 2H). 1.77-1.82 (m, 2H) |
| 67 | N-methyl-N-((3aR,5R,6aS)-2-(2,2,2-trifluoroethyl)octa-hydrocyclopenta[c]pyrrol-5-yl)-7H-pyrrolo[2,3-d]pyrimidin-4-amine | white solid | 340.3 [M + 1] | ¹H NMR (400 MHz, DMSO-$d_6$) δ 11.59 (s, 1H), 8.08 (s, 1H), 7.11 (s, 1H), 6.54 (s, 1H), 5.08 (m, 1H), 3.22-3.25 (m, 2H), 3.13 (s, 3H), 2.70-2.72 (m, 2H), 2.54 (s, 3H), 1.94-2.00 (m, 2H), 1.47-1.53 (m, 2H), 1.20-1.23 (m, 2H) |
| 68 | 3-((3aR,5R,6aS)-5-(methyl(7H-pyrrolo[2,3-d]pyrimidin-4-yl)amino)hexahydrocyclo-penta[c]pyrrol-2(1H)-yl)propanenitrile | white solid | 311.4 [M + 1] | ¹H NMR (400 MHz, CDCl₃) δ 10.72 (s, 1H), 8.32 (s, 1H), 7.05 (s, 1H), 6.57 (s, 1H), 5.28-5.32 (m, 1H), 3.74-3.82 (m, 2H), 3.27 (s, 3H), 3.16-3.20 (m, 1H), 2.73-2.76 (m, 3H), 2.54-5-2.59 (m, 3H), 2.29-2.31 (m, 1H), 1.76-1.79 (m, 2H), 1.21-1.26 (m, 2H) |

-continued

| No | Structure | Properties | MS | ¹H NMR |
|---|---|---|---|---|
| 69 | 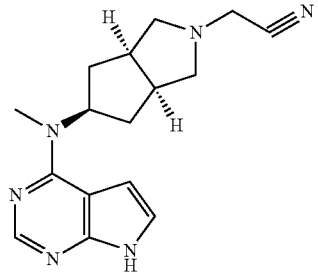<br>2-((3aR,5R,6aS)-5-(methyl(7H-pyrrolo[2,3-d]pyrimidin-4-yl)amino)hexahydrocyclopenta[c]pyrrol-2(1H)-yl)acetonitrile | white solid | 297.4 [M + 1] | ¹H NMR (400 MHz, CDCl₃) δ 10.72 (s, 1H), 8.32 (s, 1H), 7.06 (s, 1H), 6.57 (s, 1H), 5.14-5.17 (m, 1H), 3.69-3.71 (m, 2H), 3.27 (s, 3H), 3.59-3.67 (m, 5H), 2.13-2.15 (m, 2H), 1.76-1.78 (m, 1H), 1.58-1.62 (m, 2H) |
| 70 | 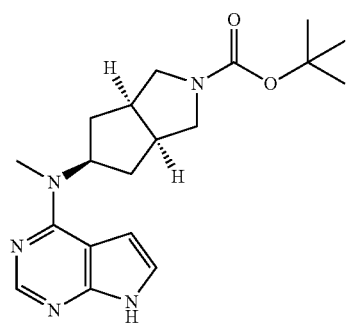<br>(3aR,5R,6aS)-tert-butyl 5-(methyl(7H-pyrrolo[2,3-d]pyrimidin-4-yl)amino)hexahydrocyclopenta[c]pyrrole-2(1H)-carboxylate | white solid | 358.2 [M + 1] | ¹H NMR (400 MHz, DMSO-d₆) δ 11.61 (s, 1H), 8.08 (s, 1H), 7.12 (s, 1H), 6.57 (s, 1H), 5.27-5.28 (m, 1H), 3.24-3.47 (m, 2H), 4.16-4.21 (m, 5H), 2.61-2.64 (m, 2H), 1.97-2.00 (m, 2H), 1.51-1.53 (m, 2H), 1.40 (s, 9H) |
| 71 | 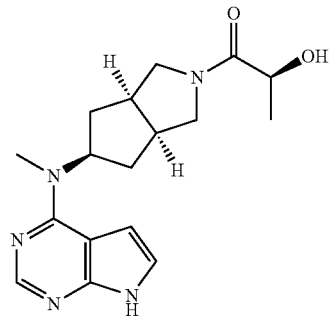<br>(S)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 330.1 [M + 1] | ¹H NMR (400 MHz, DMSO-d₆) δ 11.61 (s, 1H), 8.09 (s, 1H), 7.13 (s, 1H), 6.58 (s, 1H), 5.29-5.30 (m, 1H), 4.83-4.86 (m, 1H), 4.29-4.32 (m, 1H), 3.59-3.60 (m, 2H), 3.42-3.45 (m, 2H), 3.16 (s, 3H), 2.65-2.73 (m, 2H), 2.01-2.04 (m, 2H), 1.51-1.56 (m, 2H), 1.17-1.20 (m, 3H) |

| No | Structure | Properties | MS | ¹H NMR |
|---|---|---|---|---|
| 72 | 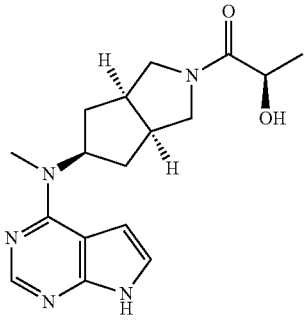<br>(R)-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)propan-1-one | white solid | 330.2 [M + 1] | ¹H NMR (400 MHz, DMSO-$d_6$) δ 11.61 (s, 1H), 8.09 (s, 1H), 7.13 (s, 1H), 6.58 (s, 1H), 5.28-5.30 (m, 1H), 4.84-4.87 (m, 1H), 4.27-4.31 (m, 1H), 3.38-3.46 (m, 3H), 3.16 (s, 3H), 2.73-2.75 (m, 2H), 1.98-2.00 (m, 2H), 1.53-1.56 (m, 2H), 1.07-1.10 (m, 3H) |
| 73 | 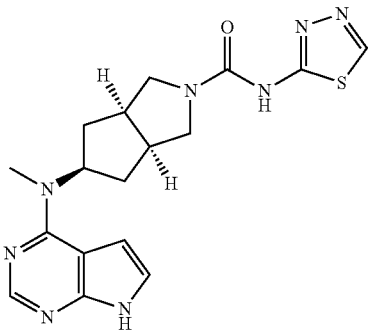<br>(3aR,5R,6aS)-5-(methyl(7H-pyrrolo[2,3-d]pyrimidin-4-yl)amino)-N-(1,3,4-thiadiazol-2-yl)hexahydrocyclopenta[c]pyrrole-2(1H)-carboxamide | white solid | 385.2 [M + 1]<br>383.2 [M − 1] | ¹H NMR (400 MHz, DMSO-$d_6$) δ 11.63 (s, 1H), 11.09 (bs, 1H), 9.00 (s, 1H), 8.10 (s, 1H), 7.13 (s, 1H), 6.59 (s, 1H), 5.30-5.34 (m, 1H), 3.62-3.67 (m, 2H), 3.46-3.52 (m, 2H), 3.17 (s, 3H), 2.72-2.75 (m, 2H), 2.02-2.07 (m, 2H), 1.57-1.60 (m, 2H) |
| 74 | 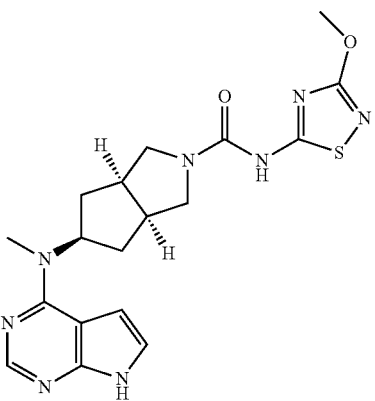<br>(3aR,5R,6aS)-N-(3-methoxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide | white solid | 415.2 [M + 1]<br>413.1 [M − 1] | ¹H NMR (400 MHz, DMSO-$d_6$) δ 11.60 (s, 1H), 11.58 (s, 1H), 8.09 (s, 1H), 7.13 (s, 1H), 6.58 (s, 1H), 5.30-5.34 (m, 1H), 3.89 (s, 3H), 3.62-3.65 (m, 2H), 3.34-3.38 (m, 2H), 3.17 (s, 3H), 2.73-2.77 (m, 2H), 1.99-2.03 (m, 2H), 1.57-1.60 (m, 2H) |

| No | Structure | Properties | MS | ¹H NMR |
|---|---|---|---|---|
| 75 | 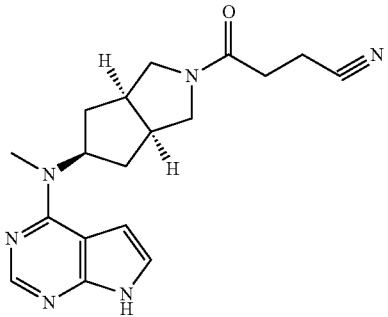<br>4-((3aR,5R,6aS)-5-(methyl(7H-pyrrolo[2,3-d]pyrimidin-4-yl)amino)hexahydrocyclopenta[c]pyrrol-2(1H)-yl)-4-oxobutanenitrile | white solid | 339.2 [M + 1] | ¹H NMR (400 MHz, CDCl₃) δ 10.65 (s, 1H), 8.26 (s, 1H), 7.09 (s, 1H), 6.58 (s, 1H), 5.44-5.50 (m, 1H), 3.67-3.72 (m, 2H), 3.42-3.49 (m, 2H), 3.28 (s, 3H), 2.67-2.77 (m, 6H), 2.19-2.22 (m, 2H), 1.56-1.62 (m, 2H) |
| 76 | 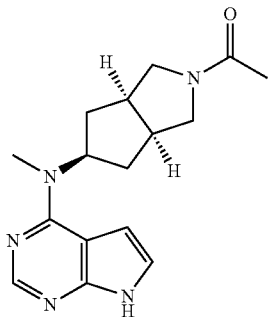<br>1-((3aR,5S,6aS)-5-(methyl(7H-pyrrolo[2,3-d]pyrimidin-4-yl)amino)hexahydrocyclopenta[c]pyrrol-2(1H)-yl)ethanone | white solid | 300.5 [M + 1] | ¹H NMR (400 MHz, CDCl₃) δ 10.83 (s, 1H), 8.28 (s, 1H), 7.07 (s, 1H), 6.58 (s, 1H), 5.42-5.48 (m, 1H), 3.67-3.70 (m, 2H), 3.44-3.55 (m, 2H), 3.27 (s, 3H), 2.74-2.81 (m, 2H), 2.21-2.22 (m, 2H), 2.16-2.17 (m, 3H), 1.53-1.60 (m, 2H) |
| 77 | 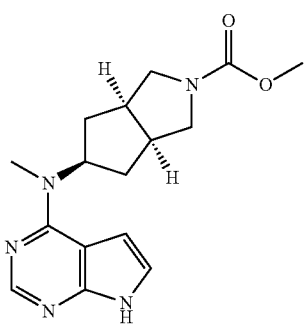<br>(3aR,5R,6aS)-methyl 5-(methyl(7H-pyrrolo[2,3-d]pyrimidin-4-yl)amino)hexahydrocyclopenta[c]pyrrole-2(1H)-carboxylate | white solid | 316.5 [M + 1] | ¹H NMR (400 MHz, CDCl₃) δ 11.16 (s, 1H), 8.27 (s, 1H), 7.07 (s, 1H), 6.57 (s, 1H), 5.38-5.41 (m, 1H), 3.72 (s, 3H), 3.40-3.56 (m, 4H), 3.27 (s, 3H), 2.70-2.72 (m, 2H), 2.16-2.18 (m, 2H), 1.56-1.57 (m, 2H) |

-continued

| No | Structure | Properties | MS | ¹H NMR |
|---|---|---|---|---|
| 78 | 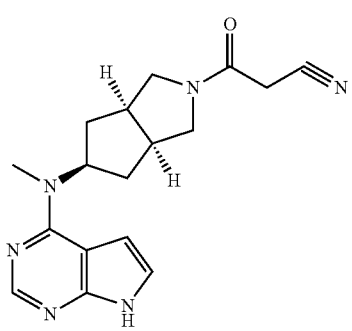<br>2-((3aR,5R,6aS)-5-(methyl(7H-pyrrolo[2,3-d]pyrimidin-4-yl)amino)hexahydrocyclopenta[c]pyrrol-2(1H)-yl)-3-oxopropanenitrile | white solid | 325.5 [M + 1] | ¹H NMR (400 MHz, CDCl₃) δ 9.55 (s, 1H), 8.30 (s, 1H), 7.05 (s, 1H), 6.59 (s, 1H), 5.49-5.51 (m, 1H), 3.62-3.77 (m, 2H), 3.61-3.62 (m, 1H), 3.46-3.51 (m, 3H), 3.28 (s, 3H), 2.80-2.89 (m, 2H), 2.23-2.26 (m, 2H), 1.61-1.69 (m, 2H). |
| 79 | 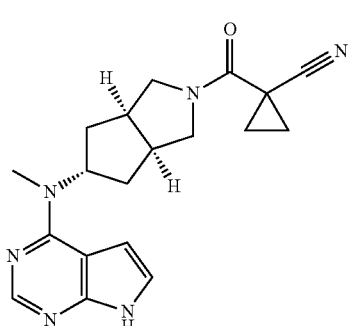<br>1-((3aR,5S,6aS)-5-(methyl(7H-pyrrolo[2,3-d]pyrimidin-4-yl)amino)octahydrocyclopenta[c]pyrrol-2-carbonyl)cyclopropanecarbonitrile | white solid | 351.4 [M + 1] | ¹H NMR (400 MHz, CDCl₃) δ 11.65 (s, 1H), 8.32 (s, 1H), 7.05-7.12 (m, 1H), 6.55-6.64 (m, 1H), 5.62-5.68 (m, 1H), 4.14-4.25 (m, 2H), 3.75-3.87 (m, 2H), 3.53-3.62 (m, 1H), 3.30 (s, 3H), 3.02-3.12 (m, 1H), 2.88-2.97 (m, 1H), 2.04-2.17 (m, 2H), 1.92-2.02 (m, 2H), 1.55-1.63 (m, 2H), 1.22-1.35 (m, 2H) |
| 80 | 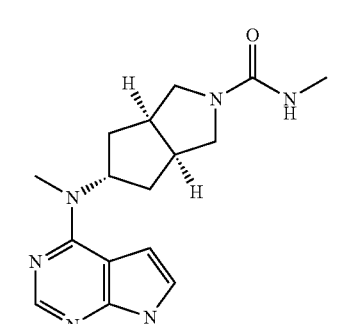<br>(3aR,5S,6aS)-N-methyl-5-(methyl(7H-pyrrolo[2,3-d]pyrimidin-4-yl)amino)hexahydrocyclopenta[c]pyrrole-2(1H)-carboxamide | white solid | 315.2 [M + 1] | ¹H NMR (400 MHz, DMSO-d₆) δ 8.19 (s, 1H), 7.26 (s, 1H), 6.78 (s, 1H), 5.35-5.38 (m, 1H), 3.71-3.75 (m, 2H), 3.52-3.54 (m, 2H), 3.20-3.24 (m, 2H), 2.96-2.98 (m, 2H), 2.73 (s, 3H), 2.17-2.19 (m, 2H), 1.94-1.96 (m, 2H), |

| No | Structure | Properties | MS | ¹H NMR |
|---|---|---|---|---|
| 81 | 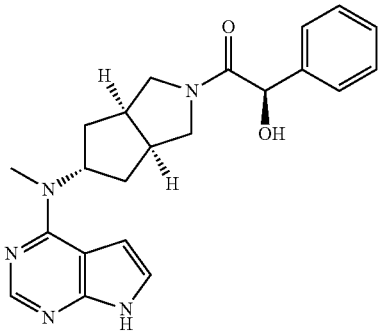<br>(R)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)-2-phenylethanone | white solid | 392.3 [M + 1] | ¹H NMR (400 MHz, CDCl$_3$) δ 10.96 (s, 1H), 8.23 (s, 1H), 7.35-7.37 (m, 5H), 7.12 (s, 1H), 6.48 (s, 1H), 5.50-5.55 (m, 1H), 5.07-5.11 (m, 1H), 3.60-3.74 (m, 1H), 3.48-3.59 (m, 2H), 3.17-3.27 (m, 4H), 2.83-2.89 (m, 2H), 1.82-1.96 (m, 4H). |
| 82 | 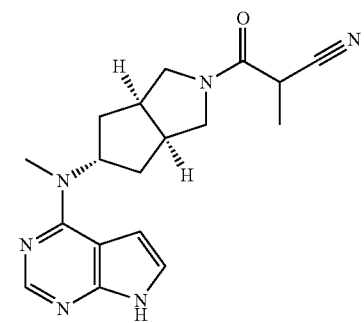<br>2-methyl-3-((3aR,5S,6aS)-5-(methyl(7H-pyrrolo[2,3-d]pyrimidin-4-yl)amino)hexahydrocyclopenta[c]pyrrol-2(1H)-yl)-3-oxopropanenitrile | white solid | 339.2 [M + 1] | ¹H NMR (400 MHz, DMSO-d$_6$) δ 11.60 (s, 1H), 8.08 (s, 1H), 7.11 (s, 1H), 6.53 (s, 1H), 5.43-5.46 (m, 1H), 4.16-4.19 (m, 1H), 3.73-3.75 (m, 1H), 3.59-3.62 (m, 1H), 3.35-3.38 (m, 1H), 3.25-3.27 (m, 1H), 3.17 (s, 3H), 3.15-3.17 (m, 1H), 3.14-3.15 (m, 1H), 1.97-2.02 (m, 2H), 1.78-1.80 (m, 2H), 1.39-1.43 (m, 3H), |
| 83 | 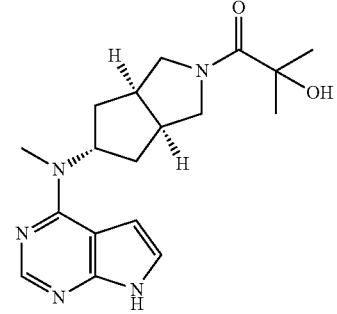<br>2-hydroxy-2-methyl-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 344.2 [M + 1] | ¹H NMR (400 MHz, DMSO-d$_6$) δ 11.59 (s, 1H), 8.07 (s, 1H), 7.11 (s, 1H), 6.54 (s, 1H), 5.42-5.46 (m, 1H), 5.20 (s, 1H), 3.91-3.94 (m, 1H), 3.61-3.67 (m, 2H), 3.26-3.28 (m, 1H), 3.14 (s, 3H), 2.72-2.82 (m, 2H), 1.93-1.96 (m, 2H), 1.70-1.75 (m, 2H), 1.30 (s, 6H) |

-continued

| No | Structure | Properties | MS | ¹H NMR |
|---|---|---|---|---|
| 84 | 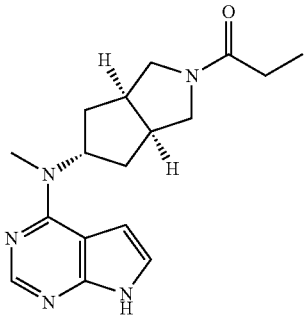<br>1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 314.1 [M + 1] | ¹H NMR (400 MHz, CDCl₃) δ 8.30 (s, 1H), 7.07 (s, 1H), 6.53 (s, 1H), 5.60-5.64 (m, 1H), 3.74-3.0-79 (m, 2H) 3.32-3.46 (m, 2H), 3.25 (s, 3H), 2.71-2.80 (m, 2H), 2.30-2.33 (m, 2H), 2.05-2.06 (m, 4H), 1.90-1.93 (m, 2H), 1.06-1.21 (m, 3H). |
| 85 | 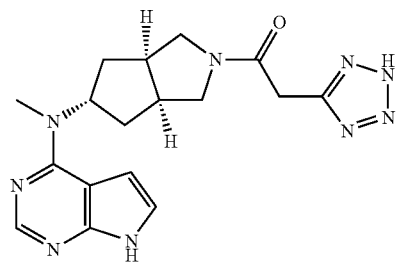<br>1-((3aR,5S,6aS)-5-(methyl(7H-pyrrolo[2,3-d]pyrimidin-4-yl)amino)hexahydrocyclopenta[c]pyrrol-2(1H)-yl)-2-(2H-tetrazol-5-yl)ethanone | white solid | 368.0 [M + 1] | ¹H NMR (400 MHz, DMSO-d₆) δ 11.61 (s, 1H), 8.10 (s, 1H), 7.12 (s, 1H), 6.55 (s, 1H), 5.51-5.53 (m, 1H), 3.99-4.00 (m, 2H), 3.80-3.82 (m, 1H), 3.58-3.61 (m, 2H), 3.46-3.47 (m, 1H), 3.16 (s, 3H), 2.65-2.70 (m, 2H), 1.96-1.99 (m, 2H), 1.75-1.79 (m, 2H), |
| 86 | 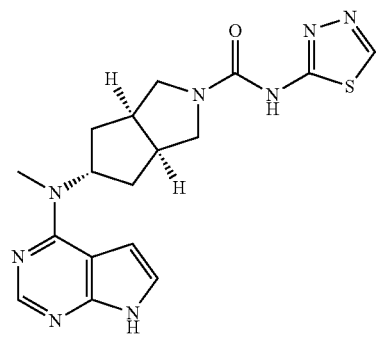<br>(3aR,5S,6aS)-5-(methyl(7H-pyrrolo[2,3-d]pyrimidin-4-yl)amino)-N-(1,3,4-thiadiazol-2-yl)hexahydrocyclopenta[c]pyrrole-2(1H)-carboxamide | white solid | 385.4 [M + 1] 383.2 [M − 1] | ¹H NMR (400 MHz, DMSO-d₆) δ 11.60 (s, 1H), 11.06 (s, 1H), 8.96 (s, 1H), 8.19 (s, 1H), 7.11 (s, 1H), 6.68 (s, 1H), 5.30-5.34 (m, 1H), 3.86-3.91 (m, 2H), 3.50-3.54 (m, 2H), 3.27 (s, 3H), 3.09-3.12 (m, 2H), 2.21-2.26 (m, 2H), 2.01-2.07 (m, 2H) |

| No | Structure | Properties | MS | ¹H NMR |
|---|---|---|---|---|
| 87 | 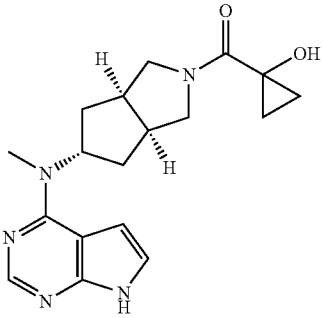<br>(1-hydroxycyclo-propyl)((3aR,5S,6aS)-5-(methyl(7H-pyrrolo[2,3-d]pyrimidin-4-yl)amino)hexahydrocyclopenta[c]pyrrol-2(1H)-yl)methanone | white solid | 342.4 [M + 1] 340.2 [M − 1] | ¹H NMR (400 MHz, CD₃OD) δ 8.20 (s, 1H), 7.06 (s, 1H), 6.78-6.86 (m, 1H), 5.35-5.52 (m, 1H), 3.80-4.11 (m, 2H), 3.46-3.60 (m, 2H), 3.00 (s, 3H), 2.98-3.13 (m, 2H), 2.26-2.22 (m, 2H), 1.97-2.01 (m, 2H), 1.13-1.29 (t, 2H), 0.88-0.93 (t, 2H) |
| 88 | 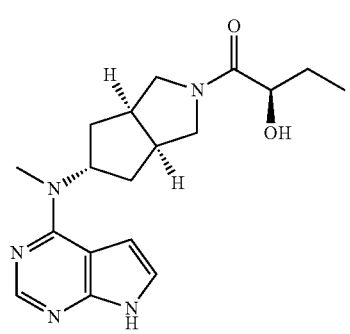<br>(R)-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)butan-1-one | white solid | 344.4 [M + 1] | ¹H NMR (400 MHz, CDCl₃) δ 9.70 (s, 1H), 8.28 (s, 1H), 7.04 (s, 1H), 6.56 (s, 1H), 6.56 (s, 1H), 5.60-5.66 (m, 1H), 4.21 (s, 1H), 3.95-3.98 (m, 1H), 3.65-3.75 (m, 3H), 3.42 (s, 1H), 3.25-3.30 (m, 4H), 2.99 (s, 2H) |
| 89 | 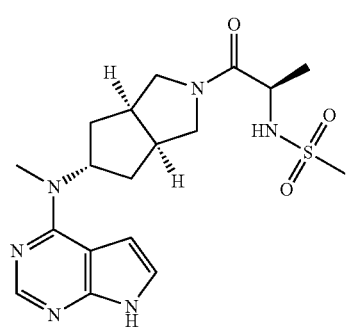<br>N-((R)-1-((3aR,5S,6aS)-5-(methyl(7H-pyrrolo[2,3-d]pyrimidin-4-yl)amino)hexahydrocyclopenta[c]pyrrol-2(1H)-yl)-1-oxopropan-2-yl)methanesulfonamide | white solid | 407.4 [M + 1] | ¹H NMR (400 MHz, CDCl₃) δ 11.63 (s, 1H), 8.27 (s, 1H), 7.08-7.15 (m, 1H), 6.57-6.63 (m, 1H), 5.58-6.05 (m, 1H), 4.32-4.42 (m, 1H), 3.88-3.97 (m, 1H), 3.71-3.78 (m, 1H), 3.57-3.64 (m, 1H), 3.38 (s, 3H), 3.02-3.09 (m, 1H), 2.98 (s, 3H), 2.06-2.17 (m, 5H), 1.90-2.02 (m, 2H), 1.50-1.52 (m, 1H), 1.41-1.44 (m, 1H), 1.29 (s, 1H) |

| No | Structure | Properties | MS | ¹H NMR |
|---|---|---|---|---|
| 90 | 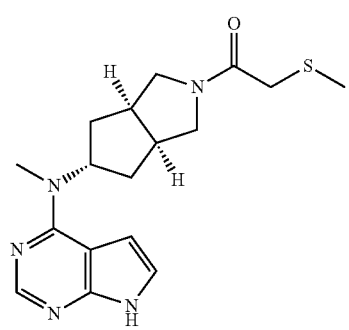<br>1-((3aR,5S,6aS)-5-(methyl(7H-pyrrolo[2,3-d]pyrimidin-4-yl)amino)hexahydrocyclopenta[c]pyrrol-2(1H)-yl)-2-(methylthio)ethanone | light yellow solid | 346.3 [M + 1] | ¹H NMR (400 MHz, CDCl$_3$) δ 11.65 (s, 1H), 8.27 (s, 1H), 7.07-7.14 (m, 1H), 6.57-6.65 (m, 1H), 5.58-5.75 (m, 1H), 3.77-3.88 (m, 2H), 3.42-3.54 (m, 2H), 3.30 (s, 3H), 3.22-3.24 (m, 2H), 2.96-3.07 (m, 1H), 2.86-2.97 (m, 1H), 2.27 (s, 3H), 2.05-2.08 (m, 2H), 1.92-2.01 (m, 2H) |
| 91 | 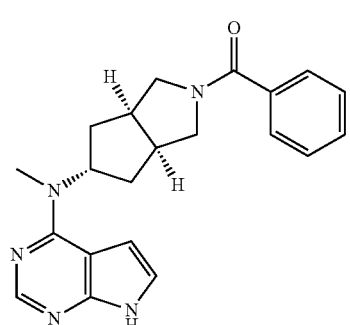<br>((3aR,5S,6aS)-5-(methyl(7H-pyrrolo[2,3-d]pyrimidin-4-yl)amino)hexahydrocyclopenta[c]pyrrol-2(1H)-yl)(phenyl)methanone | light yellow solid | 362.4 [M + 1] | ¹H NMR (400 MHz, CDCl$_3$) δ 11.65 (s, 1H), 8.31 (s, 1H), 7.55-7.61 (m, 2H), 7.44-7.48 (m, 3H), 7.07-7.14 (m, 1H), 6.56-6.67 (m, 1H), 5.58-5.75 (m, 1H), 3.97-4.12 (m, 1H), 3.62-3.83 (m, 2H), 3.34-3.45 (m, 1H), 3.30 (s, 3H), 2.85-3.07 (m, 2H), 1.92-2.04 (m, 4H) |
| 92 | 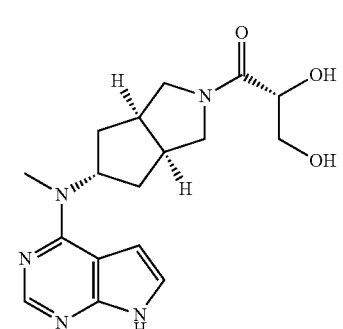<br>(R)-2,3-dihydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 346.3 [M + 1] | ¹H NMR (400 MHz, DMSO-d$_6$) δ 11.60 (s, 1H), 8.09 (s, 1H), 7.11 (s, 1H), 6.54 (s, 1H), 5.44-5.48 (m, 1H), 4.84-4.88 (m, 1H), 4.69-4.74 (m, 1H), 4.20-4.22 (m, 1H), 3.53-3.56 (m, 6H), 3.45-3.48 (m, 1H), 3.26 (s, 3H), 2.79-2.87 (m, 2H), 1.96-2.00 (m, 2H), 1.76-1.77 (m, 2H) |

| No | Structure | Properties | MS | ¹H NMR |
|---|---|---|---|---|
| 93 | 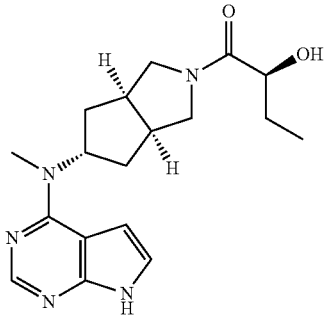<br>(S)-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)butan-1-one | white solid | 344.2 [M + 1] | ¹H NMR (400 MHz, DMSO-d₆) δ 11.59 (s, 1H), 8.07 (s, 1H), 7.10 (s, 1H), 6.53 (s, 1H), 5.42-5.46 (m, 1H), 4.67-4.73 (m, 1H), 4.06-4.09 (m, 1H), 3.64-3.66 (m, 3H), 3.28-3.29 (m, 1H), 3.23 (s, 3H), 2.79-2.88 (m, 2H), 1.95-2.00 (m, 2H), 1.51-1.73 (m, 4H), 0.85-0.92 (m, 3H) |
| 94 | 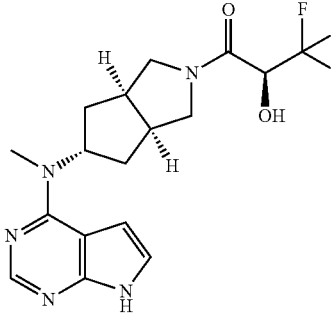<br>(S)-3,3,3-trifluoro-2-hydroxy-1-((3aR,5R,6aS)-5-(methyl(7H-pyrrolo[2,3-d]pyrimidin-4-yl)amino)hexahydrocyclopenta[c]pyrrol-2(1H)-yl)propan-1-one | white solid | 340.3 [M + 1] | ¹H NMR (400 MHz, CDCl₃) δ 10.62 (s, 1H), 8.21 (s, 1H), 7.04 (s, 1H), 6.80 (s, 1H), 5.37-5.39 (m, 1H), 3.06 (s, 3H), 3.01-3.03 (m, 2H), 2.75-2.76 (m, 6H), 1.94-1.99 (m, 4H). |
| 95 | 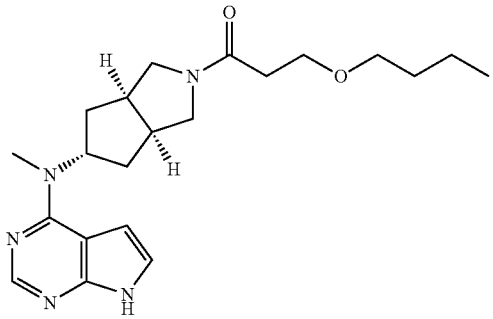<br>3-butoxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 386.0 [M + 1] | ¹H NMR (400 MHz, CDCl₃) δ 11.17 (s, 1H), 8.25 (s, 1H), 7.07 (s, 1H), 6.65 (s, 1H), 5.44-5.47 (m, 1H), 4.05-4.11 (m, 2H), 3.20 (s, 3H), 3.00-3.02 (m, 2H), 2.90-2.93 (m, 6H), 2.71-2.75 (m, 2H), 2.58-2.59 (m, 2H), 1.90-1.92 (m, 2H), 1.72-1.77 (m, 2H), 1.56-1.59 (m, 2H), 1.33-1.37 (m, 2H), 0.88-0.91 (m, 3H) |

| No | Structure | Properties | MS | ¹H NMR |
|---|---|---|---|---|
| 96 | (R)-2-hydroxy-3-methyl-1-((3aR,5S,6aS)-5-(methyl(7H-pyrrolo[2,3-d]pyrimidin-4-yl)amino)hexahydrocyclopenta[c]pyrrol-2(1H)-yl)butan-1-one | white solid | 358.4 [M + 1] | ¹H NMR (400 MHz, CDCl₃) δ 11.56 (s, 1H) 8.08 (s, 1H), 7.10 (s, 1H), 6.52 (s, 1H), 5.43-5.45 (m, 1H), 4.58-4.64 (m, 1H), 3.89-3.92 (m, 1H), 3.46-3.66 (m, 4H), 3.15-3.23 (m, 4H), 2.79-2.87 (m, 2H), 1.35 (m, 1H), 0.83-0.91 (m, 6H) |
| 97 | 3,3,3-trifluoro-2-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 384.6 [M + 1] | ¹H NMR (400 MHz, DMSO-d₆) δ 11.60 (s, 1H), 8.07-8.13 (m, 1H), 7.08-7.13 (m, 1H), 6.66-6.73 (m, 1H), 6.52-6.57 (m, 1H), 5.45-5.53 (m, 1H), 4.90-4.98 (m, 1H), 3.83-3.92 (m, 1H), 3.62-3.78 (m, 2H), 3.52-3.60 (m, 1H), 3.16 (s, 3H), 2.87-2.95 (m, 1H), 2.77-2.84 (m, 1H), 1.95-2.06 (m, 2H), 1.74-1.83 (m, 2H) |
| 98 | (3aR,5S,6aS)-phenyl 5-(methyl(7H-pyrrolo[2,3-d]pyrimidin-4-yl)amino)hexahydrocyclopenta[c]pyrrole-2(1H)-carboxylate | white solid | 378.3 [M + 1] 376.3 [M − 1] | ¹H NMR (400 MHz, DMSO-d₆) δ 11.64 (s, 1H), 8.11 (s, 1H), 7.38-7.42 (m, 2H), 7.12-7.24 (m, 4H), 6.57-6.59 (m, 1H), 5.51-5.56 (m, 1H), 3.78-3.82 (m, 1H), 3.62-3.68 (m, 1H), 3.39-3.42 (m, 1H), 3.24-3.26 (m, 1H), 3.17 (s, 3H), 2.90-2.94 (m, 2H), 1.99-2.07 (m, 2H), 1.82-1.87 (m, 2H) |

| No | Structure | Properties | MS | ¹H NMR |
|---|---|---|---|---|
| 99 | 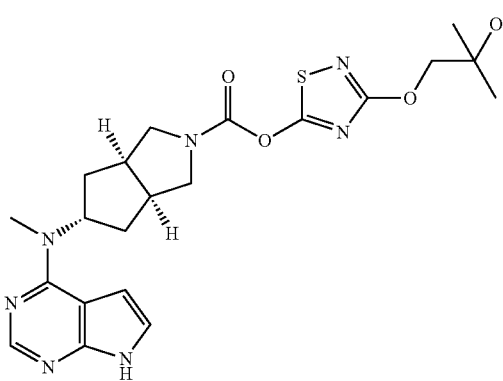<br>3aR,5S,6aS)-N-(3-(2-hydroxy-2-methylpropoxy)-1,2,4-thiadiazol-5-yl)-5-(methyl(7H-pyrrolo[2,3-d]pyrimidin-4-yl)amino)hexahydrocyclopenta[c]pyrrole-2(1H)-carboxamide | white solid | 473.4 [M + 1] | ¹H NMR (400 MHz, DMSO-d₆) δ 8.29 (s, 1H) 7.32-7.40 (m, 1H), 6.72-6.82 (m, 1H), 5.15-5.27 (m, 1H), 4.14 (s, 2H), 3.53-3.78 (m, 2H), 3.30-3.47 (m, 2H), 3.24 (s, 3H), 2.85-2.96 (m, 2H), 2.00-2.14 (m, 2H), 1.82-1.93 (m, 2H), 1.04 (s, 6H) |
| 100 | 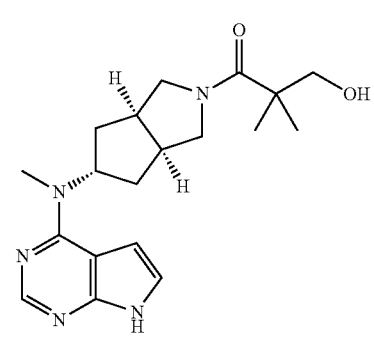<br>3-hydroxy-2,2-dimethyl-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 358.2 [M + 1] | ¹H NMR (400 MHz, CDCl₃) δ 11.18 (s, 1H) 8.30 (s, 1H), 7.08 (s, 1H), 6.53 (s, 1H), 5.53-5.57 (m, 1H), 3.75-3.80 (m, 2H), 3.58-3.62 (m, 4H), 3.24 (s, 3H), 2.85-2.87 (m, 2H), 2.01-2.07 (m, 2H), 1.87-1.92 (m, 2H), 1.23 (s, 6H) |
| 101 | 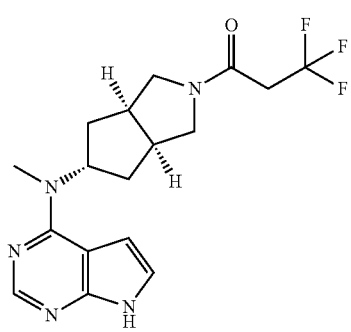<br>3,3,3-trifluoro-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 368.5 [M + 1] | ¹H NMR (400 MHz, DMSO-d₆) δ 11.60 (s, 1H), 8.10 (s, 1H), 7.05-7.20 (m, 1H), 6.50-6.65 (m, 1H), 5.40-5.61 (m, 1H), 3.65-3.75 (m, 1H), 3.47-3.59 (m, 2H), 3.49 (s, 3H), 3.31-3.21 (m, 3H), 2.73-2.96 (m, 2H), 1.93-2.08 (m, 2H), 1.72-1.86 (m, 2H) |

| No | Structure | Properties | MS | ¹H NMR |
|---|---|---|---|---|
| 102 | 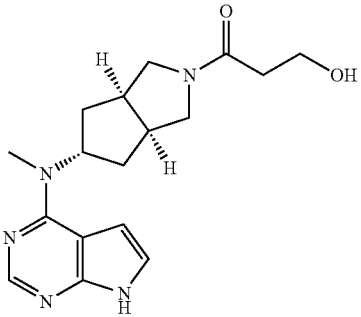<br>3-hydroxy-1-((3aR,5S,6aS)-5-(methyl(7H-pyrrolo[2,3-d]pyrimidin-4-yl)amino)hexahydrocyclopenta[c]pyrrol-2(1H)-yl)propan-1-one | white solid | 330.3 [M + 1] | ¹H NMR (400 MHz, CDCl₃) δ 10.44 (s, 1H) 8.29 (s, 1H), 7.06 (s, 1H), 6.53 (s, 1H), 5.57-5.61 (m, 1H), 3.70-3.72 (m, 2H), 3.46-3.52 (m, 4H), 3.25 (s, 3H), 2.96-3.02 (m, 2H), 2.51-2.59 (m, 2H), 2.01-2.06 (m, 2H), 1.91-1.93 (m, 2H) |
| 103 | 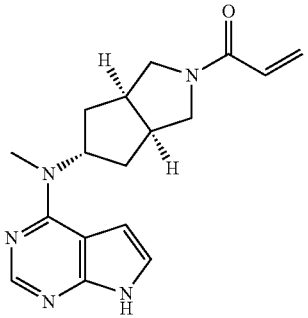<br>1-((3aR,5S,6aS)-5-(methyl(7H-pyrrolo[2,3-d]pyrimidin-4-yl)amino)hexahydrocyclopenta[c]pyrrol-2(1H)-yl)prop-2-en-1-one | white solid | 312.2 [M + 1] | ¹H NMR (400 MHz, DMSO-d₆) δ 11.60 (s, 1H), 8.08 (s, 1H),7.10 (s, 1H), 6.58-6.65 (m, 1H), 6.52 (s, 1H), 6.12-6.16 (m, 1H), 5.65-5.68 (m, 1H), 5.44-5.46 (m, 1H), 4.00-4.05 (m, 1H), 3.76-3.78 (m, 1H), 3.61-3.63 (m, 1H), 3.44-3.45 (m, 1H), 3.27 (s, 3H), 2.81-2.90 (m, 2H), 1.96-1.99 (m, 2H), 1.74-1.76 (m, 2H) |
| 104 | 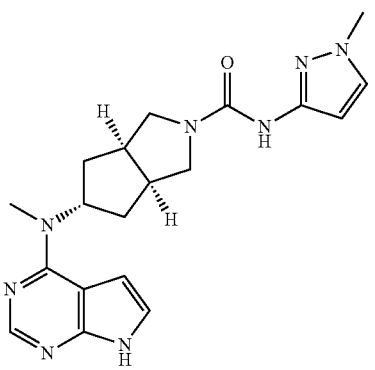<br>(3aR,5S,6aS)-5-(methyl(7H-pyrrolo[2,3-d]pyrimidin-4-yl)amino)-N-(1-methyl-1H-pyrazol-3-yl)hexahydrocyclopenta[c]pyrrole-2(1H)-carboxamide | white solid | 381.2 [M + 1] | ¹H NMR (400 MHz, CD₃OD) δ 8.09 (s, 1H) 7.43 (d, 1H), 7.05 (d, 1H), 6.62 (d, 1H), 6.31 (d, 1H), 5.52-5.56 (m, 1H), 3.78 (s, 3H), 3.68-3.72 (m, 2H), 3.40-3.44 (m, 2H), 3.25 (s, 3H), 2.27-2.31 (m, 2H), 2.10-2.16 (m, 2H), 1.89-1.93 (m, 2H) |

| No | Structure | Properties | MS | ¹H NMR |
|---|---|---|---|---|
| 105 | 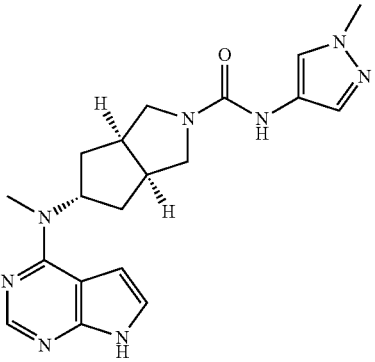<br>(3aR,5S,6aS)-5-(methyl(7H-pyrrolo[2,3-d]pyrimidin-4-yl)amino)-N-(1-methyl-1H-pyrazol-4-yl)hexahydrocyclopenta[c]pyrrole-2(1H)-carboxamide | white solid | 381.3 [M + 1] | ¹H NMR (400 MHz, DMSO-d₆) δ 11.61 (s, 1H), 8.24 (s, 1H), 8.09 (s, 1H), 7.66 (s, 1H), 7.33 (s, 1H), 7.10 (s, 1H), 6.56 (s, 1H), 5.30-5.47 (m, 1H), 3.75 (s, 3H), 3.49-3.58 (m, 2H), 3.21-3.23 (m, 2H), 3.15 (s, 3H), 2.71-2.85 (m, 2H), 2.01-2.04 (m, 2H), 1.56-1.76 (m, 2H) |
| 106 | 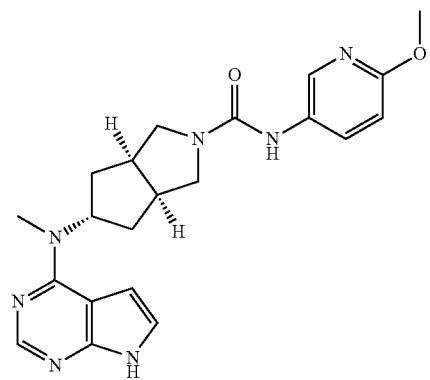<br>(3aR,5S,6aS)-N-(6-methoxypyridin-3-yl)-5-(methyl(7H-pyrrolo[2,3-d]pyrimidin-4-yl)amino)hexahydrocyclopenta[c]pyrrole-2(1H)-carboxamide | white solid | 408.2 [M + 1] | ¹H NMR (400 MHz, DMSO-d₆) δ 11.59 (s, 1H), 8.23 (s, 1H), 8.20 (s, 1H), 7.82 (s, 1H), 7.07 (s, 1H), 6.73 (s, 1H), 6.56 (s, 1H), 5.51-5.53 (m, 1H), 3.76 (s, 3H), 3.60-3.62 (m, 2H), 3.27-3.30 (m, 2H), 3.18 (s, 3H), 2.88-2.89 (m, 2H), 2.00-2.05 (m, 2H), 1.74-1.79 (m, 2H) |
| 107 | 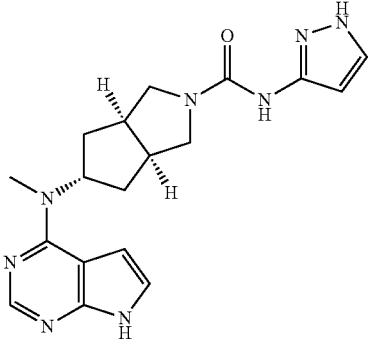<br>(3aR,5S,6aS)-5-(methyl(7H-pyrrolo[2,3-d]pyrimidin-4-yl)amino)-N-(1H-pyrazol-3-yl)hexahydrocyclopenta[c]pyrrole-2(1H)-carboxamide | white solid | 367.3 [M + 1]<br>365.2 [M − 1] | ¹H NMR (400 MHz, DMSO-d₆) δ 11.62 (s, 1H), 8.08 (s, 1H), 7.93 (s, 1H), 7.09 (s, 1H), 6.54 (s, 1H), 5.73 (s, 1H), 5.49-5.52 (m, 1H), 5.26 (s, 1H), 5.25 (s, 1H), 3.92-3.96 (m, 2H), 3.63-3.67 (m, 2H), 3.15 (s, 3H), 2.83-2.87 (m, 2H), 1.98-2.22 (m, 2H), 1.76-1.80 (m, 2H) |

| No | Structure | Properties | MS | ¹H NMR |
|---|---|---|---|---|
| 108 | 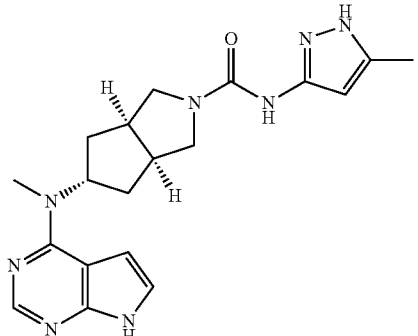<br>(3aR,5S,6aS)-5-(methyl(7H-pyrrolo[2,3-d]pyrimidin-4-yl)amino)-N-(5-methyl-1H-pyrazol-3-yl)hexahydro-cyclopenta[c]pyrrole-2(1H)-carboxamide | white solid | 381.3 [M + 1] 379.3 [M − 1] | ¹H NMR (400 MHz, DMSO-d₆) δ 11.60 (s, 1H), 8.10 (s, 1H), 7.09 (s, 1H), 6.55 (s, 1H), 6.09 (m, 2H), 5.49-5.52 (m, 1H), 5.17 (s, 1H), 3.82-3.98 (m, 2H), 3.62-3.68 (m, 2H), 3.15 (s, 3H), 2.83-2.87 (m, 2H), 2.03 (s, 3H), 1.96-2.02 (m, 2H), 1.76-1.80 (m, 2H) |
| 109 | 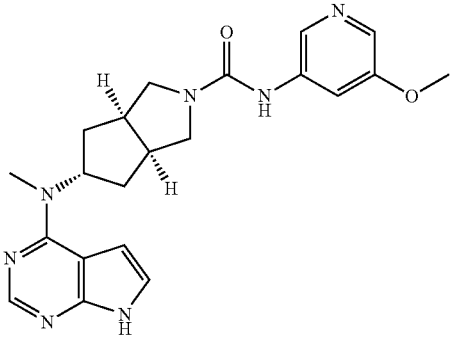<br>(3aR,5S,6aS)-N-(5-methoxy-pyridin-3-yl)-5-(methyl(7H-pyrrolo[2,3-d]pyrimidin-4-yl)amino)hexahydrocyclo-penta[c]pyrrole-2(1H)-carboxamide | white solid | 408.2 [M + 1] | ¹H NMR (400 MHz, DMSO-d₆) δ 11.61 (s, 1H), 8.34 (s, 2H), 8.08 (s, 1H), 7.88 (s, 1H), 7.66 (s, 1H), 7.06 (s, 1H), 6.55 (s, 1H), 5.51-5.53 (m, 1H), 3.78 (s, 3H), 3.62-3.67 (m, 2H), 3.31-3.33 (m, 2H), 3.16 (s, 3H), 2.88-2.89 (m, 2H), 2.01-2.06 (m, 2H), 1.77-1.79 (m, 2H) |
| 110 | 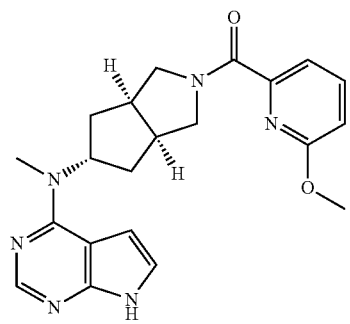<br>(6-methoxypyridin-2-yl)((3aR,5S,6aS)-5-(methyl(7H-pyrrolo[2,3-d]pyrimidin-4-yl)amino)hexahydrocyclo-penta[c]pyrrol-2(1H)-yl)methanone | white solid | 365.3 [M + 1] | ¹H NMR (400 MHz, CDCl₃) δ 9.98 (s, 1H), 8.28 (s, 1H), 7.41 (s, 1H), 6.96 (s, 1H), 6.53 (s, 1H), 6.04 (s, 1H), 5.97 (s, 1H), 5.56-5.58 (m, 1H), 3.90 (s, 3H), 3.71-3.73 (m, 2H), 3.39-3.41 (m, 2H), 3.26 (s, 3H), 2.96-2.99 (m, 2H), 2.06-2.09 (m, 2H), 1.97-1.99 (m, 2H) |

| No | Structure | Properties | MS | ¹H NMR |
|---|---|---|---|---|
| 111 | 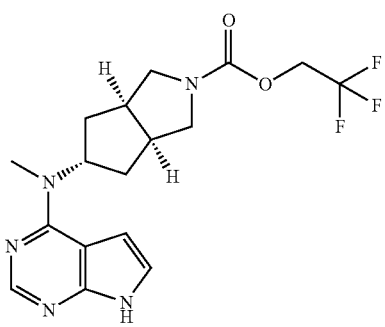<br>(3aR,5S,6aS)-2,2,2-trifluoroethyl 5-(methyl(7H-pyrrolo[2,3-d]pyrimidin-4-yl)amino)hexahydrocyclopenta[c]pyrrole-2(1H)-carboxylate | white solid | 384.1 [M + 1] | ¹H NMR (400 MHz, CDCl₃) δ 10.78 (s, 1H) 8.28 (s, 1H), 7.06 (s, 1H), 6.53 (s, 1H), 5.60-5.64 (m, 1H), 4.48-4.55 (m, 2H), 3.72-3.74 (m, 2H), 3.30-3.35 (m, 2H), 3.26 (s, 3H), 2.90-2.93 (m, 2H), 2.02-2.03 (m, 2H), 1.89-1.92 (m, 2H) |
| 112 | 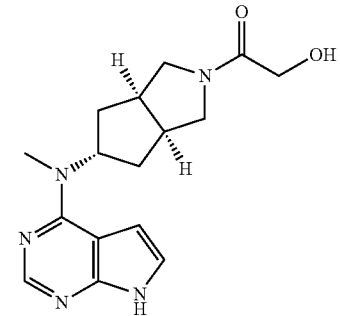<br>2-hydroxy-1-((3aR,5S,6aS)-5-(methyl(1H-pyrrolo[2,3-b]pyridin-4-yl)amino)hexahydrocyclopenta[c]pyrrol-2(1H)-yl)ethanone | white solid | 315.3 [M + 1] 313.2 [M − 1] | ¹H NMR (400 MHz, DMSO-d₆) δ 11.41 (s, 1H), 7.83 (d, 1H), 7.14 (d, 1H), 6.45 (d, 1H), 6.29 (d, 1H), 4.72-4.76 (m, 1H), 4.00 (d, 2H), 3.54-3.62 (m, 2H), 3.22-3.26 (m, 2H), 3.15 (s, 1H), 2.96 (s, 3H), 2.70-2.90 (m, 2H), 1.98-2.02 (m, 2H), 1.78-1.82 (m, 2H) |
| 113 | 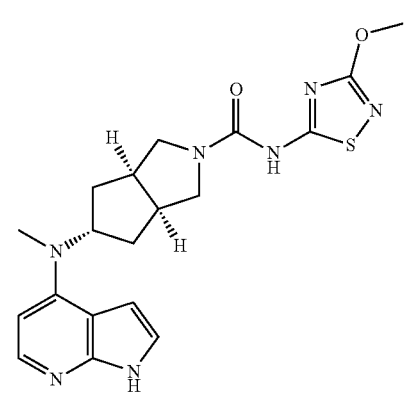<br>(3aR,5S,6aS)-N-(3-methoxy-1,2,4-thiadiazol-5-yl)-5-(methyl(1H-pyrrolo[2,3-b]pyridin-4-yl)amino)hexahydrocyclopenta[c]pyrrole-2(1H)-carboxamide | white solid | 414.3 [M + 1] 412.2 [M − 1] | ¹H NMR (400 MHz, DMSO-d₆) δ 11.60 (s, 1H), 11.40 (s, 1H), 7.83 (d, 1H), 7.06 (d, 1H), 6.50 (d, 1H), 6.34 (d, 1H), 4.77-4.82 (m, 1H), 3.90 (s, 3H), 3.62-3.66 (m, 2H), 3.37-3.41 (m, 2H), 3.00 (s, 3H), 2.88-2.92 (m, 2H), 2.00-2.06 (m, 2H), 1.80-1.86 (m, 2H) |

| No | Structure | Properties | MS | ¹H NMR |
|---|---|---|---|---|
| 114 | 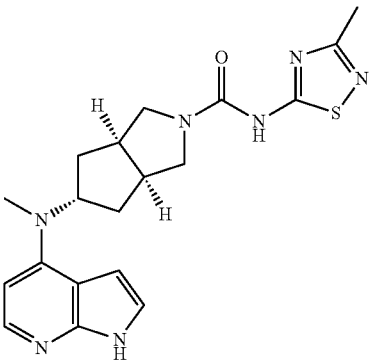<br>(3aR,5S,6aS)-5-(methyl(1H-pyrrolo[2,3-b]pyridin-4-yl)amino)-N-(3-methyl-1,2,4-thiadiazol-5-yl)hexahydro-cyclopenta[c]pyrrole-2(1H)-carboxamide | white solid | 399.3 [M + 1] 397.3 [M − 1] | ¹H NMR (400 MHz, DMSO-$d_6$) δ 11.60 (s, 1H), 10.40 (s, 1H), 8.04 (s, 1H), 7.03-7.05 (m, 1H), 6.51-6.52 (m, 1H), 5.42-5.54 (m, 1H), 3.62-3.75 (m, 2H), 3.27-3.42 (m, 2H), 3.14 (s, 3H), 2.84-2.96 (m, 2H), 2.39 (s, 3H), 1.95-2.08 (m, 2H), 1.72-1.82 (m, 2H) |
| 115 | 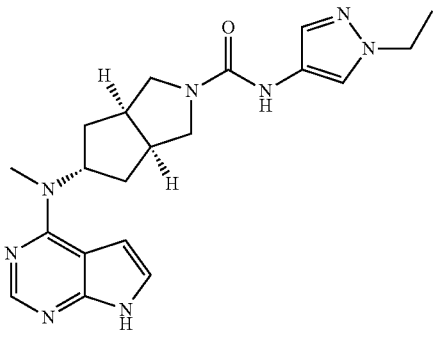<br>(3aR,5S,6aS)-N-(1-ethyl-1H-pyrazol-4-yl)-5-(methyl(7H-pyrrolo[2,3-d]pyrimidin-4-yl)amino)hexahydrocyclo-penta[c]pyrrole-2(1H)-carboxamide | white solid | 395.4 [M + 1] | ¹H NMR (400 MHz, DMSO-$d_6$) δ 11.60 (s, 1H), 8.25 (s, 1H), 8.09 (s, 1H), 7.70 (s, 1H), 7.36 (s, 1H), 7.08-7.06 (m, 1H), 6.55-6.54 (m, 1H), 5.48 (s, 1H), 4.07-4.02 (m, 1H), 3.59-3.54 (m, 2H), 3.25-3.16 (m, 5H), 2.86 (s, 2H), 2.05-1.99 (m, 2H), 1.76-1.71 (m, 2H), 1.34-1.17 (s, 3H) |
| 116 | 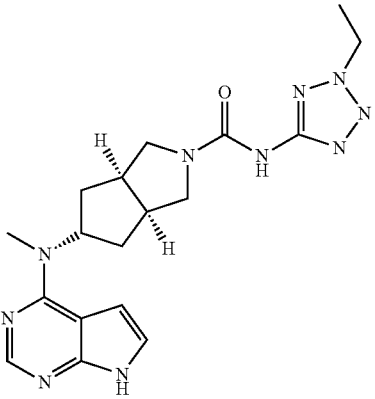<br>(3aR,5S,6aS)-N-(2-ethyl-2H-tetrazol-5-yl)-5-(methyl(7H-pyrrolo[2,3-d]pyrimidin-4-yl)amino)hexahydrocyclo-penta[c]pyrrole-2(1H)-carboxamide | white solid | 397.4 [M + 1] 395.3 [M − 1] | ¹H NMR (400 MHz, DMSO-$d_6$) δ 11.60 (s, 1H), 9.34 (s, 1H), 8.10 (s, 1H), 7.07-7.14 (m, 1H), 6.52-6.58 (m, 1H), 5.41-5.57 (m, 1H), 4.61 (q, 2H), 3.58-3.71 (m, 2H), 3.20-3.35 (m, 2H), 3.16 (s, 3H), 2.81-2.92 (m, 2H), 1.97-2.02 (m, 2H), 1.73-1.78 (m, 2H), 1.50 (t, 3H) |

| No | Structure | Properties | MS | ¹H NMR |
|---|---|---|---|---|
| 117 | 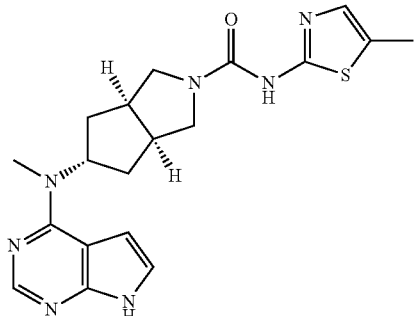<br>(3aR,5S,6aS)-5-(methyl(7H-pyrrolo[2,3-d]pyrimidin-4-yl)amino)-N-(5-methylthiazol-2-yl)hexahydrocyclopenta[c]pyrrole-2(1H)-carboxamide | white solid | 398.3 [M + 1] 396.3 [M − 1] | ¹H NMR (400 MHz, DMSO-d$_6$) δ 11.60 (s, 1H), 8.09 (s, 1H), 7.06-7.08 (m, 1H), 7.01 (s, 1H), 6.53-6.54 (m, 1H), 5.44-5.48 (m, 1H), 3.61-3.66 (m, 2H), 3.31-3.34 (m, 2H), 3.15 (s, 3H), 2.87 (s, 2H), 2.29 (s, 3H), 1.97-2.01 (m, 2H), 1.73-1.78 (m, 2H). |
| 118 | 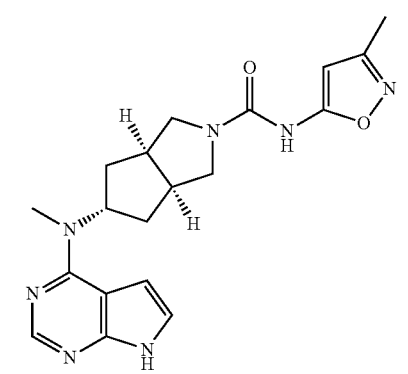<br>(3aR,5S,6aS)-5-(methyl(7H-pyrrolo[2,3-d]pyrimidin-4-yl)amino)-N-(3-methylisoxazol-5-yl)hexahydrocyclopenta[c]pyrrole-2(1H)-carboxamide | yellow solid | 382.3 [M + 1] 380.2 [M − 1] | ¹H NMR (400 MHz, DMSO-d$_6$) δ 11.60 (s, 1H), 9.97 (s, 1H), 8.09 (s, 1H), 7.04-7.09 (m, 1H), 6.50-6.56 (m, 1H), 5.93 (s, 1H), 5.40-5.54 (m, 1H), 3.55-3.70 (m, 2H), 3.25-3.42 (m, 2H), 3.15 (s, 3H), 2.79-2.91 (m, 2H), 2.15 (s, 3H), 1.92-2.06 (m, 2H), 1.69-1.80 (m, 2H) |
| 119 | 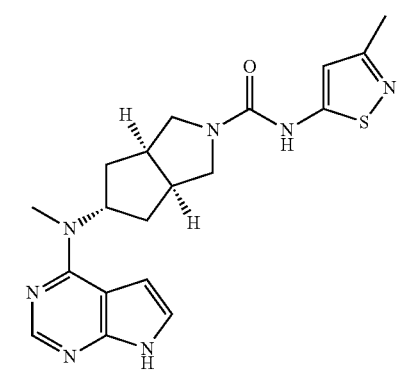<br>(3aR,5S,6aS)-5-(methyl(7H-pyrrolo[2,3-d]pyrimidin-4-yl)amino)-N-(3-methylisothiazol-5-yl)hexahydrocyclopenta[c]pyrrole-2(1H)-carboxamide | white solid | 398.4 [M + 1] 396.3 [M − 1] | ¹H NMR (400 MHz, DMSO-d$_6$) δ 11.60 (s, 1H), 10.4 (s, 1H), 8.07 (s, 1H), 7.03-7.05 (m, 1H), 6.68 (s, 1H), 6.50-6.55 (m, 1H), 5.42-5.54 (m, 1H), 3.61-3.71 (m, 2H), 3.27-3.42 (m, 2H), 3.15 (s, 3H), 2.84-2.96 (m, 2H), 2.26 (s, 3H), 1.95-2.08 (m, 2H), 1.72-1.82 (m, 2H) |

| No | Structure | Properties | MS | ¹H NMR |
|---|---|---|---|---|
| 120 | 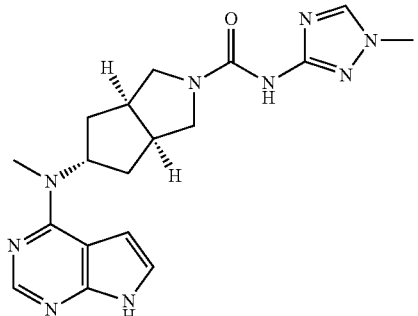<br>(3aR,5S,6aS)-5-(methyl(7H-pyrrolo[2,3-d]pyrimidin-4-yl)amino)-N-(1-methyl-1H-1,2,4-triazol-3-yl)hexahydro-cyclopenta[c]pyrrole-2(1H)-carboxamide | light yellow solid | 382.4 [M + 1] | ¹H NMR (400 MHz, DMSO-d₆) δ 12.46 (s, 1H), 8.69 (s, 1H), 8.31-8.30 (d, 1H), 7.36 (s, 1H), 6.80 (s, 1H), 5.31 (s, 1H), 3.78 (s, 3H), 3.59-3.57 (d, 2H), 3.17 (s, 1H), 2.89 (s, 2H), 2.40-2.36 (s, 3H), 2.10-2.04 (m, 2H), 1.88-1.83 (m, 2H) |
| 121 | 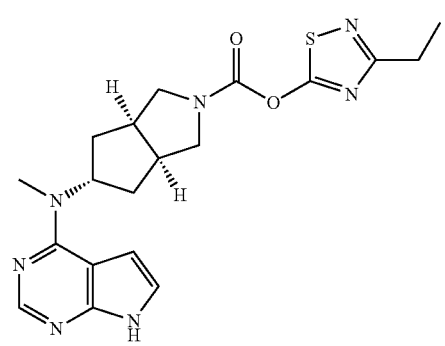<br>(3aR,5S,6aS)-N-(3-ethyl-1,2,4-thiadiazol-5-yl)-5-(methyl(7H-pyrrolo[2,3-d]pyrimidin-4-yl)amino)hexahydrocyclo-penta[c]pyrrole-2(1H)-carboxamide | white solid | 411.3 [M + 1] | ¹H NMR (400 MHz, DMSO-d₆) δ 11.60 (s, 1H), 11.52 (s, 1H), 8.08 (s, 1H), 7.10-7.00 (m, 1H), 6.58-6.48 (m, 1H), 5.55-5.38 (m, 1H), 3.78-3.60 (m, 2H), 3.49-3.36 (m, 2H), 3.15 (s, 3H), 2.96-2.84 (m, 2H), 2.74 (q, 2H), 2.10-1.94 (m, 2H), 1.85-1.72 (m, 2H), 1.25 (t, 3H) |
| 122 | 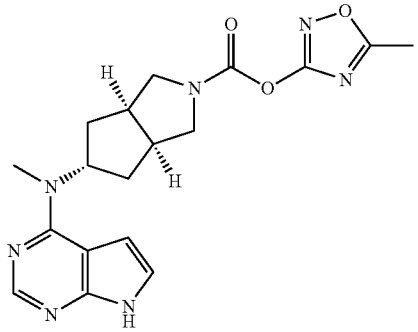<br>(3aR,5S,6aS)-5-(methyl(7H-pyrrolo[2,3-d]pyrimidin-4-yl)amino)-N-(5-methyl-1,2,4-oxadiazol-3-yl)hexahydro-cyclopenta[c]pyrrole-2(1H)-carboxamide | light yellow solid | 383.4 [M + 1]<br>381.3 [M − 1] | |

| No | Structure | Properties | MS | ¹H NMR |
|---|---|---|---|---|
| 123 | (3aR,5S,6aS)-N-(1-ethyl-1H-imidazol-4-yl)-5-(methyl(7H-pyrrolo[2,3-d]pyrimidin-4-yl)amino)hexahydrocyclopenta[c]pyrrole-2(1H)-carboxamide | yellow solid | 395.4 [M + 1] 393.3 [M − 1] | |
| 124 | (3aR,5S,6aS)-5-(methyl(7H-pyrrolo[2,3-d]pyrimidin-4-yl)amino)-N-(2-methylthiazol-5-yl)hexahydrocyclopenta[c]pyrrole-2(1H)-carboxamide | light yellow solid | 398.3 [M + 1] 396.3 [M − 1] | ¹H NMR (400 MHz, DMSO-d₆) δ 11.60 (s, 1H), 9.47 (s, 1H), 8.09 (s, 1H), 7.22 (s, 1H), 7.06-7.08 (m, 1H), 6.54-6.55 (m, 1H), 5.47-5.51 (m, 1H), 3.59-3.64 (m, 2H), 3.27-3.31 (m, 2H), 3.16 (s, 3H), 2.89-2.90 (m, 2H), 2.49 (s, 3H), 2.06-1.98 (m, 2H), 1.74-1.79 (m, 2H) |
| 125 | (3aR,5S,6aS)-N-(3-cyclopropyl-1,2,4-thiadiazol-5-yl)-5-(methyl(7H-pyrrolo[2,3-d]pyrimidin-4-yl)amino)hexahydrocyclopenta[c]pyrrole-2(1H)-carboxamide | light yellow solid | 425.4 [M + 1] 423.3 [M − 1] | ¹H NMR (400 MHz, DMSO-d₆) δ 11.53 (s, 2H), 8.07 (s, 1H), 7.03-7.05 (m, 1H), 6.52-6.53 (m, 1H), 5.43-5.47 (m, 1H), 3.65-3.70 (m, 2H), 3.32-3.37 (m, 2H), 3.15 (s, 3H), 2.89-2.90 (m, 2H), 2.07-2.12 (m, 1H), 1.98-2.05 (m, 2H), 1.74-1.80 (m, 2H), 0.93-0.97 (m, 4H) |

| No | Structure | Properties | MS | ¹H NMR |
|---|---|---|---|---|
| 126 | 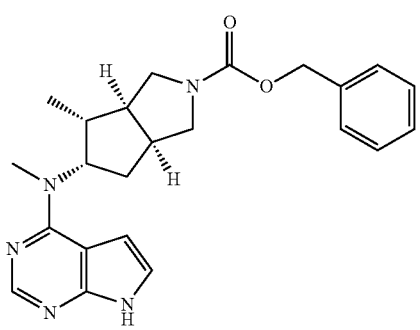<br>(3aS,4R,5S,6aS)-benzyl 4-methyl-5-(methyl(7H-pyrrolo[2,3-d]pyrimidin-4-yl)amino)hexahydrocyclopenta[c]pyrrole-2(1H)-carboxylate | white solid | 406.3 [M + 1] | ¹H NMR (400 MHz, DMSO-d₆) δ 11.61 (s, 1H), 8.08 (s, 1H), 7.36-7.38 (m, 5H), 7.12 (s, 1H), 6.60 (s, 1H), 5.10 (s, 3H), 4.94-4.96 (m, 1H), 3.60-3.62 (m, 1H), 3.27-3.32 (m, 2H), 3.18-3.20 (m, 1H), 3.11 (s, 3H), 2.10-2.12 (m, 2H), 2.07-2.09 (m, 1H), 1.77-1.80 (m, 1H), 1.47-1.48 (m, 1H) 0.86-0.87 (m, 3H) |
| 127 | 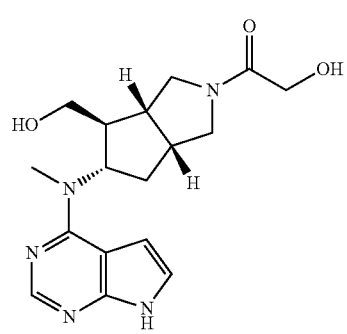<br>2-hydroxy-1-((3aR,4S,5S,6aR)-4-(hydroxymethyl)-5-(methyl-(7H-pyrrolo[2,3-d]pyrimidin-4-yl)amino)hexahydrocyclopenta[c]pyrrol-2(1H)-yl)ethanone | white solid | 346.1 [M + 1] | |
| 128 | 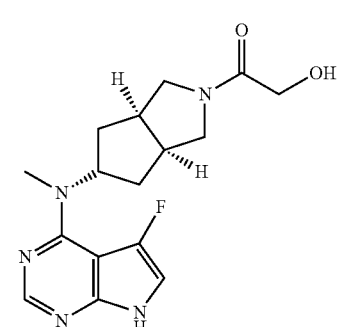<br>1-((3aR,5S,6aS)-5-((5-fluoro-7H-pyrrolo[2,3-d]pyrimidin-4-yl)(methyl)amino)hexahydrocyclopenta[c]pyrrol-2(1H)-yl)-2-hydroxyethanone | white solid | 334.2 [M + 1] | ¹H NMR (400 MHz, CDCl₃) δ 11.25 (s, 1H), 8.24 (s, 1H), 6.88 (s, 1H), 5.32-5.36 (m, 1H), 4.12-4.18 (m, 2H), 3.80-3.84 (m, 1H), 3.59-3.61 (m, 1H), 3.46-3.49 (m, 2H), 3.18-3.20 (m, 1H), 3.17 (s, 3H), 2.89-2.98 (m, 2H), 2.07-2.10 (m, 2H), 1.89-1.94 (m, 2H) |

| No | Structure | Properties | MS | ¹H NMR |
|---|---|---|---|---|
| 129 | 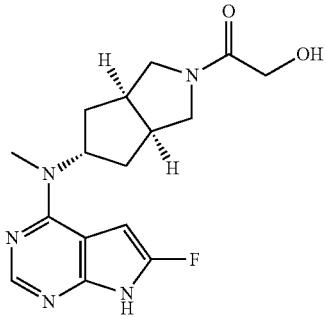<br>1-((3aR,5S,6aS)-5-((6-fluoro-7H-pyrrolo[2,3-d]pyrimidin-4-yl)(methyl)amino)hexahydrocyclopenta[c]pyrrol-2(1H)-yl)-2-hydroxyethanone | white solid | 334.2 [M + 1] | |
| 130 | 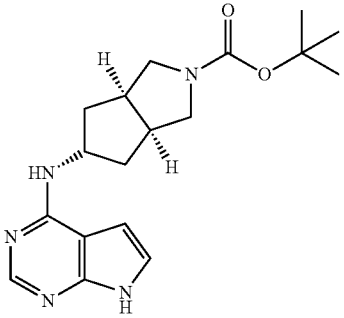<br>(3aR,5S,6aS)-tert-butyl 5-((7H-pyrrolo[2,3-d]pyrimidin-4-yl)amino)hexahydrocyclopenta[c]pyrrole-2(1H)-carboxamide | white solid | 344.4 [M + 1] | ¹H NMR (400 MHz, DMSO-$d_6$) δ 11.45 (s, 1H), 8.08 (s, 1H), 7.24 (s, 1H), 7.04 (s, 1H), 6.56 (s, 1H), 4.63-4.67 (m, 1H), 3.45-3.50 (m, 2H), 3.38-3.39 (m, 1H), 3.06-3.09 (m, 2H), 2.76-2.78 (m, 2H), 1.82-1.86 (m, 4H), 1.40 (s, 9H) |
| 131 | 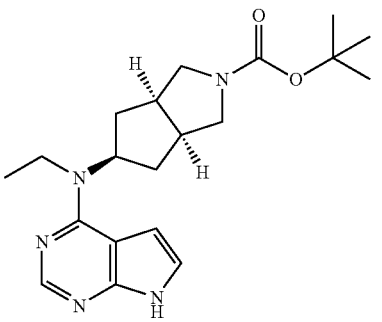<br>(3aR,5S,6aS)-tert-butyl 5-(ethyl(7H-pyrrolo[2,3-d]pyrimidin-4-yl)amino)hexahydrocyclopenta[c]pyrrole-2(1H)-carboxylate | white solid | 372.4 [M + 1] | ¹H NMR (400 MHz, CDCl$_3$) δ 10.45 (s, 1H), 8.31 (s, 1H), 7.05 (s, 1H), 6.47 (s, 1H), 5.28-5.34 (m, 1H), 3.66-3.73 (m, 2H), 3.37-3.53 (m, 4H), 2.70-2.71 (m, 2H), 2.23-2.28 (m, 2H), 1.90-2.00 (m, 2H), 1.49 (s, 9H), 1.34-1.37 (m, 3H) |

| No | Structure | Properties | MS | ¹H NMR |
|---|---|---|---|---|
| 132 | 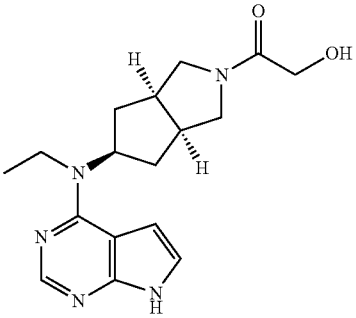<br>1-((3aR,5R,6aS)-5-(ethyl(7H-pyrrolo[2,3-d]pyrimidin-4-yl)amino)hexahydrocyclopenta[c]pyrrol-2(1H)-yl)-2-hydroxyethanone | white solid | 330.4 [M + 1] | ¹H NMR (400 MHz, DMSO-d₆) δ 11.66 (s, 1H), 8.10 (s, 1H), 7.16 (s, 1H), 6.48 (s, 1H), 5.15 (s, 1H), 4.52 (s, 1H), 3.96-4.08 (m, 2H), 3.63-3.66 (m, 2H), 3.49-3.53 (m, 2H), 3.42-3.44 (m, 2H), 2.63-2.73 (m, 2H), 2.02-2.10 (m, 2H), 1.46-1.57 (m, 2H), 1.20-1.23 (m, 3H) |
| 133 | 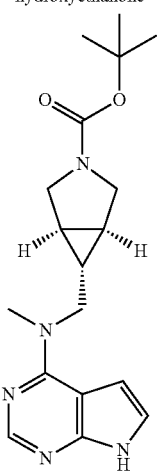<br>(1R,5S,6S)-tert-butyl 6-((methyl(7H-pyrrolo [2,3-d]pyrimidin-4-yl)amino)methyl)-3-azabicyclo[3.1.0]hexane-3-carboxylate | white solid | 344.2 [M + 1] | ¹H NMR (400 MHz, CDCl₃) δ 10.35 (s, 1H), 8.27 (s, 1H), 7.06 (s, 1H), 6.59 (s, 1H), 3.76-3.80 (m, 2H), 3.60-3.62 (m, 2H), 3.51 (s, 3H), 3.34-3.41 (m, 2H), 1.56-1.57 (m, 2H), 11.43 (s, 9H), 1.24-1.26 (m, 2H), 1.01-1.02 (m, 1H) |
| 134 | 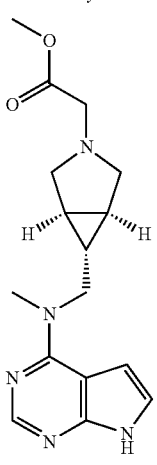<br>methyl 2-(1R,5S,6S)-6-((methyl(7H-pyrrolo[2,3-d]pyrimidin-4-yl)amino)methyl)-3-azabicyclo[3.1.0]hexan-3-yl)acetate | white solid | 316.2 [M + 1] | ¹H NMR (400 MHz, CDCl₃) δ 10.31 (s, 1H), 8.27 (s, 1H), 7.04 (s, 1H), 6.60 (s, 1H), 3.66-3.68 (m, 5H), 3.42 (s, 3H), 3.30-3.34 (m, 2H), 3.11-3.14 (m, 2H), 1.48-1.56 (m 2H), 0.82-0.90 (m, 1H) |

| No | Structure | Properties | MS | ¹H NMR |
|---|---|---|---|---|
| 135 | 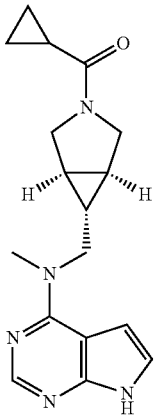<br>cyclopropyl((1R,5S,6S)-6-((methyl(7H-pyrrolo[2,3-d]pyrimidin-4-yl)amino)methyl)-3-azabicyclo[3.1.0]hexan-3-yl)methanone | white solid | 312.2 [M + 1] | ¹H NMR (400 MHz, CDCl$_3$) δ 10.32 (s, 1H), 8.29 (s, 1H), 7.06 (s, 1H), 6.60 (s, 1H), 3.82-3.86 (s, 4H), 3.72-3.73 (m, 1H), 3.45 (s, 3H), 3.40-3.43 (m, 1H), 1.75-1.77 (m, 1H), 1.60-1.64 (m, 1H), 0.94-0.95 (m, 1H), 0.72-0.74 (m, 2H), 0.69-0.70 (m, 2H) |
| 136 | 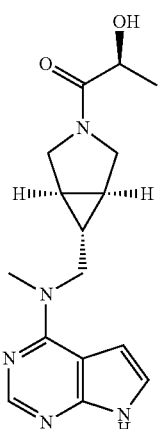<br>(S)-2-hydroxy-1-((1R,5S,6S)-6-((methyl(7H-pyrrolo[2,3-d]pyrimidin-4-yl)amino)methyl)-3-azabicyclo[3.1.0]hexan-3-yl)propan-1-one | white solid | 316.2 [M + 1] | ¹H NMR (400 MHz, DMSO-d$_6$) δ 11.60 (s, 1H), 8.05-8.15 (m, 1H), 7.06-7.18 (m, 1H), 6.49-6.58 (m, 1H), 5.38-5.55 (m, 1H), 4.76-4.91 (m, 1H), 4.22-4.38 (m, 1H), 3.55-3.71 (m, 2H), 3.19-3.30 (m, 1H), 3.18 (s, 3H), 2.70-2.81 (m, 1H), 1.92-2.05 (m, 2H), 1.68-1.82 (m, 2H), 1.15-1.25 (m, 3H) |

| No | Structure | Properties | MS | 1H NMR |
|---|---|---|---|---|
| 137 | 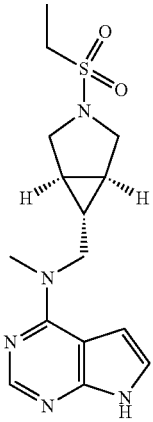<br>N-(((1R,5S,6S)-3-(ethylsulfonyl)-3-azabicyclo[3.1.0]hexan-6-yl)methyl)-7H-methyl-7H-pyrrolo[2,3-d]pyrimidin-4-amine | white solid | 336.1 [M + 1] | 1H NMR (400 MHz, CDCl$_3$) δ 10.61 (s, 1H), 8.20 (s, 1H), 7.07 (s, 1H), 6.60 (s, 1H), 3.79-3.80 (m, 2H), 3.57-3.59 (m, 2H), 3.46 (s, 3H), 3.35-3.37 (m, 2H), 2.89-2.99 (m, 2H), 1.34-1.36 (m 2H), 1.27-1.30 (m, 2H), 1.19-1.21 (m, 1H) |
| 138 | 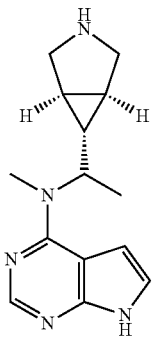<br>N-((R)-1-((1R,5S,6R)-3-azabicyclo[3.1.0]hexan-6-yl)ethyl)-N-methyl-7H-pyrrolo[2,3-d]pyrimidin-4-amine | white solid | 258.2 [M + 1] | 1H NMR (400 MHz, DMSO-d$_6$) δ 11.61 (s, 1H), 8.04 (s, 1H), 7.10 (s, 1H), 6.58 (s, 1H), 4.52-4.54 (m, 1H), 3.38-3.29 (m, 6H), 3.11-3.14 (m, 2H), 1.89-1.90 (m, 2H), 1.51-1.57 (m, 2H), 1.19-1.21 (m,3H) |
| 139 | 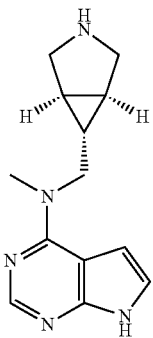<br>N-((1R,5S,6R)-3-azabicyclo[3.1.0]hexan-6-ylmethyl)-N-methyl-7H-pyrrolo[2,3-d]pyrimidin-4-amine | white solid | 244.5 [M + 1] | 1H NMR (400 MHz, DMSO-d$_6$) δ 8.38 (s, 7.07 (s, 1H), 6.61 (s, 1H), 3.74-3.76 (m, 2H), 3.48 (s, 3H), 3.08-3.15 (m, 4H), 1.29-1.33 (m, 2H), 0.98-0.99 (m, 1H) |

| No | Structure | Properties | MS | ¹H NMR |
|---|---|---|---|---|
| 140 | 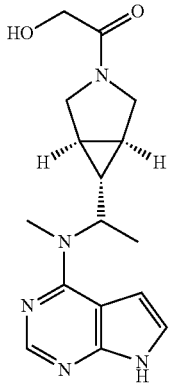<br>2-hydroxy-1-((1R,5S,6S)-6-((R)-1-(methyl(7H-pyrrolo[2,3-d]pyrimidin-4-yl)amino)ethyl)-3-azabicyclo[3.1.0]hexan-3-yl)ethanone | yellow solid | 316.2 [M + 1] | ¹H NMR (400 MHz, CDCl₃) δ 11.60 (s, 1H), 8.33 (s, 1H), 7.08-7.15 (m, 1H), 6.55-6.65 (m, 1H), 5.90-6.04 (m, 1H), 4.30-4.47 (m, 1H), 3.86-3.97 (m, 1H), 3.71-3.79 (m, 1H), 3.57-3.65 (m, 1H), 3.30-3.32 (m, 3H), 3.01-3.09 (m, 1H), 2.98 (s, 3H), 1.90-1.99 (m, 2H), 1.51-1.56 (m, 1H), 1.42-1.46 (m, 1H), 1.28-1.32 (m, 1H) |
| 141 | 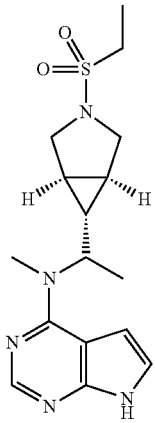<br>N-((R)-1-(1R,5S,6S)-3-(ethylsulfonyl)-3-azabicyclo-[3.1.0]hexan-6-yl)ethyl)-N-methyl-7H-pyrrolo[2,3-d]pyrimidin-4-amine | white solid | 350.2 [M + 1] | ¹H NMR (400 MHz, CDCl₃) δ 10.51 (s, 1H), 8.24 (s, 1H), 7.06 (s, 1H), 6.53 (s, 1H), 3.97-4.03 (m, 4H), 3.84-3.87 (m, 2H), 3.54-3.59 (s, 2H), 3.44-3.46 (m, 1H), 2.04-2.10 (m, 3H), 1.84-1.91 (m, 2H), 1.21-1.26 (m, 1H), 0.85-0.87 (m, 3H) |

| No | Structure | Properties | MS | ¹H NMR |
|---|---|---|---|---|
| 142 | 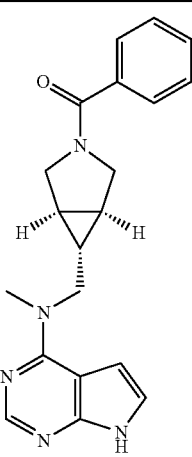 ((1R,5S,6S)-6-((methyl(7H-pyrrolo[2,3-d]pyrimidin-4-yl)amino)methyl)-3-azabicyclo-[3.1.0]hexan-3-yl)(phenyl)methanone | white solid | 348.3 [M + 1] | ¹H NMR (400 MHz, CDCl₃) δ 10.33 (s, 1H), 8.28 (s, 1H), 7.39-7.42 (m, 5H), 7.05 (s, 1H), 6.57 (s, 1H), 4.19-4.22 (m, 1H), 3.77-3.80 (m, 2H), 3.50-3.64 (m, 3H), 3.42 (s, 3H), 1.65-1.68 (m, 2H), 1.00-1.02 (m, 1H) |
| 143 | 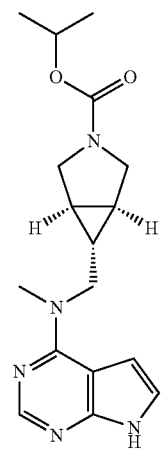 (1R,5S,6S)-isopropyl 6-((methyl(7H-pyrrolo[2,3-d]pyrimidin-4-yl)amino)methyl)-3-azabicyclo[3.1.0]hexane-3-carboxylate | white solid | 330.5 [M + 1] | ¹H NMR (400 MHz, CDCl₃) δ 10.49 (s, 1H), 8.22 (s, 1H), 7.06 (s, 1H), 6.59 (s, 1H), 4.82-4.88 (m, 1H), 3.76-3.78 (m, 2H), 3.54-3.63 (m, 2H), 3.44 (s, 3H), 1.26-1.29 (m, 2H), 1.20-1.21 (m, 6H), 0.97-0.99 (m, 1H) |

| No | Structure | Properties | MS | ¹H NMR |
|---|---|---|---|---|
| 144 | 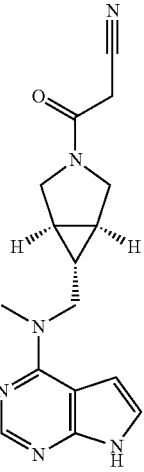<br>3-((1R,5S,6S)-6-((methyl(7H-pyrrolo[2,3-d]pyrimidin-4-yl)amino)methyl)-3-azabicyclo-[3.1.0]hexan-3-yl)-3-oxopropanenitrile | white solid | 311.5 [M + 1] | ¹H NMR (400 MHz, CDCl₃) δ 11.62 (s, 1H), 8.07 (s, 1H), 7.12 (s, 1H), 6.60 (s, 1H), 3.76-3.87 (m, 3H), 3.58-3.63 (m, 2H), 3.46-3.48 (s, 2H), 3.34 (s, 3H), 3.31-3.33 (m, 1H), 1.71-1.74 (m, 1H), 1.61-1.65 (m, 1H), 0.85-0.90 (m, 1H) |
| 145 | 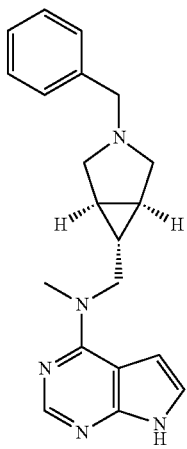<br>N-(((1R,5S,6R)-3-benzyl-3-azabicyclo[3.1.0]hexan-6-yl)methyl)-N-methyl-7H-pyrrolo[2,3-d]pyrimidin-4-amine | yellow solid | 334.4 [M + 1] | ¹H NMR (400 MHz, DMSO-d₆) δ 11.64 (s, 1H), 7.92-7.99 (m, 1H), 7.55-7.62 (m, 1H), 7.36-7.42 (m, 1H), 7.22-7.29 (m, 3H), 7.09-7.15 (m, 1H), 6.55-6.62 (m, 1H), 3.75-4.05 (m, 2H), 3.58-3.67 (m, 2H), 3.16 (s, 3H), 2.97-3.12 (m, 2H), 2.68-2.88 (m, 1H), 1.50-1.76 (m, 3H), 1.18-1.27 (m, 1H) |

| No | Structure | Properties | MS | ¹H NMR |
|---|---|---|---|---|
| 146 | 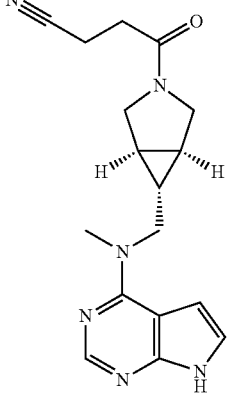<br>4-((1R,5S,6S)-6-((methyl(7H-pyrrolo[2,3-d]pyrimidin-4-yl)amino)methyl)-3-azabicyclo-[3.1.0]hexan-3-yl)-4-oxobutanenitrile | white solid | 325.4 [M + 1] | ¹H NMR (400 MHz, DMSO-d$_6$) δ 11.63 (s, 1H), 8.08 (s, 1H), 7.06-7.18 (m, 1H), 6.56-6.65 (m, 1H), 3.75-3.81 (m, 1H), 3.62-3.70 (m, 1H), 3.52-3.60 (m, 2H), 3.47-3.50 (m, 1H), 3.35 (s, 3H), 3.25-3.32 (m, 1H), 2.62-2.71 (m, 1H), 2.48-2.52 (m, 2H), 1.70-1.79 (m, 1H), 1.55-1.65 (m, 1H), 1.19-1.29 (m, 1H), 0.82-0.95 (m, 1H) |
| 147 | 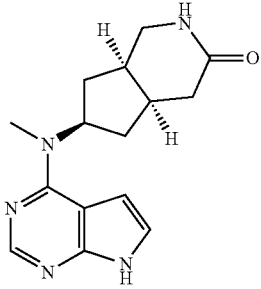<br>(4aR,6R,7aR)-6-(methyl(7H-pyrrolo[2,3-d]pyrimidin-4-yl)amino)hexahydro-1H-cyclopenta[c]pyridin-3(2H)-one | white solid | 286.0 [M + 1] | ¹H NMR (400 MHz, CDCl$_3$) δ 10.29 (s, 1H), 8.30 (s, 1H), 7.05 (s, 1H), 6.56 (s, 1H), 6.30 (s, 1H), 5.26-5.30 (m, 1H), 3.43-3.49 (m, 1H), 3.24 (s, 3H), 3.11-3.14 (m, 1H), 2.53-2.55 (m, 1H), 2.49-2.51 (m, 2H), 2.29-2.33 (m, 1H), 2.09-2.12 (m, 2H), 1.52-1.66 (m, 2H) |
| 148 | 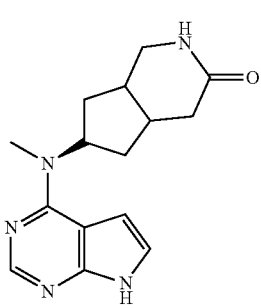<br>(6S)-6-(methyl(7H-pyrrolo[2,3-d]pyrimidin-4-yl)amino)hexahydro-1H-cyclopenta[c]pyridin-3(2H)-one | white solid | 286.0 [M + 1] | ¹H NMR (400 MHz, CDCl$_3$) δ 10.29 (s, 1H), 8.30 (s, 1H), 7.05 (s, 1H), 6.56 (s, 1H), 6.30 (s, 1H), 5.26-5.30 (m, 1H), 3.43-3.49 (m, 1H), 3.24 (s, 3H), 3.11-3.14 (m, 1H), 2.53-2.55 (m, 1H), 2.49-2.51 (m, 2H), 2.29-2.33 (m, 1H), 2.09-2.12 (m, 2H), 1.52-1.66 (m, 2H) |

-continued

| No | Structure | Properties | MS | ¹H NMR |
|---|---|---|---|---|
| 149 | 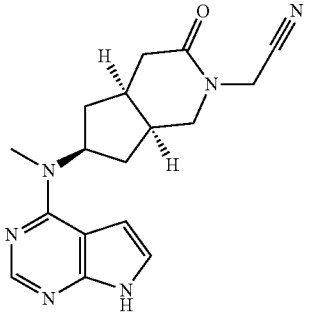<br>2-((4aS,6S,7aS)-6-(methyl(7H-pyrrolo[2,3-d]pyrimidin-4-yl)amino)-3-oxohexahydro-1H-cyclopenta[c]pyridin-2(3H)-yl)acetonitrile | white solid | 324.9 [M + 1] | ¹H NMR (400 MHz, CDCl₃) δ 9.49 (s, 1H), 8.28 (s, 1H), 7.02 (s, 1H), 6.58 (s, 1H), 5.30-5.37 (m, 1H), 4.72-4.77 (m, 1H), 4.10-4.14 (m, 1H), 3.65-3.69 (m, 1H), 3.30-3.31 (m, 1H), 3.27 (s, 3H), 2.53-2.59 (m, 2H), 2.43-2.44 (m, 1H), 2.13-2.18 (m, 3H), 1.63-1.66 (m, 1H), 1.43-1.45 (m, 1H) |
| 150 | 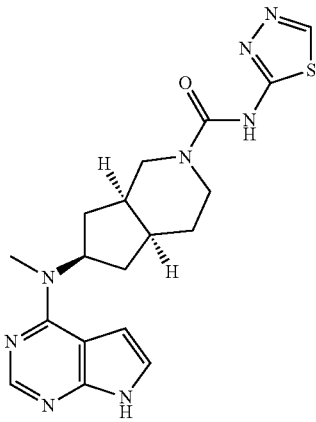 [SMILES: CN(c1ncnc2[nH]ccc12)[C@@H]1C[C@@H]2CCN(C(=O)Nc3nncs3)C[C@@H]2C1]<br>(4aS,6R,7aR)-6-(methyl(7H-pyrrolo[2,3-d]pyrimidin-4-yl)amino)-N-(1,3,4-thiadiazol-2-yl)hexahydro-1H-cyclopenta[c]pyridine-2(3H)-carboxamide | white solid | 397.2 [M + 1] | ¹H NMR (400 MHz, DMSO-d₆) δ 11.59 (s, 1H), 8.96 (s, 1H), 8.08 (s, 1H), 7.12 (s, 1H), 6.57 (s, 1H), 5.27-5.31 (m, 1H), 3.60-3.72 (m, 2H), 3.36-3.41 (m, 2H), 3.17 (s, 3H), 2.18-2.21 (m, 2H), 1.88-1.91 (m, 3H), 1.61-1.65 (m, 2H), 1.05-1.08 (m, 1H) |
| 151 | 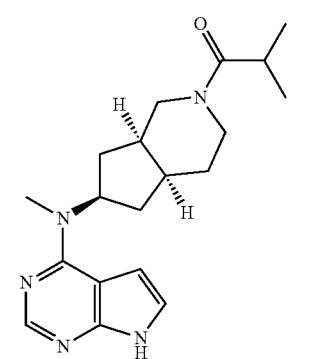 [SMILES: CC(C)C(=O)N1CC[C@H]2C[C@@H](N(C)c3ncnc4[nH]ccc34)C[C@H]2C1]<br>2-methyl-1-((4aS,6R,7aR)-6-(methyl(7H-pyrrolo[2,3-d]pyrimidin-4-yl)amino)hexahydro-1H-cyclopenta[c]pyridin-2(3H)-yl)propan-1-one | white solid | 342.3 [M + 1] | ¹H NMR (400 MHz, CDCl₃) δ 10.25 (s, 1H), 8.26 (s, 1H), 7.05 (s, 1H), 6.58 (s, 1H), 5.31-5.48 (m, 1H), 3.81-3.84 (m, 1H), 3.58-3.60 (m, 1H), 3.30-3.42 (m, 2H), 3.27 (s, 3H), 2.79-2.81 (m, 1H), 2.27-2.30 (m, 2H), 1.91-2.09 (m, 4H), 1.55-1.59 (m, 2H), 1.13-1.17 (m, 6H), |

| No | Structure | Properties | MS | ¹H NMR |
|---|---|---|---|---|
| 152 | 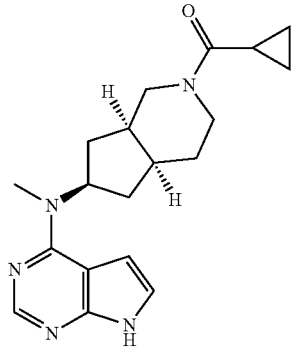 [SMILES: CN(c1ncnc2[nH]ccc12)[C@@H]1C[C@@H]2CCN(C(=O)C3CC3)C[C@@H]2C1]<br>cyclopropyl((4aS,6R,7aR)-6-(methyl(7H-pyrrolo[2,3-d]pyrimidin-4-yl)amino)hexahydro-1H-cyclopenta[c]pyridin-2(3H)-yl)methanone | white solid | 340.2 [M + 1] | ¹H NMR (400 MHz, CDCl₃) δ 10.68 (s, 1H), 8.23 (s, 1H), 7.04 (s, 1H), 6.56 (s, 1H), 5.35-5.44 (m, 1H), 3.81-3.91 (m, 2H), 3.65-3.71 (m, 1H), 3.37-3.51 (m, 2H), 3.27 (s, 3H), 2.28-2.30 (m, 2H), 1.97-2.18 (m, 3H), 1.55-1.60 (m, 3H), 0.99-1.03 (m, 2H), 0.75-0.86 (m, 2H), |
| 153 | 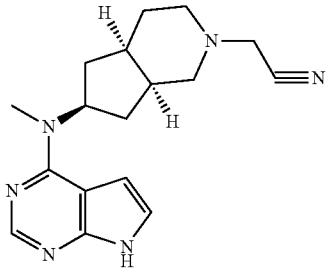 [SMILES: CN(c1ncnc2[nH]ccc12)[C@H]1C[C@H]2CCN(CC#N)C[C@H]2C1]<br>2-((4aR,6S,7aS)-6-(methyl(7H-pyrrolo[2,3-d]pyrimidin-4-yl)amino)hexahydro-1H-cyclopenta[c]pyridin-2(3H)-yl)acetonitrile | white solid | 311.5 [M + 1]<br>309.5 [M − 1] | ¹H NMR (400 MHz, DMSO-d₆) δ 11.60 (s, 1H), 8.08 (s, 1H), 7.12 (d, 1H), 6.58 (d, 1H), 5.37-5.42 (m, 1H), 3.73 (m, 2H), 3.20 (s, 3H), 2.46-2.52 (m, 2H), 2.32-2.34 (m, 1H), 2.14 -2.18 (m, 1H), 1.69-2.00 (m, 7H), 1.52-1.56 (m, 1H) |
| 154 | 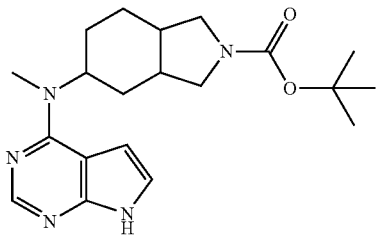 [SMILES: CN(c1ncnc2[nH]ccc12)C1CCC2CN(C(=O)OC(C)(C)C)CC2C1]<br>tert-butyl 5-(methyl(7H-pyrrolo[2,3-d]pyrimidin-4-yl)amino)hexahydro-1H-isoindole-2(3H)-carboxylate | white solid | 372.4 [M + 1]<br>370.3 [M − 1] | ¹H NMR (400 MHz, CDCl₃) δ 10.30 (s, 1H), 8.30 (s, 1H), 7.04 (d, 1H), 6.55 (d, 1H), 4.78-4.82 (m, 1H), 3.18-3.45 (m, 4H), 3.28 (s, 3H), 2.38-2.42 (m, 2H), 1.90-1.94 (m, 2H), 1.66-1.78 (m, 4H), 1.49 (d, 9H) |

-continued

| No | Structure | Properties | MS | ¹H NMR |
|---|---|---|---|---|
| 155 | 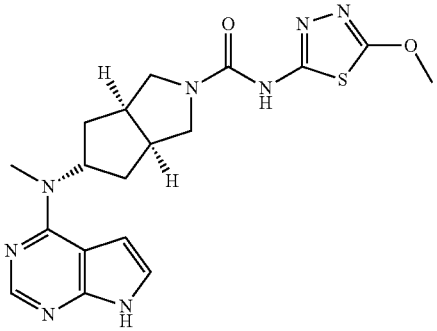(3aR,5S,6aS)-N-(5-methoxy-1,3,4-thiadiazol-2-yl)-5-(methyl(7H-pyrrolo[2,3-d]pyrimidin-4-yl)amino)hexahydrocyclopenta[c]pyrrole-2(1H)-carboxamide | white solid | 415.4 [M + 1] | ¹H NMR (400 MHz, DMSO-d₆) δ 11.60 (br. s, 1H), 8.08 (s, 1H), 6.93-7.18 (m, 1H), 6.36-6.61 (m, 1H), 5.33-5.56 (m, 1H), 4.02 (s, 3H), 3.55-3.72 (m, 2H), 3.14 (s, 3H), 2.78-2.95 (m, 2H), 1.91-2.09 (m, 2H), 1.68-1.84 (m, 2H) |
| 156 | 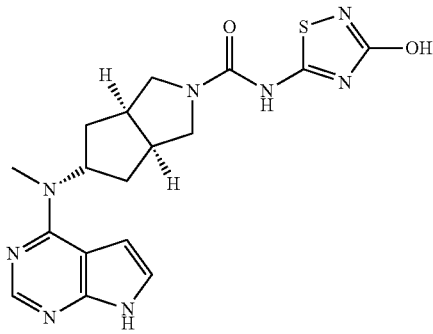(3aR,5S,6aS)-N-(3-hydroxy-1,2,4-thiadiazol-5-yl)-5-(methyl(7H-pyrrolo[2,3-d]pyrimidin-4-yl)amino)hexahydrocyclopenta[c]pyrrole-2(1H)-carboxamide | white solid | 401.3 [M + 1] | ¹H NMR (400 MHz, DMSO-d₆) δ 12.80 (s, 1H), 8.37 (s, 1H), 7.41-7.50 (m, 1H), 6.87-6.93 (m, 1H), 5.07-5.21 (m, 1H), 4.34 (s, 1H), 3.50-3.70 (m, 2H), 3.29 (s, 3H), 3.08-3.11 (m, 1H), 2.95-2.88 (m, 2H), 2.05-2.15 (m, 2H), 1.86-1.96 (m, 2H), 1.16-1.20 (m, 2H) |

TEST EXAMPLES

Biological Assays

Test Example 1

Assay for Determining the Activity of Compounds of the Present Invention for Inhibiting JAK1 Kinase In vitro activity of compounds of the present invention for inhibiting JAK1 kinase was determined by the following method.

In vitro kinase assays described below can be used to determine the activity of a test compound for inhibiting the activity of JAK1 kinase. The test compounds were dissolved in dimethyl sulfoxide and diluted with water to a serial concentration gradient as required in the experiment. JAK1 substrates (Cell Signaling Technology, Catalog Number: 1305s) and ATP (2 mM) solution were diluted with water to obtain a final concentration of 20 µM ATP and 1.2 µM substrate solution. The appropriate amount of JAK1 kinase (Invitrogen, Catalog Number: pv4774) was mixed with 4× buffer (prepared by user, and comprising 50 mM HEPES, pH 7.3, 125 mM NaCl, 24 mM MgCl₂, 1.25 mM DTT) to a final concentration of 8 ng/µL. To each well of a microplate [DELFIA® Streptavidin-coated clear plate (Perkin Elmer, Catalog Number: AAAND-0005)]17.5 µL of ATP/substrate mixture, 5 µL of an aqueous solution of a test compound (5 µL of pure water only were added to the control and blank), and 7.5 µL of the kinase solution prepared above (4× buffer only was added to the control) were added. Each well was mixed sufficiently, then incubated at room temperature (27° C.) for 50 minutes, washed with wash buffer, and dried three times, then HRP conjugated antibody was added [Phospho-Tyrosine Mouse mAb (P-Tyr-100) (HRP Conjugate, *Cell Signaling Technology*, Catalog Number: 5465)], and incubated for 1 hour. The microplate was washed with wash buffer and dried three times, and then TMB (Sigma, Catalog Number: T4444) was added, and incubated for 5 to 15 minutes to allow for color change. Stop solution (1 N sulfuric acid solution) was added to stop the reaction. Absorbance was measured on a Novostar microplate reader at a wavelength of 450 nm. IC₅₀ values of test compounds was calculated from the data of the test compounds in inhibiting the activity of JAK1 kinase at different concentrations.

The Activity of the Compounds of the Present Invention.

Biochemical activity of the compounds of the present invention was determined by the above assay, and $IC_{50}$ values are shown in the following table 1.

TABLE 1

IC$_{50}$ values of the compounds of the present invention for inhibiting the activity of JAK1 kinase.

| Example No | IC50 (JAK1/Bio) (nM) |
|---|---|
| 5 | 30 |
| 6 | 5 |
| 8 | 32 |
| 11 | 33 |
| 13 | 30 |
| 14 | 30 |
| 15 | 80 |
| 17 | 0.2 |
| 18 | 49 |
| 19 | 48 |
| 21 | 17 |
| 22 | 16 |
| 23 | 21 |
| 24 | 13 |
| 26 | 46 |
| 27 | 30 |
| 34 | 2 |
| 35 | 3 |
| 36 | 25 |
| 37 | 50 |
| 39 | 34 |
| 40 | 98 |
| 41 | 80 |
| 48 | 1 |
| 49 | 0.2 |
| 50 | 0.5 |
| 51 | 100 |
| 56 | 11 |
| 61 | 128 |
| 65 | 50 |
| 68 | 17 |
| 69 | 5 |
| 71 | 36 |
| 72 | 42 |
| 73 | 75 |
| 74 | 4 |
| 75 | 46 |
| 80 | 127 |
| 81 | 113 |
| 82 | 49 |
| 83 | 50 |
| 84 | 73 |
| 85 | 80 |
| 86 | 10 |
| 92 | 131 |
| 93 | 70 |
| 94 | 45 |
| 99 | 0.3 |
| 104 | 109 |
| 109 | 15 |
| 111 | 96 |
| 112 | 96 |
| 113 | 23 |
| 114 | 2 |
| 117 | 95 |
| 119 | 48 |
| 121 | 1 |
| 124 | 119 |
| 125 | 0.2 |
| 128 | 13 |
| 129 | 36 |
| 147 | 1 |
| 148 | 8 |
| 150 | 40 |
| 151 | 106 |
| 155 | 4 |
| 156 | 171 |

Conclusion: The compounds of the present invention had significant activity for inhibiting the proliferation of JAK1 kinase.

Test Example 2

Assay for Determining the Activity of Compounds of the Present Invention for Inhibiting JAK2 Kinase In vitro activity of compounds of the present invention for inhibiting JAK2 kinase was determined by the following method.

In vitro kinase assays described below can be used to determine the activity of a test compound for inhibiting the activity of JAK2 kinase. The test compounds were dissolved in dimethyl sulfoxide and diluted with water to a serial concentration gradient as required in the experiment. JAK2 substrates (Cell Signaling Technology, Catalog Number: 1305s) and ATP (2 mM) solution were diluted with water to obtain a final concentration of 20 µM ATP and 1.2 µM substrate solution. The appropriate amount of JAK2 kinase (Invitrogen, Catalog Number: pv4210) was mixed with 4× buffer (prepared by user, and comprising 50 mM HEPES, pH 7.3, 125 mM NaCl, 24 mM MgCl$_2$, 1.25 mM DTT) to a final concentration of 8 ng/µL. To each well of a microplate [DELFIA® Streptavidin-coated clear plate (Perkin Elmer, Catalog Number: AAAND-0005)]17.5 µL of ATP/substrate mixture, 5 µL of aqueous solution of a test compound (5 µL of pure water only were added to control and blank), and 7.5 µL of the kinase solution prepared above (4× buffer only was added to control) were added. Each well was mixed sufficiently, then incubated at room temperature (27° C.) for 50 minutes, washed with wash buffer, and dried three times, then HRP conjugated antibody [Phospho-Tyrosine Mouse mAb (P-Tyr-100) (HRP Conjugate, Cell signaling Technology, Catalog Number: 5465)] was added, and incubated for 1 hour. The microplate was washed with wash buffer and dried three times, and then TMB (Sigma, Catalog Number: T4444) was added and incubated for 5 to 15 minutes to allow for color change. Stop solution (1 N sulfuric acid solution) was added to stop the reaction. Absorbance was measured on a Novostar microplate reader at a wavelength of 450 nm. $IC_{50}$ values of test compounds were calculated from the data of the test compounds for inhibiting the activity of JAK2 kinase at different concentrations.

The Activity of the Compounds of the Present Invention

Biochemical activity of the compounds of the present invention was determined by the above assay, and $IC_{50}$ values are shown in the following table 2.

TABLE 2

IC$_{50}$ values of the compounds of the present invention for inhibiting the activity of JAK2 kinase.

| Example No | IC50 (JAK2/Bio) (nM) |
|---|---|
| 6 | 45 |
| 17 | 3 |

TABLE 2-continued

IC$_{50}$ values of the compounds of the present invention for inhibiting the activity of JAK2 kinase.

| Example No | IC50 (JAK2/Bio) (nM) |
|---|---|
| 22 | 54 |
| 24 | 77 |
| 34 | 5 |
| 35 | 16 |
| 36 | 75 |
| 37 | 72 |
| 38 | 7 |
| 39 | 113 |
| 40 | 23 |
| 48 | 31 |
| 49 | 14 |
| 50 | 7 |
| 56 | 32 |
| 61 | 25 |
| 65 | 179 |
| 68 | 18 |
| 69 | 4 |
| 73 | 47 |
| 74 | 56 |
| 75 | 156 |
| 86 | 52 |
| 92 | 203 |
| 99 | 5 |
| 111 | 146 |
| 113 | 178 |
| 114 | 140 |
| 121 | 31 |
| 125 | 14 |
| 128 | 196 |
| 134 | 60 |
| 135 | 2 |
| 147 | 5 |
| 148 | 23 |
| 150 | 23 |
| 151 | 127 |
| 155 | 41 |

Conclusion: The compounds of the present invention had significant activity for inhibiting the proliferation of JAK2 kinase.

Test Example 3

Assay for Determining the Activity of Compounds of the Present Invention for Inhibiting JAK3 Kinase In vitro activity of compounds of the present invention for inhibiting JAK3 kinase was determined by the following method.

In vitro kinase assays described below can be used to determine the activity of a test compound for inhibiting the activity of JAK3 kinase. The test compounds were dissolved in dimethyl sulfoxide and diluted with water to a serial concentration gradient as required by the experiment. JAK3 substrates (Cell Signaling Technology, Catalog Number: 1305s) and ATP (2 mM) solution were diluted with water to obtain a final concentration of 20 M ATP and 1.2 M substrate solution. The appropriate amount of JAK3 kinase (Invitrogen, Catalog Number: pv3 855) was mixed with 4× buffer (prepared by user, and comprising 50 mM HEPES, pH 7.3, 125 mM NaCl, 24 mM MgCl$_2$, 1.25 mM DTT) to a final concentration of 8 ng/μL. To each well of a microplate [DELFIA® Streptavidin-coated clear plate (Perkin Elmer, Item: AAAND-0005)]17.5 μL of ATP/substrate mixture, 5 μL of aqueous solution of a test compound (L of pure water only were added to the control and blank), and 7.5 μL of the kinase solution prepared above (4× buffer only was added to the control) were added. Each well was mixed sufficiently, then incubated at room temperature (27° C.) for 50 minutes, washed with wash buffer, and dried three times, then HRP conjugated antibody [Phospho-Tyrosine Mouse mAb (P-Tyr-100) (HRP Conjugate, Cell signaling Technology, Catalog Number: 5465)] was added, and incubated for 1 hour. The microplate was washed with wash buffer and dried three times, and then TMB (Sigma, Catalog Number: T4444) was added and incubated for 5 to 15 minutes to allow for color change. Stop solution (1 N sulfuric acid solution) was added to stop the reaction. Absorbance was measured on a Novostar microplate reader at a wavelength of 450 nm. IC$_{50}$ values of test compounds were calculated from the data of the test compounds for inhibiting the activity of JAK3 kinase at different concentrations.

The Activity of the Compounds of the Present Invention

Biochemical activity of the compounds of the present invention was determined by the above assay, and IC$_{50}$ values are shown in the following Table 3.

TABLE 3

IC$_{50}$ values of the compounds of the present invention for inhibiting the activity of JAK3 kinase.

| Example No | IC$_{50}$ (JAK3/Bio) (nM) |
|---|---|
| 6 | 11 |
| 8 | 67 |
| 17 | 0.3 |
| 31 | 93 |
| 38 | 40 |
| 40 | 71 |
| 49 | 39 |
| 50 | 201 |
| 56 | 75 |
| 68 | 43 |
| 69 | 20 |
| 73 | 191 |
| 84 | 70 |
| 97 | 110 |
| 99 | 110 |
| 111 | 101 |
| 125 | 39 |
| 128 | 4 |
| 129 | 17 |
| 133 | 90 |
| 134 | 164 |
| 147 | 31 |
| 148 | 71 |
| 150 | 148 |
| 151 | 203 |

Conclusion: The compounds of the present invention had significant activity for inhibiting the proliferation of JAK3 kinase.

Test Example 4

Proliferation Inhibition Assay of the Compounds of the Present Invention on Human Erythroid Leukemia Cell Line TF-1

The following in vitro assay is to determine the activity of the compounds of the present invention for inhibiting the proliferation of human erythroid leukemia cell line TF-1.

The following in vitro cell assay can be used to determine the activity of a test compound for inhibiting the proliferation mediated by IL-4 (said IL-4 can mediate JAK3 pathway). The activity is represented by the IC$_{50}$ value, which can not only reflect the activity of a test compound for inhibiting JAK2 and JAK3 kinase, but can also reflect the selectivity of a test compound for JAK2 and JAK3 kinase.

The general procedures of the assay are given as follows: first, the TF-1 cells (purchased from ATCC, Catalog number:

CRL 2003) were seeded in a 96-well cell culture plate at a suitable cell concentration (8000 cells/mL medium), and 10 ng/mL IL-4 (Invitrogen, Catalog Number: PHC0044) were added to each well. Then 10× serial concentration gradient of test compounds solutions (10000, 1000, 100, 10, 1 and 0.1 nM) were prepared, and then the 10× compound solutions prepared above were added to the 96-well cell culture plate containing IL-4. After the cell plates were cultured continuously for 72 hours, the activity of the test compounds for inhibiting the cell proliferation was determined by using a Cell Counting Kit-8 (purchased from Dojindo, Catalog Number: CK04). $IC_{50}$ values were calculated from the data of the inhibition rates at various concentrations of the test compounds.

The biological activity of the compounds of the present invention was tested by using the assay described above. $IC_{50}$ values were measured, and are shown in Table 4 below:

TABLE 4

$IC_{50}$ values of the compounds of the present invention for inhibiting TF-1 cell proliferation.

| Example No | $IC_{50}$ (TF-1/IL-4)/nM |
|---|---|
| 1 | 196 |
| 5 | 133 |
| 6 | 457 |
| 8 | 530 |
| 11 | 507 |
| 17 | 165 |
| 19 | 711 |
| 34 | 44 |
| 37 | 123 |
| 38 | 160 |
| 39 | 419 |
| 40 | 399 |
| 48 | 27 |
| 61 | 507 |
| 73 | 476 |
| 74 | 546 |
| 86 | 691 |
| 94 | 152 |
| 99 | 44 |
| 114 | 138 |
| 121 | 27 |
| 125 | 14 |
| 128 | 252 |
| 129 | 539 |
| 147 | 15 |
| 148 | 399 |

Conclusion: The compounds of the present invention had significant activity for inhibiting the proliferation of TF-1 cell mediated by IL-4 pathway of JAK3/JAK2.

Test Example 5

Proliferation Inhibition Assay of the Compounds of the Present Invention on T Cells The following in vitro assay is to determine the activity of the compounds of the present invention for inhibiting the proliferation of T cells.

The following in vitro cell assay can be used to determine the activity of a test compound for inhibiting the proliferation of T cells. The activity is represented by the $IC_{50}$ value.

The general procedures of the assay are given as follows: first, the PBMC cell line (purchased from Shanghai Blood Center) was centrifuged, the supernatant was removed, and the cells counted. The cells were then incubated in medium [RPMI-1640 (Hyclone, Catalog Number: SH30809.01B)+ 10% Fetal Bovine Serum (GIBCO, Catalog Number: 10099)+1% Pen Strep (GIBCO, Catalog Number: 15140)] with 200 g of Anti-Human CD3 functional Grade purified (eBioscience, Catalog Number: 16-0037-81) in a 5% carbon dioxide ($CO_2$) incubator at 37° C. for 3 days until they reached a cell concentration of $2 \times 10^6$/mL. Then, the cells were washed 3 times, resuspended, diluted to $2 \times 10^6$/mL, and then mixed with recombinant human IL-2 (purchased from Peprotech, Catalog Number: 200-02) to a concentration of 10 ng/mL, and cultured for another 3 days. The cells were washed again 3 times, and diluted to $5 \times 10^5$/mL. 80 μL of the cells were seeded in each well of a 96-well cell culture plate. The drug had an initial concentration of 1 mM. Then the drug was diluted with culture medium to 10000, 2500, 625, 156, 39, 9.8, 2.4, or 0.6 μM, and 10 μL of diluted drug was added to the corresponding well. To the control wells, 10 μL culture medium were added. The plate was placed in an incubator. After incubating for 1 hr, negative control wells were mixed with 10 μL of culture medium, and the rest of the wells were mixed with IL-2 to a concentration of 10 ng/mL, and incubated continuously for 72 hours. 3 Days later, the activity of the test compounds for inhibiting the cell proliferation was determined by using ATPlite™ Luminescence Assay System kit (PerkinElmer, Catalog Number: 6016947). $IC_{50}$ values were calculated from the data of inhibition rates at various concentrations of the test compounds.

The biological activity of the compounds of the present invention was tested by using the assay described above. $IC_{50}$ values were measured and are shown in Table 5 below:

TABLE 5

$IC_{50}$ values of the compounds of the present invention for inhibiting T cell proliferation.

| Example No | $IC_{50}$(T cell)/nM |
|---|---|
| 6 | 414 |
| 8 | 460 |
| 11 | 705 |
| 13 | 754 |
| 14 | 712 |
| 15 | 853 |
| 17 | 29 |
| 19 | 724 |
| 21 | 892 |
| 22 | 281 |
| 23 | 543 |
| 24 | 851 |
| 27 | 253 |
| 34 | 54 |
| 37 | 453 |
| 38 | 71 |
| 40 | 48 |
| 41 | 70 |
| 48 | 23 |
| 56 | 119 |
| 68 | 824 |
| 73 | 518 |
| 74 | 68 |
| 84 | 509 |
| 86 | 130 |
| 94 | 127 |
| 99 | 54 |
| 109 | 762 |
| 114 | 40 |
| 121 | 24 |
| 128 | 167 |
| 147 | 79 |
| 148 | 48 |
| 150 | 221 |

Conclusion: The compounds of the present invention had significant activity for inhibiting the proliferation of T cells.

Pharmacokinetics Assay

Test Example 6

The Pharmacokinetics Assay of the Compounds of the Present Invention

1. Abstract

Rats were used as test animals. The compounds of Example 6, Example 17, Example 22, Example 34, Example 35, Example 40, Example 48, Example 49, Example 99, Example 114, Example 121, Example 125, Example 128 and Example 148 were administered intragastrically to rats to determine the drug concentration in plasma at different time points by LC/MS/MS method. The pharmacokinetic behavior of the compounds of the present invention was studied and evaluated in rats.

2. Protocol 2.1 Samples

Compounds of Example 6, Example 17, Example 22, Example 34, Example 35, Example 40, Example 48, Example 49, Example 99, Example 114, Example 121, Example 125, Example 128, and Example 148.

2.2 Test Animals

56 Healthy adult Sprague-Dawley (SD) rats, half male and half female, purchased from SINO-BRITSH SIPPR/BK LAB. ANIMAL LTD., CO, Certificate No.: SCXK (Shanghai) 2003-0002, were divided into 14 groups, with 4 rats in each group.

2.3 Preparation of the Test Compounds

The appropriate amount of test compounds were weighed and mixed with 1.0 mL of dimethyl sulfoxide to prepare a 1.0 mg/mL suspension.

2.4 Administration

After an overnight fast, SD rats were administered intragastrically at a dose of 10.0 mg/kg and an administration volume of 10 mL/kg.

3. Process

Compounds of Example 6, Example 17, Example 22, Example 34, Example 35, Example 40, Example 48, Example 49, Example 99, Example 114, Example 121, Example 125, Example 128, and Example 148 were administered intragastrically to rats. Blood samples (0.2 mL) were taken from orbital sinus before administration and at 0.5 h, 1.0 h, 2.0 h, 3.0 h, 4.0 h, 6.0 h, 8.0 h, 12.0 h, 24.0 h, and 36.0 h after administration, stored in heparinized tubes, and centrifuged for 10 minutes at 10,000 rpm, 4° C. to separate blood plasma. The plasma samples were stored at −20° C. The rats were fed 2 hours after administration.

Content determination of the test compounds in rat plasma after intragastrically administering at different concentrations: 50 μL of rat plasmas taken at various time points after administration were mixed with 50 μL of internal standard solution and 100 μL of methanol and mixed for 3 minutes by a vortexer. The mixture was centrifuged for 10 minutes at 13,500 rpm. 10 μL of the supernatant was taken from the plasma sample and analyzed by LC-MS/MS.

4. Results of Pharmacokinetic Parameters

Pharmacokinetic Parameters of the compounds of the present invention were shown as follows:

| | Pharmacokinetics Assay (10 mg/kg) | | | | | |
|---|---|---|---|---|---|---|
| Example No | Plasma Conc. Cmax (ng/mL) | Area Under Curve AUC (ng/mL * h) | Half-Life t½ (h) | Mean Residence Time MRT (h) | Clearance CL/F (ml/min/kg) | Apparent Distribution Volume Vz/F (ml/kg) |
| Example 6 | 1227 ± 549 | 2210 ± 1472 | 4.01 ± 1.52 | 2.19 ± 0.60 | 110 ± 71 | 34475 ± 20986 |
| Example 17 | 1482 ± 177 | 4762 ± 1684 | 2.03 ± 0.82 | 3.10 ± 1.04 | 38.7 ± 13.7 | 6200 ± 1690 |
| Example 22 | 2965 ± 2113 | 6986 ± 4559 | 2.87 ± 0.70 | 2.60 ± 0.10 | 34.6 ± 22.7 | 9394 ± 8062 |
| Example 34 | 2668 ± 1449 | 14881 ± 10395 | 2.10 ± 0.73 | 3.81 ± 0.82 | 18.3 ± 14.2 | 2760 ± 1530 |
| Example 35 | 1220 ± 244 | 3075 ± 1336 | 2.11 ± 0.67 | 3.02 ± 1.33 | 63.3 ± 28.0 | 10418 ± 2040 |
| Example 40 | 1521 ± 317 | 5228 ± 1169 | 2.72 ± 1.82 | 3.27 ± 0.68/ | 33.2 ± 7.7 | 6990 ± 3390 |
| Example 48 | 2071 ± 1473 | 9617 ± 7909 | 2.43 ± 0.75 | 3.40 ± 0.91 | 31.9 ± 26.9 | 7203 ± 8113 |
| Example 49 | 1061 ± 677 | 5997 ± 4741 | 3.53 ± 1.72 | 5.32 ± 0.96 | 46.1 ± 35.6 | 18063 ± 20748 |
| Example 99 | 2668 ± 1449 | 14881 ± 10395 | 2.10 ± 0.73 | 3.81 ± 0.82 | 18.3 ± 14.2 | 2760 ± 1530 |
| Example 114 | 1226 ± 829 | 2935 ± 2217 | 2.38 ± 0.67 | 2.39 ± 0.43 | 104 ± 88 | 19115 ± 15952 |
| Example 121 | 2071 ± 1473 | 9617 ± 7909 | 2.43 ± 0.75 | 3.40 ± 0.91 | 31.9 ± 26.9 | 7203 ± 8113 |
| Example 125 | 1061 ± 677 | 5997 ± 4741 | 3.53 ± 1.72 | 5.32 ± 0.96 | 46.1 ± 35.6 | 18063 ± 20748 |
| Example 128 | 1423 ± 150 | 2322 ± 1029 | 1.62 ± 0.28 | 1.73 ± 0.50 | 84.3 ± 37.8 | 11378 ± 4148 |
| Example 148 | 1521 ± 317) | 5228 ± 1169 | 2.72 ± 1.82 | 3.27 ± 0.68 | 33.2 ± 7.7 | 6990 ± 3390 |

Conclusion: The compounds of the present invention had better pharmacokinetic data and significant advantage of pharmacokinetic properties.

What is claimed is:

1. A compound of formula (I), or a tautomer, mesomer, racemate, enantiomer, diastereomer, or mixture thereof, or a pharmaceutically acceptable salt thereof:

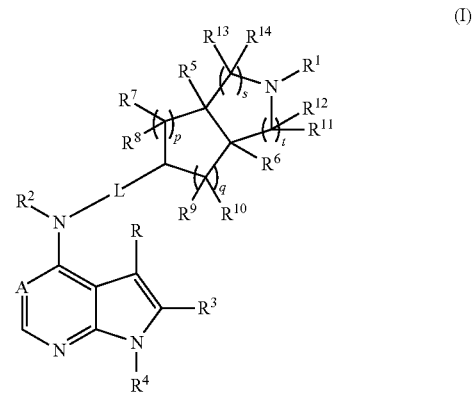

wherein:
A is CH or N;
L is a bond or alkyl;
$R^1$ is selected from the group consisting of hydrogen, alkyl, cycloalkyl, heterocyclyl, aryl, heteroaryl, —(CH₂)ₙC(O)OR¹⁵, —OC(O)R¹⁵, —C(O)R¹⁵, —C(O)NR¹⁶R¹⁷, —NHC(O)R¹⁵, —NR¹⁶R¹⁷, —OC(O)NR¹⁶R¹⁷, —NHC(O)NR¹⁶R¹⁷ and —S(O)ₘR¹⁵, wherein the alkyl, cycloalkyl, heterocyclyl, aryl or heteroaryl is optionally substituted with one or more groups selected from the group consisting of halogen, hydroxy, cyano, nitro, alkyl, alkoxy, cycloalkyl, heterocyclyl, aryl, heteroaryl, —(CH₂)ₙC(O)OR¹⁵, —OC(O)R¹⁵, —C(O)R¹⁵, —C(O)NR¹⁶R¹⁷, —NHC(O)R¹⁵, —NR¹⁶R¹⁷, —OC(O)NR¹⁶R¹⁷, —NHC(O)NR¹⁶R¹⁷, —S(O)ₘR¹⁵, —NHC(O)(O)R¹⁵, and —NHS(O)ₘR¹⁵;

R² and R⁴ are each independently selected from the group consisting of hydrogen and alkyl;

R and R³ are each independently selected from the group consisting of hydrogen, halogen, and alkyl;

R⁵ and R⁶ are each independently selected from the group consisting of hydrogen, alkyl, and aryl, wherein the alkyl or aryl is optionally substituted with one or more groups selected from the group consisting of alkyl and halogen;

R⁷, R⁸, R⁹, and R¹⁰ are each independently selected from the group consisting of hydrogen, alkyl, hydroxyalkyl, and halogen, or, R⁷ and R⁸ or R⁹ and R¹⁰ are taken together to form an oxo group;

R¹¹, R¹², R¹³, and R¹⁴ are each independently selected from the group consisting of hydrogen, alkyl, and halogen, or, R¹¹ and R¹² or R¹³ and R¹⁴ are taken together to form an oxo group;

R¹⁵ is selected from the group consisting of hydrogen, alkyl, cycloalkyl, heterocyclyl, alkenyl, alkynyl, aryl, and heteroaryl, wherein the alkyl, cycloalkyl, heterocyclyl, aryl, or heteroaryl is optionally substituted with one or more groups selected from the group consisting of alkyl, halogen, hydroxy, cyano, amino, nitro, alkoxy, cycloalkyl, heterocyclyl, aryl, heteroaryl, —(CH₂)ₙC(O)OR¹⁸, —OC(O)R¹⁸, —C(O)R¹⁸, —C(O)NR¹⁹R²⁰, —NHC(O)R¹⁸, —NR¹⁹R²⁰, —OC(O)NR¹⁹R²⁰, —NHC(O)NR¹⁹R²⁰, —S(O)ₘR¹⁸, —NHC(O)(O)R¹⁸, and —NHS(O)ₘR¹⁸;

R¹⁶ and R¹⁷ are each independently selected from the group consisting of hydrogen, alkyl, cycloalkyl, heterocyclyl, aryl, and heteroaryl, wherein the alkyl, cycloalkyl, heterocyclyl, aryl, or heteroaryl is optionally substituted with one or more groups selected from the group consisting of alkyl, halogen, hydroxy, cyano, amino, alkoxy, cycloalkyl, heterocyclyl, hydroxyalkyl, alkynyl, aryl, heteroaryl, carboxyl, alkoxycarbonyl, and —OR¹⁸;

R¹⁸ is selected from the group consisting of hydrogen, alkyl, cycloalkyl, heterocyclyl, hydroxyalkyl, aryl, and heteroaryl;

R¹⁹ and R²⁰ are each independently selected from the group consisting of hydrogen, alkyl, cycloalkyl, heterocyclyl, aryl, and heteroaryl;

m is 0, 1, or 2;
n is 0, 1, or 2;
p is 0, 1, or 2;
q is 0, 1, or 2;
s is 0, 1, or 2; and
t is 0, 1, or 2.

2. The compound of formula (I), or a tautomer, mesomer, racemate, enantiomer, diastereomer, or mixture thereof, or a pharmaceutically acceptable salt thereof according to claim 1, being a compound of formula (II), or a pharmaceutically acceptable salt thereof:

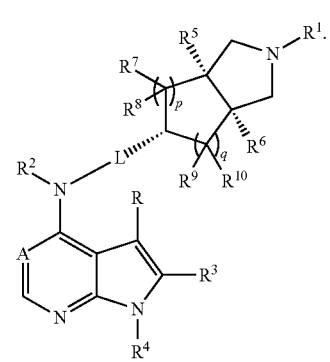

(II)

3. The compound of formula (I), or a tautomer, mesomer, racemate, enantiomer, diastereomer, or mixture thereof, or a pharmaceutically acceptable salt thereof according to claim 1, being a compound of formula (III), or a pharmaceutically acceptable salt thereof:

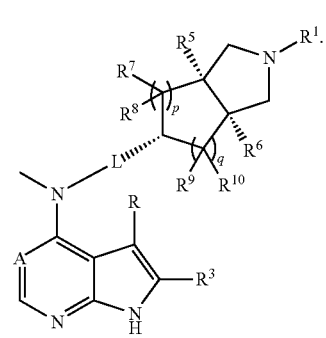

(III)

4. The compound of formula (I), or a tautomer, mesomer, racemate, enantiomer, diastereomer, or mixture thereof, or a pharmaceutically acceptable salt thereof according to claim 1, being a compound of formula (IV-a) or formula (IV-b), or a pharmaceutically acceptable salt thereof:

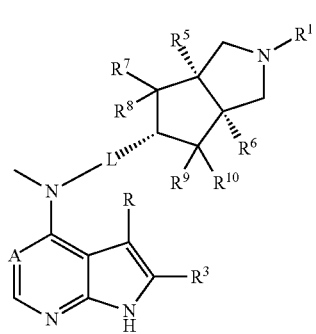

(IV-a)

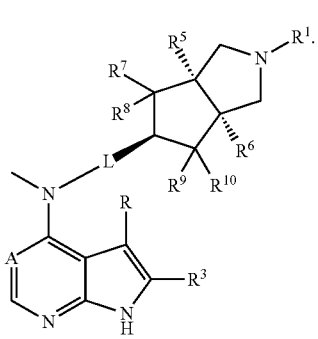

(IV-b)

5. The compound of formula (I), or a tautomer, mesomer, racemate, enantiomer, diastereomer, or mixture thereof, or a pharmaceutically acceptable salt thereof according to claim 1, being a compound of formula (V-a) or formula (V-b), or a pharmaceutically acceptable salt thereof:

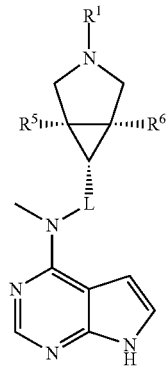
(V-a)

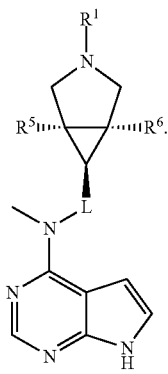
(V-b)

6. The compound of formula (I), or a tautomer, mesomer, racemate, enantiomer, diastereomer, or mixture thereof, or a pharmaceutically acceptable salt thereof according to claim 1, being a compound of formula (VI-a) or formula (VI-b), or a pharmaceutically acceptable salt thereof:

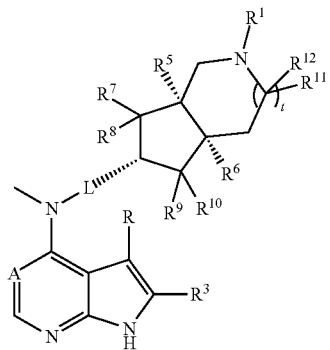
(VI-a)

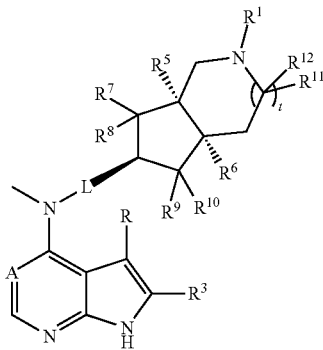
(VI-b)

wherein t is 0 or 1.

7. The compound of formula (I), or a tautomer, mesomer, racemate, enantiomer, diastereomer, or mixture thereof, or a pharmaceutically acceptable salt thereof according to claim 1, being a compound of formula (VII-a) or formula (VII-b), or a pharmaceutically acceptable salt thereof:

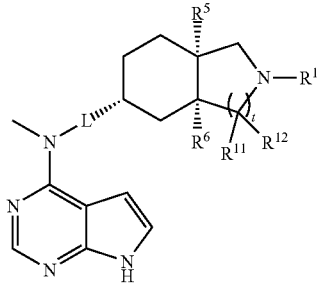
(VII-a)

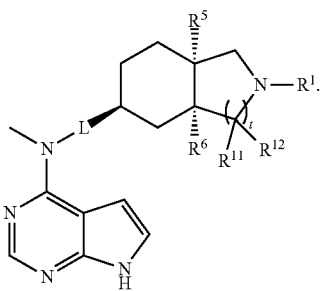
(VII-b)

8. The compound of formula (I), or a tautomer, mesomer, racemate, enantiomer, diastereomer, or mixture thereof, or a pharmaceutically acceptable salt thereof according to claim 1, wherein L is a bond.

9. The compound of formula (I), or a tautomer, mesomer, racemate, enantiomer, diastereomer, or mixture thereof, or a pharmaceutically acceptable salt thereof according to claim 1, wherein $R^1$ is selected from the group consisting of alkyl, heteroaryl, $-(CH_2)_nC(O)OR^{15}$, $-C(O)R^{15}$, $-C(O)NR^{16}R^{17}$ and $-S(O)_2R^{15}$, wherein the alkyl or heteroaryl is optionally substituted with one or more groups selected from the group consisting of halogen, hydroxyl, cyano, and $-(CH_2)_nC(O)OR^{15}$;

$R^{15}$ is selected from the group consisting of hydrogen, alkyl, cycloalkyl, heterocyclyl, alkenyl, alkynyl, aryl, and heteroaryl, wherein the alkyl, cycloalkyl, heterocyclyl, aryl, or heteroaryl is optionally substituted with one or more groups selected from the group consisting of alkyl, halogen, hydroxy, cyano, amino, nitro, alkoxy, cycloalkyl, heterocyclyl, aryl, heteroaryl, $-(CH_2)_nC(O)OR^{18}$, $-OC(O)R^{18}$, $-C(O)R^{18}$, $-S(O)_2R^{18}$, $-NHC(O)(O)R^{18}$, $-NHS(O)_2R^{18}$, and $-NR^{19}R^{20}$;

R[16] and R[17] are each independently selected from the group consisting of hydrogen, alkyl, and heteroaryl, wherein the heteroaryl is optionally substituted with one or more groups selected from the group consisting of alkoxy, cycloalkyl, hydroxyalkyl, alkynyl, and —OR[18];

R[18] is selected from the group consisting of hydrogen, alkyl, and hydroxyalkyl;

R[19] and R[20] are each independently selected from the group consisting of hydrogen and alkyl;

and n is 0, 1, or 2.

10. The compound of formula (I), or a tautomer, mesomer, racemate, enantiomer, diastereomer, or mixture thereof, or a pharmaceutically acceptable salt thereof according to claim 1, wherein R[5] and R[6] are each independently selected from the group consisting of hydrogen and alkyl.

11. The compound of formula (I), or a tautomer, mesomer, racemate, enantiomer, diastereomer, or mixture thereof, or a pharmaceutically acceptable salt thereof according to claim 1, wherein R[7], R[8], R[9] and R[10] are each independently selected from the group consisting of hydrogen, alkyl, and hydroxyalkyl.

12. The compound of formula (I), or a tautomer, mesomer, racemate, enantiomer, diastereomer, or mixture thereof, or a pharmaceutically acceptable salt thereof according to claim 1, wherein R[11], R[12], R[13] and R[14] are each independently hydrogen.

13. The compound of formula (I), or a tautomer, mesomer, racemate, enantiomer, diastereomer, or mixture thereof, or a pharmaceutically acceptable salt thereof according to claim 1, wherein R[11] and R[12] or R[13] and R[14] are taken together to form an oxo group.

14. The compound of formula (I), or a tautomer, mesomer, racemate, enantiomer, diastereomer, or mixture thereof, or a pharmaceutically acceptable salt thereof according to claim 1, wherein A is N.

15. The compound of formula (I), or a tautomer, mesomer, racemate, enantiomer, diastereomer, or mixture thereof, or a pharmaceutically acceptable salt thereof according to claim 1, wherein the compound is selected from the group consisting of:

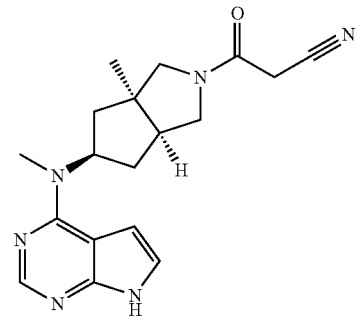

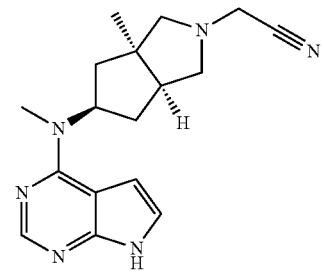

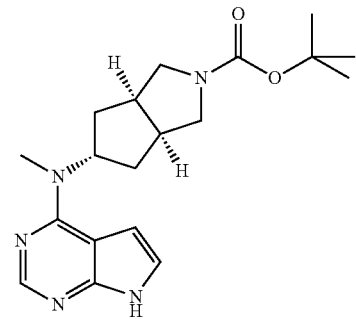

-continued

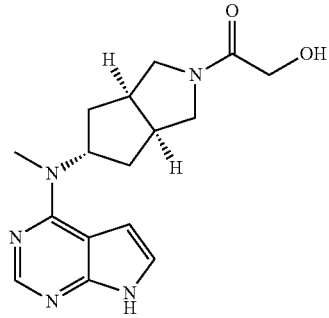

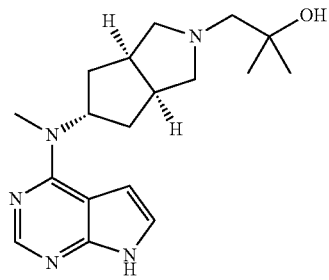

279
-continued
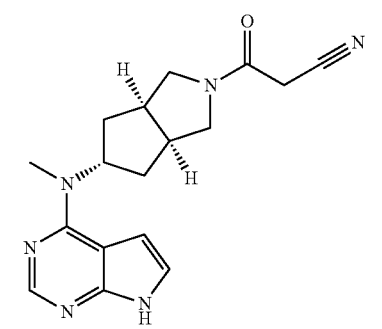
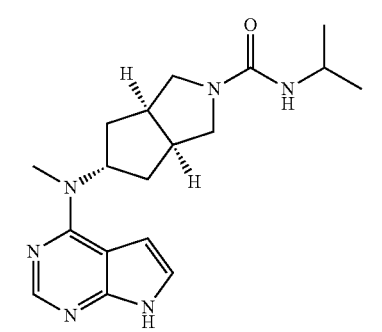
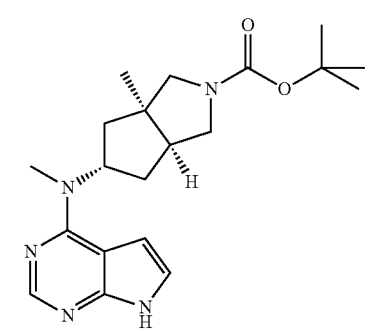
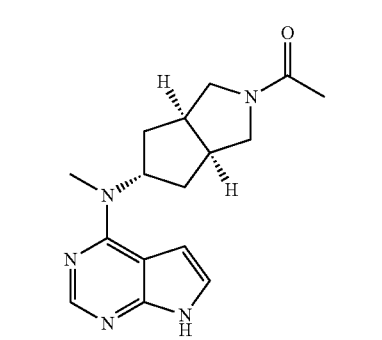
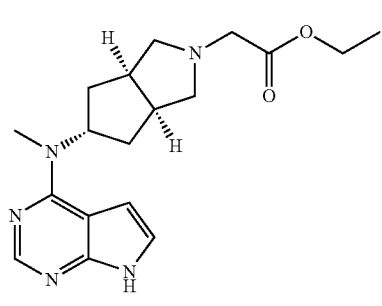
280
-continued
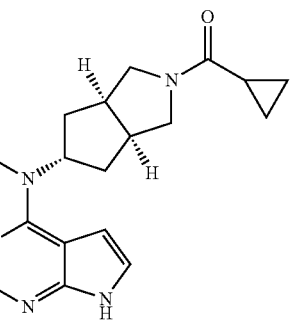
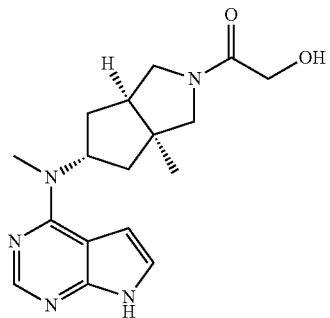
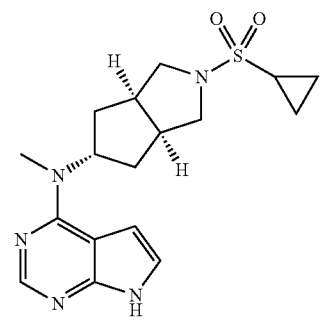
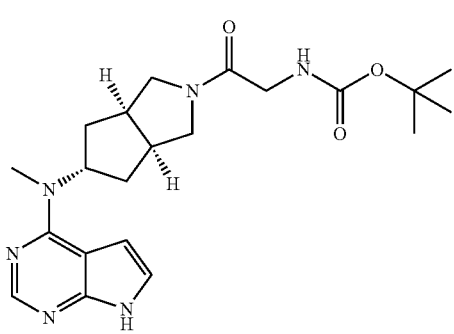
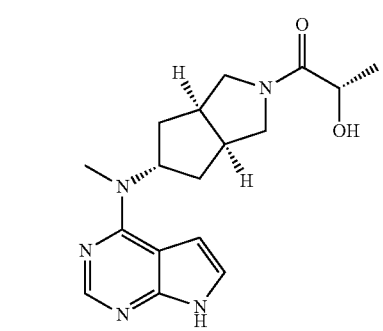

281
-continued
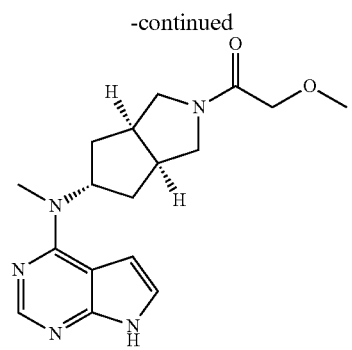
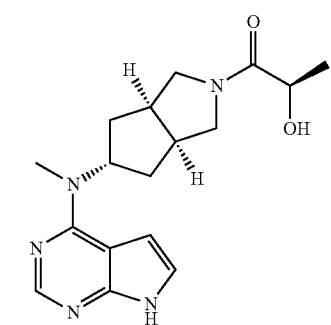
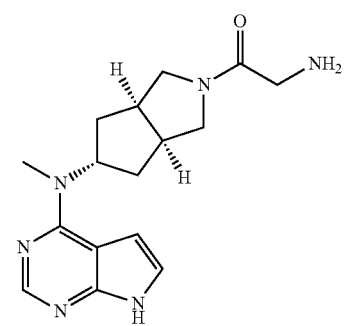
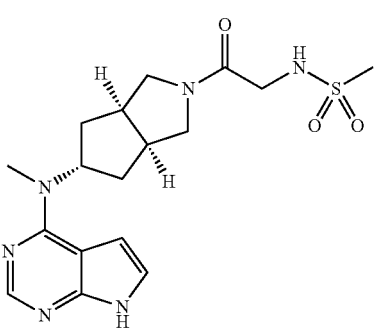
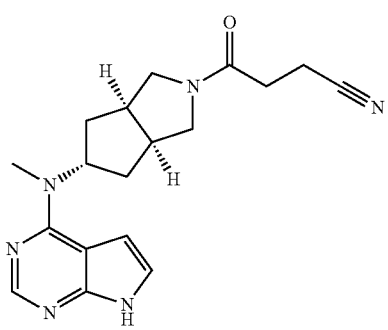
282
-continued
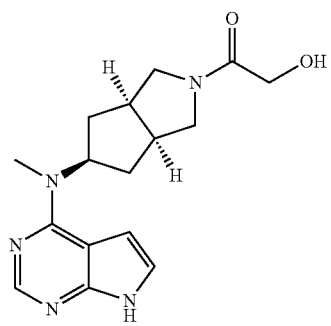
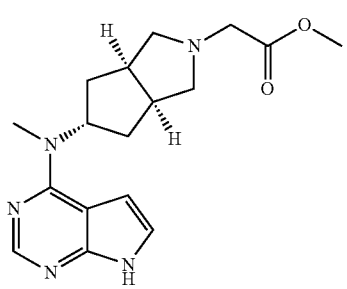
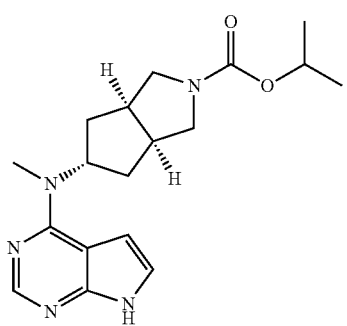
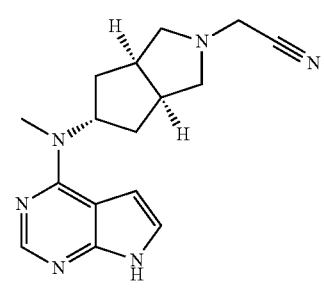
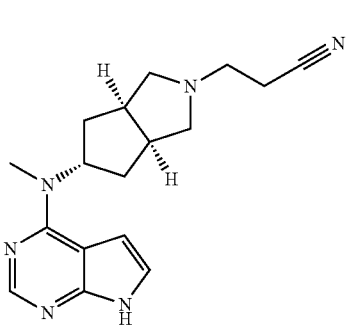

283
-continued
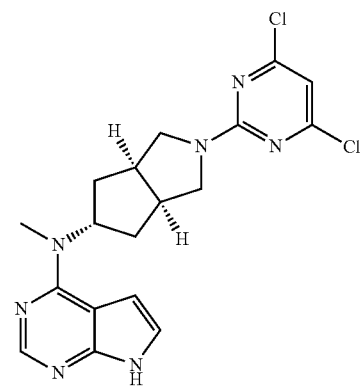
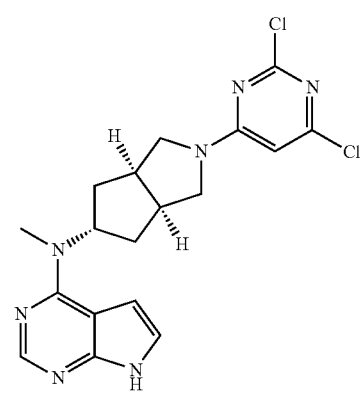
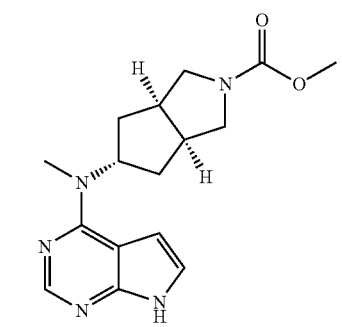
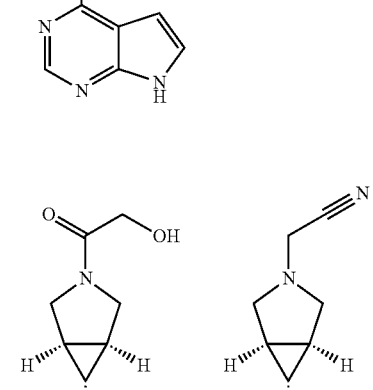
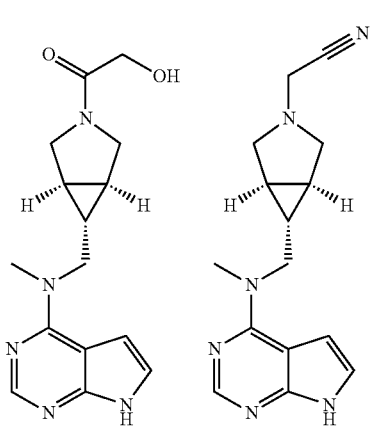
284
-continued
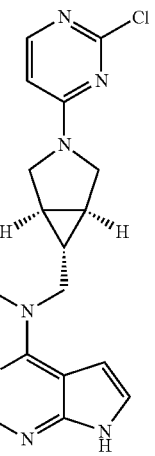
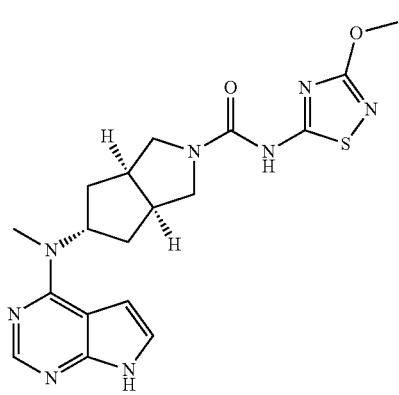
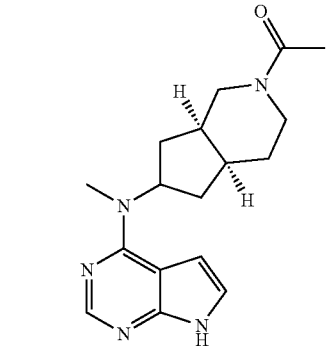
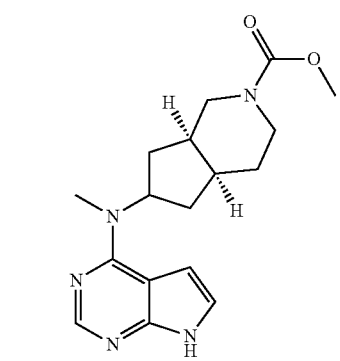

285
-continued
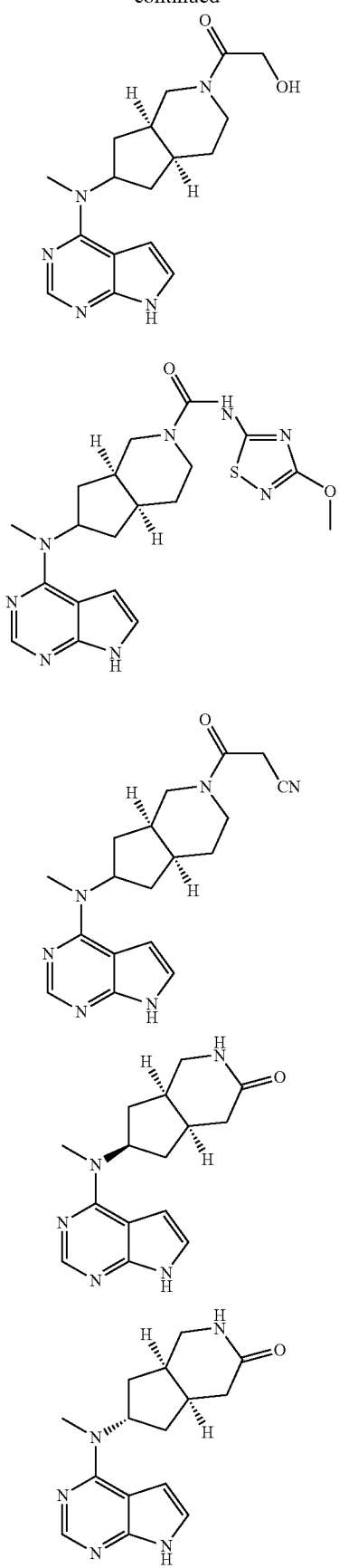
286
-continued
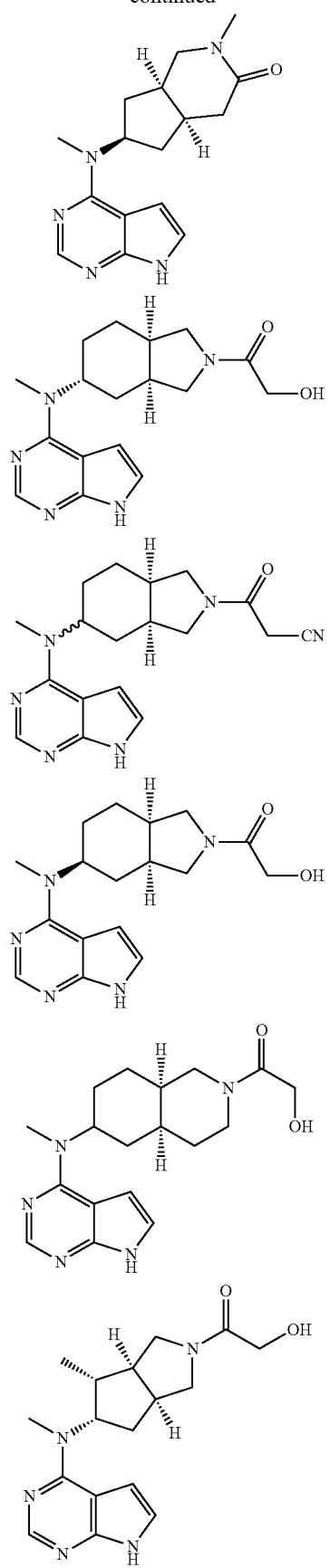

287
-continued
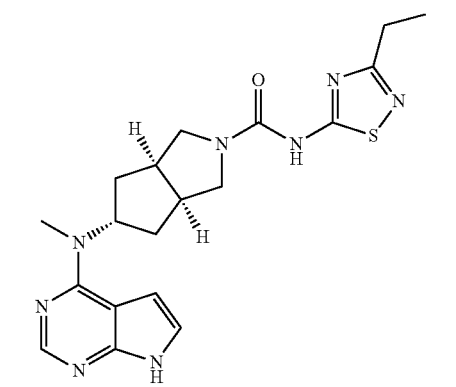
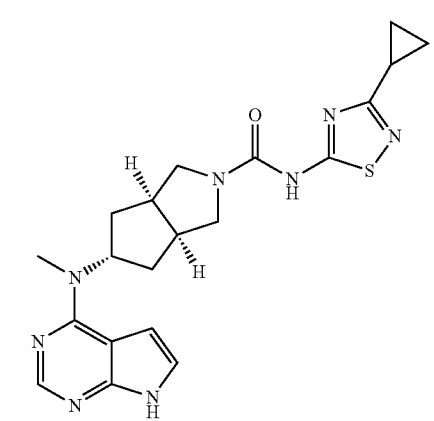
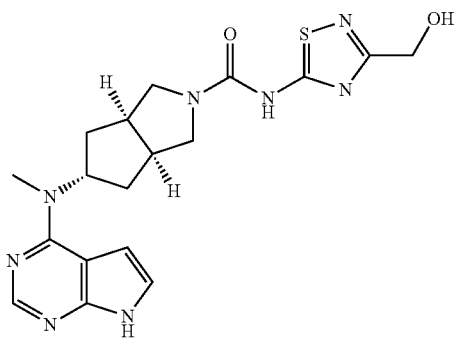
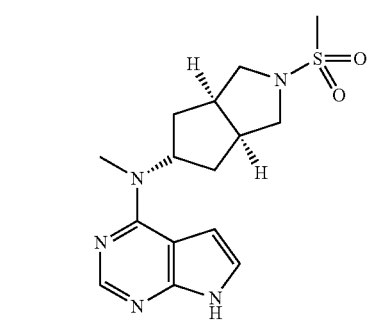
288
-continued
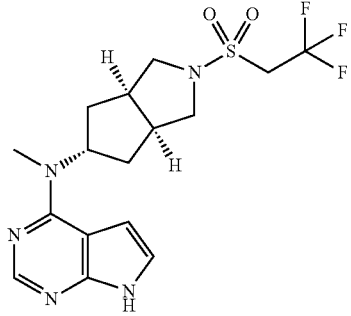
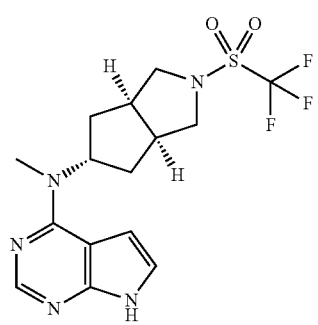
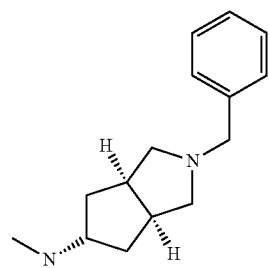
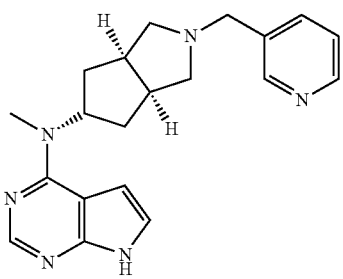
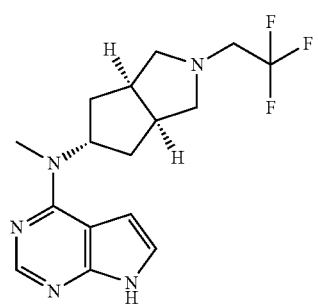

-continued
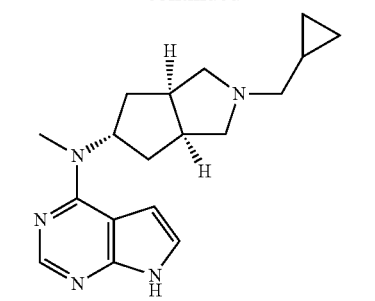
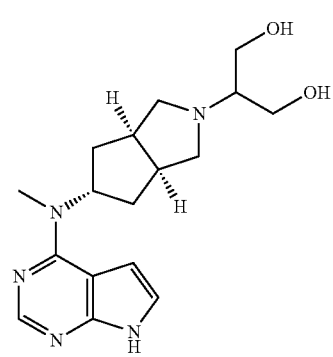
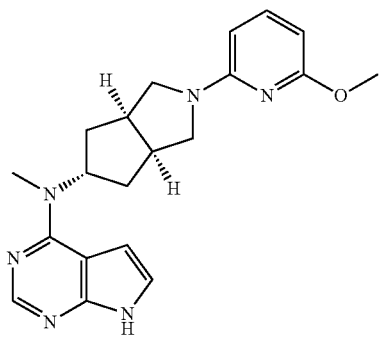
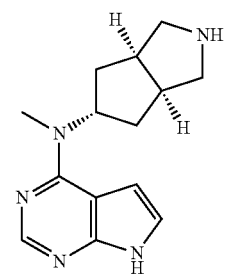
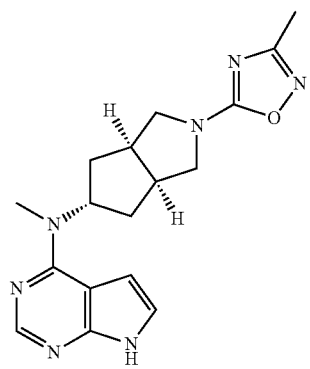
-continued
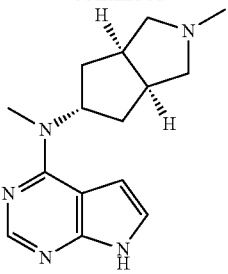
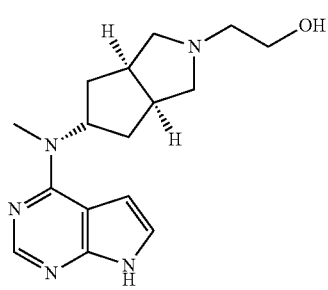
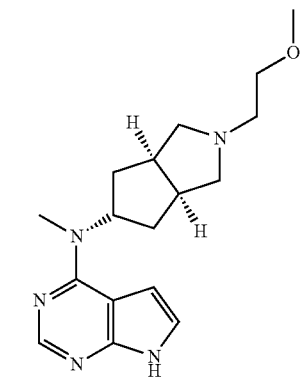
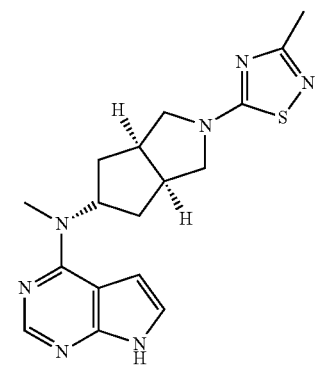
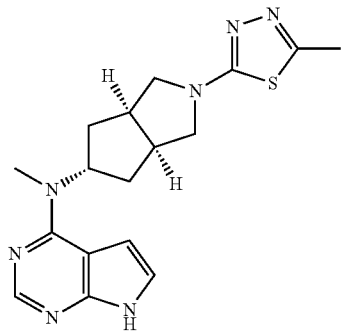

291
-continued
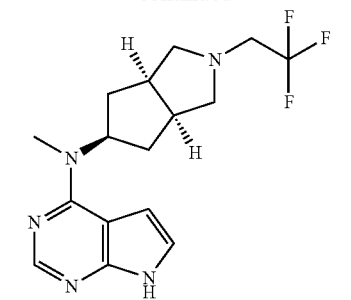
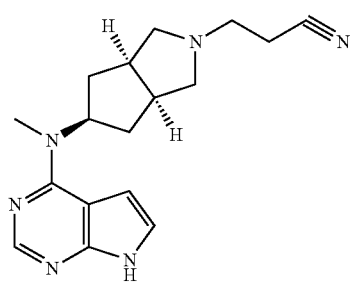
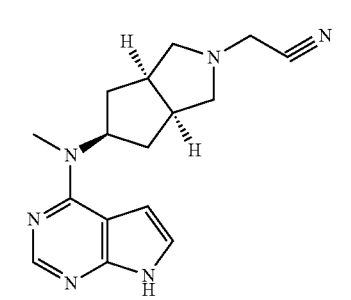
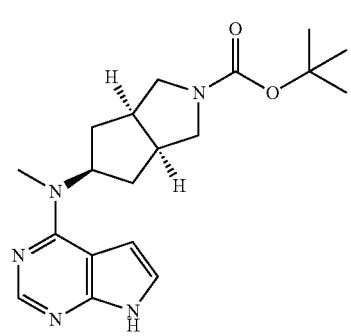
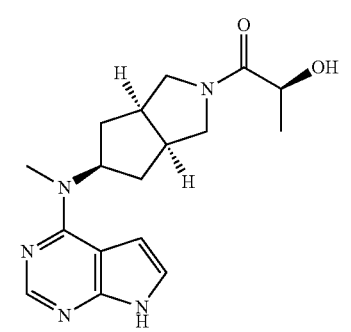
292
-continued
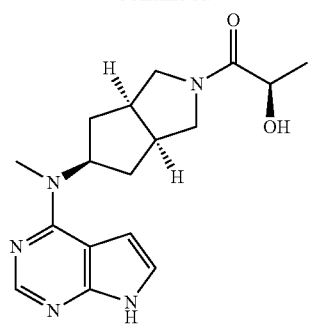
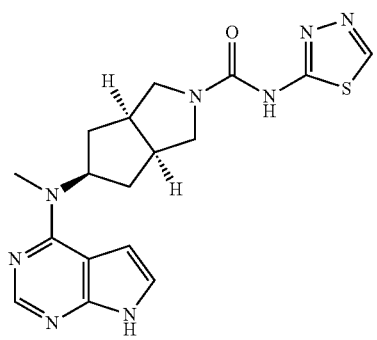
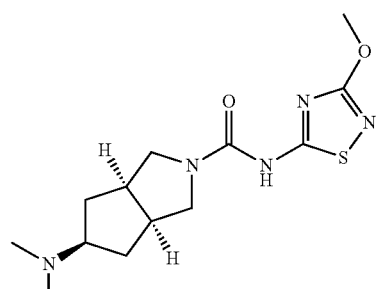
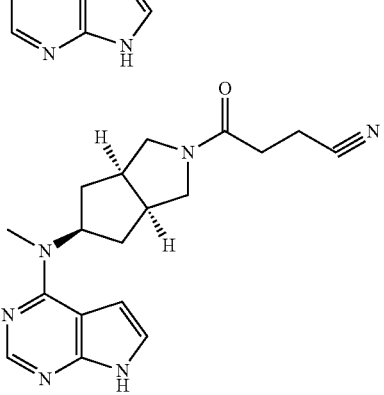
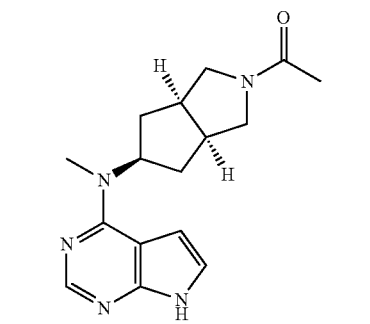

293
-continued
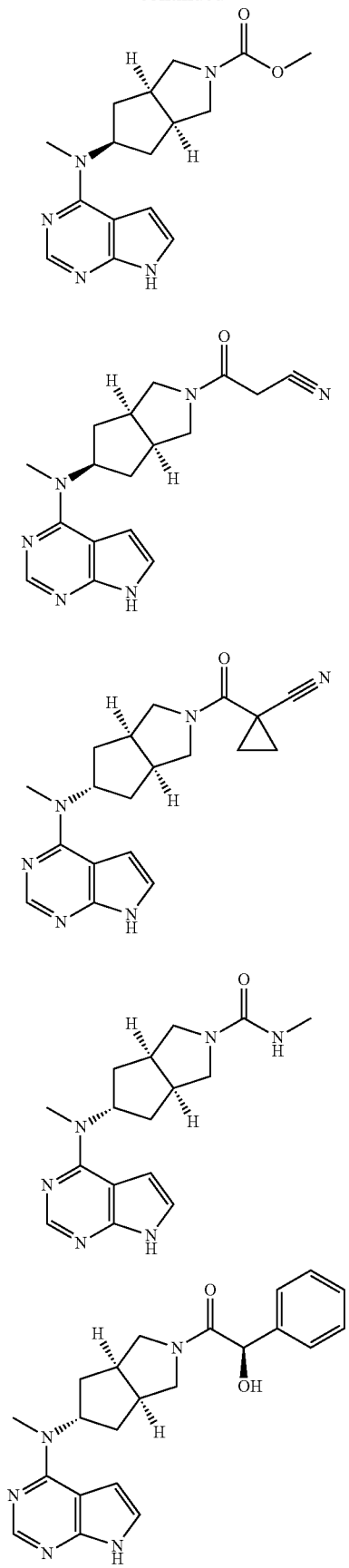
294
-continued
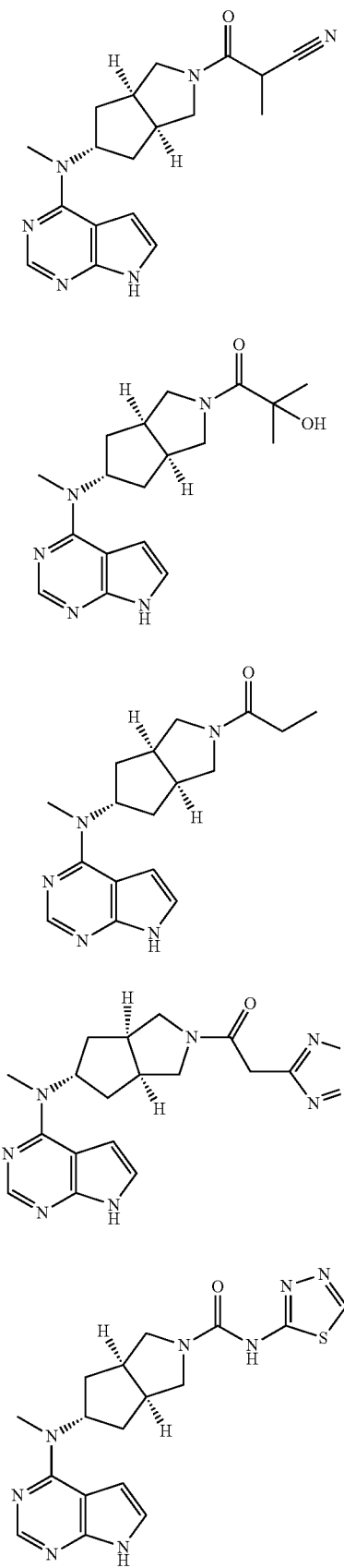

295
-continued
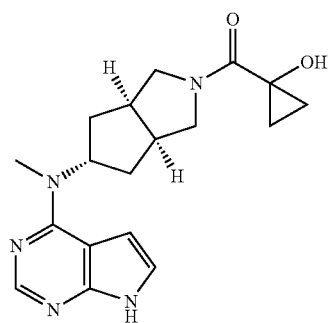
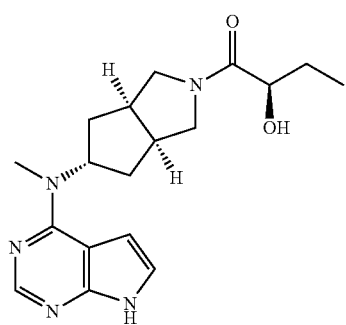
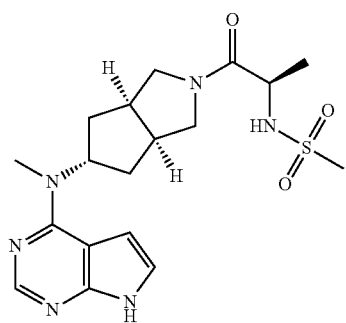
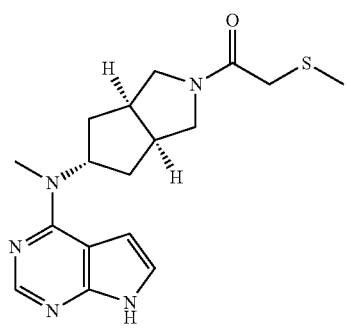
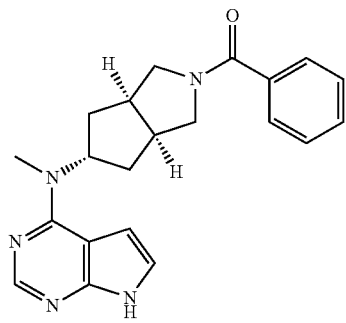
296
-continued
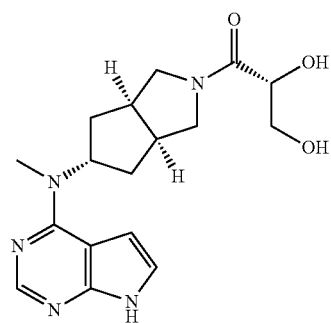
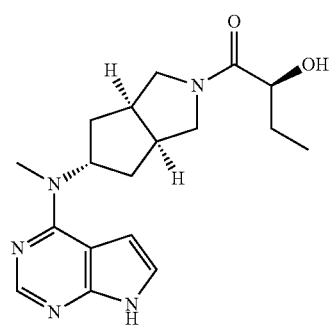
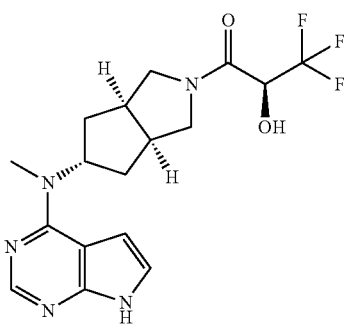
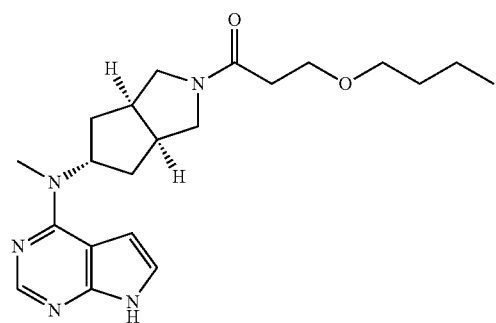
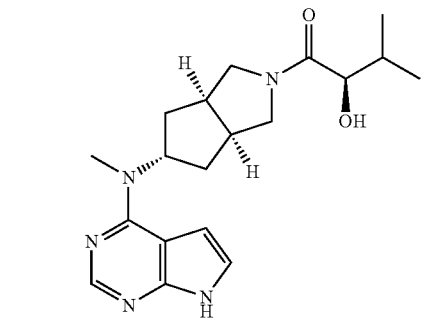

297
-continued
298
-continued
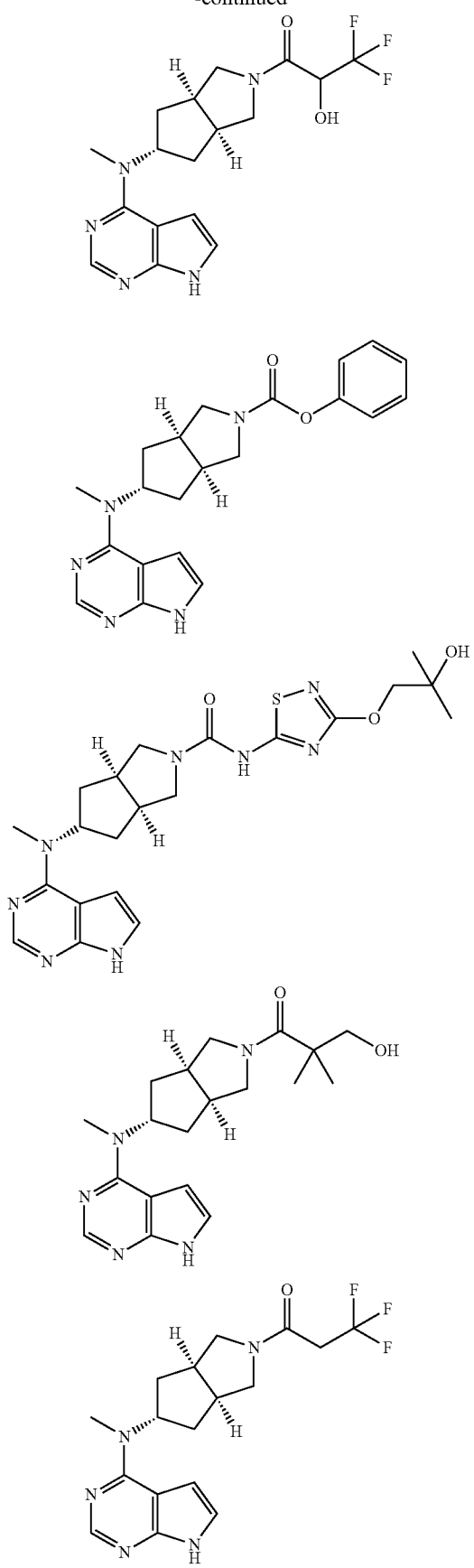
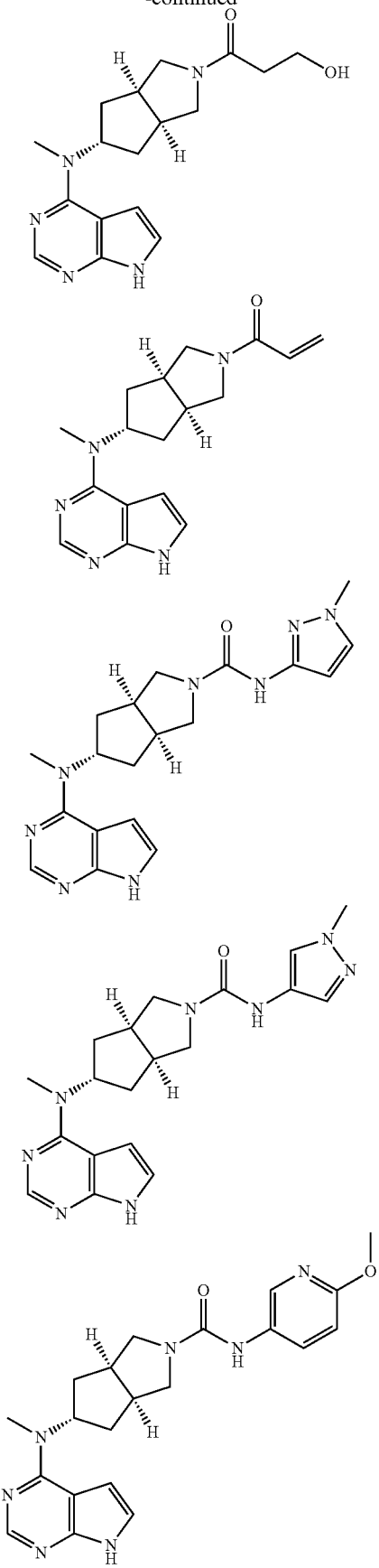

299
-continued
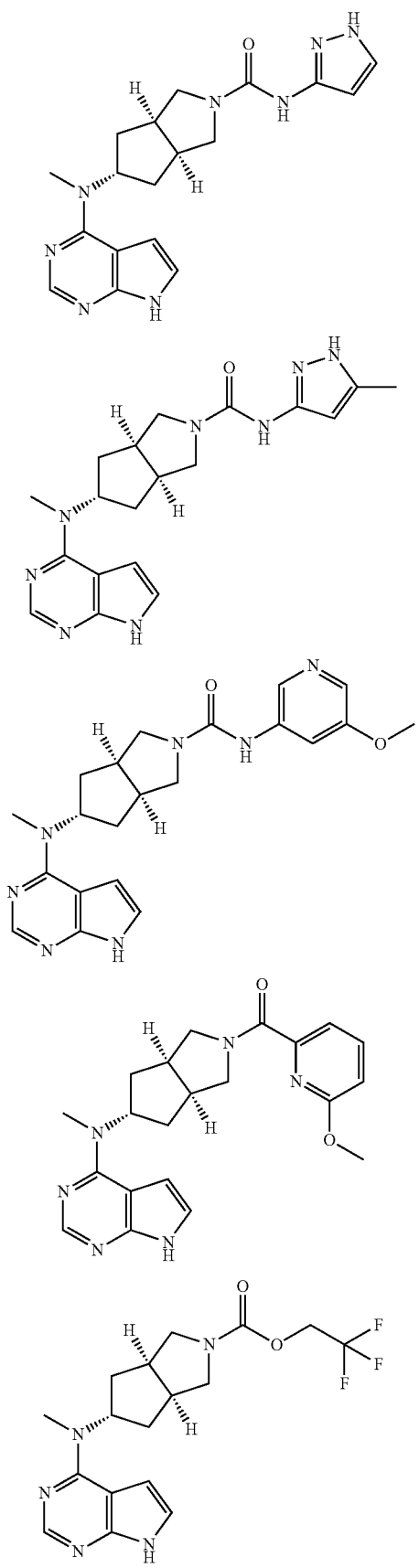
300
-continued
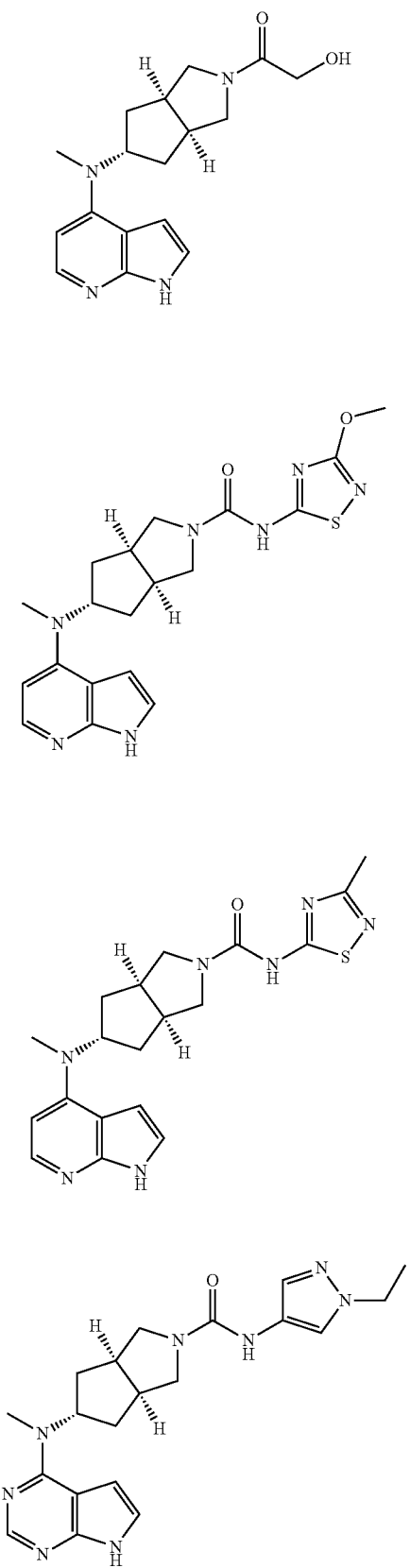

301
-continued
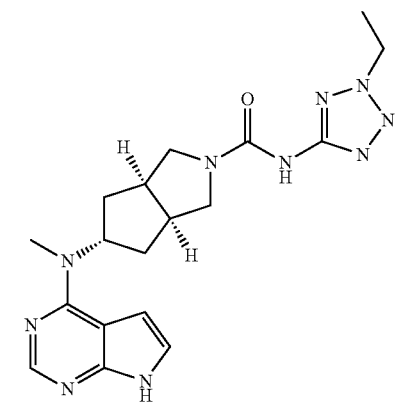
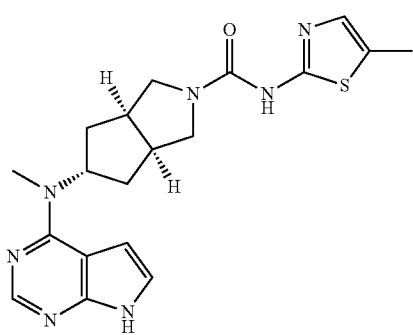
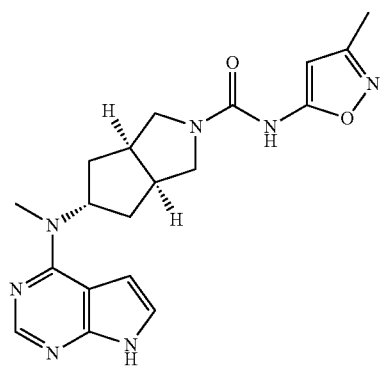
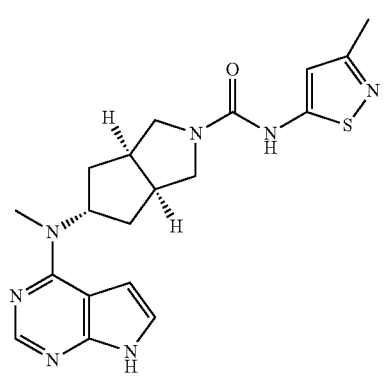
302
-continued
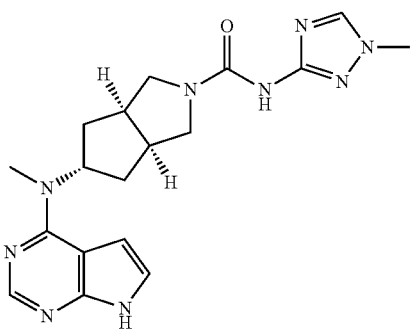
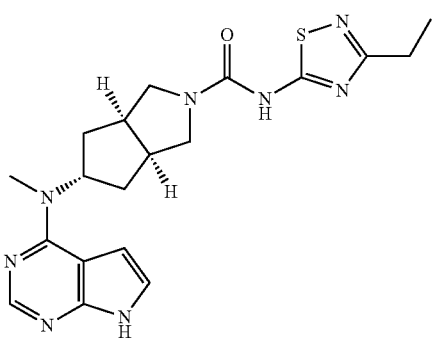
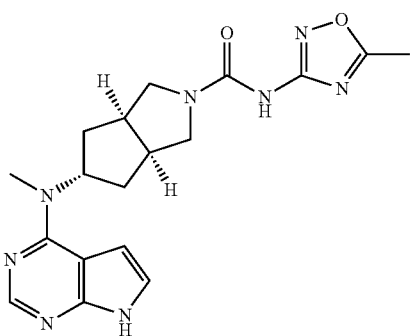
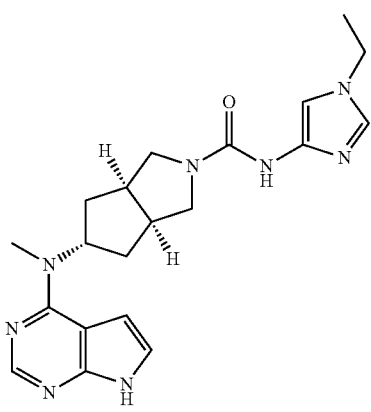

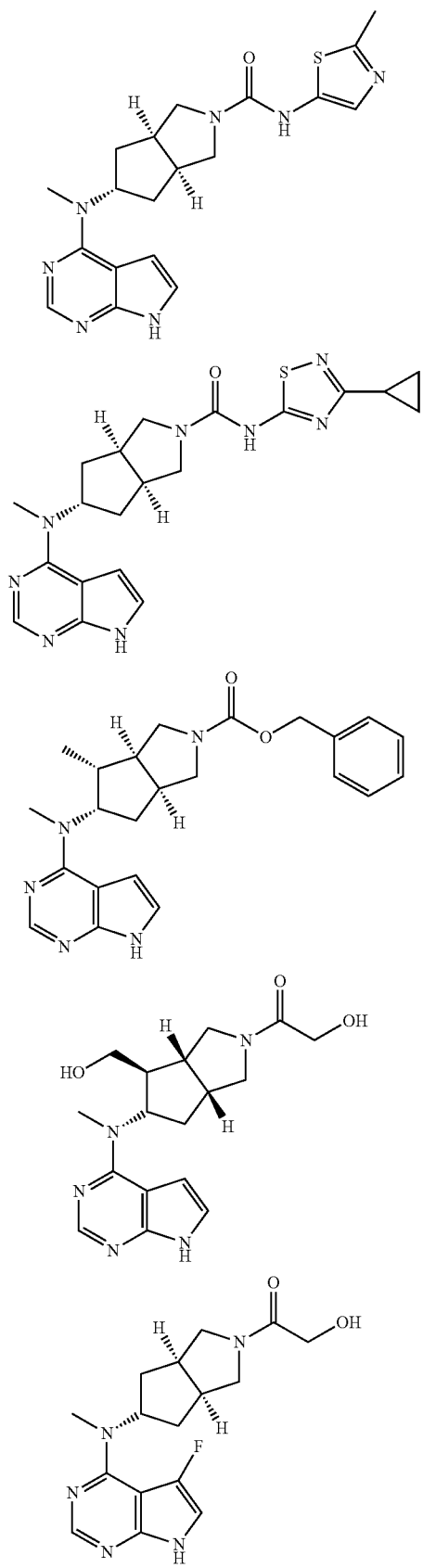
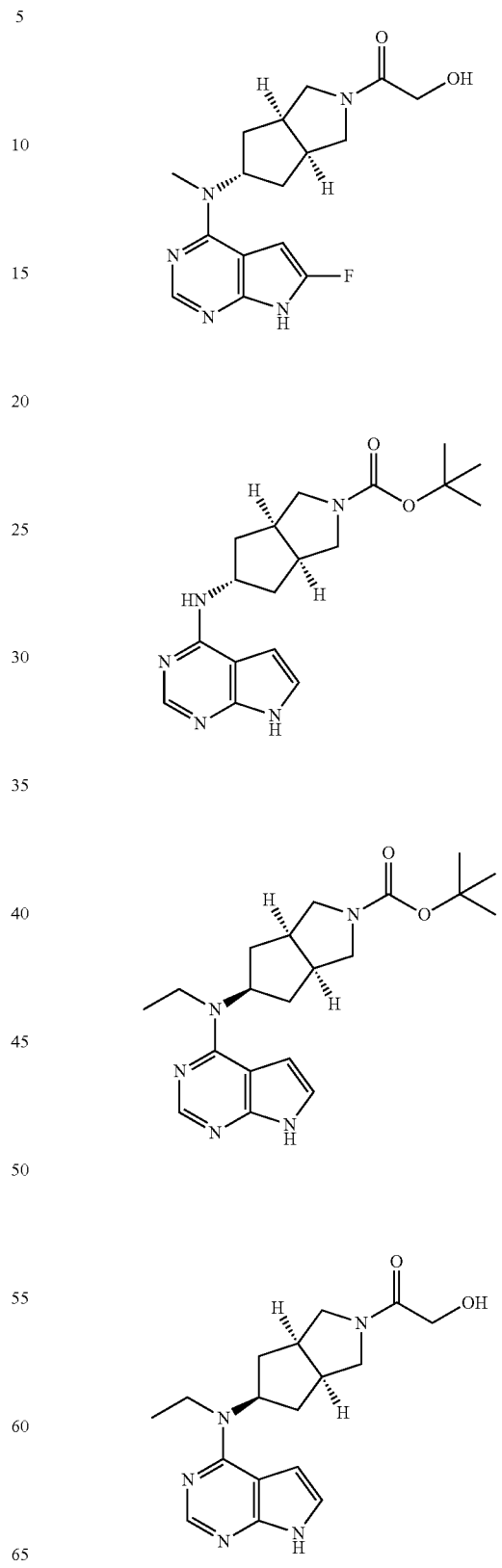

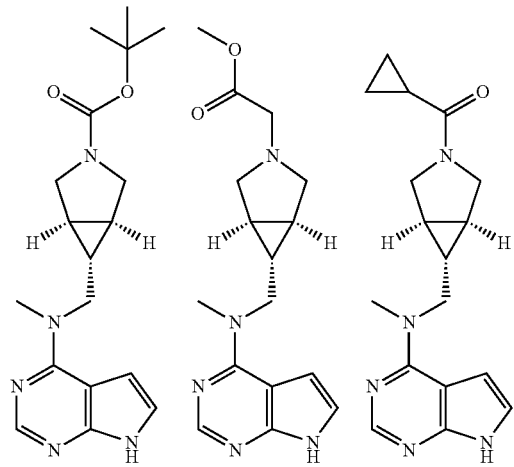
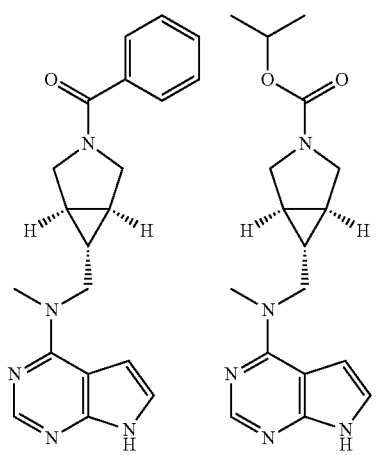
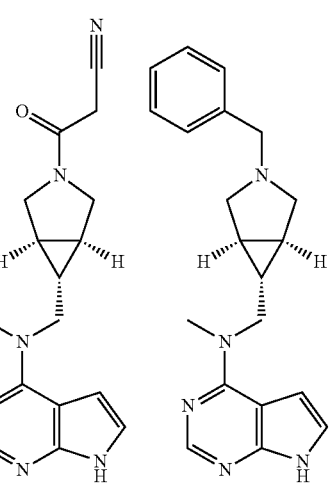
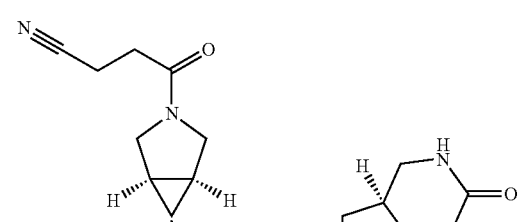
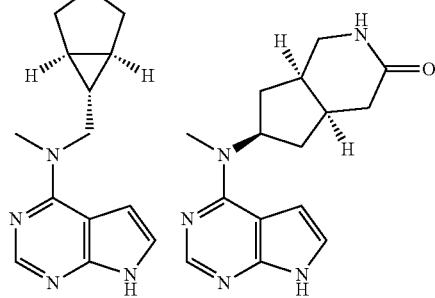
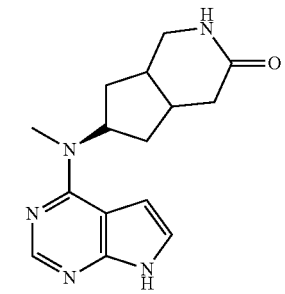

307
-continued
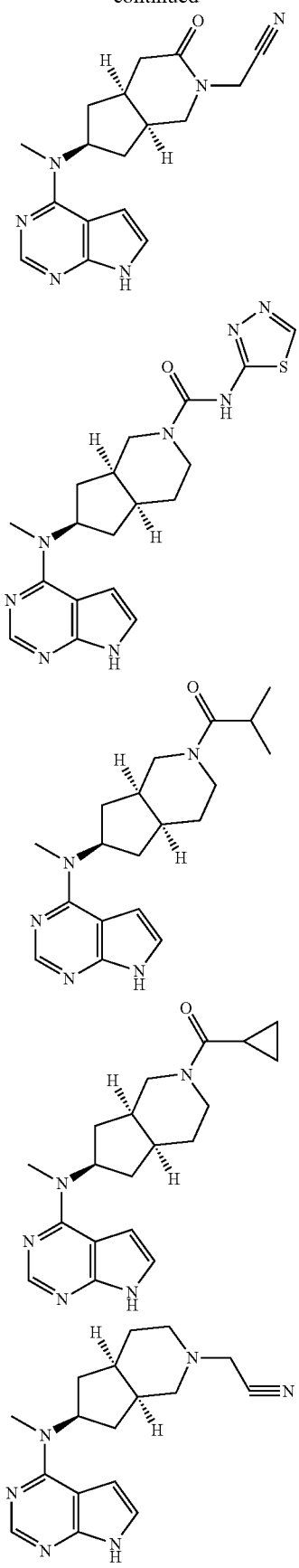
308
-continued
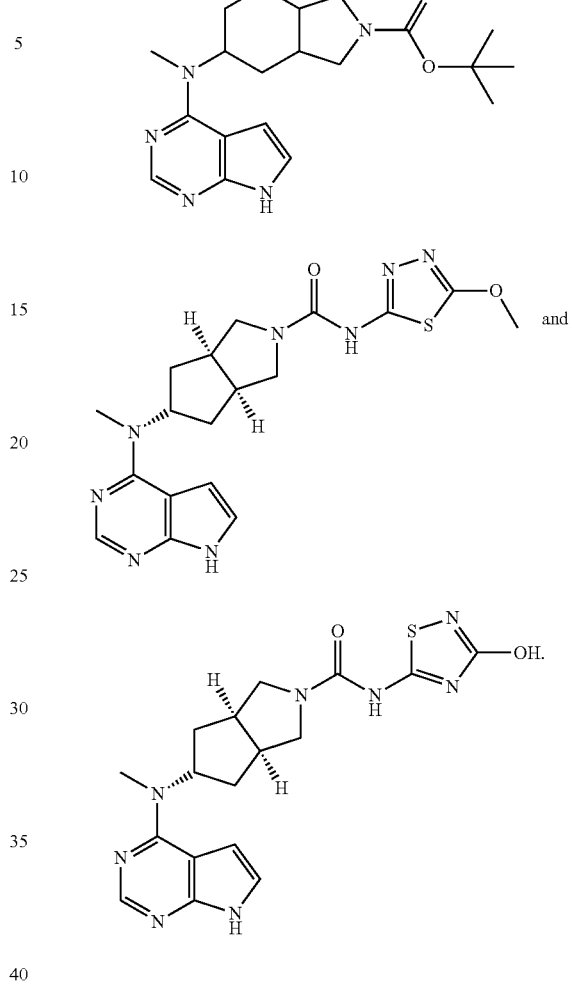
16. A process of preparing the compound of formula (I) according to claim 1, or a tautomer, mesomer, racemate, enantiomer, diastereomer, or mixture thereof, or a pharmaceutically acceptable salt thereof, comprising a step of:
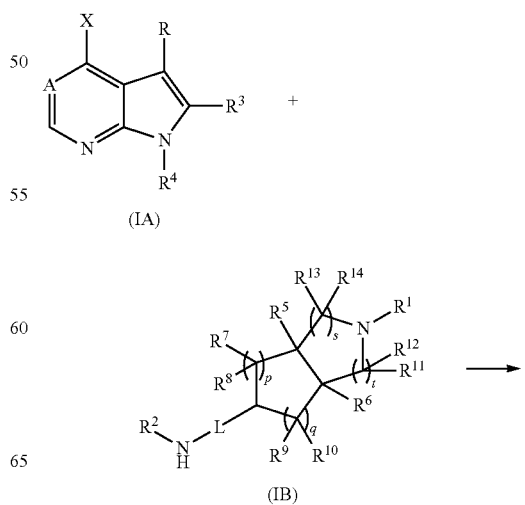

-continued

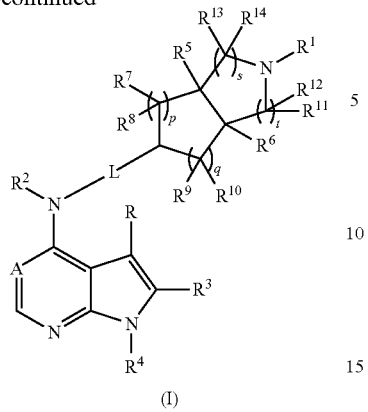

(I)

reacting a compound of formula (IA) with a compound of formula (IB) under an alkaline condition to obtain the compound of formula (I), wherein X is halogen.

17. A process of preparing the compound of formula (I) according to claim 1, or a tautomer, mesomer, racemate, enantiomer, diastereomer, or mixture thereof, or a pharmaceutically acceptable salt thereof, comprising a step of:

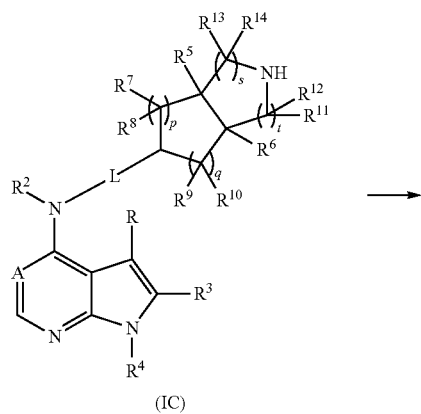

(IC)

-continued

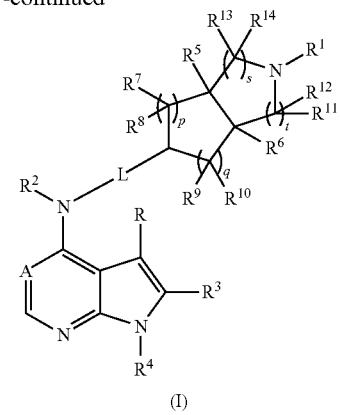

(I)

reacting a compound of formula (IC) or a pharmaceutically acceptable salt thereof with a carboxylic acid, acyl chloride, sulfonyl chloride, carboxylic ester, an ethylene oxide derivative, or halide under an alkaline condition to obtain the compound of formula (I).

18. A pharmaceutical composition comprising a therapeutically effective amount of the compound of formula (I), or a tautomer, mesomer, racemate, enantiomer, diastereomer, or mixture thereof, or a pharmaceutically acceptable salt thereof according to claim 1, and a pharmaceutically acceptable carrier.

19. A method for inhibiting JAK kinase, comprising a step of administering to a subject in need thereof the pharmaceutical composition according to claim 18.

20. The method according to claim 19, wherein the pharmaceutical composition is combined with one or more additional reagents selected from the group consisting of agents for regulating a mammalian immune system, anticancer agents, and anti-inflammatory agents.

21. A method for the treatment of a disease or disorder, comprising a step of administering to a subject in need thereof the pharmaceutical composition according to claim 18, wherein the disease or disorder is selected from the group consisting of allograft rejection; graft versus host disease; atopic dermatitis; rheumatoid arthritis; psoriasis; lymphoma; leukemia; pancreatic cancer; breast cancer; cutaneous T-cell lymphoma; and cutaneous B-cell lymphoma.

* * * * *